United States Patent
Brimble et al.

(10) Patent No.: US 11,464,853 B2
(45) Date of Patent: Oct. 11, 2022

(54) AMINO ACID AND PEPTIDE CONJUGATES AND CONJUGATION PROCESS

(71) Applicants: Auckland UniServices Limited, Auckland (NZ); Margaret Anne Brimble, Auckland (NZ); Geoffrey Martyn Williams, Auckland (NZ); Peter Roderick Dunbar, Auckland (NZ)

(72) Inventors: Margaret Anne Brimble, Auckland (NZ); Geoffrey Martyn Williams, Auckland (NZ); Peter Roderick Dunbar, Auckland (NZ); Daniel Verdon, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 81 days.

(21) Appl. No.: 16/076,912

(22) PCT Filed: Feb. 24, 2017

(86) PCT No.: PCT/IB2017/051054
§ 371 (c)(1),
(2) Date: Aug. 9, 2018

(87) PCT Pub. No.: WO2017/145097
PCT Pub. Date: Aug. 31, 2017

(65) Prior Publication Data
US 2019/0046636 A1     Feb. 14, 2019

(30) Foreign Application Priority Data
Feb. 26, 2016   (AU) ................................ 2016900701

(51) Int. Cl.
| C07K 7/00 | (2006.01) |
| A61K 39/39 | (2006.01) |
| C07C 323/59 | (2006.01) |
| A61P 35/00 | (2006.01) |
| A61K 39/00 | (2006.01) |
| A61K 39/02 | (2006.01) |
| A61K 39/12 | (2006.01) |

(52) U.S. Cl.
CPC ...... *A61K 39/39* (2013.01); *A61K 39/001104* (2018.08); *A61K 39/02* (2013.01); *A61K 39/12* (2013.01); *A61P 35/00* (2018.01); *C07C 323/59* (2013.01); *C07K 7/00* (2013.01); *A61K 2121/00* (2013.01)

(58) Field of Classification Search
CPC ...... A61K 2039/6018; A61K 2039/627; A61K 2121/00; A61K 39/001104; A61K 39/001188; A61K 39/02; A61K 39/12; A61K 39/39; A61K 47/543; A61P 35/00; C07K 14/70539; C07K 7/00; C07K 7/02; C07C 323/59; C12N 2710/16234
See application file for complete search history.

(56) References Cited

U.S. PATENT DOCUMENTS

| 4,439,425 A | 3/1984 | Tarcsay et al. |
| 4,743,543 A | 5/1988 | Kortright |
| 4,914,021 A | 4/1990 | Toth et al. |
| 4,918,164 A | 4/1990 | Hellstrom et al. |
| 4,921,789 A | 5/1990 | Salem et al. |
| 4,921,790 A | 5/1990 | O'Brien |
| 4,939,240 A | 7/1990 | Chu et al. |
| 4,963,484 A | 10/1990 | Kufe |
| 5,053,489 A | 10/1991 | Kufe |
| 5,110,911 A | 5/1992 | Samuel et al. |
| 5,808,005 A | 9/1998 | Codington et al. |
| 5,849,893 A | 12/1998 | Lubberding et al. |
| 5,855,866 A | 1/1999 | Thorpe et al. |
| 5,892,020 A | 4/1999 | Mezes et al. |
| 5,994,294 A | 11/1999 | Garvey et al. |
| 6,024,964 A | 2/2000 | Jung et al. |
| 6,074,650 A | 6/2000 | Jung et al. |
| 6,310,180 B1 | 10/2001 | Tam |
| 6,723,695 B1 | 4/2004 | Burrows et al. |
| 6,828,329 B2 | 12/2004 | Cai et al. |
| 7,491,395 B2 | 2/2009 | Stegmann |
| 7,569,225 B2 | 8/2009 | Jackson et al. |
| 7,619,057 B2 | 11/2009 | Wang et al. |
| 7,833,532 B2 | 11/2010 | Jackson et al. |

(Continued)

FOREIGN PATENT DOCUMENTS

| CA | 1333563 | 12/1994 |
| CN | 102839186 A | 12/2012 |

(Continued)

OTHER PUBLICATIONS

Schromm et al., The Journal of Biological Chemistry vol. 282, No. 15, pp. 11030-11037, Apr. 13, 2007 (Year: 2007).*
C.W. Thornber, Chem SOC, Rev. 9(4), (1979) 563-580 (Year: 1979).*
Kyrunura, "Structure-activity relationship of lipopeptide from outer membrane of *Escherichia coli* and synthesis of highly immunopotenting lipopeptide derivatives with an achiral lipo-part." Chem. Pharm. Bull. 41(3) 627-629 (1993) (Year: 1993).*

(Continued)

*Primary Examiner* — Thomas S Heard
(74) *Attorney, Agent, or Firm* — Dann, Dorfman, Herrell & Skillman, P.C.

(57) ABSTRACT

The invention relates to amino acid and peptide conjugates, methods for making amino acid and peptide conjugates, conjugates produced by the methods, and pharmaceutical compositions comprising the conjugates. Methods of eliciting immune responses in a subject and methods of vaccinating a subject, uses of the conjugates for the same, and uses of the conjugates in the manufacture of medicaments for the same are also contemplated.

18 Claims, 8 Drawing Sheets

Specification includes a Sequence Listing.

(56) References Cited

U.S. PATENT DOCUMENTS

| | | | |
|---|---|---|---|
| 7,887,833 | B2 | 2/2011 | Heldman et al. |
| 7,960,507 | B2 | 6/2011 | Eisenbach et al. |
| 8,241,639 | B2 | 8/2012 | Middeldorp |
| 8,309,096 | B2 | 11/2012 | Blais et al. |
| 8,367,067 | B2 | 2/2013 | Jackson et al. |
| 8,481,051 | B2 | 7/2013 | Kuzushima et al. |
| 8,492,514 | B2 | 7/2013 | Kessler et al. |
| 9,314,521 | B2 | 4/2016 | Ossendorp et al. |
| 2001/0039669 | A1 | 11/2001 | Douvas et al. |
| 2004/0006242 | A1 | 1/2004 | Hawkins et al. |
| 2007/0048329 | A1 | 3/2007 | Khanna et al. |
| 2007/0191314 | A1 | 8/2007 | Klucker et al. |
| 2008/0139464 | A1 | 6/2008 | Gnjatic et al. |
| 2008/0233143 | A1 | 9/2008 | Jackson et al. |
| 2009/0081248 | A1 | 3/2009 | Paterson et al. |
| 2009/0123488 | A1 | 5/2009 | Goldstein |
| 2009/0130134 | A1 | 5/2009 | Pancre et al. |
| 2009/0136537 | A1 | 5/2009 | Evans et al. |
| 2009/0202584 | A1 | 8/2009 | Thomson et al. |
| 2009/0246211 | A1 | 10/2009 | Henri et al. |
| 2009/0258917 | A1 | 10/2009 | Pelcman et al. |
| 2010/0021468 | A1 | 1/2010 | Wang et al. |
| 2010/0092500 | A1 | 4/2010 | Jackson et al. |
| 2010/0129385 | A1 | 5/2010 | Jackson et al. |
| 2010/0266623 | A1 | 10/2010 | Jackson et al. |
| 2011/0172256 | A1 | 7/2011 | Lin et al. |
| 2011/0262473 | A1 | 10/2011 | Jackson et al. |
| 2011/0280899 | A1 | 11/2011 | Jackson et al. |
| 2012/0231030 | A1 | 9/2012 | Derouazi et al. |
| 2012/0244132 | A1 | 9/2012 | Stauss et al. |
| 2012/0328660 | A1 | 12/2012 | Tsuji et al. |
| 2012/0329830 | A1 | 12/2012 | Cheng et al. |
| 2013/0018064 | A1 | 1/2013 | Paras et al. |
| 2013/0029358 | A1 | 1/2013 | Valmori et al. |
| 2013/0039942 | A1 | 2/2013 | Kombluth et al. |
| 2013/0045203 | A1 | 2/2013 | Joshi et al. |
| 2013/0183377 | A1 | 7/2013 | Agrewala et al. |
| 2013/0230544 | A1 | 9/2013 | Jackson et al. |
| 2014/0086888 | A1 | 3/2014 | Heslop et al. |
| 2014/0112975 | A1 | 4/2014 | Kiessling et al. |
| 2017/0095554 | A1 | 4/2017 | Brimble et al. |
| 2018/0002373 | A1 | 1/2018 | Brimble et al. |

FOREIGN PATENT DOCUMENTS

| | | |
|---|---|---|
| EP | 0376075 | 7/1990 |
| EP | 1666056 A1 | 6/2006 |
| EP | 2465520 | 6/2012 |
| EP | 2608806 | 10/2017 |
| JP | 8248579 | 9/1996 |
| WO | 1999/014326 A1 | 3/1993 |
| WO | 9524925 | 9/1995 |
| WO | 9745444 | 12/1997 |
| WO | 9902550 | 1/1999 |
| WO | 99/18206 A2 | 4/1999 |
| WO | 0044758 A1 | 8/2000 |
| WO | 2001/007917 A1 | 2/2001 |
| WO | 01/036453 A2 | 5/2001 |
| WO | 2001/055393 A2 | 8/2001 |
| WO | 2002/026778 A2 | 4/2002 |
| WO | 0247727 | 6/2002 |
| WO | 2003/104428 A2 | 12/2003 |
| WO | 03099195 A2 | 12/2003 |
| WO | 2004001424 | 12/2003 |
| WO | 2004/014957 A1 | 2/2004 |
| WO | 2004014956 A1 | 2/2004 |
| WO | 2004014957 | 2/2004 |
| WO | 2004041849 | 5/2004 |
| WO | 2005012270 A2 | 2/2005 |
| WO | 2006/106435 A2 | 10/2006 |
| WO | 2008/089074 A9 | 7/2008 |
| WO | 2008/151197 A2 | 12/2008 |
| WO | 2010028246 A2 | 3/2010 |
| WO | 2010/115229 A1 | 10/2010 |
| WO | 2011156686 | 12/2011 |
| WO | 2012020215 A1 | 2/2012 |
| WO | 2012/038055 A1 | 3/2012 |
| WO | 2012069188 | 5/2012 |
| WO | 2012/123755 A1 | 9/2012 |
| WO | 2012123755 | 9/2012 |
| WO | 2012158122 | 11/2012 |
| WO | 2013024282 A2 | 2/2013 |
| WO | 2013/036543 A2 | 3/2013 |
| WO | 2013/049941 A1 | 4/2013 |
| WO | 2013181597 | 12/2013 |
| WO | 2014207708 A2 | 12/2013 |
| WO | 2014/088432 A1 | 6/2014 |
| WO | 2016103192 | 6/2016 |
| WO | 2017/145097 A2 | 8/2017 |

OTHER PUBLICATIONS

Agnihotri, et al., "Structure-Activity Relationships in Toll-Like Receptor 2-Agonists Leading to Simplified Monoacyl Lipopeptides" J. Med. Chem. (2011) 54(23):8148-8160.

International Search Report and Written Opinion, Appln. No. PCT/IB2018/056611, dated Nov. 6, 2018.

Pan, et al., "Recombinant adeno-associated virus encoding Epstein-Barr virus latent membrane proteins fused with heat shock protein as a potential vaccine for nasopharyngeal carcinoma" Mol Cancer Ther. (2009) 8(9):2754-2761.

Wang, et al., "Widespread sequence variation in the Epstein-Barr virus latent membrane protein 2A gene among northern Chinese isolates" Journal of General Virology (2010) 91:2564-2573.

Buwitt-Beckmann, U. et al., "Lipopeptide structure determines TLR2 dependent cell activation level," FEBS Journal, 2005, 272: 6354-6364. doi:10.1111/j.17424658.2005.05029.x.

Zeng, W. et al., "Structural requirement for the agonist activity of the TLR2 ligand Pam2Cys," Amino Acids, 2010, 39:471-480.

Wright, T.H. et al., "An improved method for the synthesis of lipopeptide TLR2-agonists using click chemistry," Synlett, 2013, 24, 1835-1841.

Agnihotri, G. et al., "Structure-Activity Relationships in Toll-Like Receptor 2-Agonists Leading to Simplified Mionoacyl Lipopeptides," J. Med. Chem., 2011, 54, 8148-8160.

Wittrock, S. et al., "Synthetic Vaccines of Tumor-Associated Glycopeptide Antigens by Immune-Compatible Thioether Linkage to Bovine Serum Albumin," Angew Chem. Int Ed , 2007, 46, 5226-5230.

Spohn, et al., "Synthetic Lipopeptide Adjuvants and Toll-like Receptor 2—Structure-Activity Relationships" Vaccine (2004) 22:2494-2499.

Campos, L. M. et al., "Development of thermal and photochemical strategies for thiol-ene click polymer functionalization," Macromolecules, 2008, 41(19), 7063-7070.

Lanza, T. et al., "Radical additions of thiols to alkenes and alkynes in ionic liquids," Current Organic Chemistry, 2009, 13(17), 1726-1732.

Lazar, L. et al., "Synthesis of S-linked glycoconjugates and S-disaccharides by thiol-ene coupling reaction of enoses," Organic letters, 2012, 14(17), 4650-4653.

Toth, I. et al., "Recent Advances in Design and Synthesis of Self-Adjuvanting Lipopeptide Vaccines," International Journal of Peptide Research and Therapeutics, 2008, vol. 14 Issue: 4 pp. 333-340.

Zaman, M. et al., "Immunostimulation by synthetic lipopeptide-based vaccine candidates: structure-activity relationships," Front. Immunol. 2013, 4, 318, 1-12.

Isidro-Llobet, A. et al., "Amino acid-protecting groups," Chemical Reviews, 2009, 109(6), 2455-2504.

Lakshminarayanan, V. et al., "Immune recognition of tumor-associated mucin MUC1 is achieved by a fully synthetic aberrantly glycosylated MUC1 tripartite vaccine," Proceedings of the National Academy of Sciences 109, No. 1 (2012): 261-266.

Willems, M. M. et al., "N-tetradecylcarbamyl lipopeptides as novel agonists for Toll-like receptor 2," Journal of medicinal chemistry, 2014, 57(15), 6873-6878.

(56) References Cited

OTHER PUBLICATIONS

Burns, M. R. et al., "Polycationic sulfonamides for the sequestration of endotoxin," Journal of medicinal chemistry, 2007, 50(4), 877-888.
Straathof, K.C. et al., "Characterization of Latent Membrane Protein 2 Specificity in CTL Lines from Patients with EBV-Positive Nasopharyngeal Carcinoma and Lymphoma," J. Immunology, 2005, 175, 4137-4147.
Rammensee, H.-G. et al., "SYFPEITHI: database for MHC ligands and peptide motifs," Immunogenetics, 1999, 50, 213-219.
Hanley, P.J., et al., "Functionally active virus-specific T cells that target CMV, adenovirus, and EBV can be expanded from naive T-cell populations in cord blood and will target a range of viral epitopes," Blood, 2009 114:1958-1967.
Kessler, J.H. et al., "Efficient Identification of Novel HLA-A*0201-presented Cytotoxic T Lymphocyte Epitopes in the Widely Expressed Tumor Antigen PRAME by Proteasome-mediated Digestion Analysis," J. Exp. Med. 2001 193(1) 73-88. NB: C.Melief Group.
Quintarelli, C. et al., "Cytotoxic T lymphocytes directed to the preferentially expressed antigen of melanoma (PRAME) target chronic myeloid leukemia," Blood, 2008, 112(5):1876. NB: Baylor group, 1876-1885.
Quintarelli, C. et al., "High-avidity cytotoxic T lymphocytes specific for a new PRAME-derived peptide can target leukemic and leukemic-precursor cells," Blood, 2011, 117(12):3353-3362.
Ma W. et al., "Two New Tumor-Specific Antigenic Peptides Encoded By Gene MAGE-C2 and Presented to Cytolytic T Lymphocytes by HLA-A2," Int. J. Cancer, 2004 109:698-702.
Gerdemann, U. et al., "Cytotoxic T Lymphocytes Simultaneously Targeting Multiple Tumor-associated Antigens to Treat EBV Negative Lymphoma," Molecular Therapy, 2011 19(12):2258-68. (NB: original epitope from Ayyoub et al JI 168:1717-22).
Ayyoub, M. et al., "Proteasome-Assisted Identification of a SSX-2-Derived Epitope Recognized by Tumor-Reactive CTL Infiltrating Metastatic Melanoma," Journal of Immunology, 2002, 168:1717-22.
Ayyoub, M. et al., "Tumor-reactive, SSX-2-specific CD8+ T Cells are Selectively Expanded during Immune Responses to Antigen-expressing Tumors in Melanoma Patients," Cancer Research, 2003, 63(17):5601-6.
Bharadwaj, M. et al., "Contrasting Epstein-Barr virus-specific cytotoxic T cell responses to HLA A2-restricted epitopes in humans and HLA transgenic mice: implications for vaccine design," Vaccine, 2001 19:3769-77.
Duraiswamy, J. et al., "Ex Vivo Analysis of T-Cell Responses to Epstein-Barr Virus-Encoded Oncogene Latent Membrane Protein 1 Reveals Highly Conserved Epitope Sequences in Virus Isolates from Diverse Geographic Regions," Journal of Virology 2003 77(13): 7401-10.
Lee, S.P. et al., "HLA A2.1-Restricted Cytotoxic T Cells Recognizing a Range of Epstein-Barr Virus Isolates through a Defined Epitope in Latent Membrane Protein LMP2," Journal of Virology, 1993, 67(12), 7428-7435.
Liu, G. al., "Immunotherapy of Epstein-Barr Virus Associated Malignancies Using Mycobacterial HSP70 and LMP2A356-364 Epitope Fusion Protein," Cellular & Molecular Immunology, 2009 6(6):423-431.
Liu, G. et al., "Reconstituted complexes of mycobacterial HSP70 and EBV LMP2A-derived peptides elicit peptide-specific cytotoxic T lymphocyte responses and anti-tumor immunity," Vaccine 2011 29 (43):7414-23.
Catalina, M.D. et al., "Differential Evolution and Stability of Epitope-Specific CD8+ T Cell Responses in EBV Infection," The Journal of Immunology, 2001 167:4450-4457.
Fieberger, B.M. et al., "Mature proteins derived from Epstein-Barr virus fail to feed into the MHC class I antigenic pool," European Journal of Immunology, 2012 42:3167-3173.
Demachi-Okamura, A. et al., "Epstein-Barr virus (EBV) latent membrane protein-1-specific cytotoxic T lymphocytes targeting EBV-carrying natural killer cell malignancies," European Journal of Immunology, 2006 36:593-602.
Meij, P. et al., "Identification and Prevalence of CD8+ T-Cell Responses Directed Against Epstein-Barr Virus-Encoded Latent Membrane Protein 1 and Latent Membrane Protein 2," Int. J. Cancer, 2002 99:93-99.
Metzger, J. W. et al., "Synthesis of Nα-Fmoc protected derivatives of S-(2, 3-dihydroxypropyl)-cysteine and their application in peptide synthesis," Int. J. Peptide Protein Res. 38(6), 1991, 545-554.
Salunke, D. B. et al., "Design and development of stable, water-soluble, human Toll-like receptor 2 specific monoacyl lipopeptides as candidate vaccine adjuvants," Journal of Medicinal Chemistry, 2013, 56(14), 5885-5900.
Melief, C.J.M., "Cancer immunotherapy by dendritic cells," Immunity, 2008, 29(3), 372-383.
Couzin-Frankel, J., "Cancer Immunotheraphy," Science, 2013, 342, 1432-1433.
Pardoll, D. M., "The blockade of immune checkpoints in cancer immunotherapy," Nature Reviews Cancer, 2012, 12(4), 252-264.
Robert, C. et al., "Ipilimumab plus dacarbazine for previously untreated metastatic melanoma," New England Journal of Medicine, 2011, 364(26), 2517-2526.
Banchereau, J. et al., "Dendritic cells as vectors for therapy," Cell, 2001, 106(3), 271-274.
Thara, E. et al., (2011). "Vaccine therapy with sipuleucel-T (Provenge) for prostate cancer," Maturitas, 2011, 69(4), 296-303.
Kenter, G. G. et al., "Vaccination against HPV-16 Oncoproteins for Vulvar Intraepithelial Neoplasia," J. Med., 2009, 361, 1838-1847.
Cheever, M. A. et al., "The Prioritization of Cancer Antigens: A National Cancer Institute Pilot Project for the Acceleration of Translational Research," Clin. Cancer Res., 2009, 15, 5323-5337.
Van Der Burg, S. H. et al., "Therapeutic vaccination against human papilloma virus induced malignancies," Curr. Opin. Immunol., 2011, 23, 252-257.
Akira, S. et al., "Pathogen Recognition and Innate Immunity," Cell, 2006, 124, 783-801.
Banchereau, J. et al., Immunobiology of Dendritic Cells. Annu. Rev. Immunol., 2000, 18, 767-811.
Anderson, K. V. et al., "Establishment of Dorsal-Ventral Polarity in the *Drosophila* Embryo: Genetic Studies on the Role of the Toll Gene Product," Cell, 1985, 42, 779-789.
Kawai, T. et al., "The role of pattern-recognition receptors in innate immunity: update on Toll-like receptors.,". Nat. Immunol., 2010, 11, 373-384.
Jin, M. S. et al., "Structures of TLR-ligand complexes," Curr. Opin. Immunol., 2008, 20, 414-419.
Gay, N. J. et al., "Structure and Function of Toll Receptors and Their Ligands," Ann. Rev. Biochem., 2007, 76, 141-165.
Bryant, C. E. et al., "The molecular basis of the host response to lipopolysaccharide," Nat. Rev. Microbiol., 2010, 8, 8-14.
Duthie, M. S. et al., "Use of defined TLR ligands as adjuvants within human vaccines," Immunol. Rev., 2011, 239, 178-196.
Ingale, S. et al., "Robust immune responses elicited by a fully synthetic three-component vaccine," Nat. Chem. Biol., 2007, 3, 663-667.
Lake, R. A. et al., "Immunotherapy and chemotherapy—a practical partnership," Nat. Rev. Cancer, 2005, 5, 397-405.
Li, F. et al., "A Direct Method for Site-Specific Protein Acetylation," Angew. Chem. Int. Ed. 2011, 50, 9611-9614.
Takeuchi, O. et al., "Cutting Edge: Preferentially the R-stereoisomer of the Mycoplasmal Lipopeptide Macrophage-Activating Lipopeptide-2 Activates Immune Cells Through a Toll-Like Receptor 2- and MyD88-Dependent Signaling Pathway," J. Immunology, 2000, 164, 554-557.
Khan, S. et al., "Chirality of TLR-2 ligand Pam3CysSK4 in fully synthetic peptide conjugates critically influences the induction of specific CD8+ T-cells," Molecular Immunology, 2009, 46, 1084-1091.
Tokunaga, M. et al., "Asymmetric Catalysis with Water: Efficient Kinetic Resolution of Terminal Epoxides by Means of Catalytic Hydrolysis," Science, 1997, 277, 936-939.

(56) References Cited

OTHER PUBLICATIONS

Schaus, S. E. et al., "Highly Selective Hydrolytic Kinetic Resolution of Terminal Epoxides Catalyzed by Chiral (salen) ColII Complexes. Practical Synthesis of Enantioenriched Terminal Epoxides and 1,2-Diols," J. Am. Chem. Soc., 2002, 124, 1307-1315.

Wu, W. et al., "Structure-Activity Relationships in Toll-like Receptor-2 Agonistic Diacylthioglycerol Lipopeptides," J. Med Chem. 2010, 53, 3198-3213.

Nick, M. J. et al., "Major histocompatibility complex class 1 presentation of ovalbumin peptide 257-264 from exogenous sources: protein context influences the degree of TAP-independent presentation," Eur. J. Immunol., 1996, 26, 2790-2799.

Robertson, J. M. et al., "DO11.10 and OT-II T Cells Recognize a C-Terminal Ovalbumin 323-339 Epitope," J. Immunol., 2000, 164, 4706-4712.

Boyer, C. et al., "Synthesis of a New Macromonomer from 2-(Dimethylamino)ethyl Methacrylate Bearing 1-(Isopropenylphenyl)-1,1-dimethylmethyl Isocyanate Group," Macromol. Chem. Phys., 2004, 205, 645-655.

Bertrais, H. et al., "Synthese De Telomeres Photoreticulables A Partir Du Cinnamate Et De L'acetate De Vinyle," Eur. Polym. J., 1982, 18, 779-784.

Cadierno, V. et al., "Ruthenium(IV)-Catalyzed Markovnikov Addition of Carboxylic Acids to Terminal Alkynes in Aqueous Medium," Organometallics, 2011, 30, 852-862.

Wei, S. et al., "Development of an Improved Rhodium Catalyst for Z-Selective Anti-Markovnikov Addition of Carboxylic Acids to Terminal Alkynes," Chem. Eur. J., 2013, 19, 12067-12076.

Spohn, R. et al., "Synthetic lipopeptide adjuvants and Toll-like receptor 2-structure-activity relationships," Vaccine, 2004, 22, 2494-1499.

Tsukada, N. et al., "Hydrocarboxylation of unactivated internal alkynes with carboxylic acids catalyzed by dinuclear palladium complexes," Tetrahedron Lett. 2011, 52, 248-250.

Rotem, M. et al., "Addition of carboxylic acids to alkynes catalysed by ruthenium complexes," J. Organometallic Chem. 1993, 448, 189-204.

Karmee, S.K., "A Two Step Chemo-Enzymatic Method for the Synthesis of Fatty Acid Ascorbyl Esters," J. Oil Palm Res., 2012, 1518-1523.

Foster, D.J. et al., "Organomercury Chemistry. A Novel Synthesis of Vinyl Esters, Vinyl Ethers and Vinyl Thioethers," J. Am. Chem. Soc., 1961, 83, 851-855.

Luo, F. et al., "Copper(II)-Catalyzed Esterification of Arenecarboxylic Acids with Aryl- and Vinyl-Substituted Trimethoxysilanes," Synthesis, 2010, 2005-2010.

Nakamura, A. et al., "Au(I) complexes-catalyzed transfer vinylation of alcohols and carboxylic acids," Tetrahedron Lett., 2008, 49, 3729-3732.

Nakagawa, H. et al., "Synthesis of enol and vinyl esters catalyzed by an iridium complex," Tetrahedron Lett. 2003, 14, 103-106.

Rokhum, L. et al., "A practical one-pot synthesis of azides directly from alcohols," J. Chem. Sci., 2012, 124, 687-691.

Cui, H.K. et al., "Diaminodiacid-Based Solid-Phase Synthesis of Peptide Disulfide Bond Mimics," Angew. Chemie. Int. Eng. 2013, 52, 36, 9558-9562.

Rodriguez, A. R. et al. "First total synthesis of pro-resolving and tissue-regenerative Maresin sulfido-conjugates," Tetrahedron Letters, (2015) 56(25), 3936-3940.

Wang, C. et al., "Tungsten-Catalyzed Asymmetric Epoxidation of Allylic and Homoallylic Alcohols with Hydrogen Peroxide," J. Am. Chem. Soc. 2014, 136, 1222-1226.

Volkmann, R.A. et al., "2-Thioalkyl Penems: An Efficient Synthesis of Sulopenem, a (5R, 6S)-6-(1 (R)-Hydroxyethy1)-2-[(cis-1-oxo-3-thiolanyl)thio]-2-penem Antibacterial," J. Org. Chem. 1992, 57, 4352-4361.

Rasmussen, M. et al., "Describing the Peptide Binding Specificity of HLA-C (106.41)," J. Immunol., May 1, 2012, 188 (1 Supplement) 106.41; 1 -2.

Hamley I.W., "Lipopeptides: from self-assembly to bioactivity," Chemical Communications, 2015, 51, 41, 8574-8583.

Takeuchi, O. et al., "Cutting Edge: Role of Toll-Like Receptor 1 in Mediating Immune Response to Microbial Lipoproteins," J. Immunol. 2002, 169, 10-14.

Asai, Y. et al., "Toll-like receptor 2-mediated dendritic cell activation by a Porphyromonas gingivalis synthetic lipopeptide," Journal of medical microbiology, (2007) 56(4), 459-465.

Makimura, Y. et al., "Correlation between chemical structure and biological activities of Porphyromonas gingivalis synthetic lipopeptide derivatives," Clinical & Experimental Immunology, (2006) 146(1), 159-168.

Omueti, K.O. et al., "Domain Exchange between Human Toll-like Receptors 1 and 6 Reveals a Region Required for Lipopeptide Discrimination," J. Biol. Chem. 2005, 280, 36616-36625.

Schulze, O. et al., "The thio-Mitsunobu reaction: a useful tool for the preparation of 2,5-anhydro-2-thio- and 3,5-anhydro-3-thiopentofuranosides," Carbohydrate Res. 2004, 338, 1787-1802.

Reddy, C.R. et al., "Synthesis of the methylene bis-tetrahydropyran motif of (–)-exiguolide," Tetrahedron Lett. 2010, 51, 44, 5840-5842.

Saurei -Cladiere, Sauret-Cladière et al., Synthesis of (+)-2,8-dihydroxyethyl-I,4,7,10-tetraoxaspiro[5.5]undecane from (R)-4-hydroxymethyl-2,2-dimethyl- 1,3-dioxane. Tetrahedron Asymmetry, 1997, 8, 3, 417-423.

Krug, et al., "Molecular Dynamics of the alpha-Helical Epitope of a Novel Synthetic Lipopeptide Foot-and-Mouth Disease Virus Vaccine" Biopolymers (1989) 28:499-512.

Moyle, et al., "Self-Adjuvanting Lipopeptide Vaccines" Current Med. Chem. (2008) 15:506-516.

CAS RN 1690273-81-4; STN Entry Date Apr. 23, 2015; D-Valine, 3-[(1,3-dioxan-4-ylmethyl)thio]-.

CAS RN 1690246-56-0; STN Entry Date Apr. 23, 2015; D-Valine, 3-[(1,3-dioxan-4-ylmethyl)thio]-.

CAS RN 1500650-08-7; STN Entry Date Dec. 22, 2013; L-Cysteine, S-(1,3-dioxan-4-ylmethyl)-N-formyl-.

CAS RN 1500646-17-2; STN Entry Date Dec. 22, 2013; L-Homocysteine, S-(1,3-dioxan-4-ylmethyl)-, methyl ester.

CAS RN 1499966-80-1, STN Entry Date Dec. 20, 2013.

CAS RN 1498306-02-7; STN Entry Date Dec. 18, 2013; L-Cysteine, S-(1,3-dioxan-4-ylmethyl)-.

CAS RN 1190622-73-1; STN Entry Date 29Oct. 2009; L-Cysteine, S-(1,3-dioxan-4-ylmethyl)-.

Lu, X.J. et al., "Isopentenyl-Diphosphate Isomerase: Irreversible Inhibition by 3-Methly-3,4-epoxybutyl Diphosphate," Biochemistry, 1992, 31, 9955-9960.

Yang, S-H. et al., "Lipidation of Cysteine or Cysteine-Containing Peptides Using the Thiol-Ene Reaction (CLipPA)," Eur. J. Org. Chem., 2016, 2608-2616.

IPRP, Appln. No. PCT/IB2017/051054, dated Aug. 29, 2018.

Written Opinion, Appln. No. PCT/IB2017/051054, dated Aug. 17, 2017.

Luo, F. et al., "Copper(II)-Catalyzed Esterification of Arenecarboxylic Acids with Aryl- and Vinyl-Substituted Trimethoxysilanes" Synthesis (2010) 12:2005-2010.

Harndahl, M., et al., "Large scale analysis of peptide-HLA class I interactions" (2010) Immune Epitope Database (IEDB), available at http://www.iedb.org/reference/1019514.

Rasmussen, M., et al., "Large scale analysis of peptide-HLA-I stability" (2014) Immune Epitope Database (IEDB), available at http://www.iedb.org/reference/1028285.

Rasmussen, M., et al., "Describing the peptide binding specificity of HLA-C molecules" (2014) Immune Epitope Database (IEDB), available at http://www.iedb.org/reference/1028231.

Harndahl, M., et al., "Large scale analysis of peptide-HLA class I interactions" (2007) Immune Epitope Database (IEDB), available at http://www.iedb.org/reference/1006442.

Rasmussen, M., et al., "Large scale analysis of peptide-HLA-I stability" (2014) Immune Epitope Database (IEDB), available at http://www.iedb.org/reference/1028288.

Rasmussen, M., et al., "Describing the Peptide Binding Specificity of HLA-C" J. Immunol. (2012) 188 (1 Supplement):106.41, Abstract.

(56) References Cited

OTHER PUBLICATIONS

Meyer, K.H., et al., "Antibodies against neuroactive amino acids and neuropeptides. I. A new two-step procedure for their conjugation to carrier proteins and the production of an anti-Met-enkephalin antibody reactive with glutaraldehyde-fixed tissue" J. Histochem. Cytochem. (1991) 39(6):749-60.
Hauschildt, S. et al., "Induction and activity of NO synthase in bone-marrow-derived macrophages are independent of Ca2", Biochemical Journal, 1990, vol. 270, Issue: 2, pp. 351-356.
Liu, C. et al., "Chemical Ligation Approach to Form a Peptide Bond between Unprotected Peptide Segments. Concept and Model Study", Journal of the American Chemical Society, 1994, vol. 116, Issue: 10, pp. 4149-4153.
Chang, Y., et al., "Characterization of Modified Peptides by Tandem Mass Spectrometry", Analytical Science & Technology, 1995, vol. 8, Issue: 4, pp. 849-854.
Botti, P., et al., "Cyclic Peptides from Linear Unprotected Peptide Precursors through Thiazolidine Formation", Journal of the American Chemical Society, 1996, vol. 118, Issue: 42, pp. 10018-10024.
Miao, Z., et al., "Bidirectional Tandem Pseudoproline Ligations of Proline-Rich Helical Peptides", Journal of the American Chemical Society, 2000, vol. 122, Issue: 18, pp. 4253-4260.
Maruyama, Y., et al., "Synthesis of Immunoadjuvant Conjugates With HIV-Derived Peptide Inducing Peptide-Specific Antibody", Chemical & Pharmaceutical Bulletin, 1994, vol. 42, Issue: 8, pp. 1709-1711.
Shimizu, T., et al., "Antibody-Producing Effects in Mice by Synthetic Immunoactive Lipopeptides with the Conjugated Amino Acid Sequence of gp120 in Human Immunodeficiency Virus", Biological & Pharmaceutical Bulletin, 1996, vol. 19, Issue: 10, pp. 1271-1274.
Luesch, H., et al., "Isolation and Structure of the Cytotoxin Lyngbyabellin B and Absolute Configuration of Lyngbyapeptin A from the Marine Cyanobacterium Lyngbya majuscule", Journal of Natural Products, 2000, vol. 33, Issue: 10, pp. 1437-1439.
Milligan, K., et al., "Lyngbyabellin B, a Toxic and Antifungal Secondary Metabolite from the Marine Cyanobacterium Lyngbya majuscule", Journal of Natural Products, 2000, vol. 63, Issue: 10, pp. 1440-1443.
Marquez, B., et al., "Structure and Absolute Stereochemistry of Hectochlorin, a Potent Stimulator of Actin Assembly", Journal of Natural Products, 2002, vol. 65, Issue: 6, pp. 866-871.
Yokokawa, F., et al., "Total syntheses of lyngbyabellins A and B, potent cytotoxic lipopeptides from the marine cyanobacterium Lyngbya majuscule", Tetrahedron, 2002, vol. 58, Issue: 46, pp. 9445-9458.
Matthew, S., et al., "Cytotoxic Halogenated Macrolides and Modified Peptides from the Apratoxin-Producing Marine Cyanobacterium Lyngbya bouillonii from Guam", Journal of Natural Products, 2010, vol. 73, Issue: 9, pp. 1544-1552.
Hebbes, T.R., et al., "A "minimal epitope" anti-protein antibody that recognises a single modified amino acid", Mol. Immunol., 1989, vol. 26, Issue: 9, pp. 865-873.
Yi, L., et al., "Semisynthesis of prenylated Rab GTPases by click ligation" Chembiochem. (2011) 12(16):2413-7.
Boeckler, C., et al., "Design and synthesis of thiol-reactive lipopeptides" Bioorg. Med. Chem. Lett. (1998) 8(15):2055-8.
Dondoni, A., et al., "A new ligation strategy for peptide and protein glycosylation: photoinduced thiol-ene coupling" Chemistry (2009) 15(43):11444-9.

Lau, Y.F., et al., "Lipid-containing mimetics of natural triggers of innate immunity as CTL-inducing influenza vaccines" Int. Immunol. (2006) 18(12):1801-13.
Triola, G., et al., "Racemization-free synthesis of S-alkylated cysteines via thiol-ene reaction" J. Org. Chem. (2008) 73(9):3646-9.
Wright, T.H., et al., "Direct peptide lipidation through thiol-ene coupling enables rapid synthesis and evaluation of self-adjuvanting vaccine candidates" Angew Chem. Int. Ed. Engl. (2013) 52(40):10616-9.
NCBI Accession No. NP_001318.1 (http://www.ncbi.nlm.nih.gov/protein/NP_001318.1), Apr. 13, 2013.
EP Application No. 14818659.6, Europea Extended Search Report, dated Jan. 10, 2017, 6 pages.
Salunke, D.P., et al., "Structure-activity relationships in human Toll-like receptor 2-specific monoacyl lipopeptides" J Med Chem. (2012) 55(7):3353-63.
Japanese Patent Office, Examination Report—Notice of Reasons for Rejection, Patent Application No. 2016-522936, dated Jul. 10, 2018, pp. 1-7.
Kurimura, M., et al., "Structure-activity relationship of lipopeptide from outer membrane of *Escherichia coli* and synthesis of highly immunopotenting lipopeptide derivatives with an achiral lipo-part" Chem. Pharm. Bull. (1993) 41(3):627-9.
Ellervik, U., et al., "Glycosylation with N-Troc-protected glycosyl donors" Carbohydr. Res. (1996) 280(2):251-60.
Shimizu, T., et al., "Mitogenic activity and the induction of tumor necrosis factor by lipopeptide analogs of the N-terminal part of lipoprotein in the outer membrane of *Escherichia coli*" Biol. Pharm. Bull. (1994) 17(7):980-2.
IP Australia, Examination Report No. 1 for standard application, Application No. AU 2019200884, dated Oct. 31, 2019, 3 pages.
Reppe, W. et al., Justus Liebigs Annalen der Chemie, 1956, 601:81-138.
Hoyle, C. E. et al., "Thiol-ene click chemistry," Angewandte Chemie International Edition, 2010, 49(9):1540-1573.
Supplementary European Search Report, Appln. No. EP 15 87 2074, dated Mar. 2, 2018.
Cai, H. et al., "Fully Synthetic Self-Adjuvanting Thioether-Conjugated Glycopeptide-Lipopeptide Antitumor Vaccines for the Induction of Complement-Dependent Cytotoxicity against Tumor Cells," Chemistry European Journal, 2013, vol. 19, pp. 1962-1970.
CAS Registry No. 1215165-25-5, obtained from CAS SciFinder (https://www.cas.org/solutions/cas-scifinder-discovery-platform/cas-scifinder) on Nov. 5, 2021.
CAS Registry No. 1215165-26-6, obtained from CAS SciFinder (https://www.cas.org/solutions/cas-scifinder-discovery-platform/cas-scifinder) on Nov. 5, 2021.
CAS Registry No. 1215165-27-7, obtained from CAS SciFinder (https://www.cas.org/solutions/cas-scifinder-discovery-platform/cas-scifinder) on Nov. 5, 2021.
Lowe, D., "The Good Sides and Bad Sides of Polar Compounds" from In the Pipelne Blog (2017) available at https://blogs.sciencemag.org/pipeline/archives/2017/02/23/the-good-sides-and-bad-sides-of-polar-compounds.
Fisette, P.L., et al., "The Lip Lipoprotein from Neisseria gonorrhoeae Stimulates Cytokine Release and NF-kB Activation in Epithelial Cells in a Toll-like Receptor 2-dependent Manner" J. Biol. Chem. (2003) 278:46252-46260.

\* cited by examiner

SEQUENCE LISTING

```
<160> NUMBER OF SEQ ID NOS: 130

<210> SEQ ID NO 1
<211> LENGTH: 32
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or a hydrophilic amino acid
<220> FEATURE:
<221> NAME/KEY: MISC_FEATURE
<222> LOCATION: (3)..(3)
<223> OTHER INFORMATION: Xaa3 is absent or a hydrophilic amino acid
<220> FEATURE:
<221> NAME/KEY: MISC_FEATURE
<222> LOCATION: (4)..(4)
<223> OTHER INFORMATION: Xaa4 is absent or is one or more hydrophilic
      amino acids

<400> SEQUENCE: 1

Xaa Xaa Xaa Xaa Asp Arg His Ser Asp Tyr Gln Pro Leu Gly Thr Gln
1               5                   10                  15

Asp Gln Ser Leu Tyr Leu Gly Leu Gln His Asp Gly Asn Asp Gly Leu
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is from 1 to 10 hydrophilic
      amino acids

<400> SEQUENCE: 2

Xaa Xaa Xaa Asp Arg His Ser Asp Tyr Gln Pro Leu Gly Thr Gln Asp
1               5                   10                  15

Gln Ser Leu Tyr Leu Gly Leu Gln His Asp Gly Asn Asp Gly Leu
            20                  25                  30

<210> SEQ ID NO 3
<211> LENGTH: 30
```

```
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is from one to four
      hydrophilic amino acids

<400> SEQUENCE: 3

Xaa Xaa Asp Arg His Ser Asp Tyr Gln Pro Leu Gly Thr Gln Asp Gln
1               5                   10                  15

Ser Leu Tyr Leu Gly Leu Gln His Asp Gly Asn Asp Gly Leu
            20                  25                  30

<210> SEQ ID NO 4
<211> LENGTH: 33
<212> TYPE: PRT
<213> ORGANISM: Artificial Sequence
<220> FEATURE:
<223> OTHER INFORMATION: Synthetic peptide sequence

<400> SEQUENCE: 4

Ser Lys Lys Lys Lys Asp Arg His Ser Asp Tyr Gln Pro Leu Gly Thr
1               5                   10                  15

Gln Asp Gln Ser Leu Tyr Leu Gly Leu Gln His Asp Gly Asn Asp Gly
            20                  25                  30

Leu

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide sequence

<400> SEQUENCE: 5

Asp Arg His Ser Asp Tyr Gln Pro Leu Gly Thr Gln Asp Gln Ser Leu
1               5                   10                  15

Tyr Leu Gly Leu Gln His Asp Gly Asn Asp Gly Leu
            20                  25

<210> SEQ ID NO 6
<211> LENGTH: 37
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa is absent or a hydrophilic amino acid
<220> FEATURE:
<221> NAME/KEY: MISC_FEATURE
<222> LOCATION: (3)..(3)
<223> OTHER INFORMATION: Xaa3 is absent or a hydrophilic amino acid
<220> FEATURE:
<221> NAME/KEY: MISC_FEATURE
```

```
<222> LOCATION: (4)..(4)
<223> OTHER INFORMATION: Xaa4 is absent or is one or more hydrophilic
      amino acids

<400> SEQUENCE: 6

Xaa Xaa Xaa Xaa Ser Leu Tyr Leu Gly Leu Gln His Asp Gly Asn Asp
1               5                   10                  15

Gly Leu Pro Pro Pro Tyr Ser Pro Arg Asp Asp Ser Ser Gln His
            20                  25                  30

Ile Tyr Glu Glu Ala
            35

<210> SEQ ID NO 7
<211> LENGTH: 36
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or a hydrophilic amino acid
<220> FEATURE:
<221> NAME/KEY: MISC_FEATURE
<222> LOCATION: (3)..(3)
<223> OTHER INFORMATION: Xaa3 is absent or is from one to ten
      hydrophilic amino acids

<400> SEQUENCE: 7

Xaa Xaa Xaa Ser Leu Tyr Leu Gly Leu Gln His Asp Gly Asn Asp Gly
1               5                   10                  15

Leu Pro Pro Pro Pro Tyr Ser Pro Arg Asp Asp Ser Ser Gln His Ile
            20                  25                  30

Tyr Glu Glu Ala
            35

<210> SEQ ID NO 8
<211> LENGTH: 35
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is from one to four
      hydrophilic amino acids

<400> SEQUENCE: 8

Xaa Xaa Ser Leu Tyr Leu Gly Leu Gln His Asp Gly Asn Asp Gly Leu
1               5                   10                  15

Pro Pro Pro Pro Tyr Ser Pro Arg Asp Asp Ser Ser Gln His Ile Tyr
            20                  25                  30

Glu Glu Ala
            35

<210> SEQ ID NO 9
```

<211> LENGTH: 38
<212> TYPE: PRT
<213> ORGANISM: Artificial Sequence
<220> FEATURE:
<223> OTHER INFORMATION: Synthetic peptide sequence

<400> SEQUENCE: 9

Ser Lys Lys Lys Lys Ser Leu Tyr Leu Gly Leu Gln His Asp Gly Asn
1               5                   10                  15

Asp Gly Leu Pro Pro Pro Pro Tyr Ser Pro Arg Asp Asp Ser Ser Gln
            20                  25                  30

His Ile Tyr Glu Glu Ala
        35

<210> SEQ ID NO 10
<211> LENGTH: 33
<212> TYPE: PRT
<213> ORGANISM: Artificial Sequence
<220> FEATURE:
<223> OTHER INFORMATION: Synthetic peptide sequence

<400> SEQUENCE: 10

Ser Leu Tyr Leu Gly Leu Gln His Asp Gly Asn Asp Gly Leu Pro Pro
1               5                   10                  15

Pro Pro Tyr Ser Pro Arg Asp Asp Ser Ser Gln His Ile Tyr Glu Glu
            20                  25                  30

Ala

<210> SEQ ID NO 11
<211> LENGTH: 29
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is one or more hydrophilic
      amino acids

<400> SEQUENCE: 11

Xaa Xaa Xaa Xaa Ser Asp Tyr Gln Pro Leu Gly Thr Gln Asp Gln Ser
1               5                   10                  15

Leu Tyr Leu Gly Leu Gln His Asp Gly Asn Asp Gly Leu
            20                  25

<210> SEQ ID NO 12
<211> LENGTH: 28
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)

<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is from one to ten
      hydrophilic amino acids

<400> SEQUENCE: 12

Xaa Xaa Xaa Ser Asp Tyr Gln Pro Leu Gly Thr Gln Asp Gln Ser Leu
1               5                   10                  15

Tyr Leu Gly Leu Gln His Asp Gly Asn Asp Gly Leu
            20                  25

<210> SEQ ID NO 13
<211> LENGTH: 27
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S or a hydrophilic amino
      acid
<220> FEATURE:
<221> NAME/KEY: MISC_FEATURE
<222> LOCATION: (2)..(2)
<223> OTHER INFORMATION: Xaa2 is absent or is from one to four
      hydrophilic amino acids

<400> SEQUENCE: 13

Xaa Xaa Ser Asp Tyr Gln Pro Leu Gly Thr Gln Asp Gln Ser Leu Tyr
1               5                   10                  15

Leu Gly Leu Gln His Asp Gly Asn Asp Gly Leu
            20                  25

<210> SEQ ID NO 14
<211> LENGTH: 30
<212> TYPE: PRT
<213> ORGANISM: Artificial Sequence
<220> FEATURE:
<223> OTHER INFORMATION: Synthetic peptide sequence

<400> SEQUENCE: 14

Ser Lys Lys Lys Lys Ser Asp Tyr Gln Pro Leu Gly Thr Gln Asp Gln
1               5                   10                  15

Ser Leu Tyr Leu Gly Leu Gln His Asp Gly Asn Asp Gly Leu
            20                  25                  30

<210> SEQ ID NO 15
<211> LENGTH: 25
<212> TYPE: PRT
<213> ORGANISM: Artificial Sequence
<220> FEATURE:
<223> OTHER INFORMATION: Synthetic peptide sequence

<400> SEQUENCE: 15

Ser Asp Tyr Gln Pro Leu Gly Thr Gln Asp Gln Ser Leu Tyr Leu Gly
1               5                   10                  15

Leu Gln His Asp Gly Asn Asp Gly Leu
            20                  25

<210> SEQ ID NO 16
<211> LENGTH: 51
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 16

Xaa Xaa Xaa Xaa Asp Arg His Ser Asp Tyr Gln Pro Leu Gly Thr Gln
1               5                   10                  15

Asp Gln Ser Leu Tyr Leu Gly Leu Gln His Asp Gly Asn Asp Gly Leu
            20                  25                  30

Pro Pro Pro Pro Tyr Ser Pro Arg Asp Asp Ser Ser Gln His Ile Tyr
        35                  40                  45

Glu Glu Ala
    50

<210> SEQ ID NO 17
<211> LENGTH: 50
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 17

Xaa Xaa Xaa Asp Arg His Ser Asp Tyr Gln Pro Leu Gly Thr Gln Asp
1               5                   10                  15

Gln Ser Leu Tyr Leu Gly Leu Gln His Asp Gly Asn Asp Gly Leu Pro
            20                  25                  30

Pro Pro Pro Tyr Ser Pro Arg Asp Asp Ser Ser Gln His Ile Tyr Glu
        35                  40                  45

Glu Ala
    50

<210> SEQ ID NO 18
<211> LENGTH: 49
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 18

Xaa Xaa Asp Arg His Ser Asp Tyr Gln Pro Leu Gly Thr Gln Asp Gln
1               5                   10                  15

Ser Leu Tyr Leu Gly Leu Gln His Asp Gly Asn Asp Gly Leu Pro Pro
            20                  25                  30

Pro Pro Tyr Ser Pro Arg Asp Asp Ser Ser Gln His Ile Tyr Glu Glu
        35                  40                  45

Ala

<210> SEQ ID NO 19
<211> LENGTH: 52

-continued

```
<212> TYPE: PRT
<213> ORGANISM: Artificial Sequence
<220> FEATURE:
<223> OTHER INFORMATION: Synthetic peptide sequence

<400> SEQUENCE: 19

Ser Lys Lys Lys Asp Arg His Ser Asp Tyr Gln Pro Leu Gly Thr
1               5                   10                  15

Gln Asp Gln Ser Leu Tyr Leu Gly Leu Gln His Asp Gly Asn Asp Gly
                20                  25                  30

Leu Pro Pro Pro Tyr Ser Pro Arg Asp Asp Ser Ser Gln His Ile
            35                  40                  45

Tyr Glu Glu Ala
        50

<210> SEQ ID NO 20
<211> LENGTH: 47
<212> TYPE: PRT
<213> ORGANISM: Artificial Sequence
<220> FEATURE:
<223> OTHER INFORMATION: Synthetic peptide sequence

<400> SEQUENCE: 20

Asp Arg His Ser Asp Tyr Gln Pro Leu Gly Thr Gln Asp Gln Ser Leu
1               5                   10                  15

Tyr Leu Gly Leu Gln His Asp Gly Asn Asp Gly Leu Pro Pro Pro Pro
                20                  25                  30

Tyr Ser Pro Arg Asp Asp Ser Ser Gln His Ile Tyr Glu Glu Ala
            35                  40                  45

<210> SEQ ID NO 21
<211> LENGTH: 40
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 21

Xaa Xaa Xaa Xaa Leu Leu Trp Thr Leu Val Val Leu Leu Ile Cys Ser
1               5                   10                  15

Ser Cys Ser Ser Cys Pro Leu Ser Lys Ile Leu Leu Ala Arg Leu Phe
                20                  25                  30

Leu Tyr Ala Leu Ala Leu Leu Leu
            35                  40

<210> SEQ ID NO 22
<211> LENGTH: 39
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 22

Xaa Xaa Xaa Leu Leu Trp Thr Leu Val Val Leu Leu Ile Cys Ser Ser
1               5                   10                  15

Cys Ser Ser Cys Pro Leu Ser Lys Ile Leu Leu Ala Arg Leu Phe Leu
```

```
                    20                  25                  30

Tyr Ala Leu Ala Leu Leu Leu
        35

<210> SEQ ID NO 23
<211> LENGTH: 38
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 23

Xaa Xaa Leu Leu Trp Thr Leu Val Val Leu Leu Ile Cys Ser Ser Cys
1               5                   10                  15

Ser Ser Cys Pro Leu Ser Lys Ile Leu Leu Ala Arg Leu Phe Leu Tyr
            20                  25                  30

Ala Leu Ala Leu Leu Leu
        35

<210> SEQ ID NO 24
<211> LENGTH: 41
<212> TYPE: PRT
<213> ORGANISM: Artificial Sequence
<220> FEATURE:
<223> OTHER INFORMATION: Synthetic peptide sequence

<400> SEQUENCE: 24

Ser Lys Lys Lys Lys Leu Leu Trp Thr Leu Val Val Leu Leu Ile Cys
1               5                   10                  15

Ser Ser Cys Ser Ser Cys Pro Leu Ser Lys Ile Leu Leu Ala Arg Leu
            20                  25                  30

Phe Leu Tyr Ala Leu Ala Leu Leu Leu
        35                  40

<210> SEQ ID NO 25
<211> LENGTH: 36
<212> TYPE: PRT
<213> ORGANISM: Artificial Sequence
<220> FEATURE:
<223> OTHER INFORMATION: Synthetic peptide sequence

<400> SEQUENCE: 25

Leu Leu Trp Thr Leu Val Val Leu Leu Ile Cys Ser Ser Cys Ser Ser
1               5                   10                  15

Cys Pro Leu Ser Lys Ile Leu Leu Ala Arg Leu Phe Leu Tyr Ala Leu
            20                  25                  30

Ala Leu Leu Leu
        35

<210> SEQ ID NO 26
<211> LENGTH: 44
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 26
```

```
Xaa Xaa Xaa Xaa Leu Met Leu Leu Trp Thr Leu Val Val Leu Leu Ile
1               5                   10                  15

Cys Ser Ser Cys Ser Ser Cys Pro Leu Ser Lys Ile Leu Leu Ala Arg
            20                  25                  30

Leu Phe Leu Tyr Ala Leu Ala Leu Leu Leu Ala
        35                  40
```

<210> SEQ ID NO 27
<211> LENGTH: 43
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 27

```
Xaa Xaa Xaa Leu Met Leu Leu Trp Thr Leu Val Val Leu Leu Ile Cys
1               5                   10                  15

Ser Ser Cys Ser Ser Cys Pro Leu Ser Lys Ile Leu Leu Ala Arg Leu
            20                  25                  30

Phe Leu Tyr Ala Leu Ala Leu Leu Leu Ala
        35                  40
```

<210> SEQ ID NO 28
<211> LENGTH: 42
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 28

```
Xaa Xaa Leu Met Leu Leu Trp Thr Leu Val Val Leu Leu Ile Cys Ser
1               5                   10                  15

Ser Cys Ser Ser Cys Pro Leu Ser Lys Ile Leu Leu Ala Arg Leu Phe
            20                  25                  30

Leu Tyr Ala Leu Ala Leu Leu Leu Ala
        35                  40
```

<210> SEQ ID NO 29
<211> LENGTH: 45
<212> TYPE: PRT
<213> ORGANISM: Artificial Sequence
<220> FEATURE:
<223> OTHER INFORMATION: Synthetic peptide sequence

<400> SEQUENCE: 29

```
Ser Lys Lys Lys Lys Leu Met Leu Leu Trp Thr Leu Val Val Leu Leu
1               5                   10                  15

Ile Cys Ser Ser Cys Ser Ser Cys Pro Leu Ser Lys Ile Leu Leu Ala
            20                  25                  30

Arg Leu Phe Leu Tyr Ala Leu Ala Leu Leu Leu Ala
        35                  40                  45
```

<210> SEQ ID NO 30
<211> LENGTH: 40
<212> TYPE: PRT

```
<213> ORGANISM: Artificial Sequence
<220> FEATURE:
<223> OTHER INFORMATION: Synthetic peptide sequence

<400> SEQUENCE: 30

Leu Met Leu Leu Trp Thr Leu Val Val Leu Leu Ile Cys Ser Ser Cys
1               5                   10                  15

Ser Ser Cys Pro Leu Ser Lys Ile Leu Leu Ala Arg Leu Phe Leu Tyr
            20                  25                  30

Ala Leu Ala Leu Leu Leu Ala
        35                  40

<210> SEQ ID NO 31
<211> LENGTH: 30
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 31

Xaa Xaa Xaa Xaa Leu Met Leu Leu Trp Thr Leu Val Val Leu Leu Ile
1               5                   10                  15

Cys Ser Ser Cys Ser Ser Cys Pro Leu Ser Lys Ile Leu Leu
            20                  25                  30

<210> SEQ ID NO 32
<211> LENGTH: 29
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 32

Xaa Xaa Xaa Leu Met Leu Leu Trp Thr Leu Val Val Leu Leu Ile Cys
1               5                   10                  15

Ser Ser Cys Ser Ser Cys Pro Leu Ser Lys Ile Leu Leu
            20                  25

<210> SEQ ID NO 33
<211> LENGTH: 28
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 33

Xaa Xaa Leu Met Leu Leu Trp Thr Leu Val Val Leu Leu Ile Cys Ser
1               5                   10                  15

Ser Cys Ser Ser Cys Pro Leu Ser Lys Ile Leu Leu
            20                  25

<210> SEQ ID NO 34
<211> LENGTH: 31
<212> TYPE: PRT
```

<213> ORGANISM: Artificial Sequence
<220> FEATURE:
<223> OTHER INFORMATION: Synthetic peptide sequence

<400> SEQUENCE: 34

Ser Lys Lys Lys Lys Leu Met Leu Leu Trp Thr Leu Val Val Leu Leu
1               5                   10                  15

Ile Cys Ser Ser Cys Ser Ser Cys Pro Leu Ser Lys Ile Leu Leu
            20                  25                  30

<210> SEQ ID NO 35
<211> LENGTH: 26
<212> TYPE: PRT
<213> ORGANISM: Artificial Sequence
<220> FEATURE:
<223> OTHER INFORMATION: Synthetic peptide sequence

<400> SEQUENCE: 35

Leu Met Leu Leu Trp Thr Leu Val Val Leu Leu Ile Cys Ser Ser Cys
1               5                   10                  15

Ser Ser Cys Pro Leu Ser Lys Ile Leu Leu
            20                  25

<210> SEQ ID NO 36
<211> LENGTH: 35
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 36

Xaa Xaa Xaa Xaa Leu Leu Ile Cys Ser Ser Cys Ser Ser Cys Pro Leu
1               5                   10                  15

Ser Lys Ile Leu Leu Ala Arg Leu Phe Leu Tyr Ala Leu Ala Leu Leu
            20                  25                  30

Leu Leu Ala
        35

<210> SEQ ID NO 37
<211> LENGTH: 34
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 37

Xaa Xaa Xaa Leu Leu Ile Cys Ser Ser Cys Ser Ser Cys Pro Leu Ser
1               5                   10                  15

Lys Ile Leu Leu Ala Arg Leu Phe Leu Tyr Ala Leu Ala Leu Leu Leu
            20                  25                  30

Leu Ala

<210> SEQ ID NO 38
<211> LENGTH: 33
<212> TYPE: PRT
<213> ORGANISM: Artificial Sequence
<220> FEATURE:

<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 38

Xaa Xaa Leu Leu Ile Cys Ser Ser Cys Ser Ser Cys Pro Leu Ser Lys
1               5                   10                  15

Ile Leu Leu Ala Arg Leu Phe Leu Tyr Ala Leu Ala Leu Leu Leu Leu
            20                  25                  30

Ala

<210> SEQ ID NO 39
<211> LENGTH: 36
<212> TYPE: PRT
<213> ORGANISM: Artificial Sequence
<220> FEATURE:
<223> OTHER INFORMATION: Synthetic peptide sequence

<400> SEQUENCE: 39

Ser Lys Lys Lys Lys Leu Leu Ile Cys Ser Ser Cys Ser Ser Cys Pro
1               5                   10                  15

Leu Ser Lys Ile Leu Leu Ala Arg Leu Phe Leu Tyr Ala Leu Ala Leu
            20                  25                  30

Leu Leu Leu Ala
        35

<210> SEQ ID NO 40
<211> LENGTH: 31
<212> TYPE: PRT
<213> ORGANISM: Artificial Sequence
<220> FEATURE:
<223> OTHER INFORMATION: Synthetic peptide sequence

<400> SEQUENCE: 40

Leu Leu Ile Cys Ser Ser Cys Ser Ser Cys Pro Leu Ser Lys Ile Leu
1               5                   10                  15

Leu Ala Arg Leu Phe Leu Tyr Ala Leu Ala Leu Leu Leu Leu Ala
            20                  25                  30

<210> SEQ ID NO 41
<211> LENGTH: 61
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 41

Xaa Xaa Xaa Xaa Leu Asn Leu Thr Thr Met Phe Leu Leu Met Leu Leu
1               5                   10                  15

Trp Thr Leu Val Val Leu Leu Ile Cys Ser Ser Cys Ser Ser Cys Pro
            20                  25                  30

Leu Ser Lys Ile Leu Leu Ala Arg Leu Phe Leu Tyr Ala Leu Ala Leu
        35                  40                  45

Leu Leu Leu Ala Ser Ala Leu Ile Ala Gly Gly Ser Ile
    50                  55                  60

<210> SEQ ID NO 42

-continued

```
<211> LENGTH: 60
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 42

Xaa Xaa Xaa Leu Asn Leu Thr Thr Met Phe Leu Leu Met Leu Leu Trp
1               5                   10                  15

Thr Leu Val Val Leu Leu Ile Cys Ser Ser Cys Ser Ser Cys Pro Leu
            20                  25                  30

Ser Lys Ile Leu Leu Ala Arg Leu Phe Leu Tyr Ala Leu Ala Leu Leu
        35                  40                  45

Leu Leu Ala Ser Ala Leu Ile Ala Gly Gly Ser Ile
    50                  55                  60

<210> SEQ ID NO 43
<211> LENGTH: 59
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 43

Xaa Xaa Leu Asn Leu Thr Thr Met Phe Leu Leu Met Leu Leu Trp Thr
1               5                   10                  15

Leu Val Val Leu Leu Ile Cys Ser Ser Cys Ser Ser Cys Pro Leu Ser
            20                  25                  30

Lys Ile Leu Leu Ala Arg Leu Phe Leu Tyr Ala Leu Ala Leu Leu Leu
        35                  40                  45

Leu Ala Ser Ala Leu Ile Ala Gly Gly Ser Ile
    50                  55

<210> SEQ ID NO 44
<211> LENGTH: 62
<212> TYPE: PRT
<213> ORGANISM: Artificial Sequence
<220> FEATURE:
<223> OTHER INFORMATION: Synthetic peptide sequence

<400> SEQUENCE: 44

Ser Lys Lys Lys Lys Leu Asn Leu Thr Thr Met Phe Leu Leu Met Leu
1               5                   10                  15

Leu Trp Thr Leu Val Val Leu Leu Ile Cys Ser Ser Cys Ser Ser Cys
            20                  25                  30

Pro Leu Ser Lys Ile Leu Leu Ala Arg Leu Phe Leu Tyr Ala Leu Ala
        35                  40                  45

Leu Leu Leu Leu Ala Ser Ala Leu Ile Ala Gly Gly Ser Ile
    50                  55                  60

<210> SEQ ID NO 45
<211> LENGTH: 57
<212> TYPE: PRT
<213> ORGANISM: Artificial Sequence
<220> FEATURE:
<223> OTHER INFORMATION: Synthetic peptide sequence
```

<400> SEQUENCE: 45

Leu Asn Leu Thr Thr Met Phe Leu Leu Met Leu Leu Trp Thr Leu Val
1               5                   10                  15

Val Leu Leu Ile Cys Ser Ser Cys Ser Ser Cys Pro Leu Ser Lys Ile
            20                  25                  30

Leu Leu Ala Arg Leu Phe Leu Tyr Ala Leu Ala Leu Leu Leu Leu Ala
        35                  40                  45

Ser Ala Leu Ile Ala Gly Gly Ser Ile
    50                  55

<210> SEQ ID NO 46
<211> LENGTH: 48
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 46

Xaa Xaa Xaa Xaa Phe Leu Leu Met Leu Leu Trp Thr Leu Val Val Leu
1               5                   10                  15

Leu Ile Cys Ser Ser Cys Ser Ser Cys Pro Leu Ser Lys Ile Leu Leu
            20                  25                  30

Ala Arg Leu Phe Leu Tyr Ala Leu Ala Leu Leu Leu Leu Ala Ser Ala
        35                  40                  45

<210> SEQ ID NO 47
<211> LENGTH: 47
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 47

Xaa Xaa Xaa Phe Leu Leu Met Leu Leu Trp Thr Leu Val Val Leu Leu
1               5                   10                  15

Ile Cys Ser Ser Cys Ser Ser Cys Pro Leu Ser Lys Ile Leu Leu Ala
            20                  25                  30

Arg Leu Phe Leu Tyr Ala Leu Ala Leu Leu Leu Ala Ser Ala
        35                  40                  45

<210> SEQ ID NO 48
<211> LENGTH: 46
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 48

Xaa Xaa Phe Leu Leu Met Leu Leu Trp Thr Leu Val Val Leu Leu Ile
1               5                   10                  15

Cys Ser Ser Cys Ser Ser Cys Pro Leu Ser Lys Ile Leu Leu Ala Arg

-continued

```
                20                  25                  30

Leu Phe Leu Tyr Ala Leu Ala Leu Leu Leu Ala Ser Ala
        35                  40                  45

<210> SEQ ID NO 49
<211> LENGTH: 49
<212> TYPE: PRT
<213> ORGANISM: Artificial Sequence
<220> FEATURE:
<223> OTHER INFORMATION: Synthetic peptide sequence

<400> SEQUENCE: 49

Ser Lys Lys Lys Lys Phe Leu Met Leu Leu Trp Thr Leu Val Val
1               5                   10                  15

Leu Leu Ile Cys Ser Ser Cys Ser Ser Cys Pro Leu Ser Lys Ile Leu
                20                  25                  30

Leu Ala Arg Leu Phe Leu Tyr Ala Leu Ala Leu Leu Leu Ala Ser
        35                  40                  45

Ala

<210> SEQ ID NO 50
<211> LENGTH: 44
<212> TYPE: PRT
<213> ORGANISM: Artificial Sequence
<220> FEATURE:
<223> OTHER INFORMATION: Synthetic peptide sequence

<400> SEQUENCE: 50

Phe Leu Leu Met Leu Leu Trp Thr Leu Val Val Leu Leu Ile Cys Ser
1               5                   10                  15

Ser Cys Ser Ser Cys Pro Leu Ser Lys Ile Leu Leu Ala Arg Leu Phe
                20                  25                  30

Leu Tyr Ala Leu Ala Leu Leu Leu Ala Ser Ala
        35                  40

<210> SEQ ID NO 51
<211> LENGTH: 55
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 51

Xaa Xaa Xaa Xaa Leu Gln Gly Ile Tyr Val Leu Val Met Leu Val Leu
1               5                   10                  15

Leu Ile Leu Ala Tyr Arg Arg Arg Trp Arg Arg Leu Thr Val Cys Gly
                20                  25                  30

Gly Ile Met Phe Leu Ala Cys Val Leu Val Leu Ile Val Asp Ala Val
        35                  40                  45

Leu Gln Leu Ser Pro Leu Leu
    50                  55

<210> SEQ ID NO 52
<211> LENGTH: 54
<212> TYPE: PRT
<213> ORGANISM: Artificial Sequence
<220> FEATURE:
<223> OTHER INFORMATION: Synthetic peptide sequence
<220> FEATURE:
```

```
<221> NAME/KEY: misc_feature
<222> LOCATION: (1)..(3)
<223> OTHER INFORMATION: Xaa can be any naturally occurring amino acid

<400> SEQUENCE: 52

Xaa Xaa Xaa Leu Gln Gly Ile Tyr Val Leu Val Met Leu Val Leu Leu
1               5                   10                  15

Ile Leu Ala Tyr Arg Arg Arg Trp Arg Arg Leu Thr Val Cys Gly Gly
            20                  25                  30

Ile Met Phe Leu Ala Cys Val Leu Val Leu Ile Val Asp Ala Val Leu
        35                  40                  45

Gln Leu Ser Pro Leu Leu
    50

<210> SEQ ID NO 53
<211> LENGTH: 53
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 53

Xaa Xaa Leu Gln Gly Ile Tyr Val Leu Val Met Leu Val Leu Leu Ile
1               5                   10                  15

Leu Ala Tyr Arg Arg Arg Trp Arg Arg Leu Thr Val Cys Gly Gly Ile
            20                  25                  30

Met Phe Leu Ala Cys Val Leu Val Leu Ile Val Asp Ala Val Leu Gln
        35                  40                  45

Leu Ser Pro Leu Leu
    50

<210> SEQ ID NO 54
<211> LENGTH: 56
<212> TYPE: PRT
<213> ORGANISM: Artificial Sequence
<220> FEATURE:
<223> OTHER INFORMATION: Synthetic peptide sequence

<400> SEQUENCE: 54

Ser Lys Lys Lys Lys Leu Gln Gly Ile Tyr Val Leu Val Met Leu Val
1               5                   10                  15

Leu Leu Ile Leu Ala Tyr Arg Arg Arg Trp Arg Arg Leu Thr Val Cys
            20                  25                  30

Gly Gly Ile Met Phe Leu Ala Cys Val Leu Val Leu Ile Val Asp Ala
        35                  40                  45

Val Leu Gln Leu Ser Pro Leu Leu
    50                  55

<210> SEQ ID NO 55
<211> LENGTH: 51
<212> TYPE: PRT
<213> ORGANISM: Artificial Sequence
<220> FEATURE:
<223> OTHER INFORMATION: Synthetic peptide sequence

<400> SEQUENCE: 55

Leu Gln Gly Ile Tyr Val Leu Val Met Leu Val Leu Leu Ile Leu Ala
1               5                   10                  15
```

Tyr Arg Arg Arg Trp Arg Arg Leu Thr Val Cys Gly Gly Ile Met Phe
            20                  25                  30

Leu Ala Cys Val Leu Val Leu Ile Val Asp Ala Val Leu Gln Leu Ser
        35                  40                  45

Pro Leu Leu
    50

<210> SEQ ID NO 56
<211> LENGTH: 56
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 56

Xaa Xaa Xaa Xaa Ser Gly Asn Arg Thr Tyr Gly Pro Val Phe Met Cys
1               5                   10                  15

Ser Leu Gly Gly Leu Leu Thr Met Val Ala Gly Ala Val Trp Leu Thr
            20                  25                  30

Val Met Ser Asn Thr Leu Leu Ser Ala Trp Ile Leu Thr Ala Gly Phe
        35                  40                  45

Leu Ile Phe Leu Ile Gly Phe Ala
    50                  55

<210> SEQ ID NO 57
<211> LENGTH: 55
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 57

Xaa Xaa Xaa Ser Gly Asn Arg Thr Tyr Gly Pro Val Phe Met Cys Ser
1               5                   10                  15

Leu Gly Gly Leu Leu Thr Met Val Ala Gly Ala Val Trp Leu Thr Val
            20                  25                  30

Met Ser Asn Thr Leu Leu Ser Ala Trp Ile Leu Thr Ala Gly Phe Leu
        35                  40                  45

Ile Phe Leu Ile Gly Phe Ala
    50                  55

<210> SEQ ID NO 58
<211> LENGTH: 54
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 58

Xaa Xaa Ser Gly Asn Arg Thr Tyr Gly Pro Val Phe Met Cys Ser Leu
1               5                   10                  15

Gly Gly Leu Leu Thr Met Val Ala Gly Ala Val Trp Leu Thr Val Met

```
                20                  25                  30

Ser Asn Thr Leu Leu Ser Ala Trp Ile Leu Thr Ala Gly Phe Leu Ile
        35                  40                  45

Phe Leu Ile Gly Phe Ala
    50
```

<210> SEQ ID NO 59
<211> LENGTH: 57
<212> TYPE: PRT
<213> ORGANISM: Artificial Sequence
<220> FEATURE:
<223> OTHER INFORMATION: Synthetic peptide sequence

<400> SEQUENCE: 59

```
Ser Lys Lys Lys Lys Ser Gly Asn Arg Thr Tyr Gly Pro Val Phe Met
1               5                   10                  15

Cys Ser Leu Gly Gly Leu Leu Thr Met Val Ala Gly Ala Val Trp Leu
                20                  25                  30

Thr Val Met Ser Asn Thr Leu Leu Ser Ala Trp Ile Leu Thr Ala Gly
            35                  40                  45

Phe Leu Ile Phe Leu Ile Gly Phe Ala
    50                  55
```

<210> SEQ ID NO 60
<211> LENGTH: 52
<212> TYPE: PRT
<213> ORGANISM: Artificial Sequence
<220> FEATURE:
<223> OTHER INFORMATION: Synthetic peptide sequence

<400> SEQUENCE: 60

```
Ser Gly Asn Arg Thr Tyr Gly Pro Val Phe Met Cys Ser Leu Gly Gly
1               5                   10                  15

Leu Leu Thr Met Val Ala Gly Ala Val Trp Leu Thr Val Met Ser Asn
                20                  25                  30

Thr Leu Leu Ser Ala Trp Ile Leu Thr Ala Gly Phe Leu Ile Phe Leu
            35                  40                  45

Ile Gly Phe Ala
    50
```

<210> SEQ ID NO 61
<211> LENGTH: 51
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 61

```
Xaa Xaa Xaa Xaa Ser Asn Glu Glu Pro Pro Pro Tyr Glu Asp Pro
1               5                   10                  15

Tyr Trp Gly Asn Gly Asp Arg His Ser Asp Tyr Gln Pro Leu Gly Thr
                20                  25                  30

Gln Asp Gln Ser Leu Tyr Leu Gly Leu Gln His Asp Gly Asn Asp Gly
            35                  40                  45

Leu Pro Pro
    50
```

-continued

```
<210> SEQ ID NO 62
<211> LENGTH: 50
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 62

Xaa Xaa Xaa Ser Asn Glu Glu Pro Pro Pro Tyr Glu Asp Pro Tyr
1               5                   10                  15

Trp Gly Asn Gly Asp Arg His Ser Asp Tyr Gln Pro Leu Gly Thr Gln
            20                  25                  30

Asp Gln Ser Leu Tyr Leu Gly Leu Gln His Asp Gly Asn Asp Gly Leu
        35                  40                  45

Pro Pro
    50

<210> SEQ ID NO 63
<211> LENGTH: 49
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 63

Xaa Xaa Ser Asn Glu Glu Pro Pro Pro Tyr Glu Asp Pro Tyr Trp
1               5                   10                  15

Gly Asn Gly Asp Arg His Ser Asp Tyr Gln Pro Leu Gly Thr Gln Asp
            20                  25                  30

Gln Ser Leu Tyr Leu Gly Leu Gln His Asp Gly Asn Asp Gly Leu Pro
        35                  40                  45

Pro

<210> SEQ ID NO 64
<211> LENGTH: 52
<212> TYPE: PRT
<213> ORGANISM: Artificial Sequence
<220> FEATURE:
<223> OTHER INFORMATION: Synthetic peptide sequence

<400> SEQUENCE: 64

Ser Lys Lys Lys Lys Ser Asn Glu Glu Pro Pro Pro Tyr Glu Asp
1               5                   10                  15

Pro Tyr Trp Gly Asn Gly Asp Arg His Ser Asp Tyr Gln Pro Leu Gly
            20                  25                  30

Thr Gln Asp Gln Ser Leu Tyr Leu Gly Leu Gln His Asp Gly Asn Asp
        35                  40                  45

Gly Leu Pro Pro
    50

<210> SEQ ID NO 65
<211> LENGTH: 47
<212> TYPE: PRT
<213> ORGANISM: Artificial Sequence
<220> FEATURE:
<223> OTHER INFORMATION: Synthetic peptide sequence
```

<400> SEQUENCE: 65

Ser Asn Glu Glu Pro Pro Pro Tyr Glu Asp Pro Tyr Trp Gly Asn
1               5                   10                  15

Gly Asp Arg His Ser Asp Tyr Gln Pro Leu Gly Thr Gln Asp Gln Ser
            20                  25                  30

Leu Tyr Leu Gly Leu Gln His Asp Gly Asn Asp Gly Leu Pro Pro
        35                  40                  45

<210> SEQ ID NO 66
<211> LENGTH: 55
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 66

Xaa Xaa Xaa Xaa Gly Asn Asp Gly Leu Pro Pro Pro Tyr Ser Pro
1               5                   10                  15

Arg Asp Asp Ser Ser Gln His Ile Tyr Glu Glu Ala Gly Arg Gly Ser
            20                  25                  30

Met Asn Pro Val Cys Leu Pro Val Ile Val Ala Pro Tyr Leu Phe Trp
        35                  40                  45

Leu Ala Ala Ile Ala Ala Ser
    50                  55

<210> SEQ ID NO 67
<211> LENGTH: 54
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 67

Xaa Xaa Xaa Gly Asn Asp Gly Leu Pro Pro Pro Tyr Ser Pro Arg
1               5                   10                  15

Asp Asp Ser Ser Gln His Ile Tyr Glu Glu Ala Gly Arg Gly Ser Met
            20                  25                  30

Asn Pro Val Cys Leu Pro Val Ile Val Ala Pro Tyr Leu Phe Trp Leu
        35                  40                  45

Ala Ala Ile Ala Ala Ser
    50

<210> SEQ ID NO 68
<211> LENGTH: 53
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 68

Xaa Xaa Gly Asn Asp Gly Leu Pro Pro Pro Pro Tyr Ser Pro Arg Asp

```
                1               5                   10                  15
Asp Ser Ser Gln His Ile Tyr Glu Glu Ala Gly Arg Gly Ser Met Asn
                    20                  25                  30

Pro Val Cys Leu Pro Val Ile Val Ala Pro Tyr Leu Phe Trp Leu Ala
            35                  40                  45

Ala Ile Ala Ala Ser
        50
```

<210> SEQ ID NO 69
<211> LENGTH: 56
<212> TYPE: PRT
<213> ORGANISM: Artificial Sequence
<220> FEATURE:
<223> OTHER INFORMATION: Synthetic peptide sequence

<400> SEQUENCE: 69

```
Ser Lys Lys Lys Lys Gly Asn Asp Gly Leu Pro Pro Pro Tyr Ser
1               5                   10                  15

Pro Arg Asp Asp Ser Ser Gln His Ile Tyr Glu Glu Ala Gly Arg Gly
                    20                  25                  30

Ser Met Asn Pro Val Cys Leu Pro Val Ile Val Ala Pro Tyr Leu Phe
            35                  40                  45

Trp Leu Ala Ala Ile Ala Ala Ser
        50                  55
```

<210> SEQ ID NO 70
<211> LENGTH: 51
<212> TYPE: PRT
<213> ORGANISM: Artificial Sequence
<220> FEATURE:
<223> OTHER INFORMATION: Synthetic peptide sequence

<400> SEQUENCE: 70

```
Gly Asn Asp Gly Leu Pro Pro Pro Tyr Ser Pro Arg Asp Asp Ser
1               5                   10                  15

Ser Gln His Ile Tyr Glu Glu Ala Gly Arg Gly Ser Met Asn Pro Val
                    20                  25                  30

Cys Leu Pro Val Ile Val Ala Pro Tyr Leu Phe Trp Leu Ala Ala Ile
            35                  40                  45

Ala Ala Ser
        50
```

<210> SEQ ID NO 71
<211> LENGTH: 54
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(4)
<223> OTHER INFORMATION: Xaa can be any naturally occurring amino acid

<400> SEQUENCE: 71

```
Xaa Xaa Xaa Xaa Ala Ala Ile Ala Ala Ser Cys Phe Thr Ala Ser Val
1               5                   10                  15

Ser Thr Val Val Thr Ala Thr Gly Leu Ala Leu Ser Leu Leu Leu
                    20                  25                  30

Ala Ala Val Ala Ser Ser Tyr Ala Ala Ala Gln Arg Lys Leu Leu Thr
            35                  40                  45

Pro Val Thr Val Leu Thr
        50
```

<210> SEQ ID NO 72
<211> LENGTH: 53
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(3)
<223> OTHER INFORMATION: Xaa can be any naturally occurring amino acid

<400> SEQUENCE: 72

Xaa Xaa Xaa Ala Ala Ile Ala Ala Ser Cys Phe Thr Ala Ser Val Ser
1               5                   10                  15

Thr Val Val Thr Ala Thr Gly Leu Ala Leu Ser Leu Leu Leu Leu Ala
            20                  25                  30

Ala Val Ala Ser Ser Tyr Ala Ala Ala Gln Arg Lys Leu Leu Thr Pro
        35                  40                  45

Val Thr Val Leu Thr
    50

<210> SEQ ID NO 73
<211> LENGTH: 52
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
<223> OTHER INFORMATION: Xaa can be any naturally occurring amino acid

<400> SEQUENCE: 73

Xaa Xaa Ala Ala Ile Ala Ala Ser Cys Phe Thr Ala Ser Val Ser Thr
1               5                   10                  15

Val Val Thr Ala Thr Gly Leu Ala Leu Ser Leu Leu Leu Ala Ala
            20                  25                  30

Val Ala Ser Ser Tyr Ala Ala Ala Gln Arg Lys Leu Leu Thr Pro Val
        35                  40                  45

Thr Val Leu Thr
    50

<210> SEQ ID NO 74
<211> LENGTH: 55
<212> TYPE: PRT
<213> ORGANISM: Artificial Sequence
<220> FEATURE:
<223> OTHER INFORMATION: Synthetic peptide sequence

<400> SEQUENCE: 74

Ser Lys Lys Lys Lys Ala Ala Ile Ala Ala Ser Cys Phe Thr Ala Ser
1               5                   10                  15

Val Ser Thr Val Val Thr Ala Thr Gly Leu Ala Leu Ser Leu Leu Leu
            20                  25                  30

Leu Ala Ala Val Ala Ser Ser Tyr Ala Ala Ala Gln Arg Lys Leu Leu
        35                  40                  45

Thr Pro Val Thr Val Leu Thr
    50                  55

<210> SEQ ID NO 75
<211> LENGTH: 50

<212> TYPE: PRT
<213> ORGANISM: Artificial Sequence
<220> FEATURE:
<223> OTHER INFORMATION: Synthetic peptide sequence

<400> SEQUENCE: 75

```
Ala Ala Ile Ala Ala Ser Cys Phe Thr Ala Ser Val Ser Thr Val Val
1               5                   10                  15

Thr Ala Thr Gly Leu Ala Leu Ser Leu Leu Leu Ala Ala Val Ala
            20                  25                  30

Ser Ser Tyr Ala Ala Ala Gln Arg Lys Leu Leu Thr Pro Val Thr Val
        35                  40                  45

Leu Thr
    50
```

<210> SEQ ID NO 76
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 76

```
Glu Ser Asn Glu Glu Pro Pro Pro Pro Tyr
1               5                   10
```

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 77

```
Ser Asn Glu Glu Pro Pro Pro Pro Tyr
1               5
```

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 78

```
His Ser Asp Tyr Gln Pro Leu Gly Thr
1               5
```

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 79

```
Pro Leu Gly Thr Gln Asp Gln Ser Leu
1               5
```

<210> SEQ ID NO 80
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 80

Pro Leu Gly Thr Gln Asp Gln Ser Leu Tyr
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 81

Leu Gly Thr Gln Asp Gln Ser Leu Tyr
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 82

Gly Thr Gln Asp Gln Ser Leu Tyr Leu
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 83

Gly Thr Gln Asp Gln Ser Leu Tyr Leu
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 84

Gly Thr Gln Asp Gln Ser Leu Tyr Leu Gly
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 85

Gln Ser Leu Tyr Leu Gly Leu Gln His
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 86

```
Ser Leu Tyr Leu Gly Leu Gln His Asp
1               5
```

<210> SEQ ID NO 87
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 87

```
Gly Leu Gln His Asp Gly Asn Asp Gly Leu
1               5                   10
```

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 88

```
Gly Asn Asp Gly Leu Pro Pro Pro Pro Tyr
1               5                   10
```

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 89

```
Gly Leu Pro Pro Pro Pro Tyr Ser Pro
1               5
```

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 90

```
Gly Leu Pro Pro Pro Pro Tyr Ser Pro Arg
1               5                   10
```

<210> SEQ ID NO 91
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 91

```
Pro Arg Asp Asp Ser Ser Gln His Ile Tyr
1               5                   10
```

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 92

Arg Asp Asp Ser Ser Gln His Ile Tyr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 93

His Ile Tyr Glu Glu Ala Gly Arg Gly
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 94

Ile Leu Leu Ala Arg Leu Phe Leu Tyr
1               5

<210> SEQ ID NO 95
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 95

Ser Ser Cys Ser Ser Cys Pro Leu Ser Lys Ile
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 96

Leu Leu Trp Thr Leu Val Val Leu Leu
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 97

Phe Leu Tyr Ala Leu Ala Leu Leu Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 98

Cys Leu Gly Gly Leu Leu Thr Met Val

```
<210> SEQ ID NO 99
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 99

Leu Ile Val Asp Ala Val Leu Gln Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 100

Leu Thr Ala Gly Phe Leu Ile Phe Leu
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 101

Thr Val Cys Gly Gly Ile Met Phe Leu
1               5

<210> SEQ ID NO 102
<211> LENGTH: 42
<212> TYPE: PRT
<213> ORGANISM: artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is one or more hydrophilic
      amino acids

<400> SEQUENCE: 102

Xaa Xaa Xaa Xaa Gly Ala Arg Gly Pro Glu Ser Arg Leu Leu Glu Phe
1               5                   10                  15

Tyr Leu Ala Met Pro Phe Ala Thr Pro Met Glu Ala Glu Leu Ala Arg
            20                  25                  30

Arg Ser Leu Ala Gln Asp Ala Pro Pro Leu
        35                  40

<210> SEQ ID NO 103
```

```
<211> LENGTH: 41
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is from one to ten
      hydrophilic amino acids

<400> SEQUENCE: 103

Xaa Xaa Xaa Gly Ala Arg Gly Pro Glu Ser Arg Leu Leu Glu Phe Tyr
1               5                   10                  15

Leu Ala Met Pro Phe Ala Thr Pro Met Glu Ala Glu Leu Ala Arg Arg
            20                  25                  30

Ser Leu Ala Gln Asp Ala Pro Pro Leu
        35                  40

<210> SEQ ID NO 104
<211> LENGTH: 40
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is from one to four
      hydrophilic amino acids

<400> SEQUENCE: 104

Xaa Xaa Gly Ala Arg Gly Pro Glu Ser Arg Leu Leu Glu Phe Tyr Leu
1               5                   10                  15

Ala Met Pro Phe Ala Thr Pro Met Glu Ala Glu Leu Ala Arg Arg Ser
            20                  25                  30

Leu Ala Gln Asp Ala Pro Pro Leu
        35                  40

<210> SEQ ID NO 105
<211> LENGTH: 43
<212> TYPE: PRT
<213> ORGANISM: Artificial Sequence
<220> FEATURE:
<223> OTHER INFORMATION: Synthetic peptide sequence

<400> SEQUENCE: 105

Ser Lys Lys Lys Lys Gly Ala Arg Gly Pro Glu Ser Arg Leu Leu Glu
1               5                   10                  15

Phe Tyr Leu Ala Met Pro Phe Ala Thr Pro Met Glu Ala Glu Leu Ala
            20                  25                  30

Arg Arg Ser Leu Ala Gln Asp Ala Pro Pro Leu
        35                  40

<210> SEQ ID NO 106
```

<211> LENGTH: 38
<212> TYPE: PRT
<213> ORGANISM: Artificial Sequence
<220> FEATURE:
<223> OTHER INFORMATION: Synthetic peptide sequence

<400> SEQUENCE: 106

Gly Ala Arg Gly Pro Glu Ser Arg Leu Leu Glu Phe Tyr Leu Ala Met
1               5                   10                  15

Pro Phe Ala Thr Pro Met Glu Ala Glu Leu Ala Arg Arg Ser Leu Ala
                20                  25                  30

Gln Asp Ala Pro Pro Leu
        35

<210> SEQ ID NO 107
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 107

Leu Ala Met Pro Phe Ala Thr Pro Met
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 108

Phe Ala Thr Pro Met Glu Ala Glu Leu
1               5

<210> SEQ ID NO 109
<211> LENGTH: 30
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is one or more hydrophilic
      amino acids

<400> SEQUENCE: 109

Xaa Xaa Xaa Xaa Val Pro Gly Val Leu Leu Lys Glu Phe Thr Val Ser
1               5                   10                  15

Gly Asn Ile Leu Thr Ile Arg Leu Thr Ala Ala Asp His Arg
                20                  25                  30

<210> SEQ ID NO 110
<211> LENGTH: 29

```
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is from one to ten
      hydrophilic amino acids

<400> SEQUENCE: 110

Xaa Xaa Xaa Val Pro Gly Val Leu Leu Lys Glu Phe Thr Val Ser Gly
1               5                   10                  15

Asn Ile Leu Thr Ile Arg Leu Thr Ala Ala Asp His Arg
            20                  25

<210> SEQ ID NO 111
<211> LENGTH: 28
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is from one to four
      hydrophilic amino acids

<400> SEQUENCE: 111

Xaa Xaa Val Pro Gly Val Leu Leu Lys Glu Phe Thr Val Ser Gly Asn
1               5                   10                  15

Ile Leu Thr Ile Arg Leu Thr Ala Ala Asp His Arg
            20                  25

<210> SEQ ID NO 112
<211> LENGTH: 31
<212> TYPE: PRT
<213> ORGANISM: Artificial Sequence
<220> FEATURE:
<223> OTHER INFORMATION: Synthetic peptide sequence

<400> SEQUENCE: 112

Ser Lys Lys Lys Lys Val Pro Gly Val Leu Leu Lys Glu Phe Thr Val
1               5                   10                  15

Ser Gly Asn Ile Leu Thr Ile Arg Leu Thr Ala Ala Asp His Arg
            20                  25                  30

<210> SEQ ID NO 113
<211> LENGTH: 26
<212> TYPE: PRT
<213> ORGANISM: Artificial Sequence
<220> FEATURE:
<223> OTHER INFORMATION: Synthetic peptide sequence

<400> SEQUENCE: 113

Val Pro Gly Val Leu Leu Lys Glu Phe Thr Val Ser Gly Asn Ile Leu
1               5                   10                  15
```

```
Thr Ile Arg Leu Thr Ala Ala Asp His Arg
            20                  25

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 114

Glu Phe Thr Val Ser Gly Asn Ile Leu
1               5

<210> SEQ ID NO 115
<211> LENGTH: 32
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is one or more hydrophilic
      amino acids

<400> SEQUENCE: 115

Xaa Xaa Xaa Xaa Leu Gln Gln Leu Ser Leu Leu Met Trp Ile Thr Gln
1               5                   10                  15

Cys Phe Leu Pro Val Phe Leu Ala Gln Pro Pro Ser Gly Gln Arg Arg
            20                  25                  30

<210> SEQ ID NO 116
<211> LENGTH: 31
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is from one to ten
      hydrophilic amino acids

<400> SEQUENCE: 116

Xaa Xaa Xaa Leu Gln Gln Leu Ser Leu Leu Met Trp Ile Thr Gln Cys
1               5                   10                  15

Phe Leu Pro Val Phe Leu Ala Gln Pro Pro Ser Gly Gln Arg Arg
            20                  25                  30
```

```
<210> SEQ ID NO 117
<211> LENGTH: 30
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is from one to four
      hydrophilic amino acids

<400> SEQUENCE: 117

Xaa Xaa Leu Gln Gln Leu Ser Leu Leu Met Trp Ile Thr Gln Cys Phe
1               5                   10                  15

Leu Pro Val Phe Leu Ala Gln Pro Pro Ser Gly Gln Arg Arg
            20                  25                  30

<210> SEQ ID NO 118
<211> LENGTH: 33
<212> TYPE: PRT
<213> ORGANISM: Artificial Sequence
<220> FEATURE:
<223> OTHER INFORMATION: Synthetic peptide sequence

<400> SEQUENCE: 118

Ser Lys Lys Lys Lys Leu Gln Gln Leu Ser Leu Leu Met Trp Ile Thr
1               5                   10                  15

Gln Cys Phe Leu Pro Val Phe Leu Ala Gln Pro Pro Ser Gly Gln Arg
            20                  25                  30

Arg

<210> SEQ ID NO 119
<211> LENGTH: 28
<212> TYPE: PRT
<213> ORGANISM: Artificial Sequence
<220> FEATURE:
<223> OTHER INFORMATION: Synthetic peptide sequence

<400> SEQUENCE: 119

Leu Gln Gln Leu Ser Leu Leu Met Trp Ile Thr Gln Cys Phe Leu Pro
1               5                   10                  15

Val Phe Leu Ala Gln Pro Pro Ser Gly Gln Arg Arg
            20                  25

<210> SEQ ID NO 120
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 120

Ser Leu Leu Met Trp Ile Thr Gln Cys Phe Leu Pro Val Phe
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Synthetic peptide sequence
```

<400> SEQUENCE: 121

Ser Leu Leu Met Trp Ile Thr Gln Cys
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 122

Asn Leu Val Pro Met Val Ala Thr Val
1               5

<210> SEQ ID NO 123
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 123

Cys Ser Lys Lys Lys Lys Asn Leu Val Pro Cys Val Ala Thr Val
1               5                   10                  15

<210> SEQ ID NO 124
<211> LENGTH: 35
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is a hydrophilic amino acid
<220> FEATURE:
<221> NAME/KEY: MISC_FEATURE
<222> LOCATION: (4)..(4)
<223> OTHER INFORMATION: Xaa4 is absent or is one or more hydrophilic
      amino acids

<400> SEQUENCE: 124

Xaa Xaa Xaa Xaa Lys Ile Ser Gln Ala Val His Ala Ala His Ala Glu
1               5                   10                  15

Ile Asn Glu Ala Gly Arg Glu Ser Ile Ile Asn Phe Glu Lys Leu Thr
            20                  25                  30

Glu Trp Thr
        35

<210> SEQ ID NO 125
<211> LENGTH: 34
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S

```
<220> FEATURE:
<221> NAME/KEY: MISC_FEATURE
<222> LOCATION: (2)..(2)
<223> OTHER INFORMATION: Xaa2 is absent or is a hydrophilic amino acid
<220> FEATURE:
<221> NAME/KEY: MISC_FEATURE
<222> LOCATION: (3)..(3)
<223> OTHER INFORMATION: Xaa3 is absent or is from one to ten
      hydrophilic amino acids

<400> SEQUENCE: 125

Xaa Xaa Xaa Lys Ile Ser Gln Ala Val His Ala Ala His Ala Glu Ile
1               5                   10                  15

Asn Glu Ala Gly Arg Glu Ser Ile Ile Asn Phe Glu Lys Leu Thr Glu
            20                  25                  30

Trp Thr

<210> SEQ ID NO 126
<211> LENGTH: 33
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa1 is absent or is S
<220> FEATURE:
<221> NAME/KEY: MISC_FEATURE
<222> LOCATION: (2)..(2)
<223> OTHER INFORMATION: Xaa2 is absent or is from one to four
      hydrophilic amino acids

<400> SEQUENCE: 126

Xaa Xaa Lys Ile Ser Gln Ala Val His Ala Ala His Ala Glu Ile Asn
1               5                   10                  15

Glu Ala Gly Arg Glu Ser Ile Ile Asn Phe Glu Lys Leu Thr Glu Trp
            20                  25                  30

Thr

<210> SEQ ID NO 127
<211> LENGTH: 36
<212> TYPE: PRT
<213> ORGANISM: Artificial Sequence
<220> FEATURE:
<223> OTHER INFORMATION: Synthetic peptide sequence

<400> SEQUENCE: 127

Ser Lys Lys Lys Lys Lys Ile Ser Gln Ala Val His Ala Ala His Ala
1               5                   10                  15

Glu Ile Asn Glu Ala Gly Arg Glu Ser Ile Ile Asn Phe Glu Lys Leu
            20                  25                  30

Thr Glu Trp Thr
        35

<210> SEQ ID NO 128
<211> LENGTH: 31
<212> TYPE: PRT
<213> ORGANISM: Artificial Sequence
<220> FEATURE:
<223> OTHER INFORMATION: Synthetic peptide sequence

<400> SEQUENCE: 128

Lys Ile Ser Gln Ala Val His Ala Ala His Ala Glu Ile Asn Glu Ala
1               5                   10                  15
```

```
Gly Arg Glu Ser Ile Ile Asn Phe Glu Lys Leu Thr Glu Trp Thr
             20                  25                  30

<210> SEQ ID NO 129
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 129

Ser Ile Ile Asn Phe Glu Lys Leu
1               5

<210> SEQ ID NO 130
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 130

Ile Ser Gln Ala Val His Ala Ala His Ala Glu Ile Asn Glu Ala Gly
1               5                   10                  15

Arg
```

AMINO ACID AND PEPTIDE CONJUGATES AND CONJUGATION PROCESS

This application is a § 371 application of PCT/IB2017/051054, filed Feb. 24, 2017, which in turn claims priority to AU Application 2016900701, filed Feb. 26, 2016. The entire disclosure of each of the foregoing applications is incorporated by reference herein.

Incorporated herein by reference in its entirety is the Sequence Listing being concurrently submitted via EFS-Web as a text file named SeqList.txt, created Aug. 8, 2018, and having a size of 63,449 bytes.

TECHNICAL FIELD

The present invention relates to amino acid and peptide conjugates, methods for making amino acid and peptide conjugates, conjugates produced by the methods, pharmaceutical compositions comprising the conjugates, methods of eliciting immune responses in a subject and methods of vaccinating a subject, uses of the conjugates for the same, and uses of the conjugates in the manufacture of medicaments for the same. The present invention also relates to methods of making compounds useful in the synthesis of amino acid- and peptide conjugates of the invention and to such compounds.

BACKGROUND ART

Synthetic peptide vaccines generally comprise a synthetic copy of an immunogenic part of protein antigens. This approach to vaccine development has a number of advantages, including ease of synthesis, avoidance of potentially toxic biological by-products and straightforward characterisation.

A key issue in the development of peptide vaccines is the lack of immunogenicity displayed by peptides as sole vaccine components. It is usually necessary to include in the vaccine an adjuvant, designed to activate components of the innate immune system (e.g. Freund's adjuvant).

An alternative strategy in peptide vaccine design is to create self-adjuvanting vaccines in which the peptide epitope of interest is covalently linked to an appropriate adjuvant. Such self-adjuvanting vaccines may have enhanced antigen uptake, presentation and dendritic cell maturation compared to simple co-formulation of the antigen with an external adjuvant.

Several self-adjuvanting vaccines have been developed, but preparation of the vaccines can be complicated.

There is an ongoing need for new self-adjuvanting vaccines and new methods of making self-adjuvanting vaccines. It is an object of the present invention to go some way towards meeting these needs; and/or to at least provide the public with a useful choice.

Other objects of the invention may become apparent from the following description which is given by way of example only.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date.

SUMMARY OF THE INVENTION

In one aspect, the present invention broadly consists in an amino acid- or peptide conjugate compound of the formula (I):

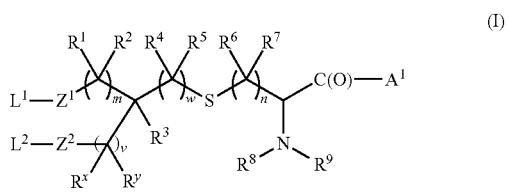

wherein
m and w are each independently an integer from 0 to 7 and v is an integer from 0 to 5,
provided that:
the sum of m, v, and w is at least 3; and
the sum of m and w is from 0 to 7;
n is 1 or 2;
Z1 and Z2 are each independently selected from the group consisting of —O—, —NR—, —S—, —S(O)—, —SO$_2$—, —C(O)O—, —OC(O)—, —C(O)NR—, —NRC(O)—, —C(O)S—, —SC(O)—, —OC(O)O—, —NRC(O)O—, —OC(O)NR—, and —NRC(O)NR—;
R1, R2, Rx, Ry, R4, R5, R6, and R7 at each instance of m, v, w, and n are each independently hydrogen or C1-6aliphatic;
R, R3, and R8 are each independently hydrogen or C1-6aliphatic;
R9 is hydrogen, C1-6aliphatic, an amino protecting group, L3-C(O)—, or A2;
L1 and L2 are each independently selected from is C5-21aliphatic or C4-20heteroaliphatic;
L3 is C1-21aliphatic or C2-20heteroaliphatic;
A1 is an amino acid, a peptide, OH, OP1, NH$_2$, or NHP2, wherein P1 is a carboxyl protecting group, and wherein P2 is a carboxamide protecting group;
A2 is an amino acid or a peptide;
wherein any aliphatic or heteroaliphatic present in any of R, R1, R2, R3, R4, R5, R6, R7, R8, R9, Rx, Ry, L1, L2, and L3 is optionally substituted;
or a pharmaceutically acceptable salt or solvate thereof.

Any of the embodiments or preferences described herein may relate to any of the aspects herein alone or in combination with any one or more embodiments or preferences described herein, unless stated or the context indicates otherwise.

In various embodiments,
R1, R2, Rx, Ry, R4, R5, R6, and R7 at each instance of m, v, w, and n are each independently hydrogen, C1-6alkyl, C2-6alkenyl, C2-6alkynyl, or C3-6cycloalkyl;
R, R3, and R8 are each independently hydrogen, C1-6alkyl, C2-6alkenyl, C2-6alkynyl, or C3-6cycloalkyl;
R9 is hydrogen, C1-6alkyl, C2-6alkenyl, C2-6alkynyl, C3-6cycloalkyl, an amino protecting group, L3-C(O), or A2;
L1 and L2 are each independently selected from C5-21alkyl, C5-21alkenyl, C5-21alkynyl, or C4-20heteroalkyl;
L3 is C1-21alkyl, C5-21alkenyl, C5-21alkynyl, C3-6cycloalkyl, or C2-20heteroalkyl;
A1 is an amino acid, a peptide, OH, OP1, NH$_2$, or NHP2, wherein P1 is a carboxyl protecting group, and wherein P2 is a carboxamide protecting group;
A2 is an amino acid or a peptide;
wherein any alkyl, alkenyl, alkynyl, cycloalkyl or heteroalkyl present in any of R, R1, R2, R3, R4, R5, R6, R7, R8, R9, Rx, Ry, L1, L2, and L3 is optionally substituted.

In various embodiments,

R1, R2, Rx, Ry, R4, R5, R6, and R7 at each instance of m, v, w, and n are each independently hydrogen, C1-6alkyl, C2-6alkenyl, or C3-6cycloalkyl;

R, R3, and R8 are each independently hydrogen, C1-6alkyl, C2-6alkenyl, or C3-6cycloalkyl;

R9 is hydrogen, C1-6alkyl, C2-6alkenyl, C3-6cycloalkyl, an amino protecting group, L3-C(O), or A2;

L1 and L2 are each independently selected from C5-21alkyl, C5-21alkenyl, or C4-20heteroalkyl;

L3 is C1-21alkyl, C5-21alkenyl, C3-6cycloalkyl, or C2-20heteroalkyl;

A1 is an amino acid, a peptide, OH, OP1, $NH_2$, or NHP2, wherein P1 is a carboxyl protecting group, and wherein P2 is a carboxamide protecting group;

A2 is an amino acid or a peptide;

wherein any alkyl, alkenyl, cycloalkyl or heteroalkyl present in any of R, R1, R2, R3, R4, R5, R6, R7, R8, R9, Rx, Ry, L1, L2, and L3 is optionally substituted.

In various embodiments,

R1, R2, Rx, Ry, R4, R5, R6, and R7 at each instance of m, v, w, and n are each independently hydrogen, C1-6alkyl, or C3-6cycloalkyl;

R, R3, and R8 are each independently hydrogen, C1-6alkyl, or C3-6cycloalkyl;

R9 is hydrogen, C1-6alkyl, C3-6cycloalkyl, an amino protecting group, L3-C(O), or A2;

L1 and L2 are each independently selected from C5-21alkyl, C5-21alkenyl, or C4-20heteroalkyl;

L3 is C1-21alkyl, C2-21alkenyl, C3-6cycloalkyl, or C2-20heteroalkyl;

A1 is an amino acid, a peptide, OH, OP1, $NH_2$, or NHP2, wherein P1 is a carboxyl protecting group, and wherein P2 is a carboxamide protecting group;

A2 is an amino acid or a peptide;

wherein any alkyl, alkenyl, cycloalkyl or heteroalkyl present in any of R, R1, R2, R3, R4, R5, R6, R7, R8, R9, Rx, Ry, L1, L2, and L3 is optionally substituted.

In various embodiments,

R1, R2, Rx, Ry, R4, R5, R6, and R7 at each instance of m, v, w, and n are each independently hydrogen, C1-6alkyl, or C3-6cycloalkyl;

R, R3, and R8 are each independently hydrogen, C1-6alkyl, or C3-6cycloalkyl;

R9 is hydrogen, C1-6alkyl, C3-6cycloalkyl, an amino protecting group, L3-C(O), or A2;

L1 and L2 are each independently selected from is C5-21alkyl or C4-20heteroalkyl;

L3 is C1-21alkyl, C3-6cycloalkyl, or C2-20heteroalkyl;

A1 is an amino acid, a peptide, OH, OP1, $NH_2$, or NHP2, wherein P1 is a carboxyl protecting group, and wherein P2 is a carboxamide protecting group;

A2 is an amino acid or a peptide;

wherein any alkyl, cycloalkyl or heteroalkyl present in any of R, R1, R2, R3, R4, R5, R6, R7, R8, R9, Rx, Ry, L1, L2, and L3 is optionally substituted.

In various embodiments, Z1 and Z2 are each independently selected from the group consisting of —C(O)O—, —C(O)NR—, and —C(O)S—.

In various embodiments, the compound of the formula (I) is a compound of the formula (IA):

(IA)

In various embodiments, v is from 0 to 4, 0 to 3, or 0 to 2, or v is 0 or 1, for example 0.

In certain embodiments, v is from 0 to 3. In exemplary embodiments, v is 0.

In various embodiments, m and w are each independently from 0 to 6, 0 to 5, 0 to 4, 0 to 3, 0 to 2, 1 to 7, 1 to 6, 1 to 5, 1 to 4, 1 to 3, or 1 to 2.

In various embodiments, m and w are each independently from 0 to 5.

In certain embodiments, m and w are each independently from 1 to 4.

In various embodiments, m is from 1 to 6, for example from 2 to 6, 1 to 5, or 2 to 5. In various embodiments, m is from 1 to 5. In various embodiments, m is from 1 to 3. In exemplary embodiments, m is 2.

In various embodiments, w is 1 or 2. In exemplary embodiments, w is 1.

In various embodiments, the sum of m and w is from 0 to 6, 0 to 5, 0 to 4, 0 to 3, 1 to 7, 1 to 6, 1 to 5, 1 to 4, 1 to 3, 2 to 7, 2 to 6, 2 to 5, 2 to 4, or 2 to 3.

In various embodiments, the sum of m and w is from 2 to 7.

In certain embodiments, the sum of m and w is from 2 to 5.

In exemplary embodiments, the sum of m and w is 3.

In various embodiments, v is from 0 to 3; m and w are each independently from 0 to 5; and the sum of m and w is from 2 to 7.

In various embodiments, v is 1 or 0; m and w are each independently from 0 to 5; and the sum of m and w is from 2 to 7.

In various embodiments, v is 1 or 0; m and w are each independently from 1 to 4; and the sum of m and w is from 2 to 7.

In various embodiments, v is 1 or 0; m and w are each independently from 1 to 4; and the sum of m and w is from 2 to 5.

In certain embodiments, v is 1 or 0; m is from 1 to 6; and w is 1 or 2. In certain embodiments, v is 1 or 0; m is from 1 to 5; and w is 1 or 2.

In certain embodiments v is 0 or 1; m is from 1 to 3; and w is 1 or 2.

In exemplary embodiments, v is 0; m is 2; and w is 1.

In exemplary embodiments, n is 1.

In certain embodiments, L1 and L2 are each independently C5-21aliphatic, for example C9-21aliphatic, C11-21aliphatic, or C11-, C13-, C15-, C17-, or C19-aliphatic.

In certain embodiments, L1 and L2 are each independently C5-21alkyl.

In various embodiments, L1 and L2 are each independently C9-21alkyl. In yet another embodiment, L1 and L2 are each independently C11-21alkyl.

In various exemplary embodiments, L1 and L2 are each independently C11, C13, C15, C17, or C19alkyl, preferably n-alkyl.

In various specifically contemplated embodiments, L1 and L2 are each independently C15alkyl.

In various embodiments, L1 and L2 each independently comprise a linear chain of 9-21 carbon atoms.

In exemplary embodiments, L1 and L2 are each independently linear C15alkyl.

In some embodiments, L3 is C1-21alkyl.

In various embodiments, L3 is methyl or linear C15alkyl.

In exemplary embodiments, L3 is methyl (that is, R9 is acetyl).

In some embodiments, the amino protecting group is Boc, Fmoc, Cbz (carboxybenzyl), Nosyl (o- or p-nitrophenylsulfonyl), Bpoc (2-(4-biphenyl)isopropoxycarbonyl) and Dde (1-(4,4-dimethyl-2,6-dioxohexylidene)ethyl).

In various embodiments, the amino protecting group is Boc or Fmoc.

In some embodiments, the amino protecting group is Fmoc.

In some embodiments, the carboxyl protecting group is tert-butyl, benzyl, or allyl.

In various embodiments, the carboxamide protecting group is Dmcp or Trityl.

In various embodiments, R1 and R2 at each instance of m are each independently C1-6alkyl or hydrogen. In various specifically contemplated embodiments, R1 and R2 at each instance of m are each hydrogen.

In various embodiments, R3 is C1-6alkyl or hydrogen. In various specifically contemplated embodiments, R3 is hydrogen.

In various embodiments, R4 and R5 at each instance of w are each independently C1-6alkyl or hydrogen, preferably hydrogen. In various specifically contemplated embodiments, R4 and R5 at each instance of w are each hydrogen.

In various embodiments, Rx and Ry at each instance of v are each independently C1-6alkyl or hydrogen. In various specifically contemplated embodiments, Rx and Ry at each instance of v are each hydrogen.

In various embodiments, R6 and R7 at each instance of n are each independently C1-6alkyl or hydrogen. In various specifically contemplated embodiments, R6 and R7 are each hydrogen.

In various embodiments, R8 is independently C1-6alkyl or hydrogen. In exemplary embodiments, R8 is hydrogen.

In various embodiments, R9 is C1-6alkyl, hydrogen, an amino protecting group, L3-C(O), or A2. In exemplary embodiments, R9 is hydrogen, an amino protecting group, L3-C(O), or A2.

In various embodiments, R8 is hydrogen and R9 is hydrogen, an amino protecting group, L3-C(O), or A2.

In various embodiments, R8 and R9 are each hydrogen; or R9 is L3-C(O) or A2.

In various exemplary embodiments, R8 is hydrogen and R9 is L3-C(O). In various specifically contemplated embodiments, R9 is L3-C(O), wherein L3 is methyl.

In various embodiments, the compound of formula (I) is a compound of the formula (IF):

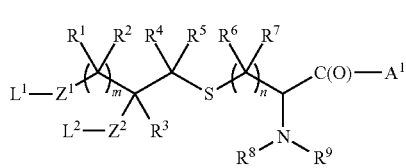

(IF)

wherein m is an integer from 2 to 6, preferably 2; and the remaining variables are as defined in the compound of formula (I) or any embodiment thereof.

In various embodiments, the compound of formula (IF) is a compound of the formula (IF-1):

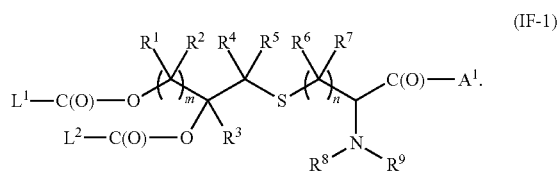

(IF-1)

In various embodiments, the compound of formula (I) is a compound of the formula (IB):

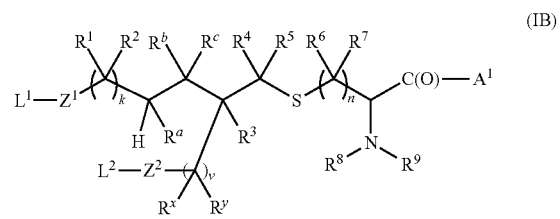

(IB)

wherein k is an integer from 0 to 4; and

Ra, Rb, and Rc are each independently hydrogen or C1-6aliphatic.

In various embodiments, the compound of formula (IB) is a compound of the formula (IC):

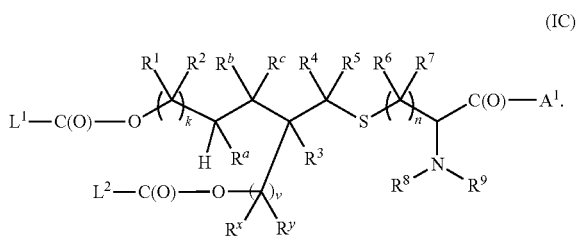

(IC)

In various embodiments, k is from 0 to 3, 0 to 2, 0 to 1, 1 to 4, 1 to 3, or 1 to 2, or k is 0 or 1.

In certain embodiments, k is 0 to 3.

In certain embodiments, k is 0 or 1.

In exemplary embodiments, k is 0.

In certain embodiments k is equal to v.

In various, embodiments, Ra, Rb, and Rc are each independently hydrogen, C1-6alkyl, C2-6alkenyl, C2-6alkynyl, or C3-6cycloalkyl.

In various, embodiments, Ra, Rb, and Rc are each independently hydrogen, C1-6alkyl, C2-6alkenyl, or C3-6cycloalkyl.

In various, embodiments, Ra, Rb, and Rc are each independently hydrogen, C1-6alkyl, or C3-6cycloalkyl.

In various embodiments, Ra, Rb, and Rc are each independently selected from hydrogen or C1-6alkyl, preferably hydrogen. In exemplary embodiments, Ra, Rb, and Rc are each hydrogen.

In various embodiments, the compound of the formula (I) is a compound of the formula (ID):

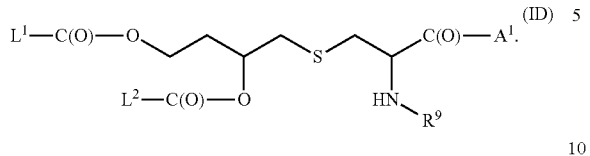

In certain embodiments, the compound is a compound of the formula (ID) wherein L1 and L2 are each linear C15alkyl.

In various embodiments, L1 and L2 are each independently C11-21alkyl; m is 2; v is 0; w is 1; R1 and R2 at each instance are each hydrogen; R3 is hydrogen; and R4 and R5 are each hydrogen.

In various embodiments, n is 1; R6, R7, and R8 are each hydrogen; and R9 is hydrogen, an amino protecting group, L3-C(O), or A2.

In various embodiments, n is 1; R6, R7, and R8 are each hydrogen; and R9 is hydrogen, an amino protecting group, or L3-C(O), wherein L3 is linear C15alkyl or methyl.

In various embodiments, L1 and L2 are each independently C11-21alkyl; m is 2; v is 0; w is 1; R1 and R2 at each instance are each hydrogen; R3 is hydrogen; R4 and R5 are each hydrogen; n is 1; R6, R7, and R8 are each hydrogen; and R9 is hydrogen, an amino protecting group, or L3-C(O), wherein L3 is linear C15alkyl or methyl.

In various embodiments, the compound of formula (I) has the formula (IE):

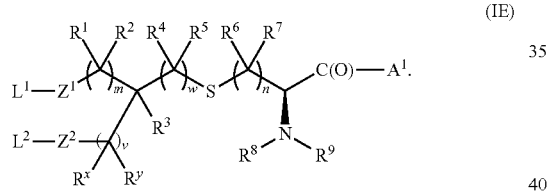

In various embodiments, the compound of formula (I) has the formula (IEE):

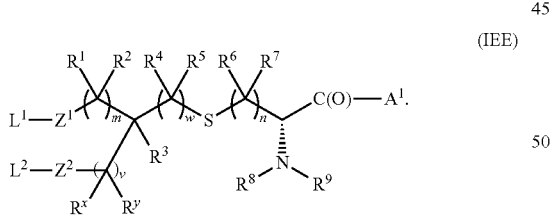

In various embodiments, the compound of formula (I) has the formula (IE-1):

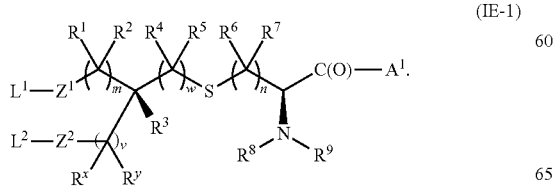

In various embodiments, the compound of formula (I) has the formula (IEE-1):

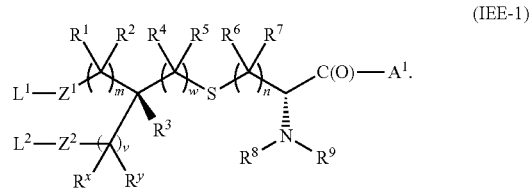

In various embodiments, the compound of formula (I) has the formula (IE-2):

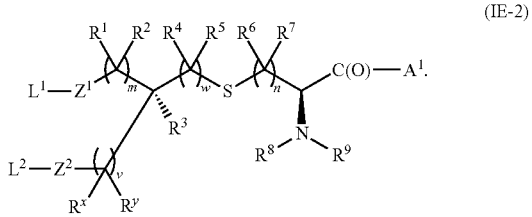

In various embodiments, the compound of formula (I) has the formula (IEE-2):

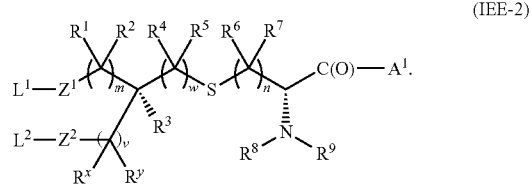

In various embodiments, the compound of formula (I) has the formula (IEE-3):

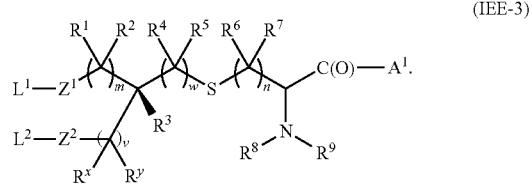

In various embodiments, the compound of formula (I) has the formula (IEE-4):

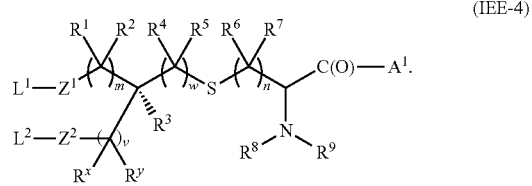

In various embodiments, the amino acid of the amino acid- or peptide conjugate to which the lipid moieties are conjugated is a cysteine residue.

Those skilled in the art will appreciate that, in certain embodiments, the moieties L1-Z1- and L2-Z2- may be fatty acid groups, for example fatty acid esters. In various embodiments, the moieties may be saturated or unsaturated fatty acid esters. In some embodiments, the fatty acid is saturated.

In various embodiments, the fatty acid is a C4-22 fatty acid. In some embodiments, the fatty acid is a C6-22 fatty acid.

In certain embodiments, the fatty acid is a C10-22 fatty acid. In certain specifically contemplated embodiments, the fatty acid is a C12-22 fatty acid. In various exemplary embodiments, the fatty acid is a C12, C14, C16, C18, or C20 fatty acid.

In some embodiments, the fatty acid is lauric acid, myristic acid, palmitic acid, stearic acid, arachic acid, palmitoleic acid, oleic acid, elaidic acid, linoleic acid, a-linolenic acid, and arachidonic acid.

In various embodiments, the fatty acid is lauric acid, myristic acid, palmitic acid, or stearic acid.

In certain exemplary embodiments, the fatty acid is palmitic acid (and the moieties L1-Z1- and L2-Z2-are each palmitoyl groups).

In various embodiments, the compound of formula (I) is an amino acid-conjugate.

In some embodiments, A1 is OH, OP1, NH2, or NHP2 and/or R9 is hydrogen, C1-6alkyl, C3-6cycloalkyl, an amino protecting group, or L3-C(O).

In some embodiments, A1 is OP1 or OH and/or R9 is hydrogen, an amino protecting group or L3-C(O).

In various embodiments, A1 is OH, OP1, NH$_2$, or NHP2 and R9 is hydrogen, C1-6alkyl, C3-6cycloalkyl, an amino protecting group, or L3-C(O).

In various embodiments, A1 is OH, or OP1, and R9 is hydrogen, an amino protecting group, or L3-C(O).

In various embodiments, R9 is hydrogen, an amino protecting group or L3-C(O). In some embodiments, R9 is hydrogen or L3-C(O).

In various embodiments, the compound of formula (I) is a peptide conjugate.

In various embodiments, A1 and/or A2 is an amino acid or a peptide.

In some embodiments, A1 and/or A2 is a peptide.

In one embodiment A1 and/or A2 is a peptide comprising an epitope.

In some embodiments, A1 and/or A2 is a peptide comprising a peptide epitope.

In another embodiment, A1 and/or A2 is a peptide, wherein the peptide comprises a peptide epitope.

In some embodiments, A1 and/or A2 is a peptide substituted with an epitope.

In some embodiments, the epitope is bound to the peptide via a linker group.

In certain embodiments, A1 is a peptide.

In certain exemplary embodiments, A1 is a peptide and R9 is not A2 (that is, R9 is not an amino acid or a peptide).

In various embodiments, the peptide comprises an epitope.

In various embodiments, the epitope is a peptide epitope.

In certain embodiments, the epitope is coupled or bound via a linker group.

In various embodiments, the amino acid of the peptide conjugate to which the lipid moieties are conjugated is an N-terminal amino acid residue.

In various embodiments, A1 is serine or a peptide comprising serine as the first N-terminal amino acid residue.

In some embodiments, A1 is a peptide comprising serine as the first N-terminal amino acid residue.

In various embodiments, the peptide conjugate comprises one or more solubilising groups.

In some embodiments, the solubilising group comprises an amino acid sequence comprising two or more hydrophilic amino acid residues in the peptide chain.

In various embodiments, the solubilising group is an amino acid sequence comprising a sequence of two or more consecutive hydrophilic amino acid residues in the peptide chain.

In various embodiments, the two or more hydrophilic amino acid residues are adjacent to the serine residue.

In some embodiments, A1 and/or A2 is a peptide comprising a solubilising group.

In various embodiments, A1 and/or A2 is a peptide comprising a solubilising group comprising an amino acid sequence comprising two or more hydrophilic amino acid residues in the peptide chain.

In certain embodiments, A1 is a peptide comprising a solubilising group comprising an amino acid sequence comprising two or more hydrophilic amino acid residues in the peptide chain.

In some embodiments, A1 is a peptide comprising serine as the first N-terminal amino acid residue and a solubilising group comprising an amino acid sequence comprising two or more hydrophilic amino acid residues in the peptide chain adjacent to the serine.

In some embodiments, the compound comprises a linker or one or more amino acids thereof. In some embodiments, the peptide comprises a linker or one or more amino acids thereof.

In some embodiments, the peptide comprises a peptide epitope bound via a linker to the amino acid to which the lipid moieties are bound.

In some embodiments, the peptide comprises two or more epitopes.

In some embodiments, the peptide comprises a peptide antigen.

In some embodiments, the linker is an amino acid sequence from about 2 to 20, 2 to 18, 2 to 16, 2 to 14, 2 to 12, 2 to 10, or 2 to 8 amino acids in length.

In some embodiments, the compound of formula (I) comprises 3 or more, 4 or more, or 5 or more contiguous amino acids.

In various embodiments, the peptide conjugate is a lipopeptide.

In some embodiments, the compound of formula (I) is a self adjuvanting peptide.

In some embodiments, A1 and/or A2 are each independently a peptide comprising from about 8 to 220, 8 to 200, 8 to 175, 8 to 150, 8 to 125, 8 to 100, 8 to 90, 8 to 80, 8 to 70, 8 to 60, 8 to 50, 8 to 40, 8 to 30, 8 to 25, 8 to 20, or 8 to 15 amino acids. In one exemplary embodiment, A1 and A2 are each independently a peptide comprising from about 8 to 60 amino acids.

In other embodiments, A1 and/or A2 are each independently a peptide comprising from about 8 to 220, 8 to 200, 8 to 175, 8 to 150, 8 to 125, 8 to 100, 8 to 90, 8 to 80, 8 to 70, 8 to 60, 8 to 50, 8 to 40, 8 to 30, 8 to 25, 8 to 20, or 8 to 15 amino acids.

In some embodiments, A1 and/or A2 are each independently a peptide comprising from about 5 to 150, 5 to 125, 5 to 100, 5 to 75, 5 to 60, 5 to 50, 5 to 40, 5 to 30, 5 to 25, 5 to 20, 8 to 150, 8 to 125, 8 to 100, 8 to 75, 8 to 60, 8 to 50, 8 to 40, 8 to 30, 8 to 25, or 8 to 20 amino acids.

In some embodiments, A1 and/or A2 are each independently a peptide, wherein the peptide comprises 8 to 60 amino acids.

In some embodiments, A1 and/or A2 are each independently a peptide comprising or substituted with a peptide epitope, wherein the peptide epitope comprises from 8 to 60 amino acids.

Suitable peptide epitopes include without limitation those described in WO 2016/103192 filed 22 Dec. 2015, the entirety of which is incorporated herein by reference.

In various embodiments, the peptide comprises, consists essentially of, or consists of one or more EBV LMP2 epitopes. In various embodiments, the one or more EBV LMP2 epitopes are MHCI epitopes. In various embodiments, the peptide comprises one or more EBV LMP2 epitopes selected from the group consisting of any one of SEQ ID NOs 76-101. In various embodiments, the peptide comprises a peptide comprising or consisting of 8 or more contiguous amino acids from the amino acid sequence of any one of SEQ ID NOs 1-75. In various embodiments, the peptide comprises a peptide comprising or consisting of 12 or more contiguous amino acids from the amino acid sequence of any one of SEQ ID NOs 1-75. In various embodiments, the peptide comprises a peptide comprising or consisting of 15 or more contiguous amino acids from the amino acid sequence of any one of SEQ ID NOs 1-75, or comprising or consisting of 20 or more contiguous amino acids from the amino acid sequence of any one of SEQ ID NOs 1-75.

In various embodiments, the peptide comprises a recombinant peptide comprising or consisting of 12 or more contiguous amino acids from the amino acid sequence of any one of SEQ ID NOs 1-75. In various embodiments, the recombinant peptide comprises or consists of 15 or more contiguous amino acids from the amino acid sequence of any one of SEQ ID NOs 1-75, or comprises or consists of 20 or more contiguous amino acids from the amino acid sequence of any one of SEQ ID NOs 1-75.

In various embodiments, the peptide comprises, consists of, or consists essentially of an amino acid sequence selected from the group consisting of any one of SEQ ID NOs 1-75.

In various embodiments, the peptide comprises, consists of, or consists essentially of an amino acid sequence selected from the group consisting of (a) 8 or more contiguous amino acid residues from the sequence $Xaa_1Xaa_2Xaa_3Xaa_4$DRHSDYQPLGTQDQSLYLGLQHDGNDGL [SEQ ID NO: 1], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (b) 8 or more contiguous amino acid residues from the sequence $Xaa_1Xaa_2Xaa_3$DRHSDYQPLGTQDQSLYLGLQHDGNDGL [SEQ ID NO:2], wherein Xaa1 is absent or is S or a hydrophilic amino acid, $Xaa_2$ is absent or is a hydrophilic amino acid, and $Xaa_3$ is absent or is from one to ten hydrophilic amino acids, (c) 8 or more contiguous amino acid residues from the sequence $Xaa_1Xaa_2$DRHSDYQPLGTQDQSLYLGLQHDGNDGL [SEQ ID NO:3], wherein Xaa1 is absent or is S or a hydrophilic amino acid, and $Xaa_2$ is absent or is from one to four hydrophilic amino acids, (d) 8 or more contiguous amino acid residues from the sequence SKKKKDRHSDYQPLGTQDQSLYLGLQHDGNDGL [SEQ ID NO:4], (e) 8 or more contiguous amino acid residues from the sequence DRHSDYQPLGTQDQSLYLGLQHDGNDGL [SEQ ID NO:5], (f) 8 or more contiguous amino acid residues from the sequence $Xaa_1Xaa_2Xaa_3Xaa_4$SLYLGLQHDGNDGLPPPPYSPRDDSSQHIYEEA [SEQ ID NO:6], wherein Xaa1 is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (g) 8 or more contiguous amino acid residues from the sequence $Xaa_1Xaa_2Xaa_3$SLYLGLQHDGNDGLPPPPYSPRDDSSQHIYEEA [SEQ ID NO:7], wherein Xaa1 is absent or is S or a hydrophilic amino acid, $Xaa_2$ is absent or is a hydrophilic amino acid, and $Xaa_3$ is absent or is from one to ten hydrophilic amino acids, (h) 8 or more contiguous amino acid residues from the sequence $Xaa_1Xaa_2$SLYLGLQHDGNDGLPPPPYSPRDDSSQHIYEEA [SEQ ID NO:8], wherein Xaa1 is absent or is S or a hydrophilic amino acid, and $Xaa_2$ is absent or is from one to four hydrophilic amino acids, (i) 8 or more contiguous amino acid residues from the sequence SKKKKSLYLGLQHDGNDGLPPPPYSPRDDSSQHIYEEA [SEQ ID NO:9], (j) 8 or more contiguous amino acid residues from the sequence SLYLGLQHDGNDGLPPPPYSPRDDSSQHIYEEA [SEQ ID NO:10], (k) 8 or more contiguous amino acid residues from the sequence $Xaa_1Xaa_2Xaa_3Xaa_4$SDYQPLGTQDQSLYLGLQHDGNDGL [SEQ ID NO:11], wherein $Xaa_1$ is absent or is S or a hydrophilic amino acid, $Xaa_2$ is absent or is a hydrophilic amino acid, $Xaa_3$ is absent or is a hydrophilic amino acid, and $Xaa_4$ is absent or is one or more hydrophilic amino acids, (l) 8 or more contiguous amino acid residues from the sequence $Xaa_1Xaa_2Xaa_3$SDYQPLGTQDQSLYLGLQHDGNDGL [SEQ ID NO:12], wherein $Xaa_1$ is absent or is S or a hydrophilic amino acid, $Xaa_2$ is absent or is a hydrophilic amino acid, and $Xaa_3$ is absent or is from one to ten hydrophilic amino acids, (m) 8 or more contiguous amino acid residues from the sequence $Xaa_1Xaa_2$SDYQPLGTQDQSLYLGLQHDGNDGL [SEQ ID NO:13], wherein $Xaa_1$ is absent or is S or a hydrophilic amino acid, and $Xaa_2$ is absent or is from one to four hydrophilic amino acids, (n) 8 or more contiguous amino acid residues from the sequence SKKKKSDYQPLGTQDQSLYLGLQHDGNDGL [SEQ ID NO:14], (o) 8 or more contiguous amino acid residues from the sequence SDYQPLGTQDQSLYLGLQHDGNDGL [SEQ ID NO:15], (p) 8 or more contiguous amino acid residues from the sequence $Xaa_1Xaa_2Xaa_3Xaa_4$DRHSDYQPLGTQDQSLYLGLQHDGNDGLPPPPYSPRDDSSQHIYEEA [SEQ ID NO:16], wherein $Xaa_1$ is absent or is S or a hydrophilic amino acid, $Xaa_2$ is absent or is a hydrophilic amino acid, Xaa₃ is absent or is a hydrophilic amino acid, and Xaa₄ is absent or is one or more hydrophilic amino acids, (q) 8 or more contiguous amino acid residues from the sequence Xaa₁Xaa₂Xaa₃DRHSDYQPLGTQDQSLYLGLQHDGN DGLPPPPYSPRDDSSQHIYEEA [SEQ ID NO:17], wherein Xaa₁ is absent or is S or a hydrophilic amino acid, Xaa₂ is absent or is a hydrophilic amino acid, and Xaa₃ is absent or is from one to ten hydrophilic amino acids, (r) 8 or more contiguous amino acid residues from the sequence Xaa₁Xaa₂DRHSDYQPLGTQDQSLYLGLQHDGNDGL PPPPYSPRDDSSQHIYEEA [SEQ ID NO:18], wherein Xaa₁ is absent or is S or a hydrophilic amino acid, and Xaa₂ is absent or is from one to four hydrophilic amino acids, (s) 8 or more contiguous amino acid residues from the sequence SKKKKDRHSDYQPLGTQDQS-LYLGLQHDGNDGLPPPPYSPRDDSSQHIYEEA [SEQ ID NO:19], (t) 8 or more contiguous amino acid residues from the sequence DRHSDYQPLGTQDQSLYLGLQHDGNDG-LPPPPYSPRDDSSQHIYEEA [SEQ ID NO:20], (u) 8 or more contiguous amino acid residues from the sequence Xaa₁Xaa₂Xaa₃Xaa₄LLWTLVVLLICSSCSSCPLSKILL ARLFLYALALLL [SEQ ID NO:21], wherein Xaa₁ is absent or is S or a hydrophilic amino acid, Xaa₂ is absent or is a hydrophilic amino acid, Xaa₃ is absent or is a hydrophilic amino acid, and Xaa₄ is absent or is one or more hydrophilic amino acids, (v) 8 or more contiguous amino acid residues from the sequence Xaa₁Xaa₂Xaa₃LLWTLVVLLICSSCSSCPLSKILLARL FLYALALLL [SEQ ID NO:22], wherein Xaa₁ is absent or is S or a hydrophilic amino acid, Xaa₂ is absent or is a hydrophilic amino acid, and Xaa₃ is absent or is from one to ten hydrophilic amino acids, (w) 8 or more contiguous amino acid residues from the sequence Xaa₁Xaa₂LLWTLVVLLICSSCSSCPLSKILLARLFLYA LALLL [SEQ ID NO:23], wherein Xaa₁ is absent or is S or a hydrophilic amino acid, and Xaa₂ is absent or is from one to four hydrophilic amino acids, (x) 8 or more contiguous amino acid residues from the sequence SKKKKLLWTLVVLLICSSCSSCPLSKIL-LARLFLYALALLL [SEQ ID NO:24], (y) 8 or more contiguous amino acid residues from the sequence LLWTLVVLLICSSCSSCPLSKILLARLFLY-ALALLL [SEQ ID NO:25], (z) 8 or more contiguous amino acid residues from the sequence Xaa₁Xaa₂Xaa₃Xaa₄LMLLWTLVVLLICSSCSSCPLSKI LLARLFLYALALLLLA [SEQ ID NO:26], wherein Xaa₁ is absent or is S or a hydrophilic amino acid, Xaa₂ is absent or is a hydrophilic amino acid, Xaa₃ is absent or is a hydrophilic amino acid, and Xaa₄ is absent or is one or more hydrophilic amino acids, (aa) 8 or more contiguous amino acid residues from the sequence Xaa₁Xaa₂Xaa₃LMLLWTLVVLLICSSCSSCPLSKILLA RLFLYALALLLLA [SEQ ID NO:27], wherein Xaa₁ is absent or is S or a hydrophilic amino acid, Xaa₂ is absent or is a hydrophilic amino acid, and Xaa₃ is absent or is from one to ten hydrophilic amino acids, (bb) 8 or more contiguous amino acid residues from the sequence Xaa₁Xaa₂LMLLWTLVVLLICSSCSSCPLSKILLARLF LYALALLLLA [SEQ ID NO:28], wherein Xaa₁ is absent or is S or a hydrophilic amino acid, and Xaa₂ is absent or is from one to four hydrophilic amino acids, (cc) 8 or more contiguous amino acid residues from the sequence SKKKKLMLLWTLVVLLICSSCSSCPLSKIL-LARLFLYALALLLLA [SEQ ID NO:29], (dd) 8 or more contiguous amino acid residues from the sequence LMLLWTLVVLLICSSCSSCPLSKILLARL-FLYALALLLLA [SEQ ID NO:30], (ee) 8 or more contiguous amino acid residues from the sequence Xaa₁Xaa₂Xaa₃Xaa₄LMLLWTLVVLLICSSCSSCPLSKI LL [SEQ ID NO:31], wherein Xaa₁ is absent or is S or a hydrophilic amino acid, Xaa₂ is absent or is a hydrophilic amino acid, Xaa₃ is absent or is a hydrophilic amino acid, and Xaa₄ is absent or is one or more hydrophilic amino acids, (ff) 8 or more contiguous amino acid residues from the sequence Xaa₁Xaa₂Xaa₃LMLLWTLVVLLICSSCSSCPLSKILL [SEQ ID NO:32], wherein Xaa₁ is absent or is S or a hydrophilic amino acid, Xaa₂ is absent or is a hydrophilic amino acid, and Xaa₃ is absent or is from one to ten hydrophilic amino acids, (gg) 8 or more contiguous amino acid residues from the sequence Xaa₁Xaa₂LMLLWTLVVLLICSSCSSCPLSKILL [SEQ ID NO:33], wherein Xaa₁ is absent or is S or a hydrophilic amino acid, and Xaa₂ is absent or is from one to four hydrophilic amino acids, (hh) 8 or more contiguous amino acid residues from the sequence SKKKKLMLLWTLVVLLICSSCSSCPL-SKILL [SEQ ID NO:34], (ii) 8 or more contiguous amino acid residues from the sequence LMLLWTLVVLLICSSCSSCPLSKILL [SEQ ID NO:35], (jj) 8 or more contiguous amino acid residues from the sequence Xaa₁Xaa₂Xaa₃Xaa₄LLICSSCSSCPLSKILLARLFLYAL ALLLLA [SEQ ID NO:36], wherein Xaa₁ is absent or is S or a hydrophilic amino acid, Xaa₂ is absent or is a hydrophilic amino acid, Xaa₃ is absent or is a hydrophilic amino acid, and Xaa₄ is absent or is one or more hydrophilic amino acids, (kk) 8 or more contiguous amino acid residues from the sequence Xaa₁Xaa₂Xaa₃LLICSSCSSCPLSKILLARLFLYALALL LLA [SEQ ID NO:37], wherein Xaa₁ is absent or is S or a hydrophilic amino acid, Xaa₂ is absent or is a hydrophilic amino acid, and Xaa₃ is absent or is from one to ten hydrophilic amino acids, (ll) 8 or more contiguous amino acid residues from the sequence Xaa₁Xaa₂LLICSSCSSCPLSKILLARLFLYALALLLLA [SEQ ID NO:38], wherein Xaa₁ is absent or is S or a hydrophilic amino acid, and Xaa₂ is absent or is from one to four hydrophilic amino acids, (mm) 8 or more contiguous amino acid residues from the sequence SKKKKLLICSSCSSCPLSKILLARLFLY-ALALLLLA [SEQ ID NO:39], (nn) 8 or more contiguous amino acid residues from the sequence LLICSSCSSCPLSKILLARLFLYALALLLLA [SEQ ID NO:40], (oo) 8 or more contiguous amino acid residues from the sequence Xaa$_1$Xaa$_2$Xaa$_3$Xaa$_4$LNLTTMFLLMLLWTLVVLLICSSCSSCPLSKILLARLFLYALALLLLASALIA GGSI [SEQ ID NO:41], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (pp) 8 or more contiguous amino acid residues from the sequence Xaa$_1$Xaa$_2$Xaa$_3$LNLTTMFLLMLLWTLVVLLICSSCSSCPLSKILLARLFLYALALLLLASALIAGGS I [SEQ ID NO:42], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (qq) 8 or more contiguous amino acid residues from the sequence Xaa$_1$Xaa$_2$LNLTTMFLLMLLWTLVVLLICSSCSSCPLSKILLARLFLYALALLLLASALIAGGSI [SEQ ID NO:43], wherein Xaa$_1$ is absent or is S or a hydrophilic amino acid, and Xaa$_2$ is absent or is from one to four hydrophilic amino acids, (rr) 8 or more contiguous amino acid residues from the sequence SKKKKLNLTTMFLLMLLWTLVVLLICSSCSSCPLSKILLARLFLYALALLLLASALIAGGSI [SEQ ID NO:44], (ss) 8 or more contiguous amino acid residues from the sequence LNLTTMFLLMLLWTLVVLLICSSCSSCPLSKILLARLFLYALALLLLASALIAGGSI [SEQ ID NO:45], (tt) 8 or more contiguous amino acid residues from the sequence Xaa$_1$Xaa$_2$Xaa$_3$Xaa$_4$FLLMLLWTLVVLLICSSCSSCPLSKILLARLFLYALALLLLASA [SEQ ID NO:46], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (uu) 8 or more contiguous amino acid residues from the sequence Xaa$_1$Xaa$_2$Xaa$_3$FLLMLLWTLVVLLICSSCSSCPLSKILLARLFLYALALLLLASA [SEQ ID NO:47], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (vv) 8 or more contiguous amino acid residues from the sequence Xaa$_1$Xaa$_2$FLLMLLWTLVVLLICSSCSSCPLSKILLARLFLYALALLLLASA [SEQ ID NO:48], wherein Xaa$_1$ is absent or is S or a hydrophilic amino acid, and Xaa$_2$ is absent or is from one to four hydrophilic amino acids, (ww) 8 or more contiguous amino acid residues from the sequence SKKKKFLLMLLWTLVVLLICSSCSSCPLSKILLARLFLYALALLLLASA [SEQ ID NO:49], (xx) 8 or more contiguous amino acid residues from the sequence FLLMLLWTLVVLLICSSCSSCPLSKILLARLFLYALALLLLASA [SEQ ID NO:50], (yy) 8 or more contiguous amino acid residues from the sequence Xaa$_1$Xaa$_2$Xaa$_3$Xaa$_4$LQGIYVLVMLVLLILAYRRRWRRLTVCGGIMFLACVLVLIVDAVLQLSPLL [SEQ ID NO:51], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (zz) 8 or more contiguous amino acid residues from the sequence Xaa$_1$Xaa$_2$Xaa$_3$LQGIYVLVMLVLLILAYRRRWRRLTVCGGIMFLACVLVLIVDAVLQLSPLL [SEQ ID NO:52], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (aaa) 8 or more contiguous amino acid residues from the sequence Xaa$_1$Xaa$_2$LQGIYVLVMLVLLILAYRRRWRRLTVCGGIMFLACVLVLIVDAVLQLSPLL [SEQ ID NO:53], wherein Xaa$_1$ is absent or is S or a hydrophilic amino acid, and Xaa$_2$ is absent or is from one to four hydrophilic amino acids, (bbb) 8 or more contiguous amino acid residues from the sequence SKKKKLQGIYVLVMLVLLILAYRRRWRRLTVCGGIMFLACVLVLIVDAVLQLSPLL [SEQ ID NO:54], (ccc) 8 or more contiguous amino acid residues from the sequence LQGIYVLVMLVLLILAYRRRWRRLTVCGIMFLACVLVLIVDAVLQLSPLL [SEQ ID NO:55], (ddd) 8 or more contiguous amino acid residues from the sequence Xaa$_1$Xaa$_2$Xaa$_3$Xaa$_4$SGNRTYGPVFM(C)(S)LGGLLTMVAGAVWLTVMSNTLLSAWILTAGFLI FLIGFA [SEQ ID NO:56], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (eee) 8 or more contiguous amino acid residues from the sequence Xaa$_1$Xaa$_2$Xaa$_3$SGNRTYGPVFM(C)(S)LGGLLTMVAGAVWLTVMSNTLLSAWILTAGFLIFLIG FA [SEQ ID NO:57], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (fff) 8 or more contiguous amino acid residues from the sequence Xaa$_1$Xaa$_2$SGNRTYGPVFM(C)(S)LGGLLTMVAGAVWLTVMSNTLLSAWILTAGFLIFLIGFA [SEQ ID NO:58], wherein Xaa$_1$ is absent or is S or a hydrophilic amino acid, and Xaa$_2$ is absent or is from one to four hydrophilic amino acids, (ggg) 8 or more contiguous amino acid residues from the sequence SKKKKSGNRTYGPVFM(C)(S)LGGLLTMVAGAVWLTVMSNTLLSAWILTAGFLIFLIGFA [SEQ ID NO:59], (hhh) 8 or more contiguous amino acid residues from the sequence SGNRTYGPVFM(C)(S)LGGLLTMVAGAVWLTVMSNTLLSAWILTAGFLIFLIGFA [SEQ ID NO:60], (iii) 8 or more contiguous amino acid residues from the sequence Xaa$_1$Xaa$_2$Xaa$_3$Xaa$_4$SNEEPPPPYEDPYWGNGDRHSDYQPLGTQDQSLYLGLQHDGNDGLPP [SEQ ID NO:61], wherein Xaa$_1$ is absent or is S or a hydrophilic amino acid, Xaa$_2$ is absent or is a hydrophilic amino acid, Xaa$_3$ is absent or is a hydrophilic amino acid, and Xaa$_4$ is absent or is one or more hydrophilic amino acids, (jjj) 8 or more contiguous amino acid residues from the sequence Xaa$_1$Xaa$_2$Xaa$_3$SNEEPPPPYEDPYWGNGDRHSDYQPLGTQDQSLYLGLQHDGNDGLPP [SEQ ID NO:62], wherein Xaa$_1$ is absent or is S or a hydrophilic amino acid, Xaa$_2$ is absent or is a hydrophilic amino acid, and Xaa$_3$ is absent or is from one to ten hydrophilic amino acids, (kkk) 8 or more contiguous amino acid residues from the sequence Xaa₁Xaa₂SNEEPPPPYEDPYWGNGDRHSDYQPLGT QDQSLYLGLQHDGNDGLPP [SEQ ID NO:63], wherein Xaa₁ is absent or is S or a hydrophilic amino acid, and Xaa₂ is absent or is from one to four hydrophilic amino acids, (lll) 8 or more contiguous amino acid residues from the sequence SKKKKSNEEPPP-PYEDPYWGNGDRHSDYQPLGTQDQS-LYLGLQHDGNDGLPP [SEQ ID NO:64], (mmm) 8 or more contiguous amino acid residues from the sequence SNEEPPP-PYEDPYWGNGDRHSDYQPLGTQDQS-LYLGLQHDGNDGLPP [SEQ ID NO:65], (nnn) 8 or more contiguous amino acid residues from the sequence Xaa₁Xaa₂Xaa₃Xaa₄GNDGLPPPPYSPRDDSSQHIYEE AGRGSMNPVCLPVIVAPYLFWLAAIAA S [SEQ ID NO:66], wherein Xaa₁ is absent or is S or a hydrophilic amino acid, Xaa₂ is absent or is a hydrophilic amino acid, Xaa₃ is absent or is a hydrophilic amino acid, and Xaa₄ is absent or is one or more hydrophilic amino acids, (ooo) 8 or more contiguous amino acid residues from the sequence Xaa₁Xaa₂Xaa₃GNDGLPPPPYSPRDDSSQHIYEEAGR GSMNPVCLPVIVAPYLFWLAAIAAS [SEQ ID NO:67], wherein Xaa₁ is absent or is S or a hydrophilic amino acid, Xaa₂ is absent or is a hydrophilic amino acid, and Xaa₃ is absent or is from one to ten hydrophilic amino acids, (ppp) 8 or more contiguous amino acid residues from the sequence Xaa₁Xaa₂GNDGLPPPPYSPRDDSSQHIYEEAGRGSM NPVCLPVIVAPYLFWLAAIAAS [SEQ ID NO:68], wherein Xaa₁ is absent or is S or a hydrophilic amino acid, and Xaa₂ is absent or is from one to four hydrophilic amino acids, (qqq) 8 or more contiguous amino acid residues from the sequence SKKKKGNDGLPPPPYSPRDDSSQHIYEEA-GRGSMNPVCLPVIVAPYLFWLAAIAAS [SEQ ID NO:69], (rrr) 8 or more contiguous amino acid residues from the sequence GNDGLPPPPYSPRDDSSQHIYEEA-GRGSMNPVCLPVIVAPYLFWLAAIAAS [SEQ ID NO:70], (sss) 8 or more contiguous amino acid residues from the sequence Xaa₁Xaa₂Xaa₃Xaa₄AAIAASCFTASVSTVVTATGLAL SLLLLAAVASSYAAAQRKLLTPVTVLT [SEQ ID NO:71], wherein Xaa₁ is absent or is S or a hydrophilic amino acid, Xaa₂ is absent or is a hydrophilic amino acid, Xaa₃ is absent or is a hydrophilic amino acid, and Xaa₄ is absent or is one or more hydrophilic amino acids, (ttt) 8 or more contiguous amino acid residues from the sequence Xaa₁Xaa₂Xaa₃AAIAASCFTASVSTVVTATGLALSLLL LAAVASSYAAAQRKLLTPVTVLT [SEQ ID NO:72], wherein Xaa₁ is absent or is S or a hydrophilic amino acid, Xaa₂ is absent or is a hydrophilic amino acid, and Xaa₃ is absent or is from one to ten hydrophilic amino acids, (uuu) 8 or more contiguous amino acid residues from the sequence Xaa₁Xaa₂AAIAASCFTASVSTVVTATGLALSLLLLAA VASSYAAAQRKLLTPVTVLT [SEQ ID NO:73], wherein Xaa₁ is absent or is S or a hydrophilic amino acid, and Xaa₂ is absent or is from one to four hydrophilic amino acids, (vvv) 8 or more contiguous amino acid residues from the sequence SKKKKAAIAASCF-TASVSTVVTATGLALSLLLLAA-VASSYAAAQRKLLTPVTVLT [SEQ ID NO:74], (www) 8 or more contiguous amino acid residues from the sequence AAIAASCFTASVSTVVTATGLALSLLL-LAAVASSYAAAQRKLLTPVTVLT [SEQ ID NO:75], (xxx) the sequence of any one of SEQ ID NOs: 1 to 75, (yyy) 8 or more contiguous amino acid residues from the sequence of any one of

ESNEEPPPPY, [SEQ ID NO: 76]

SNEEPPPPY, [SEQ ID NO: 77]

HSDYQPLGT, [SEQ ID NO: 78]

PLGTQDQSL, [SEQ ID NO: 79]

PLGTQDQSLY, [SEQ ID NO: 80]

PLGTQDQSLY, [SEQ ID NO: 80]

LGTQDQSLY, [SEQ ID NO: 81]

GTQDQSLYL, [SEQ ID NO: 82]

GTQDQSLYL, [SEQ ID NO: 83]

GTQDQSLYLG, [SEQ ID NO: 84]

QSLYLGLQH, [SEQ ID NO: 85]

SLYLGLQHD, [SEQ ID NO: 86]

SLYLGLQHD, [SEQ ID NO: 86]

GLQHDGNDGL, [SEQ ID NO: 87]

GNDGLPPPPY, [SEQ ID NO: 88]

GLPPPPYSP, [SEQ ID NO: 89]

GLPPPPYSPR, [SEQ ID NO: 90]

GLPPPPYSPR, [SEQ ID NO: 90]

PRDDSSQHIY, [SEQ ID NO: 91]

RDDSSQHIY, [SEQ ID NO: 92]

HIYEEAGRG, [SEQ ID NO: 93]

```
                                    [SEQ ID NO: 94]
         ILLARLFLY,

[SEQ ID NO: 95]
         SSCSSCPLSKI,

[SEQ ID NO: 96]
         LLWTLVVLL,

[SEQ ID NO: 97]
         FLYALALLL,

[SEQ ID NO: 98]
         CLGGLLTMV,

[SEQ ID NO: 99]
         LIVDAVLQL,

[SEQ ID NO: 100]
         LTAGFLIFL,

[SEQ ID NO: 101]
         TVCGGIMFL,
```

(zzz) the sequence of any one of SEQ ID NOs: 76-101,
(aaaa) or any combination of two or more of (a) to (zzz) above.

In one exemplary embodiment, the peptide comprises one or more epitopes derived from Latent Membrane Protein 2 (LMP2), for example, from full-length EBV LMP2 (amino acids 1-497). In one specifically contemplated embodiment, the peptide comprises, consists essentially of, or consists of an amino acid sequence selected from the group consisting of 8 or more contiguous amino acid residues from any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In another specifically contemplated embodiment, the peptide comprises, consists essentially of, or consists of an amino acid sequence selected from the group consisting of 12 or more contiguous amino acid residues from any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In another specifically contemplated embodiment, the peptide comprises, consists essentially of, or consists of an amino acid sequence selected from the group consisting of 15 or more, 18 or more, 20 or more, or 25 or more contiguous amino acid residues from any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In one embodiment, the peptide comprises, consists essentially of, or consists of an amino acid sequence selected from the group consisting of any one of SEQ ID NOs: 4, 5, 9, 10, 14, 15, 19, 20, 24, 25, 29, 30, 34, 35, 39, 40, 44, 45, 49, 50, 54, 55, 59, 60, 64, 65, 69, 70, 74, or 75.

In another specifically contemplated embodiment, the peptide comprises, consists essentially of, or consists of an amino acid sequence selected from the group consisting of 15 or more, 18 or more, 20 or more, or 25 or more contiguous amino acid residues from any one of SEQ ID NOs: 1 to 75.

In one embodiment, the peptide comprises, consists essentially of, or consists of an amino acid sequence selected from the group consisting of any one of SEQ ID NOs: 1 to 75.

In one embodiment, the peptide comprises an amino acid sequence selected from the group consisting of any one of SEQ ID NOs: 76 to 101. In one example, the peptide comprises an amino acid sequence selected from the group consisting of any one of SEQ ID NOs: 76 to 93.

In one embodiment, the peptide comprises an amino acid sequence selected from the group consisting of any two or more of SEQ ID NOs: 76 to 101. In one example, the peptide comprises an amino acid sequence selected from the group consisting of any two or more of SEQ ID NOs: 76 to 93.

In various embodiments the peptide comprises, consists of, or consists essentially of an amino acid sequence selected from the group consisting of (a) 8 or more contiguous amino acid residues from the sequence $Xaa_1Xaa_2Xaa_3Xaa_4$GARGPESRLLEFYLAMPFATPME AELARRSLAQDAPPL [SEQ ID NO:102], wherein $Xaa_1$ is absent or is S, $Xaa_2$ is absent or is a hydrophilic amino acid, $Xaa_3$ is absent or is a hydrophilic amino acid, and $Xaa_4$ is absent or is one or more hydrophilic amino acids, (b) 8 or more contiguous amino acid residues from the sequence $Xaa_1Xaa_2Xaa_3$GARGPESRLLEFYLAMPFATPMEAEL ARRSLAQDAPPL [SEQ ID NO:103], wherein $Xaa_1$ is absent or is S, $Xaa_2$ is absent or is a hydrophilic amino acid, and $Xaa_3$ is absent or is from one to ten hydrophilic amino acids, (c) 8 or more contiguous amino acid residues from the sequence $Xaa_1Xaa_2$GARGPESRLLEFYLAMPFATPMEAELARR SLAQDAPPL [SEQ ID NO:104], wherein $Xaa_1$ is absent or is S, and $Xaa_2$ is absent or is from one to four hydrophilic amino acids, (d) 8 or more contiguous amino acid residues from the sequence SKKKKGARGPESRLLEFYLAMPFATPME-AELARRSLAQDAPPL [SEQ ID NO:105], (e) the sequence of any one of SEQ ID NOs: 102 to 105, (f) 8 or more contiguous amino acid residues from the sequence GARGPESRLLEFYLAMPFATPMEAEL-ARRSLAQDAPPL [SEQ ID NO:106], (g) the sequence of SEQ ID NO: 106, (h) 8 or more contiguous amino acid residues from the sequence LAMPFATPM [SEQ ID NO:107], (i) the sequence of SEQ ID NO: 107, (j) 8 or more contiguous amino acid residues from the sequence FATPMEAEL [SEQ ID NO:108], (k) the sequence of SEQ ID NO: 108, (l) 8 or more contiguous amino acid residues from the sequence $Xaa_1Xaa_2Xaa_3Xaa_4$VPGVLLKEFTVSGNILTIRLTAAD HR [SEQ ID NO:109], wherein $Xaa_1$ is absent or is S, $Xaa_2$ is absent or is a hydrophilic amino acid, $Xaa_3$ is absent or is a hydrophilic amino acid, and $Xaa_4$ is absent or is one or more hydrophilic amino acids, (m) 8 or more contiguous amino acid residues from the sequence $Xaa_1Xaa_2Xaa_3$VPGVLLKEFTVSGNILTIRLTAADHR [SEQ ID NO:110], wherein $Xaa_1$ is absent or is S, $Xaa_2$ is absent or is a hydrophilic amino acid, and $Xaa_3$ is absent or is from one to ten hydrophilic amino acids, (n) 8 or more contiguous amino acid residues from the sequence $Xaa_1Xaa_2$VPGVLLKEFTVSGNILTIRLTAADHR [SEQ ID NO:111], wherein $Xaa_1$ is absent or is S, and $Xaa_2$ is absent or is from one to four hydrophilic amino acids, (o) 8 or more contiguous amino acid residues from the sequence SKKKKVPGVLLKEFTVSGNILTIRL-TAADHR [SEQ ID NO: 112], (p) the sequence of any one of SEQ ID NOs: 109 to 112, (q) 8 or more contiguous amino acid residues from the sequence VPGVLLKEFTVSGNILTIRLTAADHR [SEQ ID NO: 113], (r) the sequence of SEQ ID NO: 113, (s) 8 or more contiguous amino acid residues from the sequence EFTVSGNIL [SEQ ID NO:114], (t) the sequence of SEQ ID NO: 114, (u) 8 or more contiguous amino acid residues from the sequence $Xaa_1Xaa_2Xaa_3Xaa_4$LQQLSLLMWITQCFLPVFLAQPPSGQRR [SEQ ID NO:115], wherein $Xaa_1$ is absent or is S, $Xaa_2$ is absent or is a hydrophilic amino acid, $Xaa_3$ is absent or is a hydrophilic amino acid, and $Xaa_4$ is absent or is one or more hydrophilic amino acids (v) 8 or more contiguous amino acid residues from the sequence $Xaa_1Xaa_2Xaa_3$LQQLSLLMWITQCFLPVFLAQPPSGQRR [SEQ ID NO:116], wherein $Xaa_1$ is absent or is S, $Xaa_2$ is absent or is a hydrophilic amino acid, and $Xaa_3$ is absent or is from one to ten hydrophilic amino acids, (w) 8 or more contiguous amino acid residues from the sequence $Xaa_1Xaa_2$LQQLSLLMWITQCFLPVFLAQPPSGQRR [SEQ ID NO:117], wherein $Xaa_1$ is absent or is S, and $Xaa_2$ is absent or is from one to four hydrophilic amino acids, (x) 8 or more contiguous amino acid residues from the sequence SKKKKLQQLSLLMWITQCFLPVFLAQPPSGQRR [SEQ ID NO:118], (y) the sequence of any one of SEQ ID NOs: 115 to 118, (z) 8 or more contiguous amino acid residues from the sequence LQQLSLLMWITQCFLPVFLAQPPSGQRR [SEQ ID NO: 119], (aa) the sequence of SEQ ID NO: 119, (bb) 8 or more contiguous amino acid residues from the sequence SLLMWITQCFLPVF [SEQ ID NO:120], (cc) the sequence of SEQ ID NO: 120, (dd) 8 or more contiguous amino acid residues from the sequence SLLMWITQC [SEQ ID NO:121], (ee) the sequence of SEQ ID NO: 121, (ff) or any combination of two or more of (a) to (ee) above.

In one exemplary embodiment, the peptide epitope is derived from NY-ESO-1. In one specifically contemplated embodiment, the peptide comprises, consists essentially of, or consists of an amino acid sequence selected from the group consisting of 8 or more contiguous amino acid residues from any one of SEQ ID NO: 106, 107, 108, 113, 114, 119, 120, and 121.

In one embodiment, the peptide comprises, consists essentially of, or consists of an amino acid sequence selected from the group consisting of any one of SEQ ID NO: 106, 107, 108, 113, 114, 119, 120, and 121.

In one embodiment, the peptide comprises, consists essentially of, or consists of an amino acid sequence selected from the group consisting of any one of SEQ ID NO: 106, 113, and 119.

In one embodiment, the peptide comprises, consists essentially of, or consists of an amino acid sequence selected from the group consisting of any one of SEQ ID NO: 105, 112, and 118.

In various embodiments, the peptide comprises, consists essentially of, or consists of one or more ovalbumin protein epitopes. In various embodiments, the one or more ovalbumin protein are MHCI epitopes. In various embodiments, the one or more ovalbumin protein are MHCII epitopes.

In various embodiments, the peptide comprises, consists essentially of, or consists of:

(a) 8 or more contiguous amino acid residues from the sequence $Xaa_1Xaa_2Xaa_3Xaa_4$KISQAVHAAHAEINEAGRESIINFEKLTEWT [SEQ ID NO:124], wherein $Xaa_1$ is absent or is S, $Xaa_2$ is absent or is a hydrophilic amino acid, $Xaa_3$ is absent or is a hydrophilic amino acid, and $Xaa_4$ is absent or is one or more hydrophilic amino acids (b) 8 or more contiguous amino acid residues from the sequence $Xaa_1Xaa_2Xaa_3$ KISQAVHAAHAEINEAGRESIINFEKLTEWT [SEQ ID NO:125], wherein $Xaa_1$ is absent or is S, $Xaa_2$ is absent or is a hydrophilic amino acid, and $Xaa_3$ is absent or is from one to ten hydrophilic amino acids, (c) 8 or more contiguous amino acid residues from the sequence $Xaa_1Xaa_2$ KISQAVHAAHAEINEAGRESIINFEKLTEWT [SEQ ID NO:126], wherein $Xaa_1$ is absent or is S, and $Xaa_2$ is absent or is from one to four hydrophilic amino acids, (d) 8 or more contiguous amino acid residues from the sequence SKKKKKISQAVHAAHAEINEAGRESIINFEKLTEWT [SEQ ID NO: 127], (e) the sequence of any one of SEQ ID NOs: 124 to 127, (f) 8 or more contiguous amino acid residues from the sequence KISQAVHAAHAEINEAGRESIINFEKLTEWT [SEQ ID NO:128], (g) the sequence of SEQ ID NO: 128, (h) 8 or more contiguous amino acid residues from the sequence SIINFEKL [SEQ ID NO: 129], (i) the sequence of SEQ ID NO: 129, (j) 8 or more contiguous amino acid residues from the sequence ISQAVHAAHAEINEAGR [SEQ ID NO: 130], (k) the sequence of SEQ ID NO: 130, (l) or any combination of any two or more of (a) to (k) above.

In various embodiments, the peptide comprises one or more ovalbumin protein epitopes selected from the group consisting of any one of SEQ ID NOs 124-130. In various embodiments, the peptide comprises a peptide comprising or consisting of 8 or more contiguous amino acids from the amino acid sequence of any one of SEQ ID NOs 124-130.

In various embodiments, the peptide comprises, consists of, or consists essentially of an amino acid sequence selected from the group consisting of any one of SEQ ID NOs 124-130.

In one embodiment, the peptide conjugate comprises two or more epitopes, such as two or more peptide epitopes.

In some embodiments, the peptide conjugate comprises an antigenic peptide.

In specifically contemplated embodiments, the peptide is a synthetic peptide.

In various embodiments, the compound of formula (I) is an isolated compound of formula (I).

In various embodiments, the compound of formula (I) is a pure, purified or substantially pure compound of formula (I).

In another aspect, the present invention broadly consists in a method of making a compound of the formula (XV), the method comprising reacting an epoxide of the formula (XVI):

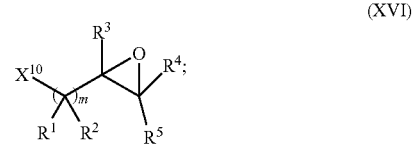

(XVI)

and
an amino acid-comprising conjugation partner comprising a thiol of the formula (III):

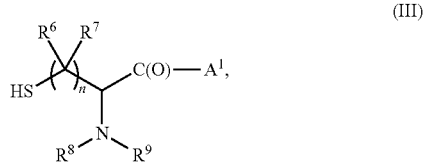

under conditions effective to conjugate the epoxide and amino acid-comprising conjugation partner and provide the compound of formula (XV):

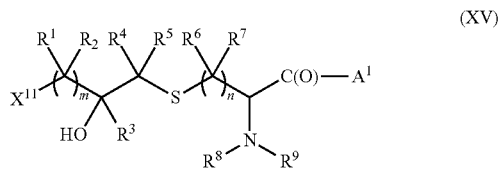

wherein
X10 is L1-Z1-, —OH, —SH, —NHR, HNRC(O)O—, P10-O—, P11-S—, P12-NR—, or P12-NRC(O)O—;
X11 is X10 or —OH, —SH, —NHR, or HNRC(O)O— when X10 is P10-O—, P11-S—, P12-NR—, or P12-NRC(O)O— and said conditions are effective to remove P10, P11, or P12;
P10, P11, and P12 are each independently a protecting group;
m is an integer from 2 to 6; and
n, L1, Z1, R, R1, R2, R3, R4, R5, R6, R7, R8, R9, and A1 are as defined in the compound of formula (I) or any embodiment thereof; or a salt or solvate thereof.

In various embodiments m is from 2 to 5, 2 to 4, or 2 to 3. In exemplary embodiments, m is 2.

In various embodiments, X10 is L1-Z1- or —OH, —SH, —NHR, P10-O—, P11-S—, or P12-NR—; and X11 is X10 or —OH, —SH, or —NHR.

In various embodiments, X10 is L1-Z1-, —OH, or P10-O—; and X11 is X10 or —OH.

In various embodiments, X10 is L1-C(O)O—, OH, or P10-O—; and X11 is L1-C(O)O—, P10-O—, or OH.

In various embodiments, X10 is L1-C(O)O— or P10-O—; and X11 is L1-C(O)O—, P10-O—, or OH.

In exemplary embodiments, X10 is P10-O—; and X11 is P10-O— or OH.

In various embodiments, R9 is not hydrogen and/or A1 is not OH.

In various embodiments, the amino acid-comprising conjugation partner is a peptide containing conjugation partner comprising 15 or less, 14 or less, 13 or less, 12 or less, 11 or less, 10 or less, 9 or less, 8 or less, 7 or less, 6 or less, 5 or less, 4 or less, or 3 or less amino acid residues.

In various embodiments, the C-terminus of the amino acid comprising conjugation partner is protected with a carboxyl protecting group or a carboxamide protecting group and/or the Na-amino group of the amino acid comprising conjugation partner is protected with an amino protecting group.

In exemplary embodiments, R9 is an amino protecting group.

In various embodiments, A1 is OP1 or NHP2. In certain embodiments, A1 is OP1.

In exemplary embodiments, R9 is an amino protecting group and A1 is OP1.

In various embodiments, the method comprises reacting the epoxide and amino acid-comprising conjugation partner in the presence of an acid, for example a strong acid.

In certain embodiments, the acid comprises hydrochloric acid, sulfuric acid, or a mixture thereof.

In certain embodiments, the acid comprises a lewis acid, for example BF$_3$.

In other embodiments, the method comprises reacting the epoxide and amino acid-comprising conjugation partner under neutral conditions.

In various embodiments, the neutral conditions comprise a protic solvent, such as an alcohol, for example ethanol.

In other embodiments, the method comprises reacting the epoxide and amino acid-comprising conjugation partner in the presence of a base, for example a mild base.

In some embodiments, the base is an organic amine, for example triethylamine.

In various embodiments, the method comprises providing the epoxide by reacting an alkene of the formula (XVII):

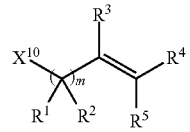

and an oxidant under conditions effective to epoxidise the alkene.

In various embodiments, the oxidant is a peroxide, such as an organic peroxide, for example m-chloro peroxybenzoic acid, or an organic N-oxide, for example pyridine N-oxide.

In various embodiments, the method comprises providing the epoxide by reacting an compound of the formula (XVII-A) wherein LG is a leaving group:

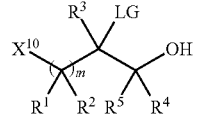

and a base under conditions effective for epoxidation.

In various embodiments, the compound of formula (XVII-A) is prepared from L-aspartic acid.

In various embodiments, the method further comprises providing a single stereoisomer or a stereoisomerically enriched mixture of the epoxide of formula (XVI).

In various embodiments, providing the single stereoisomer or a stereoisomerically enriched mixture of the epoxide of formula (XVI) comprises resolving a racemic mixture of the epoxide.

In various embodiments, the method comprises providing a single stereoisomer or a stereoisomerically enriched mixture of the compound of formula (XVII-A).

In various embodiments, the method comprises converting the compound of formula (XV) to an amino acid- or peptide conjugate of the formula (IF) or a pharmaceutically acceptable salt or solvate thereof of the present invention by one or more additional synthetic steps:

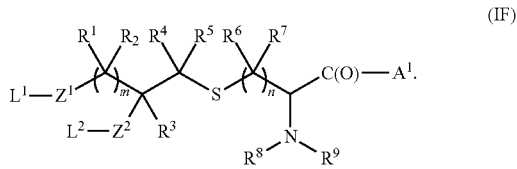

(IF)

In various embodiments, the method comprises converting the compound of formula (XV) to an amino acid- or peptide conjugate of the formula (IF-1) or a pharmaceutically acceptable salt or solvate thereof of the present invention by one or more additional synthetic steps:

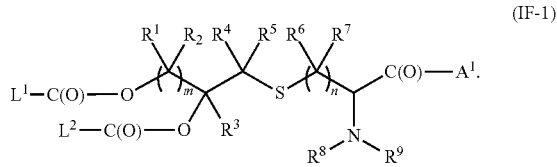

(IF-1)

In various embodiments, the one or more synthetic steps comprises converting the hydroxyl group bound to the carbon to which R3 is attached to L2-Z2-.

In various embodiments, the one or more synthetic steps comprises acylating the compound of formula (XV) so as to replace the hydrogen atom of the hydroxyl group bound to the carbon to which R3 is attached with L2-C(O)—.

In various embodiments, X11 is P10-O— or OH; and the one or more synthetic steps comprise acylating the compound of formula (XV) so as to replace P10 or the hydrogen atom of the hydroxyl group of X11 with L1-C(O)—; and/or acylating the compound of formula (XV) so as to replace the hydrogen atom of the hydroxyl group bound to the carbon to which R3 is attached with L2-C(O)—.

In another aspect, the present invention broadly consists in a compound of the formula (XV):

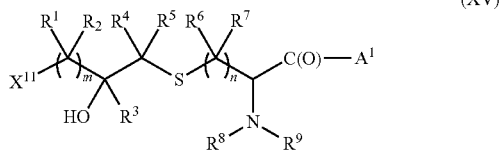

(XV)

wherein
X11 is L1-Z1-, —OH, —SH, —NHR, HNRC(O)O—, P10-O—, P11-S—, P12-NR—, or P12-NRC(O)O—;
P10, P11, and P12 are each independently a protecting group;
m is an integer from 2 to 6; and
n, L1, Z1, R, R1, R2, R3, R4, R5, R6, R7, R8, R9, and A1 are as defined in the compound of formula (I) or any embodiment thereof; or a salt or solvate thereof.

In another aspect, the present invention broadly consists in the use of a compound of the formula (XV) or (XVI) in the synthesis of an amino acid- or peptide-conjugate of the formula (IF) of the present invention or a pharmaceutically acceptable salt or solvate thereof.

In another aspect, the present invention broadly consists in a method of making a compound of the formula (XX), the method comprising reacting a compound of the formula (XXI):

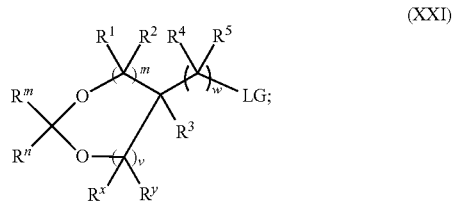

(XXI)

and
an amino acid-comprising conjugation partner comprising a thiol of the formula (III):

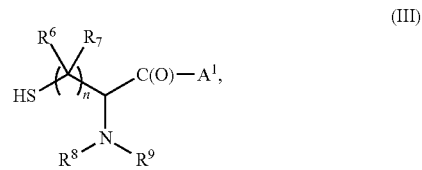

(III)

under conditions effective to conjugate the compound of formula (XXI) and amino acid-comprising conjugation partner and provide the compound of formula (XX):

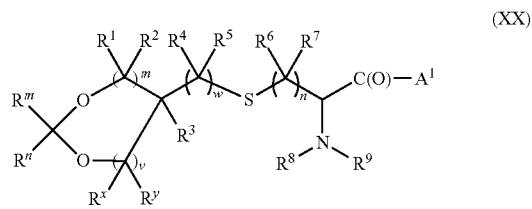

(XX)

wherein
Rm and Rn are each independently hydrogen, C1-6alkyl, aryl, or heteroaryl;
LG is a leaving group;
m and w are each independently an integer from 0 to 7 and v is an integer from 0 to 5,
provided that:
the sum of m, v, and w is at least 3; and
the sum of m and w is from 0 to 7; and
n, Rx, Ry, R1, R2, R3, R4, R5, R6, R7, R8, R9, and A1 are as defined in the compound of formula (I) or any embodiment thereof; or a salt or solvate thereof.

In various embodiments, Rm and Rn are each independently selected from hydrogen, C1-6alkyl, or aryl.

In certain embodiments, Rm is hydrogen, C1-6alkyl, or aryl; and Rn is C1-6alkyl or aryl.

In various embodiments, the leaving group is a halo (for example chloro, bromo, or iodo) or sulfonate (for example a tosylate or mesylate).

In various embodiments, m and v are such that the compound comprises a 5-7-membered cyclic acetal.

In certain embodiment, the cyclic acetal is a 6-membered cyclic acetal.

In various embodiments, the cyclic acetal is a 5-membered cyclic acetal and w is an integer greater than 1.

In various embodiments, m is 2 and v is 1.

In various embodiments, R9 is not hydrogen and/or A1 is not OH.

In various embodiments, the amino acid-comprising conjugation partner is a peptide containing conjugation partner comprising 15 or less, 14 or less, 13 or less, 12 or less, 11 or less, 10 or less, 9 or less, 8 or less, 7 or less, 6 or less, 5 or less, 4 or less, or 3 or less amino acid residues.

In various embodiments, the C-terminus of the amino acid comprising conjugation partner is protected with a carboxyl protecting group or a carboxamide protecting group and/or the Nα-amino group of the amino acid comprising conjugation partner is protected with an amino protecting group.

In exemplary embodiments, R9 is an amino protecting group.

In various embodiments, A1 is OP1 or NHP2. In certain embodiments, A1 is OP1.

In exemplary embodiments, R9 is an amino protecting group and A1 is OP1.

In various embodiments, the method comprises reacting the compound of formula (XXI) and the amino acid-comprising conjugation partner of formula (III) in the presence of a base.

In various embodiments, the base comprises an organic amine, for example triethylamine, N-methylmorpholine, or collidine.

In various embodiments, the cyclic acetal of formula (XXI) is provided in the form of a single stereoisomer or a stereoisomerically enriched mixture.

In various embodiments, the method comprises converting the compound of formula (XX) to an amino acid- or peptide conjugate of the formula (I) or a pharmaceutically acceptable salt or solvate thereof of the present invention by one or more additional synthetic steps:

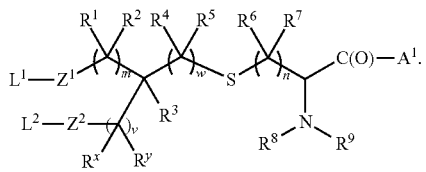

(I)

In various embodiments, the method comprises converting the compound of formula (XX) to an amino acid- or peptide conjugate of the formula (IA) or a pharmaceutically acceptable salt or solvate thereof of the present invention by one or more synthetic steps:

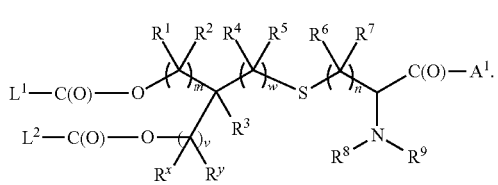

(IA)

In various embodiments, the one or more synthetic steps comprises removing the acetal in the compound of formula (XX) to provide a compound of the formula (XXIII-1):

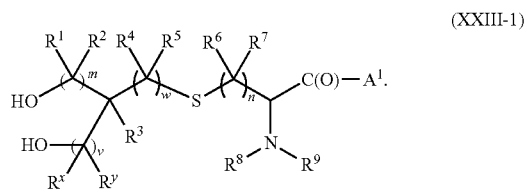

(XXIII-1)

In various embodiments, wherein Rm is optionally substituted aryl, for example phenyl or methoxy substituted phenyl, the method comprises removing the acetal in the compound of formula (XX) to provide a compound of the formula (XXIII-2) or (XXIII-3):

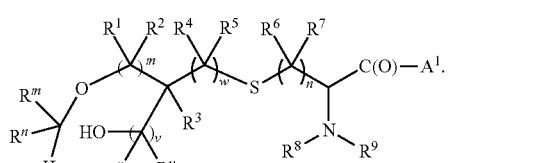

(XXIII-2)

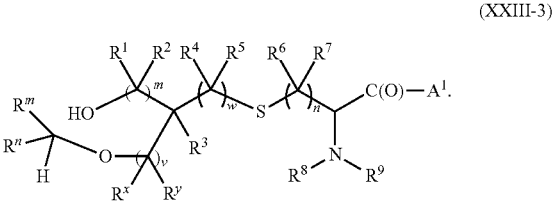

(XXIII-3)

In various embodiments, the one or more synthetic steps comprise converting the hydroxyl group bound to the carbon to which R1 and R2 are attached in the compound of formula (XXIII-1) to L1-Z1-, and/or converting the hydroxyl group bound to the carbon to which Rx and Ry are attached to L2-Z2.

In various embodiments, the one or more synthetic steps comprise
  converting the hydroxyl group bound to the carbon atom to which Rx and Ry are attached in the compound of formula (XXIII-2) to L2-Z2-, removing the RmRnCH— group to provide a hydroxyl group, and converting the hydroxyl group to L1-Z1; or
  converting the hydroxyl group bound to the carbon to which Rx and Ry are attached in the compound of formula (XXIII-2) to L1-Z1-, removing the RmRnCH— group to provide a hydroxyl group, and converting the hydroxyl group to L2-Z2-.

In various embodiments, converting said hydroxyl group to L1-Z1- or L2-Z2-comprises acylating so as to replace the hydrogen atom of the hydroxyl group with L1-C(O)— or L2-C(O)—.

In another aspect, the present invention broadly consists in a compound of the formula (XX):

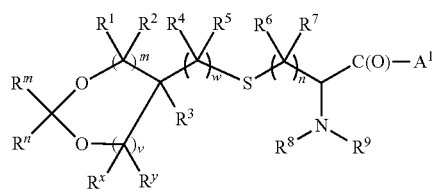

(XX)

wherein:
Rm and Rn are each independently hydrogen, C1-6alkyl, aryl, or heteroaryl;
m and w are each independently an integer from 0 to 7 and v is an integer from 0 to 5,
provided that:
the sum of m, v, and w is at least 3; and
the sum of m and w is from 0 to 7; and
n, Rx, Ry, R1, R2, R3, R4, R5, R6, R7, R8, R9, and A1 are as defined in the compound of formula (I) or any embodiment thereof; or a salt or solvate thereof.

In another aspect, the present invention broadly consists in the use of a compound of the formula (XX) or (XXI) in the synthesis of an amino acid- or peptide-conjugate of the formula (IA) of the present invention or a pharmaceutically acceptable salt or solvate thereof.

In another aspect, the present invention broadly consists in a method of making an amino acid- or peptide conjugate of the formula (I) or a pharmaceutically acceptable salt or solvate thereof of the present invention, the method comprising reacting
a first lipid-containing conjugation partner comprising a carbon-carbon double bond,
a second lipid-containing conjugation partner comprising a carbon-carbon double bond, and
an amino acid-comprising conjugation partner comprising a thiol under conditions effective to conjugate the first lipid-containing conjugation partner and the second lipid-containing conjugation partner to the amino acid-comprising conjugation partner and provide the amino acid or peptide-conjugate of formula (I) or salt or solvate thereof,
wherein in the amino acid- or peptide conjugate the sulfur atom from the thiol of the amino acid-comprising conjugation partner is conjugated to a carbon atom from the carbon-carbon double bond of the first lipid-containing conjugation partner, and a carbon atom from the carbon-carbon double bond of the first lipid-containing conjugation partner is conjugated to a carbon atom from the carbon-carbon double bond of the second lipid-containing conjugation partner.

In one embodiment, the amino acid-comprising conjugation partner is a peptide-containing conjugation partner, and the lipid-containing conjugation partners are coupled to the peptide of the peptide-containing conjugation partner.

In some embodiments, the lipid-containing conjugation partners are conjugated to the or an amino acid of the amino acid-comprising conjugation partner or the peptide of the peptide-containing conjugation partner.

In certain embodiments, the lipid-containing conjugation partners are conjugated to the or an amino acid of the amino acid-comprising conjugation partner.

Accordingly, in another aspect, the present invention broadly consists in a method of making a peptide conjugate of formula (I) or a pharmaceutically acceptable salt or solvate thereof of the present invention, the method comprising reacting
a first lipid-containing conjugation partner comprising a carbon-carbon double bond,
a second lipid-containing conjugation partner comprising a carbon-carbon double bond, and
peptide-containing conjugation partner comprising a thiol under conditions effective to conjugate the first lipid-containing conjugation partner and the second lipid-containing conjugation partner to the peptide-containing conjugation partner and provide the peptide conjugate of formula (I) or salt or solvate thereof,
wherein in the peptide conjugate the sulfur atom from the thiol of the peptide-containing conjugation partner is conjugated to a carbon atom from the carbon-carbon double bond of the first lipid-containing conjugation partner, and a carbon atom from the carbon-carbon double bond of the first lipid-containing conjugation partner is conjugated to a carbon atom from the carbon-carbon double bond of the second lipid-containing conjugation partner.

In various embodiment, the conjugate is a lipopeptide, such that the method is for making a lipopeptide.

In various embodiments, the first and second lipid-containing conjugation partners have the same structure (that is, the first and second lipid-containing conjugation partners are identical).

In various embodiments, the method comprises conjugating the sulfur atom of the thiol to a carbon atom of the carbon-carbon double bond of the first lipid containing conjugation partner and then conjugating a carbon atom from the carbon-carbon double bond to which the thiol is conjugated to a carbon atom of the carbon-carbon double bond of the second lipid-containing conjugation partner.

In various embodiments, the first lipid-containing conjugation partner is a compound of the formula (IIA):

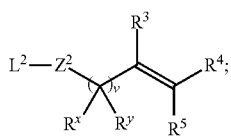

(IIA)

the second lipid-containing conjugation partner is a compound of the formula (IIB):

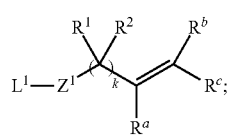

(IIB)

and
the amino acid-comprising conjugation partner comprises a structure of the formula (III):

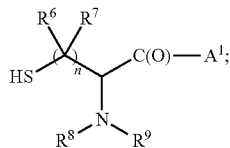
(III)

and
wherein Ra, Rb, Rc, L1, L2, Z1, Z2, R1, R2, Rx, Ry, R3, R4, R5, R6, R7, R8, R9, A1, k, v, and n are as defined in the compound of formula (I) or any embodiment thereof.

In various embodiments, the amino acid- or peptide conjugate is a compound of the formula (IB):

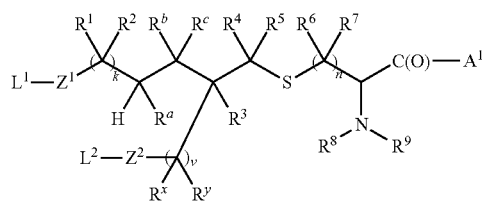
(IB)

wherein Ra, Rb, Rc, L1, L2, Z1, Z2, R1, R2, Rx, Ry, R3, R4, R5, R6, R7, R8, R9, A1, k, v, and n are as defined in the compound of formula (I) or any embodiment thereof.

In various embodiments, the lipid containing conjugation partners are in stoichiometric excess to the amino acid-comprising conjugation partner.

In various embodiments, the mole ratio of the lipid containing conjugation partners (combined) to amino acid-comprising conjugation partner is at least 7:1.

In various embodiments, the first lipid-containing conjugation partner is a compound of the formula (IIA-1):

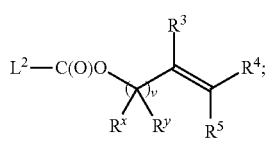
(IIA-1)

the second lipid-containing conjugation partner is a compound of the formula (IIB):

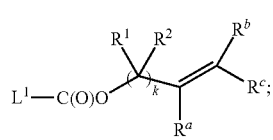
(IIB)

the amino acid-comprising conjugation partner comprises a structure of the

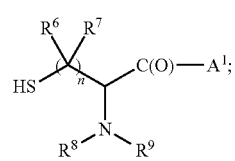
(III)

and
the conjugate is a compound of the formula (IC):

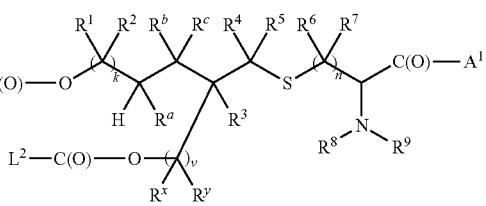
(IC)

wherein Ra, Rb, Rc, L1, L2, Z1, Z2, R1, R2, Rx, Ry, R3, R4, R5, R6, R7, R8, R9, A1, k, v, and n are as defined in the compound of formula (I) or any embodiment thereof.

In various embodiments, L1 is C11-21alkyl; k is 0-3, preferably 0; and Ra, Rb, and Rc are each hydrogen.

In various embodiments, L2 is C11-21alkyl; v is 0-3, preferably 0; and R3, R4, and R5 are each hydrogen.

In various embodiments, n is 1; R6, R7, and R8 are each hydrogen; and R9 is hydrogen, an amino protecting group, L3-C(O), or A2.

In various embodiments, n is 1; R6, R7, and R8 are each hydrogen; and R9 is hydrogen, an amino protecting group, or L3-C(O), wherein L3 is linear C15alkyl or methyl.

In various embodiments, the compounds of formula (IIA) and (IIB) are each vinyl palmitate.

In various embodiments, the amino-acid comprising conjugation partner is cysteine, a protected cysteine (including Na-amine and/or carboxyl protected cysteine), or a peptide comprising a cysteine residue (including an Na-amine or carboxyl protected cysteine residue), for example, an N-terminal cysteine residue (including an Na-amine protected cysteine residue).

In some embodiments, the method comprises reacting vinyl palmitate and an Na-amino protected cysteine, such as Fmoc-Cys-OH, Boc-Cys-OH, Fmoc-Cys-OP1, or Boc-Cys-OP1. In some embodiments, the carboxyl group of the Na-amino protected cysteine is protected.

In one embodiment, the conditions effective to conjugate the lipid-containing conjugation partners to the amino acid-comprising conjugation partner comprises the generation of one or more free radicals. In one embodiment, the conditions effective to conjugate the lipid-containing conjugation partners to the peptide-containing conjugation partner comprises the generation of one or more free radicals.

In some embodiments, the generation of one or more free radicals is initiated thermally and/or photochemically. In certain embodiments, the generation of one or more free radicals is initiated by the thermal and/or photochemical degradation of a free radical initiator. In exemplary embodiments, the generation of one or more free radicals is initiated by the thermal degradation of a thermal initiator or the photochemical degradation of a photochemical initiator.

In some embodiments, thermal degradation of the free radical initiator comprises heating the reaction mixture at a suitable temperature. In some embodiments, the reaction mixture is heated at a temperature is from about 40° C. to about 200° C., from about 50° C. to about 180° C., from about 60° C. to about 150° C., from about 65° C. to about 120° C., from about 70° C. to about 115° C., from about 75° C. to about 110° C., or from about 80° C. to about 100° C. In other embodiments, the reaction mixture is heated at a temperature of at least about 40° C., at least about 50° C., at least about 60° C., or at least about 65° C. In one specifically contemplated embodiment, the reaction mixture is heated at a temperature of about 90° C.

In some embodiments, photochemical degradation of the free radical initiator comprises irradiation with ultraviolet light, preferably having a frequency compatible with the side chains of naturally occurring amino acids. In a specifically contemplated embodiment, the ultraviolet light has a wavelength of about 365 nm. In exemplary embodiments, photochemical degradation of the free radical initiator is carried out at about ambient temperature.

In one specifically contemplated embodiment, the thermal initiator is 2,2'-azobisisobutyronitrile (AIBN). In one specifically contemplated embodiment, the photoinitiator is 2,2-dimethoxy-2-phenylacetophenone (DMPA).

In certain embodiments, the reaction is carried out in a liquid medium. In one embodiment, the liquid medium comprises a solvent. In one embodiment, the solvent is selected from the group consisting of N-methylpyrrolidone (NMP), dimethylsulfoxide (DMSO), N,N-dimethylformamide (DMF), dichloromethane (DCM), 1,2-dichloroethane, and mixtures thereof. In one specifically contemplated embodiment, the solvent comprises NMP, DMF, DMSO, or a mixture thereof.

In one specifically contemplated embodiment, the solvent comprises DMSO or NMP. In exemplary embodiments, the solvent comprises NMP.

In some embodiments, the reaction is carried out in the presence of one or more additives that inhibit the formation of by-products and/or that improve the yield of or conversion to the desired product compound of formula (I).

In various embodiments, the one or more additive is an extraneous thiol, an acid, an organosilane, or a combination of any two or more thereof.

In some exemplary embodiments, the extraneous or exogenous thiol is selected from the group consisting of reduced glutathione (GSH), 2,2'-(ethylenedioxy)diethanethiol (DODT), 1,4-dithiothreitol (DTT), protein, and sterically hindered thiols. In a specifically contemplated embodiment, the extraneous or exogenous thiol is DTT. In some embodiments, the extraneous or exogenous thiol is a sterically hindered thiol, for example tert-butyl mercaptan.

In various embodiments, the acid additive is a strong inorganic or organic acid. In various embodiments, the acid is a strong organic acid. In various embodiments, the acid is TFA.

In various embodiments, the organosilane is a trialkylsilane, for example TIPS.

In some embodiments, the one or more additive is selected from the group consisting of TFA, tert-butyl mercaptan, TIPS, and combinations of any two or more thereof.

In certain embodiments, the one or more additive is a combination of an acid and an extraneous thiol, for example TFA and tert-butyl mercaptan.

In other embodiments, the one or more additive is a combination of an acid and an organosilane, for example TFA and TIPS.

In other embodiments, the one or more additive is a combination of an extraneous thiol and an organosilane, and optionally an acid, for example a combination of t-BuSH and TIPS, and TFA.

In some embodiments, the reaction is carried out for a period of time from about 5 minutes to about 48 h, 5 minutes to about 24 h, from about 5 minutes to about 12 hours, from about 5 minutes to about 6 hours, from about 5 minutes to about 3 hours, 5 minutes to 2 hours, or form about 5 minutes to about 1 hour. In exemplary embodiments, the reaction is carried out for a period of time from about 5 minutes to about 1 h. In some embodiments, the reaction is carried out until one of the conjugation partners is at least about 70%, 80%, 90%, 95%, 97%, 99%, or 100% consumed.

In certain embodiments, the reaction is carried out under substantially oxygen free conditions.

In various embodiments, the amino acid-comprising conjugation partner is a peptide-containing conjugation partner.

In one embodiment, the amino acid-comprising conjugation partner comprises an epitope. In one embodiment, the peptide-containing conjugation partner comprises an epitope, such as a peptide epitope.

In one embodiment, the amino acid-comprising conjugation partner comprises two or more epitopes. In one embodiment, the peptide-containing conjugation partner comprises two or more epitopes.

In one embodiment, the amino acid-comprising conjugation partner consists of a peptide.

In one embodiment, the amino acid-comprising conjugation partner consists of a peptide comprising a peptide epitope. In one embodiment, the peptide-containing conjugation partner consists of a peptide. In one embodiment, the peptide-containing conjugation partner consists of a peptide comprising a peptide epitope.

In some embodiments, the amino acid-comprising conjugation partner comprises an epitope bound to the or an amino acid of the conjugation partner. In some embodiments, the peptide-containing conjugation partner comprises an epitope bound to the peptide of the peptide containing conjugation partner. In some embodiments, the epitope is bound to the peptide via linker group.

In some embodiments, the amino acid-comprising conjugation partner comprises a peptide epitope bound to the or an amino acid of the conjugation partner via a linker group. In some embodiments, the peptide-containing conjugation partner comprises a peptide epitope bound to the peptide via a linker group.

In some embodiments, the amino acid-comprising conjugation partner and/or the peptide-containing conjugation partner comprises an antigenic peptide.

In one embodiment, the amino acid-comprising conjugation partner and/or peptide conjugate comprises a synthetic peptide. In some embodiments, the synthetic peptide is a peptide prepared by a method comprising solid phase peptide synthesis (SPPS).

In various embodiments, the method comprises coupling the amino acid of the amino acid conjugate or an amino acid of the peptide conjugate to an amino acid or an amino acid of a peptide to provide a peptide conjugate.

In various embodiments, the method comprises coupling the amino acid of the amino acid conjugate to an amino acid or an amino acid of a peptide to provide a peptide conjugate.

In various embodiments, the peptide comprises an epitope. In various embodiments, the epitope is a peptide epitope.

In some embodiments, the method further comprises coupling the amino acid of the amino acid conjugate to an amino acid or a peptide to provide a peptide conjugate.

In some embodiments, coupling a peptide comprises individually coupling one or more amino acids and/or one or more peptides.

In some embodiments, the method further comprises coupling the amino acid of the amino acid conjugate or an amino acid of the peptide conjugate to an amino acid or a peptide so as to provide a peptide conjugate comprising a linker group or one or more amino acids thereof.

In some embodiments, the method further comprises coupling an amino acid of the peptide conjugate comprising a linker group or one or more amino acids thereof to an amino acid or a peptide so as to provide a peptide conjugate comprising a peptide epitope bound to the amino acid to which lipid moieties are conjugated via a linker group.

In some embodiments, the amino acid of the peptide conjugate to which the lipid moeities are conjugated is an N-terminal amino acid residue.

In some embodiments, the method further comprises coupling the amino acid of the amino acid conjugate or an amino acid of the peptide conjugate to an amino acid or a peptide so as to provide a peptide conjugate comprising a peptide epitope.

In some embodiments, the method further comprises coupling an epitope to the amino acid of the amino acid conjugate or an amino acid of the peptide conjugate.

In some embodiments, the method further comprises coupling a peptide epitope to the amino acid of the amino acid conjugate or an amino acid of the peptide conjugate.

In some embodiments, the epitope is coupled or bound via a linker group.

In some embodiments, the method further comprises coupling an epitope to the peptide of the peptide conjugate.

In some embodiments, the method further comprises coupling a peptide epitope to the peptide of the peptide conjugate.

In some embodiments, the epitope is bound to the peptide via a linker group.

In various embodiments, the amino acid-comprising conjugation partner consists of an amino acid, for example cysteine (including Na-amino and/or C-terminus protected cysteines).

In various embodiments, the C-terminus of the amino acid comprising conjugation partner is protected with a protecting group and/or the Na-amino group of the amino acid comprising conjugation partner is protected with a protecting group.

In various embodiments, the carboxyl group of the C-terminus of the amino acid is protected with a carboxyl protecting group or a carboxamide protecting group and/or the Na-amino group of the amino acid is protected with an amino protecting group.

In various embodiments, the carboxyl group of the C-terminus of the amino acid is protected with a carboxyl protecting group and/or the Na-amino group of the amino acid is protected with an amino protecting group.

In some embodiments, the carboxyl group of the C-terminus of the peptide is protected with a carboxyl protecting group and/or the Na-amino group of the peptide is protected with an amino protecting group.

In some embodiments, the amino acid residue comprising the thiol is a terminal amino acid residue. In some embodiments, the amino acid residue comprising the thiol is an N-terminal residue.

In some embodiments, A1 and/or R9 is a group other than an amino acid or a peptide, and the method comprises coupling an amino acid or a peptide so as to replace A1 and/or R9 with the amino acid or peptide.

In some embodiments, A1 a group other than an amino acid or a peptide, and the method comprises coupling an amino acid or a peptide so as to replace A1 with the amino acid or peptide.

In some embodiments, A1 is a OH, OP1, NH$_2$, or NHP2 and/or R9 is hydrogen, an amino protecting group or L3-C(O), and the method comprises coupling an amino acid or a peptide so as to replace A1 and/or R9 with the amino acid or peptide.

In some embodiments, A1 is a OH, OP1, NH$_2$, or NHP2 and R9 is hydrogen, an amino protecting group or L3-C(O) and the method further comprises coupling an amino acid or a peptide so as to replace A1 and/or R9 with the amino acid or peptide.

In some embodiments, coupling a peptide comprises individually coupling one or more amino acids and/or one or more peptides.

In some embodiments, coupling the amino acid or peptide provides a peptide conjugate comprising a peptide epitope. In some embodiments, the coupling the amino acid or peptide provides a peptide conjugate comprising a linker group or one or more amino acids thereof. In some embodiments, coupling the amino acid or peptide provides a peptide conjugate comprising a peptide epitope bound to the amino acid to which the lipid moieties are conjugated via a linker group.

In some embodiments, the Na-amino group of the amino acid comprising the thiol to which the lipid moieties are conjugated is acylated. In some embodiments, R9 in the amino acid comprising conjugation partner comprising the thiol is L3-C(O)—.

In certain embodiments, the method further comprises acylating the Na-amino group of the amino acid of the amino acid conjugate or the amino acid residue of the peptide conjugate to which the lipid moieties are conjugated. In certain embodiments, the method further comprises acylating the Na-amino group with a C2-20 fatty acid, such as acetyl.

In some embodiments, R9 is hydrogen or an amino protecting group, and the method further comprises acylating the amino acid conjugate or peptide conjugate so as to replace the hydrogen or amino protecting group at R9 with L3-C(O).

In some embodiments, acylating the amino acid conjugate or peptide conjugate so as to replace the amino protecting group at R9 with L3-C(O) comprises removing the amino protecting group at R9 to provide a hydrogen at R9.

In certain embodiments, the or an amino acid of the amino acid-comprising conjugation partner comprises the thiol. In certain embodiments, an amino acid residue of the peptide of the peptide-containing conjugation partner comprises the thiol.

In certain embodiments, the thiol is the thiol of a cysteine residue.

In certain embodiments, the cysteine residue is a terminal residue. In certain embodiments, the cysteine residue is an N-terminal residue.

In some embodiments, the amino group of the cysteine residue is acylated.

In one embodiment, the amino group is acylated with a C2-20 fatty acid.

In one exemplary embodiment, the C2-20 fatty acid is acetyl or palmitoyl. In another exemplary embodiment, the C2-20 fatty acid is acetyl.

In some embodiments, the amino acid-comprising conjugation partner and/or peptide conjugate comprises from 8 to 220, 8 to 200, 8 to 175, 8 to 150, 8 to 125, 8 to 100, 8 to 90, 8 to 80, 8 to 70, 8 to 60, 8 to 50, 8 to 40, 8 to 30, 8 to 25, 8 to 20, or 8 to 15 amino acids. In some embodiments, the peptide-containing conjugation partner comprises from 8 to 220, 8 to 200, 8 to 175, 8 to 150, 8 to 125, 8 to 100, 8 to 90, 8 to 80, 8 to 70, 8 to 60, 8 to 50, 8 to 40, 8 to 30, 8 to 25, 8 to 20, or 8 to 15 amino acids.

In one exemplary embodiment, the amino acid-comprising conjugation partner and/or peptide conjugate comprises a peptide comprising from 8 to 60 amino acids. In one exemplary embodiment, the peptide comprises from 8 to 60 amino acids.

In other embodiments, the amino acid-comprising conjugation partner and/or peptide conjugate comprises from 5 to 220, 8 to 220, 5 to 175, 8 to 175, 8 to 150, 10 to 150, 15 to 125, 20 to 100, 20 to 80, 20 to 60, 25 to 100, 25 to 80, 25 to 60, 30 to 80, 40 to 60, or 50 to 60 amino acids. In other embodiments, the peptide-containing conjugation partner comprises from 5 to 220, 8 to 220, 5 to 175, 8 to 175, 8 to 150, 10 to 150, 15 to 125, 20 to 100, 20 to 80, 20 to 60, 25 to 100, 25 to 80, 25 to 60, 30 to 80, 40 to 60, or 50 to 60 amino acids.

In other embodiments, the amino acid comprising conjugation partner and/or peptide conjugate comprises from 5 to 150, 5 to 125, 5 to 100, 5 to 75, 5 to 60, 5 to 50, 5 to 40, 5 to 30, 5 to 25, 5 to 20, 8 to 150, 8 to 125, 8 to 100, 8 to 75, 8 to 60, 8 to 50, 8 to 40, 8 to 30, 8 to 25, or 8 to 20 amino acids. In other embodiments, the peptide-containing conjugation partner comprises from 5 to 150, 5 to 125, 5 to 100, 5 to 75, 5 to 60, 5 to 50, 5 to 40, 5 to 30, 5 to 25, 5 to 20, 8 to 150, 8 to 125, 8 to 100, 8 to 75, 8 to 60, 8 to 50, 8 to 40, 8 to 30, 8 to 25, or 8 to 20 amino acids.

In various embodiments, the amino acid comprising conjugation partner is a short peptide. In some embodiments, the short peptide comprises less than 10, 9, 8, 7, 6, 5, 4, or 3 amino acids.

In one embodiment, the amino acid-comprising conjugation partner and/or peptide conjugate comprises one or more solubilising groups. In one embodiment, the peptide-containing conjugation partner comprises one or more solubilising groups.

In certain embodiments, the solubilising group is an amino acid sequence comprising two or more hydrophilic amino acid residues in the peptide chain. In certain embodiments, the solubilising group is an amino acid sequence comprising a sequence of two or more consecutive hydrophilic amino acid residues in the peptide chain. In one embodiment, the hydrophilic amino acid residues are cationic amino acid residues. In one embodiment, the cationic amino acid residues are arginine or lysine residues. In one specifically contemplated embodiment, the cationic amino acid residues are lysine residues. In one embodiment, the sequence comprises from 2 to 20, 2 to 15, 2 to 10, 3 to 7, or 3 to 5 amino acids. In one embodiment, the solubilising group is a tri-, tetra-, penta-, hexa-, or hepta-lysine sequence. In one specifically contemplated embodiment, the solubilising group is a tetralysine sequence.

In some embodiments, the peptide conjugate and/or amino-acid comprising conjugation partner comprises a serine residue adjacent to the amino acid residue to which the lipid moieties are conjugated. In a specifically contemplated embodiment, the peptide of the peptide-containing conjugation partner comprises a serine residue adjacent to the amino acid residue to which the lipid moieties are conjugated. In an exemplary embodiment, the amino acid residue to which the lipid moieties are conjugated is N-terminal. In a specifically contemplated embodiment, the peptide further comprises a consecutive sequence of two or more hydrophilic amino acid residues adjacent to the serine residue.

In certain embodiments, the peptide conjugate and/or amino-acid comprising conjugation partner comprises a consecutive sequence of two or more hydrophilic amino acid residues adjacent to the serine residue.

In certain embodiments, the peptide conjugate and/or amino acid-comprising conjugation partner comprises only naturally occurring amino acids. In certain embodiments, the peptide-containing conjugation partner comprises only naturally occurring amino acids. In other embodiments, 75% or more, 80% or more, 85% or more, 90% or more, 95% or more, 97% or more, or 99% or more of the amino acid residues in the peptide are naturally occurring amino acids.

In other embodiments, 75% or more, 80% or more, 85% or more, 90% or more, 95% or more, 97% or more, or 99% or more of the amino acid residues in the peptide conjugate and/or amino acid-comprising conjugation partner are naturally occurring amino acids.

In exemplary embodiments, the peptide conjugate and/or amino acid-comprising conjugation partner comprises a peptide comprising a peptide epitope. In exemplary embodiments, the peptide of the peptide-containing conjugation partner comprises one or more peptide epitopes.

In various embodiments, the peptide comprises, consists essentially of, or consists of one or more EBV LMP2 epitopes. In various embodiments, the one or more EBV LMP2 epitopes are MHCI epitopes. In various embodiments, the peptide comprises one or more EBV LMP2 epitopes selected from the group consisting of any one of SEQ ID NOs 76-101. In various embodiments, the peptide comprises a peptide comprising or consisting of 12 or more contiguous amino acids from the amino acid sequence of any one of SEQ ID NOs 1-75. In various embodiments, the peptide comprises a peptide comprising or consisting of 15 or more contiguous amino acids from the amino acid sequence of any one of SEQ ID NOs 1-75, or comprising or consisting of 20 or more contiguous amino acids from the amino acid sequence of any one of SEQ ID NOs 1-75.

In various embodiments, the peptide comprises a recombinant peptide comprising or consisting of 12 or more contiguous amino acids from the amino acid sequence of any one of SEQ ID NOs 1-75. In various embodiments, the recombinant peptide comprises or consists of 15 or more contiguous amino acids from the amino acid sequence of any one of SEQ ID NOs 1-75, or comprises or consists of 20 or more contiguous amino acids from the amino acid sequence of any one of SEQ ID NOs 1-75.

In one exemplary embodiment, the peptide epitope is derived from NY-ESO-1. In one specifically contemplated embodiment, the peptide comprises, consists essentially of, or consists of an amino acid sequence selected from the group consisting of 8 or more contiguous amino acid residues from any one of SEQ ID NO: 106, 107, 108, 113, 114, 119, 120, and 121.

In various embodiments, the peptide comprises, consists essentially of, or consists of one or more NY-ESO-1 epitopes. In various embodiments, the one or more NY-ESO-1 epitopes are MHCI epitopes. In various embodiments, the the peptide comprises, consists essentially of, or consists of an amino acid sequence selected from the group consisting of 8 or more contiguous amino acid residues from any one of SEQ ID NO: 106, 107, 108, 113, 114, 119, 120, and 121. In various embodiments, the peptide comprises a peptide comprising or consisting of 12 or more contiguous amino acids from the amino acid sequence of any one of SEQ ID NO: 106, 107, 108, 113, 114, 119, 120, and 121. In various embodiments, the peptide comprises a peptide comprising or consisting of 15 or more contiguous amino acids from the amino acid sequence of any one of SEQ ID NO: 106, 107, 108, 113, 114, 119, 120, and 121, or comprising or consisting of 20 or more contiguous amino acids from the amino acid sequence of any one of SEQ ID NO: 106, 107, 108, 113, 114, 119, 120, and 121.

In one specifically contemplated embodiment, the reactive functional groups of the amino acids of the peptide-containing conjugation partner are unprotected.

In certain embodiments, one or more reactive functional groups of one or more amino acids of the peptide conjugate are unprotected.

In certain embodiments, one or more reactive functional groups of the amino acid of the amino acid conjugate are unprotected.

In certain embodiments, one or more reactive functional groups of one or more amino acids of the amino acid-comprising conjugation partner are unprotected.

In certain embodiments, the amino acid-comprising conjugation partner comprises a peptide, wherein the reactive functional groups of the side chains of the amino acids of the peptide are unprotected, with the exception of any thiols other than the thiol to be reacted.

In certain specifically contemplated embodiments, the reactive functional groups of the amino acids of the peptide of the peptide-containing conjugation partner are unprotected.

In certain specifically contemplated embodiments, the reactive functional groups of the amino acids of the peptide of the peptide-containing conjugation partner are unprotected, with the exception of any thiols other than the thiol to be reacted.

Those skilled in the art will appreciate that the peptide of the peptide conjugate and/or peptide-containing conjugation partner may, as described herein, be optionally substituted, modified, or bound to various other moieties as described herein to provide the peptide conjugate and/or peptide containing conjugation partner.

In some embodiments, the method comprises
synthesising the amino acid sequence of a peptide by solid phase peptide synthesis (SPPS);
coupling the amino acid of an amino acid conjugate or an amino acid of a peptide conjugate to the solid phase bound peptide by SPPS so as to provide a peptide conjugate comprising a peptide epitope, a peptide conjugate comprising a linker group or one or more amino acids thereof, or a peptide conjugate comprising a peptide epitope bound to the amino acid to which lipid moeities are conjugated via a linker group.

In some embodiments, the method comprises
reacting the lipid-containing conjugation partners and an amino acid-comprising conjugation partner to provide an amino acid or peptide conjugate;
synthesising the amino acid sequence of a peptide by solid phase peptide synthesis (SPPS);
coupling the amino acid of the amino acid conjugate or an amino acid of the peptide conjugate to the solid phase bound peptide by SPPS so as to provide a peptide conjugate comprising a peptide epitope, a peptide conjugate comprising a linker group or one or more amino acids thereof, or a peptide conjugate comprising a peptide epitope bound to the amino acid to which lipid moeities are conjugated via a linker group.

In some embodiments, the method further comprises acylating the Nα-amino group of the amino acid of the amino acid conjugate or the amino acid to which the lipid-moieties are conjugated of any one of the peptide conjugates.

In some embodiments, the method comprises cleaving the peptide conjugate from the solid phase support.

In some embodiments, the method comprises
synthesising the amino acid sequence of the peptide of the peptide-containing conjugation partner by solid phase peptide synthesis (SPPS); and
reacting the lipid-containing conjugation partners and peptide-containing conjugation partner in accordance with any of the embodiments described herein.

In exemplary embodiments, the method comprises
synthesising the amino acid sequence of the peptide of the peptide-containing conjugation partner by SPPS,
cleaving the peptide from the solid phase support; and
reacting the lipid-containing conjugation partners and peptide-containing conjugation partner in accordance with any of the embodiments described herein.

In one embodiment, the peptide-containing conjugation partner is not purified prior to reaction with the lipid-containing conjugation partners.

In some embodiments, one or more protecting groups are removed on cleaving the peptide from the solid phase support. In certain embodiments, all of the protecting groups present in the peptide are removed.

In one embodiment, the SPPS is Fmoc-SPPS.

In some embodiments, the amino acid residue in the peptide of the peptide-containing conjugation partner bearing the thiol to be reacted is an N-terminal amino acid residue and the method comprises acylating the N-terminal amino group prior to cleaving the peptide from the solid phase. In specifically contemplated embodiments, the N-terminal residue is a cysteine residue.

In one embodiment, the method further comprises separating the peptide conjugate from the reaction medium and optionally purifying the peptide conjugate.

In another aspect, the present invention broadly consists in a method of making a peptide conjugate, the method comprising
providing an amino acid- or peptide conjugate of the formula (I) of the present invention or a salt or solvate thereof, and
coupling the amino acid of the amino acid conjugate or an amino acid of the peptide conjugate to an amino acid or an amino acid of a peptide to provide a peptide conjugate.

In various embodiments, the product peptide conjugate is a compound of the formula (I) or a pharmaceutically acceptable salt thereof of the present invention.

In various embodiments, the amino acid of the amino acid conjugate is coupled under conditions that reduce epimerisation at the α-carbon of the amino acid. In various embodiments, the conditions are such that less than about 35, 30, 25, 20, 15, 10, 5, 3, 2, or 1% by mol of the amino acid is epimerised. In various embodiments, the conditions that reduce epimerisation comprise the use of PyBOP as the coupling reagent.

In various embodiments, the conditions comprise the use of PyBOP and 2,4,6-trimethylpyridine.

In another aspect, the present invention broadly consists in use of an amino acid- or peptide-conjugate of the formula (I) of the present invention or a salt or solvate thereof in the synthesis of an immunogenic peptide-conjugate.

In various embodiments, the immunogenic peptide conjugate is a compound of the formula (I) of the present invention or a pharmaceutically acceptable salt thereof.

In another aspect, the present invention broadly consists in an amino acid-conjugate or peptide conjugate of the present invention produced by a method of the present invention.

In another aspect, the present invention broadly consists in a peptide conjugate made by a method of the present invention.

In another aspect, the present invention broadly consists in a composition comprising an amino acid- or peptide conjugate of formula (I) of the present invention or a salt or solvate thereof.

In various embodiments, the composition comprises isolated, pure, purified or substantially purified compound of formula (I) or a salt or solvate thereof.

In various embodiments, the composition comprises at least about 60, 70, 75, 80, 85, 90, 95, 97, 98, or 99% by weight compound of formula (I) or a salt or solvate thereof.

In various embodiments, the composition is free of substantially free of amino acid- or peptide containing compounds other than compounds of formula (I).

In another aspect, the present invention broadly consists in a pharmaceutical composition comprising an effective amount of a peptide conjugate compound of the formula (I) of the present invention or a pharmaceutically acceptable salt or solvate thereof, and a pharmaceutically acceptable carrier.

In various embodiments, the pharmaceutical composition of claim comprises an effective amount of two or more peptide conjugate compounds of the formula (I) of the present invention.

In one embodiment, the pharmaceutical composition is an immunogenic composition.

In one embodiment, the pharmaceutical composition does not include an extrinsic adjuvant.

In some embodiments, the pharmaceutical composition is a vaccine.

In one embodiment, the pharmaceutical composition comprises an effective amount of two or more peptide conjugates of the present invention, for example the pharmaceutical composition comprises an effective amount of three or more peptide conjugates of the present invention.

In one embodiment, the pharmaceutical composition comprises an effective amount of one or more peptide conjugates of the present invention together with one or more peptides described herein, or any combination thereof. For example, the pharmaceutical composition comprises an effective amount of two or more peptide conjugates of the present invention and one or more peptides described herein, or an effective amount of one or more peptide conjugates of the present invention and two or more peptides described herein.

In another aspect, the present invention broadly consists in a method of vaccinating or eliciting an immune response in a subject comprising administering to the subject an effective amount of one or more peptide conjugate compounds of the formula (I) of the invention or a pharmaceutically acceptable salt or solvate thereof, or an effective amount of a pharmaceutical composition of of the present invention.

In another aspect, the present invention broadly consists in use of one or more peptide conjugate compounds of formula (I) of the present invention or a pharmaceutically acceptable salt or solvate thereof or a pharmaceutical composition of the present invention in the manufacture of a medicament for vaccinating or eliciting an immune response in a subject.

In another aspect, the present invention broadly consists in one or more peptide conjugate compounds of the formula (I) of the present invention or a pharmaceutically acceptable salt or solvate thereof or a pharmaceutical composition of the present invention for vaccinating or eliciting an immune response in a subject.

In another aspect, the present invention broadly consists in use of one or more peptide conjugate compounds of the formula (I) of the invention or a pharmaceutically acceptable salt or solvate thereof or a pharmaceutical composition of the present invention for vaccinating or eliciting an immune response in a subject.

In various embodiments, the method, use, one or more compounds, or pharmaceutical composition is for eliciting an immune response in a subject.

In various embodiments, the method, use, one or more compounds, or pharmaceutical composition is for vaccinating a subject.

In some embodiments, the method comprises the administration of one or more peptides described herein and one or more peptide conjugates of the present invention or two or more peptide conjugates of the present invention, for example one or more peptides in combination with one or more peptide conjugates to the subject.

In some embodiments, one or more peptides described herein and one or more peptide conjugates of the present invention or two or more peptide conjugates of the present invention, for example one or more peptides in combination with one or more peptide conjugates, are used for vaccinating or eliciting an immune response in the subject or in the manufacture of a medicament for vaccinating or eliciting an immune response in the subject.

In some embodiment, two or more peptide conjugates are used or administered.

In some embodiments the two or more peptide conjugates, or one or more peptides and one or more peptide conjugates are used or administered simultaneously, sequentially, or separately.

Asymmetric centers may exist in the compounds described herein. The asymmetric centers may be designated as (R) or (S), depending on the configuration of substituents in three dimensional space at the chiral carbon atom. All stereochemical isomeric forms of the compounds, including diastereomeric, enantiomeric, and epimeric forms, as well as d-isomers and l-isomers, and mixtures thereof, including enantiomerically enriched and diastereomerically enriched mixtures of stereochemical isomers, are within the scope of the invention.

Individual enantiomers can be prepared synthetically from commercially available enantiopure starting materials or by preparing enantiomeric mixtures and resolving the mixture into individual enantiomers. Resolution methods include conversion of the enantiomeric mixture into a mixture of diastereomers and separation of the diastereomers by, for example, recrystallization or chromatography, and any other appropriate methods known in the art. Starting materials of defined stereochemistry may be commercially available or made and, if necessary, resolved by techniques well known in the art.

The compounds described herein may also exist as conformational or geometric isomers, including cis, trans, syn, anti, entgegen (E), and zusammen (Z) isomers. All such isomers and any mixtures thereof are within the scope of the invention.

Also within the scope of the invention are any tautomeric isomers or mixtures thereof of the compounds described. As would be appreciated by those skilled in the art, a wide variety of functional groups and other structures may exhibit tautomerism. Examples include, but are not limited to, keto/enol, imine/enamine, and thioketone/enethiol tautomerism.

The compounds described herein may also exist as isotopologues and isotopomers, wherein one or more atoms in the compounds are replaced with different isotopes. Suitable isotopes include, for example, $^1H$, $^2H$ (D), $^3H$ (T), $^{12}C$, $^{13}C$, $^{14}C$, $^{16}O$, and $^{18}O$. Procedures for incorporating such isotopes into the compounds described herein will be apparent to those skilled in the art. Isotopologues and isotopomers of the compounds described herein are also within the scope of the invention.

Also within the scope of the invention are salts of the compounds described herein, including pharmaceutically acceptable salts. Such salts include, acid addition salts, base addition salts, and quaternary salts of basic nitrogen-containing groups.

Acid addition salts can be prepared by reacting compounds, in free base form, with inorganic or organic acids. Examples of inorganic acids include, but are not limited to, hydrochloric, hydrobromic, nitric, sulfuric, and phosphoric acid. Examples of organic acids include, but are not limited to, acetic, trifluoroacetic, propionic, succinic, glycolic, lactic, malic, tartaric, citric, ascorbic, maleic, fumaric, pyruvic, aspartic, glutamic, stearic, salicylic, methanesulfonic, benzenesulfonic, isethionic, sulfanilic, adipic, butyric, and pivalic.

Base addition salts can be prepared by reacting compounds, in free acid form, with inorganic or organic bases. Examples of inorganic base addition salts include alkali metal salts, alkaline earth metal salts, and other physiologically acceptable metal salts, for example, aluminium, calcium, lithium, magnesium, potassium, sodium, or zinc salts. Examples of organic base addition salts include amine salts, for example, salts of trimethylamine, diethylamine, ethanolamine, diethanolamine, and ethylenediamine.

Quaternary salts of basic nitrogen-containing groups in the compounds may be may be prepared by, for example, reacting the compounds with alkyl halides such as methyl, ethyl, propyl, and butyl chlorides, bromides, and iodides, dialkyl sulfates such as dimethyl, diethyl, dibutyl, and diamyl sulfates, and the like.

The compounds described herein may form or exist as solvates with various solvents. If the solvent is water, the solvate may be referred to as a hydrate, for example, a mono-hydrate, a di-hydrate, or a tri-hydrate. All solvated forms and unsolvated forms of the compounds described herein are within the scope of the invention.

The general chemical terms used in the formulae herein have their usual meaning.

The term "aliphatic" is intended to include saturated and unsaturated, nonaromatic, straight chain, branched, acyclic, and cyclic hydrocarbons. Those skilled in the art will appreciate that aliphatic groups include, for example, alkyl, alkenyl, alkynyl, cycloalkyl, and cycloalkenyl groups, and hybrids thereof such as (cycloalkyl)alkyl, (cycloalkenyl) alkyl and (cycloalkyl)alkenyl groups. In various embodiments, aliphatic groups comprise from 1-12, 1-8, 1-6, or 1-4 carbon atoms. In some embodiments, aliphatic groups comprise 5-21, from 9-21, or from 11-21 carbon atoms, such as from 11, 13, 15, 17, or 19 carbon atoms. In some embodiments, the aliphatic group is saturated.

The term "heteroaliphatic" is intended to include aliphatic groups, wherein one or more chain and/or ring carbon atoms are independently replaced with a heteroatom, preferably a heteroatom selected from oxygen, nitrogen and sulfur. In some embodiments, the heteroaliphatic is saturated. Examples of heteroaliphatic groups include linear or branched, heteroalkyl, heteroalkenyl, and heteroalkynyl groups.

The term "alkyl" is intended to include saturated straight chain and branched chain hydrocarbon groups. In some embodiments, alkyl groups have from 1 to 12, 1 to 10, 1 to 8, 1 to 6, or from 1 to 4 carbon atoms. In some embodiments, alkyl groups have from 5-21, from 9-21, or from 11-21 carbon atoms, such as from 11, 13, 15, 17, or 19 carbon atoms. Examples of straight chain alkyl groups include, but are not limited to, methyl, ethyl, n-propyl, n-butyl, n-pentyl, n-hexyl, n-heptyl, and n-octyl. Examples of branched alkyl groups include, but are not limited to, isopropyl, iso-butyl, sec-butyl, tert-butyl, neopentyl, isopentyl, and 2,2-dimethylpropyl.

The term "alkenyl" is intended to include straight and branched chain alkyl groups having at least one double bond between two carbon atoms. In some embodiments, alkenyl groups have from 2 to 12, from 2 to 10, from 2 to 8, from 2 to 6, or from 2 to 4 carbon atoms. In some embodiments, alkenyl groups have from 5-21, from 9-21, or from 11-21 carbon atoms, such as from 11, 13, 15, 17, or 19 carbon atoms. In some embodiments, alkenyl groups have one, two, or three carbon-carbon double bonds. Examples of alkenyl groups include, but are not limited to, vinyl, allyl, —CH═CH(CH$_3$), —CH═C(CH$_3$)$_2$, —C(CH$_3$)═CH$_2$, and —C(CH$_3$)═CH(CH$_3$).

The term "alkynyl" is intended to include straight and branched chain alkyl groups having at least one triple bond between two carbon atoms. In some embodiments, the alkynyl group have from 2 to 12, from 2 to 10, from 2 to 8, from 2 to 6, or from 2 to 4 carbon atoms. In some embodiments, alkynyl groups have one, two, or three carbon-carbon triple bonds. Examples include, but are not limited to, —C≡CH, —C≡CH$_3$, —CH$_2$C≡CH$_3$, and —C≡CH$_2$CH(CH$_2$CH$_3$)$_2$.

The term "heteroalkyl" is intended to include alkyl groups, wherein one or more chain carbon atoms are replaced with a heteroatom, preferably a heteroatom selected from the group consisting of oxygen, nitrogen, and sulfur. In some embodiments, the heteroalkyl is saturated. Heteroalkyl groups include, for example, polyethylene glycol groups and polyethylene glycol ether groups, and the like.

The term "cycloalkyl" is intended to include mono-, bi- or tricyclic alkyl groups. In some embodiments, cycloalkyl groups have from 3 to 12, from 3 to 10, from 3 to 8, from 3 to 6, from 3 to 5 carbon atoms in the ring(s). In some embodiments, cycloalkyl groups have 5 or 6 ring carbon atoms. Examples of monocyclic cycloalkyl groups include, but are not limited to, cyclopropyl, cyclobutyl, cyclopentyl, cyclohexyl, cycloheptyl, and cyclooctyl. In some embodiments, the cycloalkyl group has from 3 to 8, from 3 to 7, from 3 to 6, from 4 to 6, from 3 to 5, or from 4 to 5 ring carbon atoms. Bi— and tricyclic ring systems include bridged, spiro, and fused cycloalkyl ring systems. Examples of bi- and tricyclic ring cycloalkyl systems include, but are not limited to, bicyclo[2.1.1]hexanyl, bicyclo[2.2.1]heptanyl, adamantyl, and decalinyl.

The term "cycloalkenyl" is intended to include non-aromatic cycloalkyl groups having at least one double bond between two carbon atoms. In some embodiments, cycloalkenyl groups have one, two or three double bonds. In some embodiments, cycloalkenyl groups have from 4 to 14, from 5 to 14, from 5 to 10, from 5 to 8, or from 5 to 6 carbon atoms in the ring(s). In some embodiments, cycloalkenyl groups have 5, 6, 7, or 8 ring carbon atoms. Examples of cycloalkenyl groups include cyclohexenyl, cyclopentenyl, cyclohexadienyl, butadienyl, pentadienyl, and hexadienyl.

The term "aryl" is intended to include cyclic aromatic hydrocarbon groups that do not contain any ring heteroatoms. Aryl groups include monocyclic, bicyclic and tricyclic ring systems. Examples of aryl groups include, but are not limited to, phenyl, azulenyl, heptalenyl, biphenyl, fluorenyl, phenanthrenyl, anthracenyl, indenyl, indanyl, pentalenyl, and naphthyl. In some embodiments, aryl groups have from 6 to 14, from 6 to 12, or from 6 to 10 carbon atoms in the ring(s). In some embodiments, the aryl groups are phenyl or naphthyl. Aryl groups include aromatic-aliphatic fused ring systems. Examples include, but are not limited to, indanyl and tetrahydronaphthyl.

The term "heterocyclyl" is intended to include non-aromatic ring systems containing 3 or more ring atoms, of which one or more is a heteroatom. In some embodiments, the heteroatom is nitrogen, oxygen, or sulfur. In some embodiments, the heterocyclyl group contains one, two, three, or four heteroatoms. In some embodiments, heterocyclyl groups include mono-, bi- and tricyclic rings having from 3 to 16, from 3 to 14, from 3 to 12, from 3 to 10, from 3 to 8, or from 3 to 6 ring atoms. Heterocyclyl groups include partially unsaturated and saturated ring systems, for example, imidazolinyl and imidazolidinyl. Heterocyclyl groups include fused and bridged ring systems containing a heteroatom, for example, quinuclidyl. Heterocyclyl groups include, but are not limited to, aziridinyl, azetidinyl, azepanyl, diazepanyl, 1,3-dioxanyl, 1,3-dioxolanyl, isoxazolidinyl, morpholinyl, piperazinyl, piperidinyl, pyranyl, pyrazolidinyl, pyrrolinyl, pyrrolidinyl, tetra hydrofuranyl, tetrahydrothienyl, thiadiazolidinyl, and trithianyl.

The term "heteroaryl" is intended to include aromatic ring systems containing 5 or more ring atoms, of which, one or more is a heteroatom. In some embodiments, the heteroatom is nitrogen, oxygen, or sulfur. In some embodiments, heteroaryl groups include mono-, bi- and tricyclic ring systems having from 5 to 16, from 5 to 14, from 5 to 12, from 5 to 10, from 5 to 8, or from 5 to 6 ring atoms. Heteroaryl groups include, but are not limited to, pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, pyrazolopyridinyl, triazolopyridinyl, benzotriazolyl, benzoxazolyl, benzothiazolyl, imidazopyridinyl, isoxazolopyridinylxanthinyl, guaninyl, quinolinyl, isoquinolinyl, tetrahydroquinolinyl, quinoxalinyl, and quinazolinyl. Heteroaryl groups include fused ring systems in which all of the rings are aromatic, for example, indolyl, and fused ring systems in which only one of the rings is aromatic, for example, 2,3-dihydroindolyl.

The term "halo" or "halogen" is intended to include F, Cl, Br, and I.

The term "heteroatom" is intended to include oxygen, nitrogen, sulfur, or phosphorus. In some embodiments, the heteroatom is selected from the group consisting of oxygen, nitrogen, and sulfur.

As used herein, the term "substituted" is intended to mean that one or more hydrogen atoms in the group indicated is replaced with one or more independently selected suitable substituents, provided that the normal valency of each atom to which the substituent/s are attached is not exceeded, and that the substitution results in a stable compound. In various embodiments, optional substituents in the compounds described herein include but are not limited to halo, CN, $NO_2$, OH, $NH_2$, NHR10, NR10R20, C1-6haloalkyl, C1-6haloalkoxy, $C(O)NH_2$, C(O)NHR10, C(O)NR10R20, $SO_2R10$, OR10, SR10, S(O)R10, C(O)R10, and C1-6aliphatic; wherein R10 and R20 are each independently C1-6aliphatic, for example C1-6alkyl.

The term "carboxyl protecting group" as used herein is means a group that is capable of readily removed to provide the OH group of a carboxyl group and protects the carboxyl group against undesirable reaction during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504. Examples include, but are not limited to, alkyl and silyl groups, for example methyl, ethyl, tert-butyl, methoxymethyl, 2,2,2-trichloroethyl, benzyl, diphenylmethyl, trimethylsilyl, and tert-butyldimethylsilyl, and the like.

The term "amine protecting group" as used herein means a group that is capable of being readily removed to provide the $NH_2$ group of an amine group and protects the amine group against undesirable reaction during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504. Examples include, but are not limited to, acyl and acyloxy groups, for example acetyl, chloroacetyl, trichloroacetyl, o-nitrophenylacetyl, o-nitrophenoxy-acetyl, trifluoroacetyl, acetoacetyl, 4-chlorobutyryl, isobutyryl, picolinoyl, aminocaproyl, benzoyl, methoxy-carbonyl, 9-fluorenylmethoxycarbonyl, 2,2,2-trifluoroethoxycarbonyl, 2-trimethylsilylethoxy-carbonyl, tert-butyloxycarbonyl, benzyloxycarbonyl, p-nitrobenzyloxycarbonyl, 2,4-dichloro-benzyloxycarbonyl, and the like. Further examples include Cbz (carboxybenzyl), Nosyl (o- or p-nitrophenylsulfonyl), Bpoc (2-(4-biphenyl)isopropoxycarbonyl) and Dde (1-(4,4-dimethyl-2,6-dioxohexylidene)ethyl).

The term "carboxamide protecting group" as used herein means a group that is capable of being readily removed to provide the $NH_2$ group of a carboxamide group and protects the carboxamide group against undesirable reaction during synthetic procedures. Such protecting groups are described in Protective Groups in Organic Synthesis edited by T. W. Greene et al. (John Wiley & Sons, 1999) and 'Amino Acid-Protecting Groups' by Fernando Albericio (with Albert Isidro-Llobet and Mercedes Alvarez) Chemical Reviews 2009 (109) 2455-2504. Examples include, but are not limited to, 9-xanthenyl (Xan), trityl (Trt), methyltrityl (Mtt), cyclopropyldimethylcarbinyl (Cpd), and dimethylcyclopropylmethyl (Dmcp).

As used herein, the term "and/or" means "and", or "or", or both.

The term "(s)" following a noun contemplates the singular and plural form, or both.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. The "containing" is also to be interpreted in the same manner.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Although the present invention is broadly as defined above, those persons skilled in the art will appreciate that the invention is not limited thereto and that the invention also includes embodiments of which the following description gives examples.

BRIEF DESCRIPTION OF THE FIGURES

The invention will be described with reference to the accompanying figures in which.

DETAILED DESCRIPTION OF THE INVENTION

Figure 1:
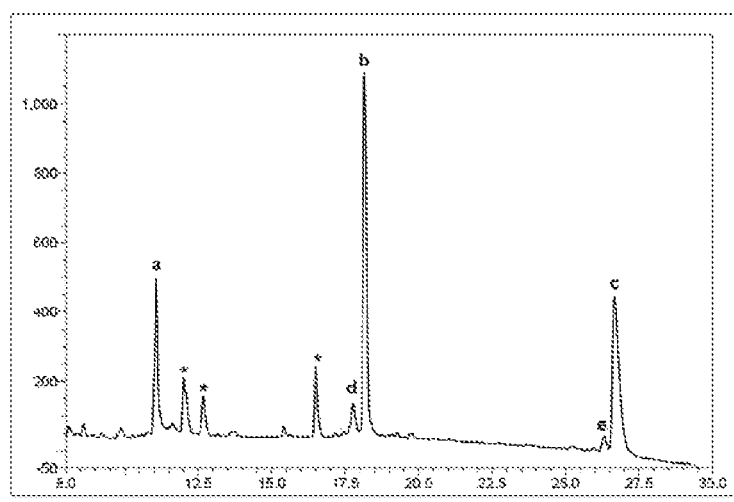
FIG. 1 is an HPLC chromatogram of reaction mixture following irradiation of solution of AcCSKKKKNLVPC(tBu)VATV 1, vinyl palmitate (70 equivalents) and DMPA at 365 nm. Peak a (11.05 min): residual starting peptide 1; b (18.58 min): mono-pamitoylated peptide 2; c (26.66 min): bis-palmitoylated peptide 3; e, f: sulfoxides of 2 and 3; *: by-products from the DMPA photoinitiator. Column: Phenomenex Gemini C18 (3μ, 110 Å, 4.6×150 mm); eluent A, water/0.1% TFA; eluent B: MeCN/0.1% TFA; gradient: 5-95% B over 30 min @ 1 mL/min.

The present invention provides amino acid- and peptide conjugate compounds of the formula (I) as defined herein. The inventors have advantageously found that such conjugates have surprising immunogenic activity.

The amino acid- and peptide conjugate compounds of formula (I) may be prepared using the methods and procedures described herein.

Starting materials and/or intermediates useful in the methods may be prepared using known synthetic chemistry techniques (for example, the methods generally described in Louis F Fieser and Mary F, *Reagents for Organic Synthesis* v. 1-19, Wiley, New York (1967-1999 ed.) or *Beilsteins Handbuch der organischen Chemie*, 4, Aufl. Ed. Springer-Verlag Berlin, including supplements (also available via the Beilstein online database)) or, in some embodiments, may be commercially available.

Preparation of the compounds may involve the protection and deprotection of various chemical groups. The need for protection and deprotection, and the selection of appropriate protecting groups, can be readily determined by a person skilled in the art. Protecting groups and methods for protection and deprotection are well known in the art (see e.g. T. W. Greene and P. G. M. Wuts, *Protective Groups in Organic Synthesis*, 3$^{rd}$ Ed., Wiley & Sons, Inc., New York (1999)).

As shown in Scheme A1 and described below, compounds of formula (IF) that are compounds of formula (I) wherein w is 1, v is 0, and m is from 2 to 6, preferably 2, may be prepared via a method involving the conjugation of an epoxide to an amino acid-comprising conjugation partner.

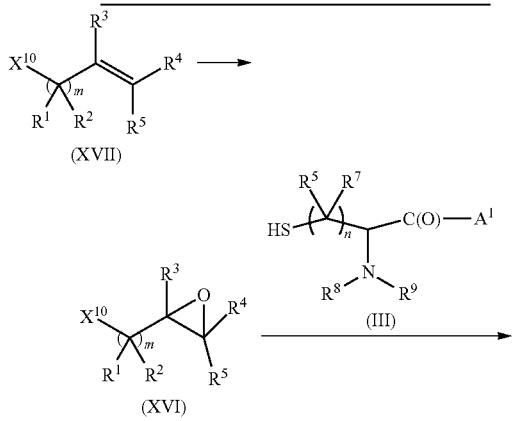

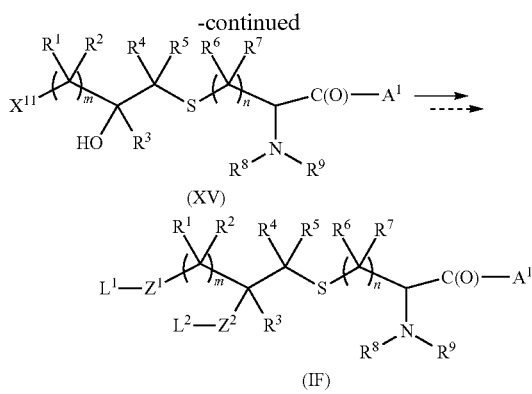

(XV)

(IF)

The present invention provides a method of making a compound of the formula (XV), comprising reacting an epoxide of the formula (XVI) and an amino acid-comprising conjugation partner comprising a thiol of the formula (III) under conditions effective to provide the compound of formula (XV) by conjugation of the thiol to the epoxide.

The amino acid comprising conjugation partner reacted with the epoxide may consist of an amino acid, for example an Nα-amine protected and/or C-terminus protected cysteine. Alternatively, the amino acid comprising conjugation partner may comprise a peptide, for example a short peptide. In such embodiments, the amino acid comprising conjugation partner may comprise about 15 amino acid residues or less, for example 5, 4, or 3 amino acid residues. The Nα-amino group of the amino acid comprising conjugation partner is preferably protected or otherwise substituted (i.e. is not in the form of a free amine —$NH_2$ group) to prevent reaction during the conjugation reaction. The C-terminus of the amino acid comprising conjugation partner may also be protected.

X10 in the compound of formula (XVI) may be a protected hydroxyl, thiol, amine, or carbamate group (P10-O—, P11-S—, P12-NR—, or P12-NRC(O)O—, respectively) from which L1-Z1- and L2-Z2-may subsequently be formed. Where X10 is a protected group, the protecting group may be removed in the conjugation reaction to provide a compound of the formula (XV) wherein X11 is the corresponding deprotected group. For example, where X10 is a P10-O— group conjugation may provide the corresponding hydroxyl group as X11 in the compound of formula (XV).

The epoxide of formula (XVI) comprises a stereogenic centre at the carbon atom to which R3 is attached. Thus, a single stereoisomer of the epoxide or a stereoisomerically enriched mixture of the epoxide may used in the reaction to control the stereochemistry of the carbon atom to which R3 is attached in the compound of formula (XV) and subsequent products formed, including the compound of formula (IF). Various methods for providing enantiopure or enantioenriched mixtures of epoxides are known in the art. In various embodiments, providing the single stereoisomer or a stereoisomerically enriched mixture of the epoxide of formula (XVI) comprises resolving a racemic mixture of the epoxide. For example, resolving a racemic epoxide mixture by kinetic hydrolysis, as described by Jacobsen et al, *Science*, 1997, 277, 936-938.

The epoxide of formula (XVI) may be provided by reacting an alkene of the formula (XVII) with an oxidant under conditions effective to epoxidise the alkene. Numerous methods for epoxidising alkenes are known in the art. In certain embodiments, the epoxidation is carried out by reacting the alkene with a peroxide or an organic N-oxide as the oxidant. Examples of suitable peroxides include organic peroxides, for example m-chloro peroxybenzoic acid. Examples of N-oxides include, for example, pyridine N-oxide and the like. Other suitable oxidants will be apparent to those skilled in the art. The reaction may be carried out in a liquid reaction medium comprising a suitable solvent, for example dichloromethane. Alkenes of the formula (XVII) may be commercially available or prepared from commercially available precursors using standard synthetic chemistry techniques.

Those skilled in the art will appreciate that certain X10 groups may be susceptible to oxidation in the epoxidation reaction, for example when X10 comprises an amine group (which may form an N-oxide) or thioether group (which may form e.g. sulfoxides or sulfones). Such groups may be protected during the reaction to prevent oxidation or reduced back to the desired group at an appropriate point in the synthetic sequence after the epoxidation reaction has been carried out.

Alternatively, the epoxide of formula (XVI) may be prepared by treating a compound of formula (XVII-A), wherein LG is a suitable leaving group such as a halogen, with a base in a suitable solvent to displace the leaving group as shown in scheme A2.

Scheme A2. Epoxidation via leaving group displacement.

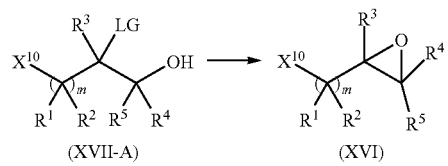

(XVII-A)  (XVI)

Compounds of the formula (XVII-A) may be commercially available or may be prepared from commercially available precursors. Advantageously, in some embodiments, the compound of formula (XVII-A) may be prepared from an enantiopure α-amino acid. The epoxidation reaction proceeds stereospecifically with inversion of stereochemistry at the carbon to which R3 is attached.

For example, as shown in scheme A2-1, the compound of formula (XVII-A1), which corresponds to a compound of formula (XVII-A) wherein m is 2 and each R1 and R2, and R3, R4, and R5 are hydrogen, X10 is —OH, and LG is bromo, may be prepared from L-aspartic acid (see Volkmann, R. A. et al. *J. Org. Chem.*, 1992, 57, 4352-4361).

L-Aspartic acid may be converted to be bromosuccinic acid (AA-1) by, for example, treatment with sodium nitrite and a strong acid such as sulfuric acid, to generate nitrous acid in situ, in the presence of sodium bromide at a temperature from −10 to 0° C. The reaction proceeds stereospecifically with overall retention of stereochemistry.

Reduction of bromosuccinic acid (AA-1) to bromodiol (XVII-A1) may be carried out using a suitable reductant, for example by treatment with borane or borane-dimethyl sulfide complex in THF at −78° C. allowing the reaction mixture to warm to room temperature. Epoxidation to provide the compound of formula (XVI-1a) may be carried out by reacting bromodiol (XVII-A1) with a base, for example cesium carbonate in dichloromethane at room temperature. As noted above, the reaction proceeds stereospecifically with overall inversion of stereochemistry.

The opposite enantiomer of epoxide (XVI-1a) can be prepared from D-aspartic acid by the same procedure.

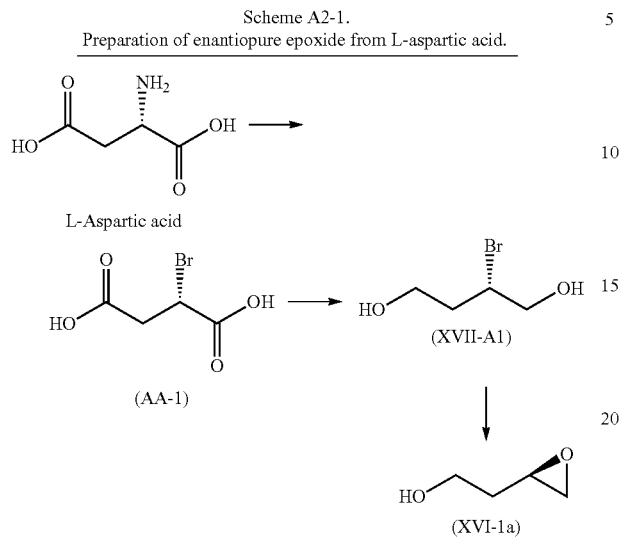

Scheme A2-1.
Preparation of enantiopure epoxide from L-aspartic acid.

Referring again to Scheme A1, the compound of formula (XV) may be subsequently converted by one or more synthetic steps to an amino acid or peptide conjugate of the formula (IF). In the one or more steps, the hydroxyl group bound to the carbon to which R3 is attached is converted to an L2-Z2-group.

If X11 is not L1-Z1-, then the one or more steps also comprises converting X11 to L1-Z1-. The L1-Z1- and L2-Z2-groups may be introduced simultaneously or sequentially in any order.

In certain embodiments, the one or more steps comprises acylating the compound of formula (XV) so as to replace the hydrogen atom of the hydroxyl group bound to the carbon to which R3 is attached with L2-C(O)—.

In exemplary embodiments, X10 is P10-O— or OH; and X11 is P10-O— or OH.

In various embodiments, X11 is P10-O— or OH; and the one or more synthetic steps comprise acylating the compound of formula (XV) so as to replace P10 or the hydrogen atom of the hydroxyl group of X11 with L1-C(O)—; and/or the hydrogen atom of the hydroxyl group bound to the carbon to which R3 is attached with L2-C(O)—.

In certain embodiments, as shown below in Scheme A3 and described in the Examples, the method comprises reacting an epoxide of formula (XVI-1) bearing a protected hydroxyl group with an amino acid comprising conjugation partner of the formula (III) to provide a compound of the formula (XV-1a).

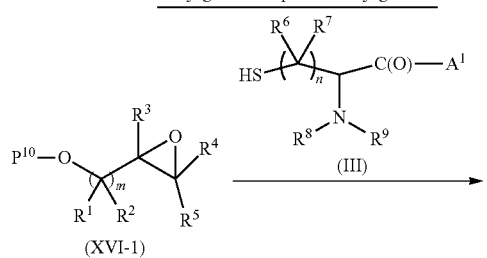

Scheme A3: Preparation of bis-ester conjugates via epoxide conjugation.

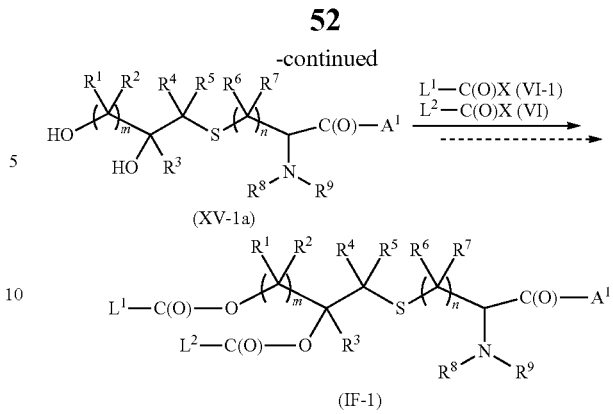

The conjugation reaction may be carried out under acidic conditions by reacting the epoxide and thiol in the presence of an acid, for example hydrochloric acid, sulfuric acid, or a mixture thereof. The reaction may be carried out in a liquid reaction medium comprising a suitable solvent, such as dichloromethane, at a temperature from about −10 to about 50° C., for example from 0 to 40° C.

The hydroxyl protecting group P10 is selected such that it is removable under the conditions effective for conjugation and is therefore removed during the conjugation reaction to provide the desired diol of formula (XV-1a). Suitable protecting groups will be apparent to those skilled in the art and may include, for example, acid labile silyl protecting groups.

Alternatively, the conjugation reaction may be carried using an epoxide of the formula (XVI) wherein X10 is a hydroxyl group, such as the epoxide of formula (XVI-1a).

The diol of the formula (XV-1a) may be converted to the compound of formula (IF-1) by reaction with the compounds of formula (VI-1) and (VI), wherein X is OH or a suitable leaving group (for example a halide, such as chloro or bromo), under conditions effective for esterification.

The conditions effective for esterification depend on the nature of the compound of formula (IV) and/or (VI-1). For example, where X is OH, the reaction may be carried out in the presence of a base, such as DMAP, and activating agent, such as N,N'-diisopropylcarbodiimide (DIC) in a liquid medium comprising a suitable solvent, such as THF.

In various embodiments, the compound of formula (VI) and (VI-1) are identical. For example, the compound of formula (VI) and (VI-1) may each be palmitic acid. In such embodiments, conversion of the diol of formula (XV-1a) to the compound of formula (IF-1) may be accomplished in a single step.

In certain embodiments, different L1 and L2 groups may be introduced by reacting the diol with a stoichiometric amount of a compound of formula (VI-1) or (VI) to esterify the more reactive of the two alcohols, and then reacting the resultant ester with the other a compound of formula (VI) or (VI-1) to esterify the second alcohol of the diol.

In other embodiments, the method comprises reacting an epoxide of formula (XVI-1) and an amino acid comprising conjugation partner of the formula (III) to provide a compound of the formula (XV-1b) as shown in Scheme A4 below. In such embodiments, the hydroxyl protecting group P10 is stable and is not removed under the conjugation reaction conditions.

The protected alcohol of the formula (XV-1b) provides ready access to compounds of formula (IF-1) wherein L1 and L2 are different. Using the compound of formula (XV-1b) to access such compounds, rather than the diol of formula (XV-1a), may be more convenient in certain embodiments, for example where there is poor selectivity between the alcohols of the diol of formula (XV-1a).

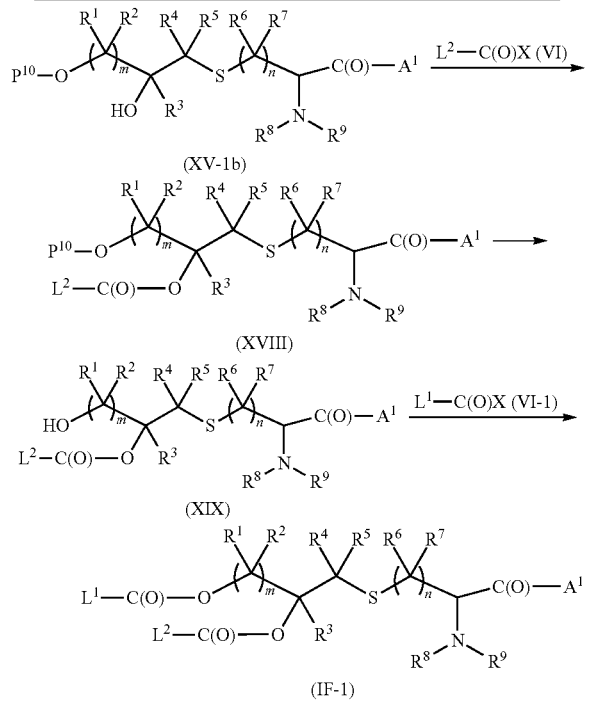

The β-sulfanylhydroxyl group of the compound of formula (XV-1b) may be acylated with a compound of formula (VI) under conditions effective for esterification to provide protected ester (XVIII), then the protecting group P10 removed to provide the alcohol of formula (XIX). The conditions for removal of the protecting group depend on the protecting group used. For example, dilute HF may be used to remove silyl protecting groups, such as TBDMS, TBDPS, and the like. The alcohol of formula (XIX) may then be acylated with a compound of formula (VI-1) under conditions effective for esterification to provide the desired compound of formula (IF-1).

Those skilled in the art will appreciate that hydroxyl groups, for example those in the compounds of formulae (XV-1a), (XV-1b), and (XIX), may be converted to various other functional groups, such as thiols and amines, to provide access compounds of formula (I) bearing L1-Z1- and L2-Z2-groups other than esters.

For example, the compound of formula (XV-1b) can be used to prepare thioester and amide analogues of the compound of formula (IF-1), as shown below in Scheme A5. To prepare amide analogue (IF-3), the hydroxyl group in the compound of formula (XV-1b) may first be converted to an azide and then reduced to the corresponding amine. The reaction may be carried out under modified Mitsunobu conditions (e.g. L. Rokhum et al, 3. Chem. Sci, 2012, 124, 687-691) using $PPh_3$, $I_2$, imidazole, and $NaN_3$ to provide the azide, and then $PPh_3$ to reduce azide to the amine. Alternatively, the azide may be obtained by first converting the hydroxyl group to a suitable leaving group, for example a tosyl or mesyl group, and then treating with $NaN_3$.

Acylation of the amine with a compound of formula (VI) provides the amide of formula (XVIII-2). The acylation reaction may be carried out by reacting a carboxylic acid of the formula (VI) in the presence of a base, for example DMAP, and an activating agent, for example DIC, in a suitable solvent such as THF. Deprotection of the protecting group P10 and esterification of the resultant alcohol (XIX-2) provides the compound of the formula (IF-3).

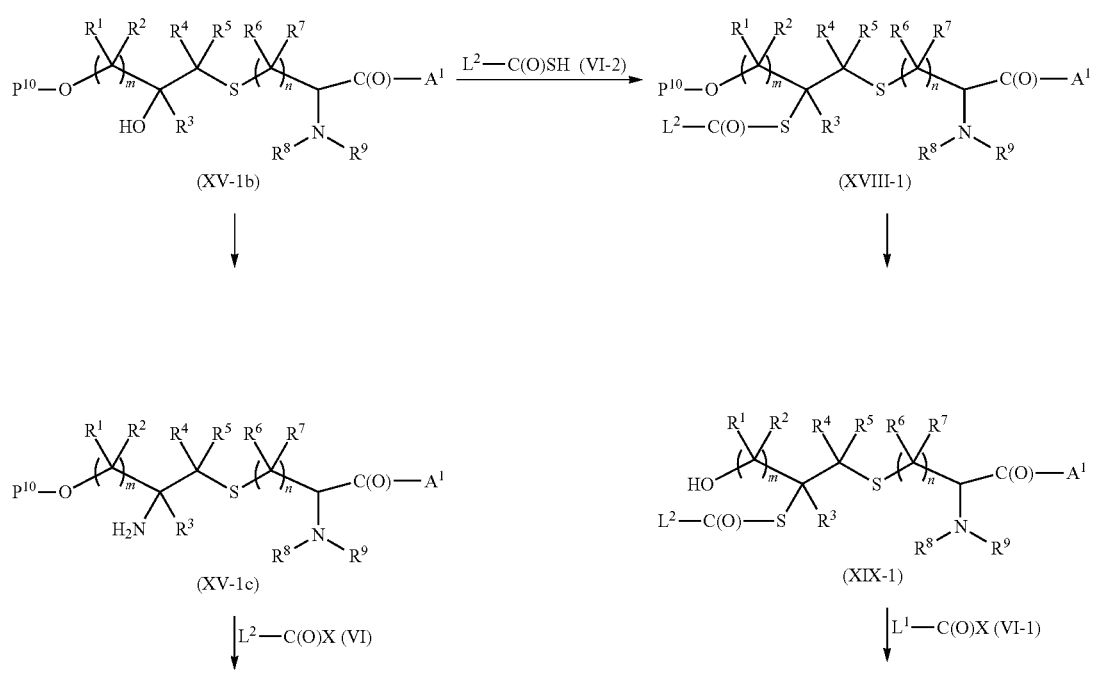

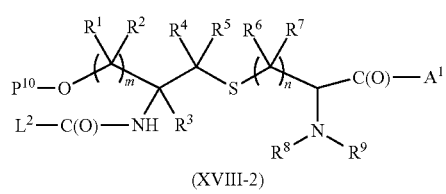

(XVIII-2)

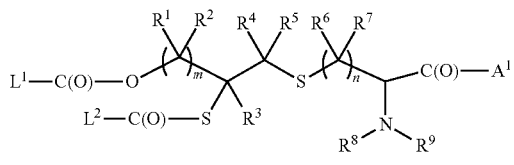

(IF-2)

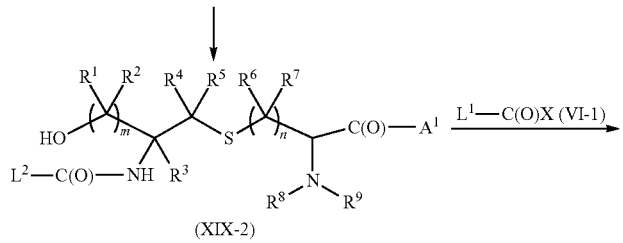

(XIX-2)

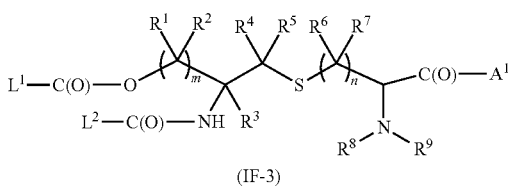

(IF-3)

Thioester analogue (IF-2) may be prepared by first reacting the compound of formula (XV-1b) under Mitsunobu conditions (e.g. PPh₃, diethylazodicarboxylate (DEAD)) and trapping with the desired thioacid of formula (VI-2), for example thiopalmitic acid, to provide the compound of formula (XVIII-1) (see e.g. O. Schulze et al, Carbohydrate Res., 2004, 339, 1787-1802). Deprotection of the protecting group P10 and esterification of the resultant alcohol (XIX-1) provides the compound of the formula (IF-2).

Thioester and amide analgoues of bis-ester (IF-1) may also be prepared from the compound of formula (XIX), as shown in Scheme A6. The compound of formula (XIX) may be converted to the compound of formula (IF-4) by methods analogous to those described above for the conversion of the compound formula (XV-1b) to the compound of formula (XVIII-1).

Similarly, the compound of formula (XIX) may be converted to the compound of formula (IF-5) by methods analogous to those described above for the conversion of the compound of formula (XV-1b) to the compound of formula (XVIII-2).

Further analogues of bis-ester (IF-1) may be prepared by replacing the compound of formula (XIX) in Scheme A6 with a compound of formula (XIX-1) or (XIX-2) and then following the synthetic sequences described.

Numerous other compounds of formula (IF) may be prepared by analogous methods, as will be appreciated by those skilled in the art.

Compounds of formula (VI), (VI-1), (VI-2), and (VI-3) may be commercially available or prepared from commercially available precursors using standard synthetic chemistry techniques.

Compounds of formula (I) may also be prepared by a method comprising the conjugation of an amino acid comprising conjugation partner and an acetal, as shown in Scheme B1.

Scheme A6. Preparation of thioesters and amides via the compound of formula (XIX).

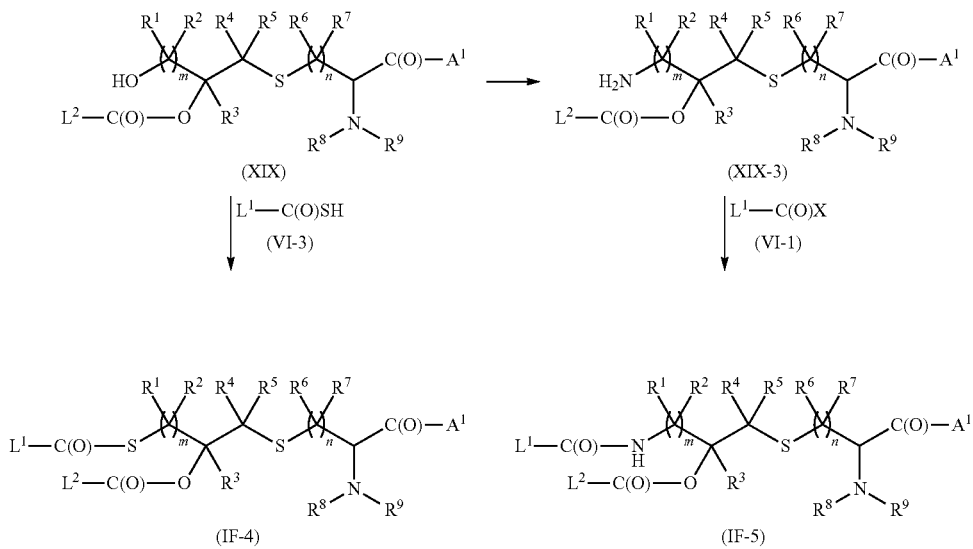

Scheme B1. Preparation of compounds of formula (I) via acetal (XXI).

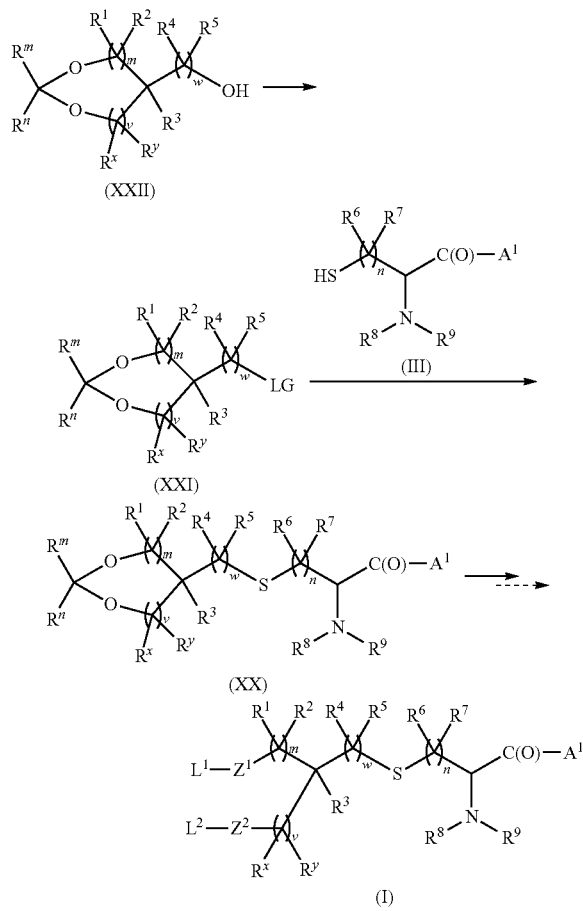

The present invention provides a method of making the compound of formula (XX) comprising reaching an amino acid comprising conjugation partner of the formula (III) and an acetal of the formula (XXI), wherein LG is a suitable leaving group, under conditions effective to provide a compound of the formula (I). In the reaction, the thiol of the compound of formula (III) displaces the leaving group (LG) in the acetal of formula (XXI). Suitable leaving groups include but are not limited to halo (for example chloro, bromo, or iodo) or sulfonate (for example a tosylate or mesylate). Other suitable leaving groups will be apparent to those skilled in the art.

The size of the acetal ring in the compound of formula (XXI) may vary. The acetal ring may comprise from 5 to 7 ring atoms (i.e. may be a 5-7-membered cyclic acetal). In certain embodiments, the cyclic acetal is 6-membered. It will be appreciated that when the cyclic acetal is a 5-membered cyclic acetal, in order to provide a compound of the formula (I), w is at least 2 (such that the sum of m, v, and w is at least 3).

The amino acid comprising conjugation partner reacted with the acetal may consist of an amino acid, for example an Nα-amine protected and/or C-terminus protected cysteine. Alternatively, the amino acid comprising conjugation partner may comprise a peptide, for example a short peptide. In such embodiments, the amino acid comprising conjugation partner may comprise about 15 amino acid residues or less, for example 5, 4, or 3 amino acid residues. The Nα-amino group of the amino acid comprising conjugation partner is preferably protected or otherwise substituted (i.e. is not in the form of a free amine —NH$_2$ group) to prevent reaction during the conjugation reaction. The C-terminus of the amino acid comprising conjugation partner may also be protected.

The conjugation reaction may be carried out in the presence of a base. For example, the reaction may be carried out in the presence of organic amine, in a suitable solvent, for example DMF, at a temperature of about 50° C. Suitable organic amines include but are not limited to triethylamine, N-methylmorpholine, collidine, and the like.

The compound of formula (XXI) may be provided in stereoisomerically pure form or a stereoisomerically enriched mixture by reacting stereoisomerically pure or a stereoisomerically enriched mixture of the compound of the compound of formula (XXII). Advantageously, stereoisomerically pure compounds of formula (XXII) are readily commercially available, such as (4R)- or (4S)-(2,2-dimethyl-1,3-dioxan-4-yl)-methanol.

Other compounds of formula (XXII) may be prepared by routine methods known in the art. As shown in Scheme B1-1, a compound of formula (XXII-B), wherein Pg is a suitable hydroxyl protecting group, may be reacted with a compound of the formula (XXII-C1) to provide the acetal of formula (XXII-D), which may then be converted to the compound of formula (XXII) by removal of the protecting group Pg. Alternatively, the compound of formula (XXII-B) may be reacted with an acyclic acetal of the formula (XXII-C2), wherein Ro and Rp are each independently C1-4alkyl. The acetylisation reaction may be carried out using an acid, such as camphorsulfonic acid, in a suitable solvent, such as dichloromethane.

The conditions for removal of the protecting group Pg, depend on the protecting group used. For example, a silyl ether protecting group, such as TBDMS, may be removed by treatment with a source of fluorine, such as tetrabutylammonium fluoride (TBAF) in suitable solvent, such as THF. See, for example C. R. Reddy et al, (Tetrahedron Letters, 2010, 51(44) 5840-5842); and Sauret-Cladiere et al (Tetrahedron Asymmetry, 1997, 8(3), 417-423).

Scheme B1-1. Preparation of compounds of formula (XXII).

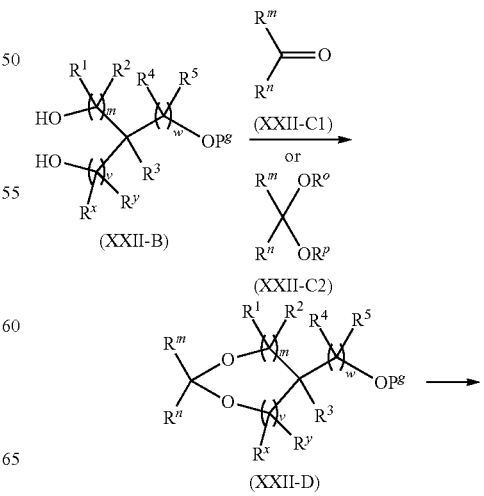

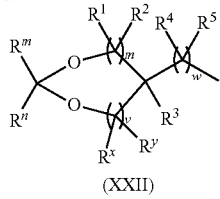

(XXII)

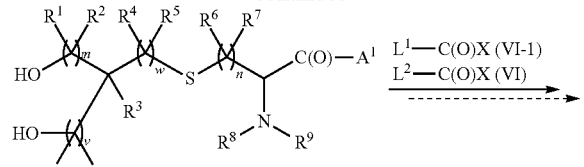

(XXIII-1)

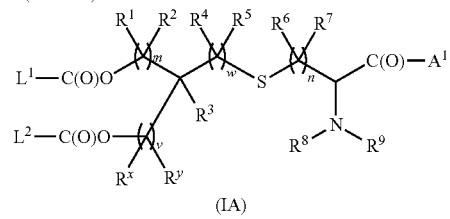

(IA)

Referring again to Scheme B1, compounds of formula (XXI) may be prepared from compounds of formula (XXII) by reaction with a suitable precursor of the leaving group. For example, tosylate or mesylate leaving groups may be prepared by reaction with tosyl chloride or mesyl chloride in the presence of a base and a suitable solvent, and an iodo leaving group may be prepared by reaction with $PPh_3$ and $I_2$.

The compound of formula (XX) may subsequently be converted by one or more synthetic steps to a compound of the formula (I), for example a compound of the formula (IA).

The one or more synthetic steps may comprise removing the acetal to provide a diol of the formula (XXIII-1). The hydroxyl group bound to the carbon to which R1 and R2 are attached in the compound of formula (XXIII-1) may be converted to L1-Z1-, and/or the hydroxyl group bound to the carbon to which Rx and Ry are attached may be converted to L2-Z2.

For example, as shown in Scheme B2, the acetal in the compound of formula (XX) may be removed to provide the diol of formula (XXIII-1) by treatment with an acid such as p-toluene sulfonic acid in a solvent such as dichloromethane. The diol of formula (XXIII-1) may be converted to the bis-ester compound of formula (IA) via one or more acylation steps in a manner analogous to that described for the conversion of the compound of formula (XV-1a) to the compound of formula (IF-1).

Alternatively, in various embodiments wherein Rm is optionally substituted aryl, for example phenyl or methoxy substituted phenyl, the one or more synthetic steps may comprise removing the acetal to provide a compound of the formula (XXIII-2) or (XXIII-3). The one or more steps may comprise converting the hydroxyl group bound to the carbon atom to which Rx and Ry are attached in the compound of formula (XXIII-2) to L2-Z2-, removing the RmRnCH— group to provide a hydroxyl group, and converting the hydroxyl group to L1-Z1; or converting the hydroxyl group bound to the carbon to which Rx and Ry are attached in the compound of formula (XXIII-2) to L1-Z1-, removing the RmRnCH— group to provide a hydroxyl group, and converting the hydroxyl group to L2-Z2-. Such methods advantageously allows allow the introduction of different L1-Z1 and L2-Z2-groups.

As illustrated in Scheme B3, the acetal in the compound of formula (XX) may be removed by, for example, treatment with a suitable reducing agent, for example diisobutylaluminium hydride (DIBAL). The resulting compound of formula compound of formula (XXIII-2) may then be acylated with the compound of formula (VI) to introduce the desired L2-C(O)O— group. Removal of the RmRnCH— group to provide the compound of formula (XXV-2) may be carried out by hydrogenolysis (e.g. for a benzyl or p-methoxybenzyl group) or any other suitable method having regard to the nature of RmRnCH— group. The compound of formula (XXV-2) may then be converted to the compound of formula (IA) by acylating with the compound of formula (IV-1). The acylation steps may be carried out as described herein with respect to the preparation of the compound of formula (IF-1).

Scheme B2. Preparation of bis-ester conjugates of formula (IA).

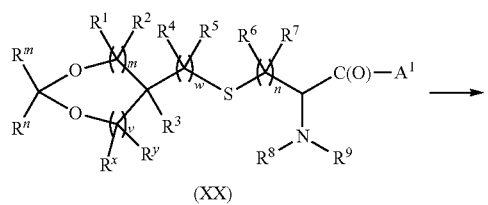

(XX)

Scheme B3. Bis-ester conjugates via compounds of formula (XXIII-2).

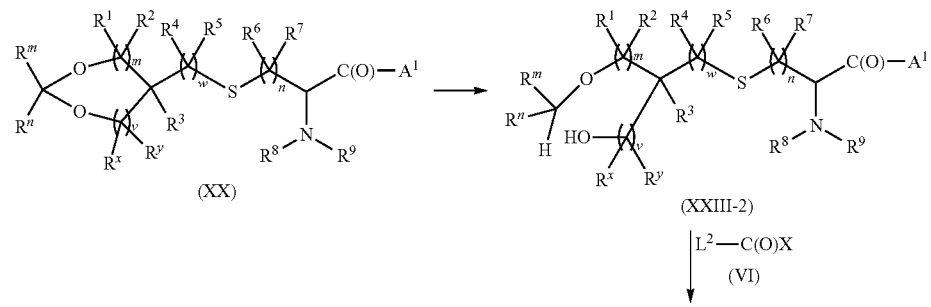

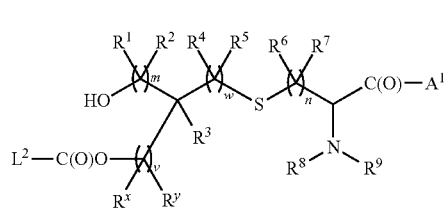

(XXV-2)

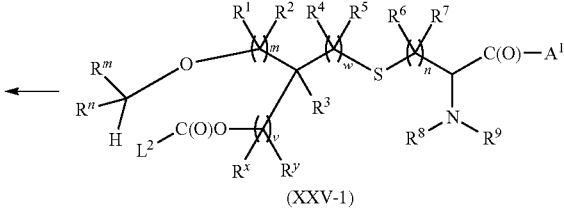

(XXV-1)

$$L^1\text{—}C(O)X$$

(VI-1)

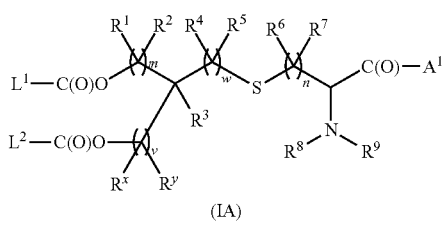

(IA)

It will be apparent to those skilled in the art that compounds of formula (IA) may be prepared from compounds of formula (XXIII-3) by a replacing the compounds of formulae (XXIII-2), (VI) and (VI-1) in Scheme B3 with the compounds of formulae (XXIII-3), (VI-1), and (VI), respectively, and then following the synthetic sequence described.

Hydroxyl groups produced on removal of the acetal or RmRnCH— group, such as those in the compounds formulae (XXIII-1), (XXIII-2), (XXIII-3), and (XXV-2), may be converted to various other functional groups, such as thiols and amines, to provide access compounds of formula (I) bearing other Z1 and Z2 groups.

It will be appreciated that amide and thioester analogues of the bis-ester compound of formula (IA) may be prepared by methods analogous to those described above with respect to the amide and thioester analogues of the bis-ester compound of formula (IF-1).

The present invention also provides a method for preparing compounds of formula (I) via a thiol-ene reaction. The method comprises reacting a first lipid-containing conjugation partner comprising a carbon-carbon double bond, a second lipid-containing conjugation partner a carbon-carbon double bond, and an amino acid-comprising conjugation partner comprising a thiol, under conditions effective to conjugate the first and second lipid-containing conjugation partners to the amino acid-comprising conjugation partner. Each lipid containing conjugation partner comprises and therefore in the reaction provides to the compound of formula (I) a lipid moiety one comprising L1, the other comprising L2.

The thiol-ene reaction involves the addition of a thiol across a non-aromatic carbon-carbon double bond (i.e. hydrothiolation of the carbon-carbon double bond). The reaction proceeds via a free radical mechanism. There are three distinct phases in the reaction: initiation, coupling, and termination.

Typically, radical generation gives rise to an electrophilic thiyl radical which propagates across the ene group of an alkene, forming a carbon-centred radical and chain transfer from an additional thiol molecule quenches the radical on carbon to give the final product.

Without wishing to be bound by theory, the inventors believe that in the method of the present invention, the thiol is conjugated to a carbon atom of the carbon-carbon double bond of the first lipid containing conjugation partner to form a carbon-centred radical, and that this carbon-centred radical, instead of being quenched, is then conjugated with a carbon atom of the carbon-carbon double bond of the second lipid-containing conjugation partner to provide a compound of the formula (I).

The method thus provides amino acid- and peptide conjugates of the formula (I) in which the sulfur atom from the thiol is conjugated to a carbon atom from the carbon-carbon double bond of the first lipid-containing conjugation partner, and a carbon atom from the carbon-carbon double bond of the first lipid-containing conjugation partner is conjugated to a carbon atom from the carbon-carbon double bond of the second lipid-containing conjugation partner.

The first and second lipid containing conjugation partners may be the same or different. Those skilled in the art will appreciate that reacting different lipid containing conjugation partners at the same time may provide a mixture of (potentially up to four different) compounds of formula (I). Accordingly, in certain exemplary embodiments, the first and second lipid containing conjugation partners are the same.

The thiolene reaction may be regioselective with respect to which carbon atom of the carbon-carbon double bond of the first lipid-containing conjugation partner is conjugated to the thiol and also with respect to which carbon atom of the carbon-carbon double bond of the second lipid-containing conjugation partner is conjugated to which carbon atom of the carbon-carbon double bond from the first lipid-containing conjugation partner. Those skilled in the art will appreciate that various regioisomers may be formed in the reaction.

In certain embodiments, the method comprises reacting a first lipid containing conjugation partner of the formula (IIA) and a second lipid containing conjugation partner of the formula (IIB) with a thiol containing amino acid comprising conjugation partner (III) under conditions effective to provide a compound of the formula (IB) (Scheme C1).

Scheme C1. Preparation of compounds of formula (IB) via a thiolene reaction.

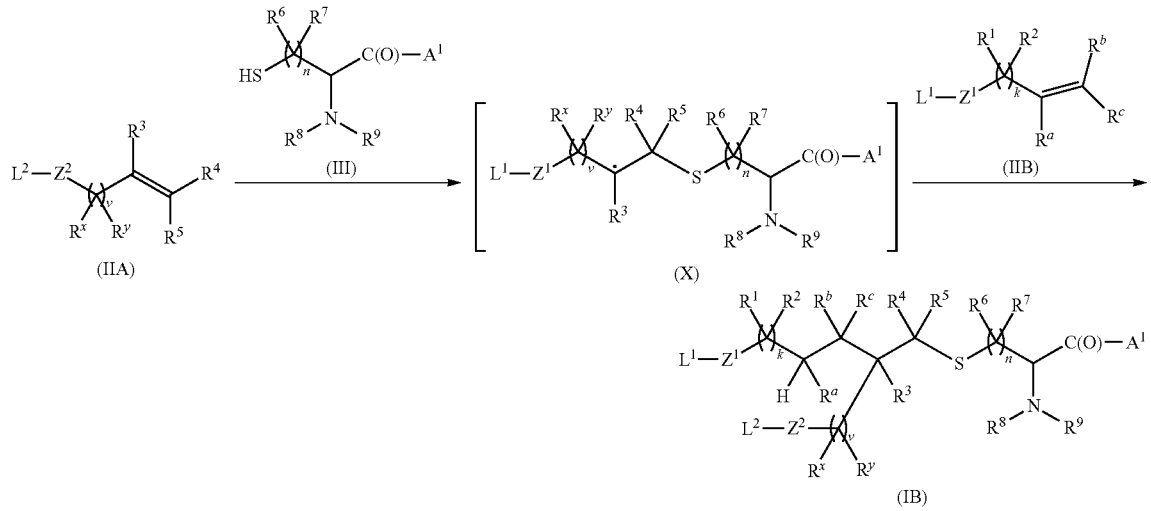

The conditions effective for formation of the compound of formula (IB) may vary. In various embodiments, the conditions effective for formation of the compound of formula (IB) may comprise carrying out the reaction with a stoichiometric excess of lipid containing conjugation partner to thiol, such as a stoichiometric ratio of the lipid containing conjugation partners (IIA) and (IIB) (combined) to amino acid-comprising conjugation partner of at least 7:1, for example 8:1, 9:1, 10:1, 20:1, 30:1, 40:1, 50:1, 60:1, or 70:1.

The degree of conversion of the amino acid-comprising conjugation partner to the product compound of formula (IB) may vary. Preferably, at least 5, 10, 15, 20, 25, 30, 35, 40, 45, 50, 60, or 70% of the amino acid-comprising conjugation partner is converted to the compound of formula (IB). Conversion may be determined by HPLC.

As noted above, without wishing to be bound by theory, the inventors believe that under such conditions reaction of the alkene of formula (IA) with the thiol of formula (III) results in the formation of a carbon-centred radical of the formula (X), which is trapped with the second alkene of the formula (IIB), rather than quenched by abstraction of a proton from the thiol of another molecule of the formula (III), to provide the desired amino acid- or peptide conjugate.

The reaction may result in the production of a mixture of stereoisomers as it may not be possible to control or influence the stereochemistry of bond formation between the carbon atom to which R3 is bound and the carbon atom to which Rb and Rc are bound owing to the radical intermediate generated in the course of the reaction. The reaction typically produces a mixture of epimers with respect to the carbon atom to which R3 is bound.

In certain embodiments, the Z1 and Z2 in the lipid containing-conjugation partners are each —C(O)O—, and the compound of formula (I) formed in the thiolene method is a compound of formula (IC) as defined herein.

In exemplary embodiments, the thiolene method of the present invention comprises reacting an amino acid-comprising conjugation partner comprising a structure of the formula (III) with lipid containing-conjugation partners of the formula (IIA) and (IIB) that are vinyl esters to provide a compound of the formula (ID). The reaction may be carried out, for example as described in the Examples below, by irradiating a reaction mixture comprising the amino acid comprising conjugation partner; lipid containing-conjugation partners; a photochemical initiator, such as DMPA. One or more additives may be included that reduce the formation of by products, such as a sterically hindered thiol (for example tert-butylmercaptan), an acid (for example TFA), or an organosilane (for example triisopropylsilane), or a combination of any two or more thereof. The reaction may be carried out in a suitable solvent, such as NMP, at ambient temperature for a suitable period of time, such as 30 minutes.

The reaction is typically initiated by the generation of one or more free radicals in the reaction mixture. One or more free radicals may be generated in the method by any method known in the art. The free radicals may be generated thermally and/or photochemically. One or more free radical initiators may be used to initiate the generation of free radicals. Suitable free radical initiators include thermal initiators and photoinitiators.

Free radicals are generated from thermal initiators by heating. The rate of degradation of the thermal initiator and resulting free radical formation depends on the initiator and the temperature at which the initiator is heated. Higher temperatures generally result in faster decomposition. A person skilled in the art will be able to select an appropriate temperature for heating the initiator without undue experimentation.

Numerous thermal initiators are commercially available. Examples of thermal initiators include but are not limited to tert-amyl peroxybenzoate, 1,1'-azobis(cyclohexanecarbonitrile), 2,2'-azobisisobutyronitrile (AIBN), benzoyl peroxide, tert-butyl hydroperoxide, tert-butyl peracetate, tert-butyl peroxide, tert-butyl peroxybenzoate, tert-butylperoxy isopropyl carbonate, lauroyl peroxide, peracetic acid, and potassium persulfate.

Free radicals may be generated from photoinitiators by irradiation with light. The frequency of light necessary to induce degradation of the photoinitiators and free radical formation depends on the initiator. Many photoinitiators can be initiated with ultraviolet light.

Light of a specific wavelength or wavelength range may be used to selectively irradiate the initiator, where the lipid-containing conjugation partners or amino acid-comprising conjugation partner, for example a peptide-containing conjugation partner, comprises photosensitive groups. In certain embodiments, a frequency of about 365 nm is used. Light of this frequency is generally compatible with the side chains of naturally occurring amino acids.

A wide range of photoinitiators are commercially available. Examples of photoinitiators include but are not limited to acetophenone, anisoin, anthraquinone, anthraquinone-2-sulfonic acid, benzil, benzoin, benzoin ethyl ether, benzoin isobutyl ether, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4'-bis(diethylamino)benzophenone, 4,4'-bis(dimethylamino)benzophenone, camphorquinone, 2-chlorothioxanthen-9-one, dibenzosuberenone, 2,2-diethoxyacetophenone, 4,4'-dihydroxybenzophenone, 2,2-dimethoxy-2-phenylacetophenone (DMPA), 4-(dimethylamino)benzophenone, 4,4'-dimethylbenzil, 2,5-dimethylbenzophenone, 3,4-dimethylbenzophenone, 4'-ethoxyacetophenone, 2-ethylanthraquinone, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, and thioxanthen-9-one.

A person skilled in the art will be able to select appropriate free radical initiators for use in the method having regard to, for example, the nature of the lipid-containing conjugation partners, amino acid-comprising conjugation partner, for example a peptide-containing conjugation partner, and any other components present in the reaction mixture. In some embodiments, the initiator is present in the reaction in a stoichiometric ratio relative to the starting material comprising the thiol of from about 20:1 to about 0.05:1, from about 10:1 to about 0.05:1, from about 5:1 to about 0.05:1, from about 3:1 to about 0.5:1.

The lipid-containing conjugation partners and amino acid-comprising conjugation partner, for example a peptide-containing conjugation partner, may be prepared using known synthetic chemistry techniques (for example, the methods generally described in Louis F Fieser and Mary F, *Reagents for Organic Synthesis* v. 1-19, Wiley, New York (1967-1999 ed.) or *Beilsteins Handbuch der organischen Chemie*, 4, Aufl. Ed. Springer-Verlag Berlin, including supplements (also available via the Beilstein online database)) or, in some embodiments, may be commercially available.

For example, lipid-containing conjugation partner compounds of the formula (IIA-1) may be prepared by reacting a compound of the formula (VI) wherein X is OH or a suitable leaving group with a compound of the formula (VII) wherein Y is H, a metal or metalloid, or acyl (for example, alkylcarbonyl) under conditions effective for esterification (or transesterification where Y is an acyl group) (Scheme C2).

Scheme C2. Preparation of compounds of the formula (IIA-1).

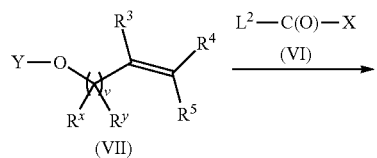

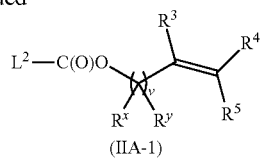

Methods for esterification (or transesterification) are well known in the art. For example, when X is chloro and Y is H, the reaction may be carried out in the presence of a base, such as pyridine or triethylamine, in a suitable solvent. The acid chloride may be converted in situ to a more reactive species (e.g. to the corresponding iodide, using sodium iodide). The temperature at which the reaction is carried out depends on the reactivity of the acid species and the solvent used.

For example, vinyl esters of the formula (IIA-1) may be produced by transesterification with vinyl acetate (itself produced industrially by the reaction of acetic acid and acetylene or acetic acid and ethylene over a suitable catalyst) using an acid or metal catalyst. See, for example, EP0376075A2 and S. K. Karmee, *J. Oil Palm Res.*, 2012, 1518-1523.

Vinyl esters of the formula (IIA-1) may also be prepared by the addition a carboxylic acid to a terminal acetylene in the presence of a catalyst (usually a palladium or ruthenium complex). See, for example, V. Cadierno, J. Francos, J. Gimeno *Organometallics*, 2011, 30, 852-862; S. Wei, J. Pedroni, A. Meissner, A. Lumbroso, H.-J. Drexler, D. Heller, B. Breit, *Chem. Eur. J.*, 2013, 19, 12067-12076. Nonterminal acetylenes may also be reacted. See, for example, N. Tsukada, A. Takahashi, Y. Inoue, *Tetrahedron Lett.*, 2011, 52, 248-250 and M. Rotem, Y. Shvo, *J. Organometallic Chem.* 1993, 448, 159-204.

Further examples of methods for preparing vinyl esters of formula (IIA-I) include: reaction of divinylmercury with aromatic and aliphatic acids [see, for example, D. J. Foster, E. Tobler, *J. Am. Chem. Soc.* 1961, 83, 851]; Cu(II)-catalyzed esterification of arene carboxylic acids with trimethoxy(vinyl)silane in the presence of AgF [see, for example, F. Luo, C. Pan, P. Qian, J. Cheng, *Synthesis* 2010, 2005]; vinyl transfer reactions from vinyl acetate to primary and secondary alcohols, and also to carboxylic acids with a catalyst system consisting of 2 mol-% of [AuCl(PPh$_3$)] and 2 mol-% of AgOAc [see, for example, A. Nakamura, M. Tokunaga, *Tetrahedron Lett.* 2008, 49, 3729]; and Ir complex ([Ir(cod)Cl]$_2$/P(OMe)$_3$)-catalyzed transvinylation [see, for example, H. Nakagawa, Y. Okimoto, S. Sakaguchi, Y. Ishii, *Tetrahedron Lett.* 2003, 44, 103].

Other suitable methods for preparing compounds of formula (II-A) will be apparent to those skilled in the art.

Lipid containing conjugation partner compounds of the formula (IIB-1) may be prepared in an analogous fashion, where the compounds of formula (IIA-1) and (IIB-1) are different.

Numerous compounds of formula (VI) are commercially available. Others may be prepared using standard synthetic chemistry techniques from commercially available precursors. For example, compounds of formula (VI) wherein X is chloro may be prepared treating the corresponding carboxylic acid with thionyl chloride in a suitable solvent or mixture of solvents.

Similarly, compounds of formula (VII) are also commercially available or may be prepared from commercially available precursors using standard synthetic chemistry techniques.

The order in which the lipid-containing conjugation partners and amino acid-comprising conjugation partner, for example a peptide-containing conjugation partner, and any other components present in the reaction mixture are introduced into the reaction vessel may vary. The reaction may be carried out as a one-pot procedure.

The ratio of the lipid-containing conjugation partners to amino acid-comprising conjugation partner, for example a peptide-containing conjugation partner, in the reaction may vary. In some embodiments, the mole ratio of the first lipid-containing conjugation partner and second lipid-containing conjugation partner combined (i.e. in total) to the amino acid-comprising conjugation partner is at least 7:1, for example 8:1, 9:1, 10:1, 20:1, 30:1, 40:1, 50:1, 60:1, or 70:1.

The reaction may be carried out at any suitable temperature. In some embodiments, the reaction is carried out at a temperature from about −25° C. to about 200° C., from about −10° C. to about 150° C., from about 0° C. to about 125° C., from about ambient temperature to about 100° C. In some embodiments, the reaction is carried out at a temperature of less than about 200° C., less than about 175° C., less than about 150° C., less than about 125° C., or less than about 100° C.

In some embodiments, the reaction is carried out at a temperature above ambient temperature. In one embodiment, the reaction is carried out at a temperature from 40 to 200° C., from 50 to 150° C., from 60 to 100° C., from 65 to 90° C., or from 70 to 80° C. In some embodiments, the reaction is carried out at a temperature greater than 40° C., greater than 50° C., greater than 75° C., greater than 100° C., or greater than 150° C.

The temperature at which the reaction is carried out may depend on how free radicals are generated in the reaction. The temperature used may be selected to control the rate of the reaction. The temperature may be adjusted during the course of the reaction to control the rate of the reaction.

If free radicals are generated thermally (e.g. using a thermal initiator), the reaction will generally be carried out at a temperature above ambient temperature. The temperature will depend on the reactivity of the species from which free radicals are generated.

If free radicals are generated photochemically the reaction may be carried out, advantageously, at ambient temperature. In certain embodiments, it may be desirable to cool the reaction mixture to slow the rate of reaction or conversely heat the reaction mixture to increase the rate of reaction.

A person skilled in the art will be able to select appropriate temperatures for carrying out the method having regard to the reactivity of the starting materials and other reactants present.

The temperature at which the reaction is carried out may be controlled by heating or cooling the reaction mixture by suitable method known in the art. Heat may be applied to the reaction mixture, for example, using a heat exchanger within the reaction vessel, a heating jacket surrounding the reaction vessel, or by immersing the reaction vessel in a heated liquid (e.g. an oil or sand bath). In certain exemplary embodiments, the reaction mixture is heated by microwave irradiation.

The progress of the reaction may be monitored by any suitable means, for example, by thin layer chromatography (TLC) or high performance liquid chromatography (HPLC). The reaction may be allowed to proceed to substantial completion, as monitored by the consumption of at least one of the starting materials. In some embodiments, the reaction is allowed to proceed for a period of time from 1 minute to 7 days, 5 minutes to 72 hours, 10 minutes to 48 hours, 10 minutes to 24 hours. In other embodiments, the reaction is allowed to proceed for a period of time less than 72 h, less than 48 h, less than 24 h, less than 12 h, less than 6 h, less than 4 h, less than 2 h, or less than 1 h.

In some embodiments, the reaction is carried out until at least about 50%, at least about 60%, at least about 70%, at least about 75%, at least about 80%, at least about 85%, at least about 90%, at least about 95%, at least about 97%, at least about 99% of the amino acid-comprising conjugation partner has been consumed. The consumption of starting materials may be monitored by any suitable method, for example, HPLC.

The reaction mixture may be mixed by any suitable method known in the art, for example, using a magnetic or mechanical stirrer. The method used may depend on the scale on which the reaction is carried out.

The reaction is generally carried out in a liquid reaction medium. The liquid reaction medium may comprise a solvent. Examples of suitable solvents include N-methylpyrrolidone (NMP), dimethylformamide, dichloromethane, 1,2-dichloroethane, chloroform, carbon tetrachloride, water, methanol, ethanol, dimethylsulfoxide, trifluoroacetic acid, acetic acid, acetonitrile, and mixtures thereof.

The solvent may be selected based on the solubility of the starting materials and other reactants present, for example the free radical initiator. In some embodiments, the lipid-containing conjugation partners are hydrophobic. The hydrophobicity or hydrophilicity of an amino acid-comprising conjugation partner may vary depending on, for example, the amino acid sequence of the peptide of a peptide-containing conjugation partner. The presence of a solubilising group in the peptide-containing conjugation partner may increase solubility in polar solvents, such as water. A person skilled in the art will be able to select an appropriate solvent without undue experimentation.

The reaction may be carried out under substantially oxygen-free conditions. Oxygen may quench free radicals formed in the reaction. The reaction mixture may be degassed with an inert gas (e.g. nitrogen or argon) that is substantially oxygen-free to remove any dissolved oxygen before free radicals are generated. Alternatively, individual components of the reaction mixture may be degassed with inert gas that is substantially oxygen-free prior to being combined in the reaction vessel. The reaction may be carried out under an atmosphere of inert gas that is substantially oxygen-free.

The method of the present invention may be carried out at ambient pressure.

An additive that inhibits the formation of undesirable by-products and/or that improves the yield of or conversion to the desired product may be included in the reaction mixture in the thiolene method of the present invention. The one or more additive may be an extraneous thiol, an acid, an organosilane, or a combination of any two or more thereof.

The inventors have found that in some embodiments the inclusion of an extraneous or exogenous thiol as an additive in the reaction mixture reduces the formation of undesirable by products. The extraneous thiol may, in some embodiments, increase the efficiency or conversion of the desired thiolene reaction. Examples of suitable extraneous thiols include but are not limited to reduced glutathione, DODT, DTT, protein, sterically hindered thiols, and the like.

In some embodiments, the extraneous thiol is DTT.

In other embodiments, the extraneous thiol is a sterically hindered thiol. Non-limiting examples of a suitable sterically hindered extraneous thiol include tert-butyl mercaptan and 1-methylpropyl mercaptan.

Without wishing to be bound by theory, the inventors believe that in certain embodiments an extraneous thiol such as tert-butylmercaptan can provide a proton to quench the radical intermediate formed on propagation of the radical of formula (X) with the alkene of formula (IIB) to provide the desired compound of formula (IB) and the resulting thiyl radical can propagate the reaction by generating another mole of thiyl radical from the amino acid comprising conjugation partner of formula (III).

It will be apparent that extraneous thiols may in certain embodiments also be capable of prematurely quenching the reaction by providing a proton radical of formula (X). In such embodiments, the extraneous thiol and the amount in which it is used may be selected such that the yield of or conversion to (as determined by HPLC) the compound of formula (IB) is optimised.

In various embodiments, the extraneous thiol is present in the reaction in a stoichiometric ratio relative to the amino acid comprising conjugation partner of from about 200:1 to about 0.05:1, 100:1 to 0.05:1, 80:1 to 0.05:1, 60:1 to 0.05:1, 40:1 to 0.05:1, 20:1 to about 0.05:1, 10:1 to about 0.5:1, 5:1 to about 1:1, or 3:1 to about 1:1. In certain embodiments, a sterically hindered thiol such as t-BuSH is present in the reaction in a stoichiometric ratio relative to the amino acid comprising conjugation partner of from about 100:1 to 0.05:1, for example about 80:1, about 40:1, or about 3:1.

The inclusion of an acid in some embodiments may also reduce the formation of undesirable by-products. The acid may be a strong inorganic acid, for example HCl, or organic acid, for example TFA. In certain embodiments, the additive is TFA. Without wishing to be bound by theory, the inventors believe that decreasing the pH of the reaction mixture may result in the protonation of electron rich side chains of residues such as lysine, etc. which could otherwise participate in single electron transfers and form radical species in the reaction. In various embodiments, the reaction mixture comprises from about 0.01 to 25, 0.01 to 15, 0.01 to 10, or 1 to 10% v/v acid additive. In certain embodiments, the reaction mixture comprises from 1-10% v/v TFA, for example 5% v/v TFA.

The inventors have found that in some embodiments including both tert-butyl mercaptan and TFA as additives in the reaction mixture can reduce the the formation of undesirable by products and increase the conversion of starting material to the desired product. Accordingly, in certain exemplary embodiments, the reaction mixture comprises a combination of an acid and an exogenous thiol, such as a combination of a strong organic acid and a sterically hindered thiol, for example a combination of TFA and tert-butyl mercaptan.

An organosilane may also be included as an additive in the thiolene reaction. Organosilanes are radical-based reducing agents, the activity of which can be modulated by varying the substituents on the silicon atom. In various embodiments, the organosilane is a compound of the formula $(R^q)_3SiH$, wherein Rq at each instance is independently hydrogen or an organic group, for example alkyl or aryl, provided that at least one Rq is not hydrogen. Examples of organosilanes include but are not limited to triethylsilane (TES), triphenylsilane, diphenylsilane, triisopropylsilane (TIPS), and the like. In various embodiments, the organosilane is a trialkylsilane, for example TIPS or TES.

Without wishing to be bound by theory, the inventors believe that, as with an extraneous thiol, in certain embodiments an organosilane such as TIPS can act as a hydrogen donor to provide the desired compound of formula (IB) and promote propagation of the reaction.

In various embodiments, the organosilane is present in the reaction in a stoichiometric ratio relative to the amino acid comprising conjugation partner of from about 200:1 to about 0.05:1, 100:1 to 0.05:1, 80:1 to 0.05:1, 60:1 to 0.05:1, 40:1 to 0.05:1, 20:1 to 0.05:1, 10:1 to 0.5:1, 5:1 to about 1:1, or 3:1 to about 1:1. In certain embodiments, a trialkylsilane such as TIPS is present in the reaction in a stoichiometric ratio relative to the amino acid comprising conjugation partner of from about 100:1 to 0.05:1, for example about 80:1 or about 40:1.

The organosilane may be used as an additive in combination with an extraneous thiol. Alternatively, the organosilane may be used instead of an extraneous thiol. An acid, such as TFA, may also be present. The inventors have found that in certain embodiments using TIPS in the reaction together with TFA but without any extraneous thiol can provide higher conversion to the desired compound of formula (IB) than when a combination of TIPS, t-BuSH, and TFA are used.

The additive is generally used in an amount sufficient to minimise the formation of undesirable by products without adversely affecting the reaction or any, optional, subsequent steps in the method.

The products formed in the reaction and conversion to the desired product may be determined by, for example, HPLC.

The concentration of the lipid-containing conjugation partners and amino acid-comprising conjugation partner, for example a peptide-containing conjugation partner, respectively, in the reaction mixture may also affect the reaction. Those skilled in the art will be able to vary the concentration of the lipid-containing conjugation partners and peptide-containing conjugation partner in the reaction mixture to e.g. optimise yield and purity without undue experimentation.

In some embodiments, the starting material comprising the thiol is present in a concentration from about 0.05 mM to about 1 M, from about 0.5 mM to about 1 M, from about 1 mM to about 1 M. In some embodiments, the concentration is at least about 0.05 mM, 0.5 mM, or 1 mM.

In some embodiments, the concentration of the starting materials comprising the alkenes is at least about 0.05 mM, 0.5 mM, or 1 mM.

In some embodiments, the amino acid conjugate or peptide conjugate is separated from the reaction medium after the reaction and optionally purified. The conjugate may be separated from the reaction medium using any suitable method known in the art, for example, by precipitation.

In some embodiments, the amino acid or peptide conjugate is purified after separating it from the reaction medium. For example, the conjugate may be purified by HPLC using one or more suitable solvents.

The present invention also provides a method of making a peptide conjugate, the method comprising
    providing an amino acid- or peptide conjugate of the formula (I) of the invention or a salt or solvate thereof, and
    coupling the amino acid of the amino acid conjugate or an amino acid of the peptide conjugate to an amino acid or an amino acid of a peptide to provide a peptide conjugate.

The peptide conjugate produced by and/or the peptide-containing conjugation partner and/or the peptides coupled in the methods of the present invention may comprise a synthetic peptide. Synthetic peptides may be prepared using solid phase peptide synthesis (SPPS).

The basic principle for solid phase peptide synthesis (SPPS) is a stepwise addition of amino acids to a growing polypeptide chain anchored via a linker molecule to a solid phase support, typically a resin particle, which allows for cleavage and purification once the polypeptide chain is complete. Briefly, a solid phase resin support and a starting amino acid are attached to one another via a linker molecule. Such resin-linker-acid matrices are commercially available.

The amino acid to be coupled to the resin is protected at its Na-terminus by a chemical protecting group.

The amino acid may also have a side-chain protecting group. Such protecting groups prevent undesired or deleterious reactions from taking place during the process of forming the new peptide bond between the carboxyl group of the amino acid to be coupled and the unprotected Na-amino group of the peptide chain attached to the resin.

The amino acid to be coupled is reacted with the unprotected Na-amino group of the N-terminal amino acid of the peptide chain, increasing the chain length of the peptide chain by one amino acid. The carboxyl group of the amino acid to be coupled may be activated with a suitable chemical activating agent to promote reaction with the Na-amino group of the peptide chain. The Na-protecting group of N-terminal amino acid of the peptide chain is then removed in preparation for coupling with the next amino acid residue. This technique consists of many repetitive steps making automation attractive whenever possible. Those skilled in the art will appreciate that peptides may be coupled to the Na-amino group of the solid phase bound amino acid or peptide instead of an individual amino acid, for example where a convergent peptide synthesis is desired.

When the desired sequence of amino acids is achieved, the peptide is cleaved from the solid phase support at the linker molecule.

SPPS may be carried out using a continuous flow method or a batch flow method. Continuous flow permits real-time monitoring of reaction progress via a spectrophotometer, but has two distinct disadvantages—the reagents in contact with the peptide on the resin are diluted, and scale is more limited due to physical size constraints of the solid phase resin. Batch flow occurs in a filter reaction vessel and is useful because reactants are accessible and can be added manually or automatically.

Two types of protecting groups are commonly used for protecting the N-alpha-amino terminus: "Boc" (tert-butyloxycarbonyl) and "Fmoc" (9-fluorenylmethyloxycarbonyl). Reagents for the Boc method are relatively inexpensive, but they are highly corrosive and require expensive equipment and more rigorous precautions to be taken. The Fmoc method, which uses less corrosive, although more expensive, reagents is typically preferred.

For SPPS, a wide variety of solid support phases are available. The solid phase support used for synthesis can be a synthetic resin, a synthetic polymer film or a silicon or silicate surface (e.g. controlled pore glass) suitable for synthesis purposes. Generally, a resin is used, commonly polystyrene suspensions, or polystyrene-polyethylenegly-col, or polymer supports for example polyamide. Examples of resins functionalized with linkers suitable for Boc-chemistry include PAM resin, oxime resin SS, phenol resin, brominated Wang resin and brominated PPOA resin. Examples of resins suitable for Fmoc chemistry include amino-methyl polystyrene resins, AMPB-BHA resin, Sieber amide resin, Rink acid resin, Tentagel S AC resin, 2-chlorotrityl chloride resin, 2-chlorotrityl alcohol resin, TentaGel S Trt-OH resin, Knorr-2-chlorotrityl resin, hydrazine-2-chlorotrityl resin, ANP resin, Fmoc photolable resin, HMBA-MBHA resin, TentaGel S HMB resin, Aromatic Safety Catch resinBAI resin and Fmoc-hydroxylamine 2 chlorotrityl resin. Other resins include PL Cl-Trt resin, PL-Oxime resin and PL-HMBA Resin. Generally resins are interchangeable.

For each resin appropriate coupling conditions are known in the literature for the attachment of the starting monomer or sub-unit.

Preparation of the solid phase support includes solvating the support in an appropriate solvent (e.g. dimethylformamide). The solid phase typically increases in volume during solvation, which in turn increases the surface area available to carry out peptide synthesis.

A linker molecule is then attached to the support for connecting the peptide chain to the solid phase support. Linker molecules are generally designed such that eventual cleavage provides either a free acid or amide at the C-terminus. Linkers are generally not resin-specific. Examples of linkers include peptide acids for example 4-hydroxymethylphenoxyacetyl-4'-methylbenzyhydrylamine (HMP), or peptide amides for example benzhydrylamine derivatives.

The first amino acid of the peptide sequence may be attached to the linker after the linker is attached to the solid phase support or attached to the solid phase support using a linker that includes the first amino acid of the peptide sequence. Linkers that include amino acids are commercially available.

The next step is to deprotect the Na-amino group of the first amino acid. For Fmoc SPPS, deprotection of the Na-amino group may be carried out with a mild base treatment (piperazine or piperidine, for example). Side-chain protecting groups may be removed by moderate acidolysis (trifluoroacetic acid (TFA), for example). For Boc SPPS, deprotection of the Na-amino group may be carried out using for example TFA.

Following deprotection, the amino acid chain extension, or coupling, proceeds by the formation of peptide bonds. This process requires activation of the C-a-carboxyl group of the amino acid to be coupled. This may be accomplished using, for example, in situ reagents, preformed symmetrical anhydrides, active esters, acid halides, or urethane-protected N-carboxyanhydrides. The in situ method allows concurrent activation and coupling. Coupling reagents include carbodiimide derivatives, for example N,N'-dicyclohexylcarbodiimide or N,N-diisopropylcarbodiimide. Coupling reagents also include uronium or phosphonium salt derivatives of benzotriazol. Examples of such uronium and phosphonium salts include HBTU (O-1H-benzotriazole-1-yl)-N,N,N',N'-tetramethyluronium hexafluorophosphate), BOP (benzotriazole-1-yl-oxy-tris-(dimethylamino)-phosphonium hexafluorophosphate), PyBOP (Benzotriazole-1-yl-oxytripyrrolidinophosphonium hexafluorophosphate), PyAOP, HCTU (O-(1H-6-chloro-benzotriazole-1-yl)-1,1,3,3-tetramethyluronium hexafluorophosphate), TCTU (O-1H-6-chlorobenzotriazole-1-yl)-1,1,3,3-tetramethyluronium tetrafluoroborate), HATU (O-(7-azabenzotriazol-1-yl)-1,1,3,3-tetramethyluronium hexafluorophosphate), TATU (O-(7-azabenzotriazol-1-yl)-1,1,3,3-tetramethyluronium tetrafluoroborate), TOTU (O-[cyano(ethoxycarbonyl)methyleneamino]-N,N,N',N'''-tetramethyluronium tetrafluoroborate), and HAPyU (O-(benzotriazol-1-yl)oxybis-(pyrrolidino)-uronium hexafluorophosphate. In some embodiments, the coupling reagent is HBTU, HATU, BOP, or PyBOP.

After the desired amino acid sequence has been synthesized, the peptide is cleaved from the resin. The conditions used in this process depend on the sensitivity of the amino acid composition of the peptide and the side-chain protecting groups. Generally, cleavage is carried out in an environment containing a plurality of scavenging agents to quench the reactive carbonium ions that originate from the protective groups and linkers. Common cleaving agents include, for example, TFA and hydrogen fluoride (HF). In some embodiments, where the peptide is bound to the solid phase support via a linker, the peptide chain is cleaved from the solid phase support by cleaving the peptide from the linker.

The conditions used for cleaving the peptide from the resin may concomitantly remove one or more side-chain protecting groups.

The use of protective groups in SPPS is well established. Examples of common protective groups include but are not limited to acetamidomethyl (Acm), acetyl (Ac), adamantyloxy (AdaO), benzoyl (Bz), benzyl (Bzl), 2-bromobenzyl, benzyloxy (BzlO), benzyloxycarbonyl (Z), benzyloxymethyl (Bom), 2-bromobenzyloxycarbonyl (2-Br—Z), tert-butoxy (tBuO), tert-butoxycarbonyl (Boc), tert-butoxymethyl (Bum), tert-butyl (tBu), tert-buthylthio (tButhio), 2-chlorobenzyloxycarbonyl (2-Cl—Z), cyclohexyloxy (cHxO), 2,6-dichlorobenzyl (2,6-DiCl-Bzl), 4,4'-dimethoxybenzhydryl (Mbh), 1-(4,4-dimethyl-2,6-dioxo-cyclohexylidene)3-methyl-butyl (ivDde), 4-{N-[1-(4,4-dimethyl-2,6-dioxo-cyclohexylidene)3-methylbutyl]-amino) benzyloxy (ODmab), 2,4-dinitrophenyl (Dnp), fluorenylmethoxycarbonyl (Fmoc), formyl (For), mesitylene-2-sulfonyl (Mts), 4-methoxybenzyl (MeOBzl), 4-methoxy-2,3,6-trimethyl-benzenesulfonyl (Mtr), 4-methoxytrityl (Mmt), 4-methylbenzyl (MeBzl), 4-methyltrityl (Mtt), 3-nitro-2-pyridinesulfenyl (Npys), 2,2,4,6,7-pentamethyldihydrobenzofurane-5-sulfonyl (Pbf), 2,2,5,7,8-pentamethyl-chromane-6-sulfonyl (Pmc), tosyl (Tos), trifluoroacetyl (Tfa), trimethylacetamidomethyl (Tacm), trityl (Trt) and xanthyl (Xan).

Where one or more of the side chains of the amino acids of the peptide contains functional groups, such as for example additional carboxylic, amino, hydroxy or thiol groups, additional protective groups may be necessary. For example, if the Fmoc strategy is used, Mtr, Pmc, Pbf may be used for the protection of Arg; Trt, Tmob may be used for the protection of Asn and Gln; Boc may be used for the protection of Trp and Lys; tBu may be used for the protection of Asp, Glu, Ser, Thr and Tyr; and Acm, tBu, tButhio, Trt and Mmt may be used for the protection of Cys. A person skilled in the art will appreciate that there are numerous other suitable combinations.

The methods for SPPS outlined above are well known in the art. See, for example, Atherton and Sheppard, "Solid Phase Peptide Synthesis: A Practical Approach," New York: IRL Press, 1989; Stewart and Young: "Solid-Phase Peptide Synthesis 2nd Ed.," Rockford, Ill.: Pierce Chemical Co., 1984; Jones, "The Chemical Synthesis of Peptides," Oxford: Clarendon Press, 1994; Merrifield, J. Am. Soc. 85:2146-2149 (1963); Marglin, A. and Merrifield, R. B. Annu. Rev. Biochem. 39:841-66 (1970); and Merrifield R. B. JAMA. 210(7):1247-54 (1969); and "Solid Phase Peptide Synthesis—A Practical Approach" (W. C. Chan and P. D. White, eds. Oxford University Press, 2000). Equipment for automated synthesis of peptides or polypeptides is readily commercially available from suppliers such as Perkin Elmer/Applied Biosystems (Foster City, Calif.) and may be operated according to the manufacturer's instructions.

Following cleavage from the resin, the peptide may be separated from the reaction medium, e.g. by centrifugation or filtration. The peptide may then be subsequently purified, e.g. by HPLC using one or more suitable solvents.

Advantageously, the inventors have found that in some embodiments the peptide-containing conjugation partner may be used in the methods of the present invention without purification following cleavage of the peptide from the resin.

The inventors have also advantageously found that in some embodiments the thiolene method of the present invention can be carried out using a peptide-containing conjugation partner, wherein the peptide does not contain an Na-amino group protecting group or any side chain protecting groups. The reaction is generally selective for reaction of a thiol and a non-aromatic carbon-carbon double bond.

It may be necessary to protect thiol groups present in the peptide-containing conjugation partner (e.g. in cysteine residues of the peptide) with a protective group to prevent undesirable competing reactions in the methods of the present invention. The thiol groups may be protected with a protective group that is not removable under the conditions used to remove one or more other protecting groups present in the peptide or to cleave the peptide from the resin.

Typically, the peptide will be synthesised using amino acids bearing the appropriate protecting groups. A person skilled in the art will be able to select appropriate protecting groups without undue experimentation.

The amino acid-comprising conjugation partner and/or lipid-containing conjugation partners may comprise one or more unsaturated carbon-carbon bonds in addition to the carbon-carbon double bonds of the lipid containing conjugation partners to be reacted. Those skilled in the art will appreciate that the selectivity of the thiol for the carbon-carbon double bond to be reacted in such embodiments may depend on, for example, the steric and/or electronic environment of the carbon-carbon double bond relative to the one or more additional unsaturated carbon-carbon bonds. In certain embodiments, the carbon-carbon double bonds to be reacted are activated relative to any other unsaturated carbon-carbon bonds in the amino acid-comprising conjugation partner and lipid-containing conjugation partner. In certain embodiments, the carbon-carbon double bonds to be reacted are activated relative to any other unsaturated carbon-carbon bonds in the peptide-containing conjugation partner and lipid-containing conjugation partner.

In some embodiments, the Na-amino group of the amino acid of the amino acid-comprising conjugation partner comprising the thiol is acylated, for example acetylated. In some embodiments, the methods of the present invention may comprise acylating, for example acetylating, the Na-amino group of the amino acid of the amino acid-comprising conjugation partner comprising the carbon-carbon double bond or thiol to be reacted.

Where a peptide-containing conjugation partner has been synthesised by SPPS, acylation may be carried out prior to or after cleavage from the resin. In some embodiments, the amino acid residue of the peptide-containing conjugation partner bearing the thiol to be reacted is an N-terminal amino acid residue, for example cysteine, and the method comprises acylating the N-terminal amino group prior to cleaving the peptide.

In some embodiments, the method further comprises acylating, for example acetylating, the Na-amino group of the amino acid of the amino acid conjugate or the amino acid residue of the peptide conjugate to which the lipid moieties are conjugated.

Acylation of the Na-amino group of an amino acid may be carried out by reacting an amino acid or peptide with an acylating agent in the presence of base in a suitable solvent, for example DMF. Non-limiting examples of acylating agents include acid halides, for example acid chlorides such as acetyl chloride, and acid anhydrides, for example acetic anhydride. Such agents maybe commercially available or may be prepared by methods well known in the art. Non-limiting examples of suitable bases include triethylamine, diisopropylethylamine, 4-methylmorpholine, and the like.

In other embodiments, the synthesising the peptide of the peptide-containing conjugation partner comprises coupling an amino acid or a peptide comprising an amino acid that is acylated, for example acetylated, at the Nα-amino group and comprises the thiol to be reacted to one or more amino acids and/or one or more peptides.

In some embodiments, the method comprises coupling the amino acid of the amino acid conjugate to an amino acid or a peptide to provide a peptide conjugate. In some embodiments, the method comprises coupling the amino acid of the amino acid conjugate to an amino acid or peptide bound to a solid phase resin support by SPPS. In some embodiments, the method comprises coupling the amino acid of the amino acid conjugate to a peptide bound to a solid phase resin support by SPPS. The method may comprise synthesising the peptide bound to the solid phase resin support by SPPS.

In some embodiments, the method further comprises coupling the amino acid of the amino acid conjugate or an amino acid of the peptide conjugate to an amino acid or a peptide so as to provide a peptide conjugate comprising a peptide epitope. In some embodiments, the peptide to be coupled comprises a peptide epitope. In other embodiments, a peptide epitope is formed on coupling. The coupling may be carried out by SPPS as described herein.

In some embodiments, the method comprises coupling the amino acid of the amino acid conjugate to a peptide bound to a solid phase resin support by SPPS so as to provide a peptide conjugate comprising a peptide epitope.

In one embodiment, the peptide of the peptide conjugate to be coupled is bound to a solid phase resin support, and the method comprises coupling an amino acid of the peptide conjugate to be coupled to an amino acid or a peptide so as to provide a peptide conjugate comprising a peptide epitope.

In an alternate embodiment, the method comprises coupling an amino acid of the peptide conjugate to an amino acid or peptide bound to a solid phase resin support by SPPS so as to provide peptide conjugate comprising a peptide epitope.

In some embodiments, the method further comprises coupling an epitope, for example a peptide epitope, to the amino acid conjugate or peptide conjugate. Where the method comprises coupling a peptide epitope, the coupling may be carried out by SPPS as described herein.

In certain embodiments, the epitope, for example a peptide epitope, is coupled or bound via a linker group. In certain embodiments, the linker group is an amino sequence, for example a sequence of two or more, three or more, or four or more contiguous amino acids. In certain embodiments, the linker comprises from about 2 to 20, 2 to 18, 2 to 16, 2 to 14, 2 to 12, 2 to 10, 4 to 20, 4 to 18, 4 to 16, 4 to 14, 4 to 12, or 4 to 10 amino acids.

It will be appreciated by those skilled in the art that coupling an amino acid or a peptide to another amino acid or peptide as described herein may comprise forming a peptide bond between the Nα-terminus of the amino acid or an amino acid of the peptide of one coupling partner and the C-terminus of the amino acid or an amino acid of the peptide of the other coupling partner.

In the method of the present invention comprises synthesising the amino acid sequence of the peptide of the peptide-containing conjugation partner by SPPS; and reacting the peptide-containing conjugation partner.

In some embodiments, the method of the present invention comprises synthesising the amino acid sequence of the peptide of the peptide-containing conjugation partner by SPPS; and reacting the lipid-containing conjugation partners with the peptide-containing conjugation partner.

In some embodiments, synthesising the amino acid sequence of the peptide of the peptide-containing conjugation partner by SPPS comprises coupling an amino acid or peptide to an amino acid or peptide bound to a solid phase resin support to provide the amino acid sequence of the peptide or a portion thereof. In certain embodiments, the amino acid sequence of the entire peptide of the peptide-containing conjugation partner is synthesised by SPPS.

The peptide-containing conjugation partner may be reacted, for example with the lipid-containing conjugation partners in the thiolene method, while bound to a solid phase resin support. Alternatively, the peptide may be cleaved from the solid phase resin support, and optionally purified, prior to reaction, for example with the lipid-containing conjugation partners.

The peptide conjugate and/or amino acid-comprising conjugation partner, for example a peptide-containing conjugation partner, may comprise one or more solubilising groups. The one or more solubilising groups increase the solubility of, for example, the peptide-containing conjugation partner in polar solvents, such as water. In exemplary embodiments, the solubilising group does not adversely affect the biological activity of the peptide conjugate.

The presence of a solubilising group may be advantageous for formulation and/or administration of the peptide conjugate as a pharmaceutical composition.

In some embodiments, the solubilising group is bound to the peptide of the peptide conjugate and/or peptide-containing conjugation partner. In some embodiments, the solubilising group is bound to the peptide of the peptide-containing conjugation partner. In some embodiments, the peptide of the peptide conjugate and/or the peptide of the peptide-containing partner comprises a solubilising group. In some embodiments, the peptide of the peptide-containing partner comprises a solubilising group.

In some embodiments, the solubilising group is bound to the side chain of an amino acid in the peptide chain. In some embodiments, the solubilising group is bound to the C- or N-terminus of the peptide chain. In some embodiments, the solubilising group is bound between two amino acid residues in the peptide chain. In some embodiments, the solubilising group is bound to the Nα-amino group of one amino acid residue in the peptide chain and the carboxyl group of another amino acid residue in the peptide chain.

Examples of suitable solubilising groups include, but are not limited to, hydrophilic amino acid sequences or polyethylene glycols (PEGs).

In one embodiment, the solubilising group is a hydrophilic amino acid sequence comprising two or more hydrophilic amino acid residues in the peptide chain. In some embodiments, the solubilising group is an amino acid sequence comprising a sequence of two or more consecutive hydrophilic amino acid residues in the peptide chain. Such solubilising groups may be formed by adding each amino acid of the solubilising group to the peptide chain by SPPS.

In another embodiment, the solubilising group is a polyethylene glycol. In some embodiments, the polyethylene glycol is bound to the Nα-amino group of one amino acid residue in the peptide chain and the carboxyl group of another amino acid residue in the peptide chain.

In some embodiments, the polyethylene glycol comprises from about 1 to about 100, about 1 to about 50, about 1 to about 25, about 1 to about 20, about 1 to about 15, about 1 to about 15, about 1 to about 10, about 2 to about 10, or about 2 to about 4 ethylene glycol monomer units. Methods for coupling polyethylene glycols to peptides are known.

In some embodiments, the peptide conjugate and/or peptide-containing conjugation partner comprises an antigen, for example, an antigenic peptide. In one embodiment, the peptide of the peptide conjugate or peptide-containing conjugation partner is or comprises an antigen; or an antigen is bound to peptide, optionally via a linker. In some embodiments, the peptide-containing conjugation partner comprises an antigen, for example, an antigenic peptide. In one embodiment, the peptide of the peptide-containing conjugation partner is or comprises an antigen; or an antigen is bound to peptide, optionally via a linker.

In one embodiment, the antigen comprises a peptide comprising an epitope. In one embodiment, the peptide comprising an epitope is a glycopeptide comprising an epitope. In one embodiment, the antigen comprises a glycopeptide comprising an epitope.

In some embodiments, the peptide conjugate and/or peptide-containing conjugation partner comprises an epitope. In some embodiments, the peptide of the peptide conjugate and/or peptide-containing conjugation partner comprises an epitope. In some embodiments, the peptide-containing conjugation partner comprises an epitope. In some embodiments, the peptide of the peptide-containing conjugation partner comprises an epitope.

In some embodiments, the peptide conjugate and/or peptide-containing conjugation partner comprises two or more epitopes, for example, the peptide of the peptide conjugate and/or peptide-containing conjugation partner comprises two or more epitopes.

In some embodiments, the peptide conjugate and/or peptide-containing conjugation partner is or comprises a glycopeptide comprising an epitope. In some embodiments, the peptide of the peptide conjugate and/or peptide-containing conjugation partner is a glycopeptide. In some embodiments, the peptide conjugate and/or peptide-containing conjugation partner comprises a glycopeptide comprising an epitope bound to the peptide of the peptide conjugate and/or peptide-containing conjugation partner. In some embodiments, the peptide-containing conjugation partner is or comprises a glycopeptide comprising an epitope. In some embodiments, the peptide of the peptide-containing conjugation partner is a glycopeptide. In some embodiments, the peptide-containing conjugation partner comprises a glycopeptide comprising an epitope bound to the peptide of the peptide-containing conjugation partner.

In some embodiments, the peptide conjugate and/or peptide-containing conjugation partner comprises a proteolytic cleavage site. In some embodiments, the peptide of the peptide conjugate and/or peptide-containing conjugation partner comprises a proteolytic cleavage site. In some embodiments, the peptide-containing conjugation partner comprises a proteolytic cleavage site. In some embodiments, the peptide of the peptide-containing conjugation partner comprises a proteolytic cleavage site.

In some embodiments, the peptide of the peptide conjugate and/or peptide-containing conjugation partner comprises one or more linker groups. In some embodiments, the peptide of the peptide-containing conjugation partner comprises one or more linker groups.

In some embodiments, the peptide conjugate and/or peptide-containing conjugation partner comprises a linker group. In some embodiments, the peptide-containing conjugation partner comprises a linker group.

In some embodiments, the peptide conjugate and/or peptide-containing conjugation partner comprises an epitope bound to the peptide of the peptide conjugate and/or peptide-containing conjugation partner via a linker group. In some embodiments, the peptide-containing conjugation partner comprises an epitope bound to the peptide of the peptide-containing conjugation partner via a linker group.

Examples of linker groups include but are not limited to amino acid sequences (for example, a peptide), polyethylene glycol, alkyl amino acids, and the like. In some embodiments, the linker is or comprises a proteolytic cleavage site. In some embodiments, the linker is or comprises a solubilising group.

In some embodiments, the linker is bound between two amino acid residues in the peptide chain.

In some embodiments, the linker group is bound to the Na-amino group of one amino acid residue in the peptide conjugate and/or peptide-containing conjugation partner and the carboxyl group of another amino acid residue in the peptide-containing conjugation partner. In some embodiments, the linker group is bound to the Na-amino group of one amino acid residue in the peptide-containing conjugation partner and the carboxyl group of another amino acid residue in the peptide-containing conjugation partner.

In certain embodiments, the linker group is cleavable in vivo from the amino acids to which it is bound. In certain embodiments, the linker group is cleavable by hydrolysis in vivo. In certain embodiments, the linker group is cleavable by enzymatic hydrolysis in vivo. Linker groups may be introduced by any suitable method known in the art.

The method may further comprise coupling an epitope to the amino acid of the amino acid conjugate or the peptide of the peptide conjugate. The epitope may be bound via a linker group, as described above. In some embodiments, the epitope is a peptide epitope. In some embodiments, the method comprises coupling a glycopeptide comprising an epitope.

It will be appreciated that in certain desirable embodiments, the peptide conjugates of the invention maintain appropriate uptake, processing, and presentation by antigen presenting cells. Desirably, the lipid-containing conjugate does not interfere with presentation of any antigenic peptide present in the conjugate by antigen presenting cells. The examples presented herein establish that conjugates of the invention are presented by antigen presenting cells comparably with non-conjugated, related peptides.

Confirmation of the identity of the peptides synthesized may be conveniently achieved by, for example, amino acid analysis, mass spectrometry, Edman degradation, and the like.

The method of the present invention may further comprise separating the amino acid conjugate from the liquid reaction medium. Alternatively, the method of the present invention may further comprise separating the peptide conjugate from the liquid reaction medium. Any suitable separation methods known in the art may be used, for example, precipitation and filtration. The conjugate may be subsequently purified, for example, by HPLC using one or more suitable solvents.

The present invention also relates to amino acid conjugates and peptide conjugates made by the methods of the present invention.

The present invention also relates to a compound of the formula (I), which is an amino acid conjugate.

The present invention also relates to a compound of the formula (I), which is a peptide conjugate.

The peptide conjugates may be pure or purified, or substantially pure.

As used herein "purified" does not require absolute purity; rather, it is intended as a relative term where the material in question is more pure than in the environment it was in previously. In practice the material has typically, for example, been subjected to fractionation to remove various other components, and the resultant material has substantially retained its desired biological activity or activities. The term "substantially purified" refers to materials that are at least about 60% free, preferably at least about 75% free, and most preferably at least about 90% free, at least about 95% free, at least about 98% free, or more, from other components with which they may be associated during manufacture.

The term "a-amino acid" or "amino acid" refers to a molecule containing both an amino group and a carboxyl group bound to a carbon which is designated the a-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

In certain embodiments the peptide-containing conjugation partner comprises only natural amino acids. The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" or "non-naturally occurring amino acid" refers to a molecule which is structurally similar to an amino acid and which can be substituted for an amino acid. Amino acid analogs include, without limitation, compounds which are structurally identical to an amino acid, as defined herein, except for the inclusion of one or more additional methylene groups between the amino and carboxyl group (e.g., a-amino β-carboxy acids), or for the substitution of the amino or carboxy group by a similarly reactive group (e.g., substitution of the primary amine with a secondary or tertiary amine, or substitution or the carboxy group with an ester or carboxamide).

Unless otherwise indicated, conventional techniques of molecular biology, microbiology, cell biology, biochemistry and immunology, which are within the skill of the art may be employed in practicing the methods described herein. Such techniques are explained fully in the literature, such as, Molecular Cloning: A Laboratory Manual, second edition (Sambrook et al., 1989); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); The Immunoassay Handbook (David Wild, ed., Stockton Press NY, 1994); Antibodies: A Laboratory Manual (Harlow et al., eds., 1987); and Methods of Immunological Analysis (R. Masseyeff, W. H. Albert, and N. A. Staines, eds., Weinheim: VCH Verlags gesellschaft mbH, 1993).

The term "peptide" and the like is used herein to refer to any polymer of amino acid residues of any length. The polymer can be linear or non-linear (e.g., branched), it can comprise modified amino acids or amino acid analogs. The term also encompasses amino acid polymers that have been modified naturally or by intervention, for example, by disulfide bond formation, glycosylation, lipidation, acetylation, phosphorylation, or any other modification or manipulation, for example conjugation with labeling or bioactive components.

The inventors have found that peptide conjugates of the present invention have immunological activity.

Cell-mediated immunity is primarily mediated by T-lymphocytes. Pathogenic antigens are expressed on the surface of antigen presenting cells (such as macrophages, B-lymphocytes, and dendritic cells), bound to either major histocompatibility MHC Class I or MHC Class II molecules. Presentation of pathogenic antigen coupled to MHC Class II activates a helper (CD4+) T-cell response. Upon binding of the T-cell to the antigen-MHC II complex, CD4+ T-cells, release cytokines and proliferate.

Presentation of pathogenic antigens bound to MHC Class I molecules activates a cytotoxic (CD8+) T-cell response. Upon binding of the T-cell to the antigen-MHC I complex, CD8+ cells secrete perforin and other mediators, resulting in target cell death. Without wishing to be bound by any theory, the applicants believe that in certain embodiments an enhanced response by CD8+ cells is achieved in the presence of one or more epitopes recognised by CD4+ cells.

Methods to assess and monitor the onset or progression of a cell-mediated response in a subject are well known in the art. Convenient exemplary methods include those in which the presence of or the level of one or more cytokines associated with a cell-mediated response, such as those identified herein, is assessed. Similarly, cell-based methods to assess or monitor the onset and progression of a cell-mediated response are amenable to use in the present invention, and may include cell proliferation or activation assays, including assays targeted at identifying activation or expansion of one or more populations of immune cells, such as T-lymphocytes.

In certain embodiments, methods of the invention elicit both a cell-mediated immune response and a humoral response.

The humoral immune response is mediated by secreted antibodies produced by B cells. The secreted antibodies bind to antigens presented on the surface of invading pathogens, flagging them for destruction.

Again, methods to assess and monitor the onset or progression of a humoral response are well known in the art. These include antibody binding assays, ELISA, skin-prick tests and the like.

Without wishing to be bound by theory, the inventors believe that the peptide conjugates in some embodiments stimulate Toll like receptors (TLRs).

Toll-like receptors (TLRs) are highly conserved pattern recognition receptors (PRRs) that recognise pathogen-associated molecular patterns and transmit danger signals to the cell (Kawai, T., Akira, S., *Immunity* 2011, 34, 637-650). TLR2 is a cell-surface receptor expressed on a range of different cell types, including dendritic cells, macrophages and lymphocytes (Coffman, R. L., Sher, A., Seder, R. A., *Immunity* 2010, 33, 492-503).

TLR2 recognises a wide range of microbial components including lipopolysaccharides, peptidoglycans and lipoteichoic acid. It is unique amongst TLRs in that it forms heterodimers, with either TLR1 or TLR6; the ability to form complexes with other PRRs may explain the wide range of agonists for TLR2 (Feldmann, M., Steinman, L., *Nature* 2005, 435, 612-619). Upon ligand binding and heterodimerisation, signalling takes place via the MyD88 pathway, leading to NFκB activation and consequent production of inflammatory and effector cytokines.

Di- and triacylated lipopeptides derived from bacterial cell-wall components have been extensively studied as TLR2 agonists (Eriksson, E. M. Y., Jackson, D. C., *Curr. Prot. and Pept. Sci.* 2007, 8, 412-417). Lipopeptides have been reported to promote dendritic cell maturation, causing the up-regulation of co-stimulatory molecules on the cell surface and enhanced antigen-presentation. Lipopeptides have also been reported to stimulate macrophages to release cytokines and promote the activation of lymphocytes including B cells and CD8+ T cells.

In some embodiments, the peptide conjugate has TLR2 agonist activity. In some embodiments, the peptide conjugate has TLR2 agonist activity comparable to Pam3CSK4. In some embodiments, the peptide conjugate has TLR2 agonist activity at least about 50%, about 60%, about 70%, about 80%, about 90% that of Pam3CSK4. In some embodiments, for example in embodiments where a modulated immune response is desirable, the peptide conjugate has TLR2 agonist activity less that that of Pam3CSK4. For example, the peptide conjugate has TLR2 agonist activity less than about 50%, less than about 40%, less than about 30%, less than about 20%, or less than about 10% that of Pam3CSK4.

In some embodiments, the peptide of the peptide conjugate and/or peptide-containing conjugation partner comprises a serine amino acid residue adjacent to the amino acid through which the lipid moieties are conjugated to the peptide. In some embodiments, the serine is bound to the C-termini of the amino acid. The presence of the serine amino acid residue in this position may enhance TLR2 binding.

As will be appreciated by those skilled in the art on reading this disclosure, the peptide conjugate may comprise an epitope, including, for example two or more epitopes. The epitope may be coupled or bound to the peptide via a linker group. In some embodiments, the epitope is a peptide epitope. A person skilled in the art will appreciate that a wide range of peptide epitopes may be employed in the present invention.

Antigens

It will be appreciated that a great many antigens, for example tumour antigens or antigens from various pathogenic organisms, have been characterised and are suitable for use in the present invention. All antigens, whether or not presently characterized, that are capable of eliciting an immune response are contemplated.

Accordingly, depending on the choice of antigen the conjugates of the present invention find application in a wide range of immunotherapies, including but not limited to the treatment and prevention of infectious disease, the treatment and prevention of cancer, and the treatment of viral re-activation during or following immunosuppression, for example in patients who have had bone marrow transplants or haematopoietic stem cell transplants.

Also contemplated are antigens comprising one or more amino acid substitutions, such as one or more conservative amino acid substitutions.

A "conservative amino acid substitution" is one in which an amino acid residue is replaced with another residue having a chemically similar or derivatised side chain. Families of amino acid residues having similar side chains, for example, have been defined in the art. These families include, for example, amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid analogs (e.g., phosphorylated or glycosylated amino acids) are also contemplated in the present invention, as are peptides substituted with non-naturally occurring amino acids, including but not limited to N-alkylated amino acids (e.g. N-methyl amino acids), D-amino acids, β-amino acids, and γ-amino acids.

Fragments and variants of antigens are also specifically contemplated.

A "fragment" of a peptide, is a subsequence of the peptide that performs a function that is required for the enzymatic or binding activity and/or provides three dimensional structure of the peptide, such as the three dimensional structure of a polypeptide.

The term "variant" as used herein refers to peptide sequences, including for example peptide sequences different from the specifically identified sequences, wherein one or more amino acid residues is deleted, substituted, or added. Variants are naturally-occurring variants, or non-naturally occurring variants. Variants are from the same or from other species and may encompass homologues, paralogues and orthologues. In certain embodiments, variants of peptides including peptides possess biological activities that are the same or similar to those of the wild type peptides. The term "variant" with reference to peptides encompasses all forms of peptides as defined herein.

Those of skill in the art will appreciate that the conjugates of the present invention are in certain embodiments particularly suited for stimulating T-cell responses, for example in the treatment of neoplastic diseases, including cancer. Conjugates of the present invention comprising one or more tumour antigens are specifically contemplated. It will be appreciated that tumour antigens contemplated for use in the preparation of peptide conjugates of the invention will generally comprise one or more peptides. In certain embodiments of the invention, including for example pharmaceutical compositions of the invention, one or more additional tumour antigens may be present, wherein the one or more tumour antigens does not comprise peptide. Tumour antigens are typically classified as either unique antigens, or shared antigens, with the latter group including differentiation antigens, cancer-specific antigens, and over-expressed antigens. Examples of each class of antigens are amenable to use in the present invention. Representative tumour antigens for use in the treatment, for example immunotherapeutic treatment, or vaccination against neoplastic diseases including cancer, are discussed below. Compounds, vaccines and compositions comprising one or more antigens prepared using those methods of immunisation are specifically contemplated.

In certain embodiments, the tumour antigen is a peptide-containing tumour antigen, such as a polypeptide tumour antigen or glycoprotein tumour antigens. In certain embodiments, the tumour antigen is a saccharide-containing tumour antigen, such as a glycolipid tumour antigen or a ganglioside tumour antigen. In certain embodiments, the tumour antigen is a polynucleotide-containing tumour antigen that expresses a polypeptide-containing tumour antigen, for instance, an RNA vector construct or a DNA vector construct, such as plasmid DNA.

Tumour antigens appropriate for the use in the present invention encompass a wide variety of molecules, such as (a) peptide-containing tumour antigens, including peptide epitopes (which can range, for example, from 8-20 amino acids in length, although lengths outside this range are also common), lipopolypeptides and glycoproteins, (b) saccharide-containing tumour antigens, including poly-saccharides, mucins, gangliosides, glycolipids and glycoproteins, including and (c) polynucleotides that express antigenic polypeptides. Again, those skilled in the art will recognise that a tumour antigen present in a conjugate or composition of the present invention will typically comprise peptide. However, embodiments of the invention where one or more conjugates comprises a tumour antigen that does not itself comprise peptide, but for example is bound to the amino acid-comprising or peptide-containing conjugation partner, are contemplated. Similarly, compositions of the invention in which one or more tumour antigens that does not itself comprise peptide is present are contemplated.

In certain embodiments, the tumour antigens are, for example, (a) full length molecules associated with cancer cells, (b) homologues and modified forms of the same, including molecules with deleted, added and/or substituted portions, and (c) fragments of the same, provided said fragments remain antigenic or immunogenic. In certain embodiments, the tumour antigens are provided in recombinant form. In certain embodiments, the tumour antigens include, for example, class I-restricted antigens recognized by CD8+ lymphocytes or class II-restricted antigens recognized by CD4+ lymphocytes. In certain embodiments, tumor antigens include synthetic peptides comprising class I-restricted antigens recognized by CD8+ lymphocytes or class II-restricted antigens recognized by CD4+ lymphocytes.

Shared tumour antigens are generally considered to be native, unmutated sequences that are expressed by tumours due to epigenetic changes that allow de-repression of developmentally-repressed genes. Accordingly, shared antigens are typically considered preferable to over-expressed or differentiation-associated antigens because there is no expression in normal tissues. Also, the same antigens can be targeted in a number of cancer patients. For example, the cancer-testis antigen NY-ESO-1 is present in the majority of patients with many tumours, and a sizeable minority of patients with other tumours. In another example, breast differentiation tumour antigens NYBR-1 and NYBR-1.1 are found in a proportion of breast cancer sufferers. Shared tumour antigens thus represent an attractive target for development.

The use of shared tumour antigens, such cancer-testis antigens including NY-ESO-1, CTSP-1, CTSP-2, CTSP-3, CTSP-4, SSX2, and SCP1, and breast cancer antigens NYBR-1 and NYBR-1.1, in conjugates of the present invention is specifically contemplated herein.

In one exemplary embodiment, the peptide of the peptide-containing conjugation partner or of the peptide conjugate comprises one or more epitopes derived from NY-ESO-1. In one embodiment, the peptide comprises one or more epitopes derived from NY-ESO-1 residues 79-116. In one embodiment, the peptide comprises one or more epitopes derived from NY-ESO-1 residues 118-143. In one embodiment, the peptide comprises one or more epitopes derived from NY-ESO-1 residues 153-180.

In one specifically contemplated embodiment, the peptide of the peptide-containing conjugation partner or of the peptide conjugate, comprises, consists essentially of, or consists of an amino acid sequence selected from the group consisting of 8 or more contiguous, 10 or more contiguous, 12 or more contiguous, 15 or more contiguous, 20 or more contiguous, or 25 or more contiguous amino acids from any one of SEQ ID NOs: 1 to 20.

In various embodiments, the peptide comprises more that one amino acid sequence selected from the group consisting of any one of SEQ ID NOs: 1 to 20. In one embodiment, the peptide comprises one or more amino acid sequences selected from the group consisting of SEQ ID NOs: 4-7, 12, 13, and 18-20.

Similarly, the prostate vaccine Sipuleucel-T (APC8015, Provenge™), which comprises the antigen prostatic acid phosphatase (PAP), is present in 95% of prostate cancer cells. At least in part due to this potential for efficacy in a significant proportion of prostate cancer sufferers, Sipuleucel-T was approved by the FDA in 2010 for use in the treatment of asymptomatic, hormone-refractory prostate cancer. The use of PAP antigen in conjugates of the present invention is specifically contemplated in the present invention.

Unique antigens are considered to be those antigens that are unique to an individual or are shared by a small proportion of cancer patients, and typically result from mutations leading to unique protein sequences. Representative examples of unique tumour antigens include mutated Ras antigens, and mutated p53 antigens. As will be appreciated by those skilled in the art having read this specification, the methods of the present invention enable the ready preparation of conjugates comprising one or more unique tumour antigens, for example to elicit specific T-cell responses to one or more unique tumour antigens, for example in the preparation of patient-specific therapies.

Accordingly, representative tumour antigens include, but are not limited to, (a) antigens such as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumours), (b) mutated antigens, for example, p53 (associated with various solid tumours, for example, colorectal, lung, head and neck cancer), p21/Ras (associated with, for example, melanoma, pancreatic cancer and colorectal cancer), CDK4 (associated with, for example, melanoma), MUM1 (associated with, for example, melanoma), caspase-8 (associated with, for example, head and neck cancer), CIA 0205 (associated with, for example, bladder cancer), HLA-A2-R1701, beta catenin (associated with, for example, melanoma), TCR (associated with, for example, T-cell non-Hodgkins lymphoma), BCR-abl (associated with, for example, chronic myelogenous leukemia), triosephosphate isomerase, MA 0205, CDC-27, and LDLR-FUT, (c) over-expressed antigens, for example, Galectin 4 (associated with, for example, colorectal cancer), Galectin 9 (associated with, for example, Hodgkin's disease), proteinase 3 (associated with, for example, chronic myelogenous leukemia), Wilm's tumour antigen-1 (WT 1, associated with, for example, various leukemias), carbonic anhydrase (associated with, for example, renal cancer), aldolase A (associated with, for example, lung cancer), PRAME (associated with, for example, melanoma), HER-2/neu (associated with, for example, breast, colon, lung and ovarian cancer), alpha-fetoprotein (associated with, for example, hepatoma), KSA (associated with, for example, colorectal cancer), gastrin (associated with, for example, pancreatic and gastric cancer), telomerase catalytic protein, MUC-1 (associated with, for example, breast and ovarian cancer), G-250 (associated with, for example, renal cell carcinoma), p53 (associated with, for example, breast, colon cancer), and carcinoembryonic antigen (associated with, for example, breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, for example, melanoma), (e) prostate associated antigens such as PAP, prostatic serum antigen (PSA), PSMA, PSH-P1, PSM-P1, PSM-P2, associated with for example, prostate cancer, (f) immunoglobulin idiotypes (associated with myeloma and B cell lymphomas, for example), and (g) other tumour antigens, such as polypeptide- and saccharide-containing antigens including (i) glycoproteins such as sialyl Tn and sialyl Le.sup.x (associated with, for example, breast and colorectal cancer) as well as various mucins; glycoproteins are coupled to a carrier protein (for example, MUC-1 are coupled to KLH); (ii) lipopolypeptides (for example, MUC-1 linked to a lipid moiety); (iii) polysaccharides (for example, Globo H synthetic hexasaccharide), which are coupled to a carrier proteins (for example, to KLH), (iv) gangliosides such as GM2, GM12, GD2, GD3 (associated with, for example, brain, lung cancer, melanoma), which also are coupled to carrier proteins (for example, KLH).

Other representative tumour antigens amenable to use in the present invention include TAG-72, (See, e.g., U.S. Pat. No. 5,892,020; human carcinoma antigen (See, e.g., U.S. Pat. No. 5,808,005); TP1 and TP3 antigens from osteocarcinoma cells (See, e.g., U.S. Pat. No. 5,855,866); Thomsen-Friedenreich (TF) antigen from adenocarcinoma cells (See, e.g., U.S. Pat. No. 5,110,911); KC-4 antigen from human prostate adenocarcinoma (See, e.g., U.S. Pat. No. 4,743,543); a human colorectal cancer antigen (See, e.g., U.S. Pat. No. 4,921,789); CA125 antigen from cystadenocarcinoma (See, e.g., U.S. Pat. No. 4,921,790); DF3 antigen from human breast carcinoma (See, e.g., U.S. Pat. Nos. 4,963,484 and 5,053,489); a human breast tumour antigen (See, e.g., U.S. Pat. No. 4,939,240); p97 antigen of human melanoma (See, e.g., U.S. Pat. No. 4,918,164); carcinoma or orosomucoid-related antigen (CORA) (See, e.g., U.S. Pat. No. 4,914,021); T and Tn haptens in glycoproteins of human breast carcinoma, MSA breast carcinoma glycoprotein; MFGM breast carcinoma antigen; DU-PAN-2 pancreatic carcinoma antigen; CA125 ovarian carcinoma antigen; YH206 lung carcinoma antigen, Alphafetoprotein (AFP) hepatocellular carcinoma antigen; Carcinoembryonic antigen (CEA) bowel cancer antigen; Epithelial tumour antigen (ETA) breast cancer antigen; Tyrosinase; the raf oncogene product; gp75; gp100; EBV-LMP 1 & 2; EBV-EBNA 1, 2 & 3C; HPV-E4, 6, 7; C017-1A; GA733; gp72; p53; proteinase 3; telomerase; and melanoma gangliosides. These and other tumour antigens, whether or not presently characterized, are contemplated for use in the present invention.

In certain embodiments, the tumour antigens are derived from mutated or altered cellular components. Representative examples of altered cellular components include, but are not limited to ras, p53, Rb, altered protein encoded by the Wilms' tumour gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Polynucleotide-containing antigens used in the present invention include polynucleotides that encode polypeptide tumour antigens such as those listed above. In certain embodiments, the polynucleotide-containing antigens include, but are not limited to, DNA or RNA vector constructs, such as plasmid vectors (e.g., pCMV), which are capable of expressing polypeptide tumour antigens in vivo.

The present invention also contemplates the preparation of conjugates comprising viral antigens that are capable of stimulating T-cell to elicit effective anti-viral immunity in patients who are or have been immunosuppressed, for example patients who have had bone marrow transplants, haematopoietic stem cell transplants, or are otherwise undergoing immunosuppression.

Similarly, antigens derived from viruses associated with increased incidence of cancer, or that are reported to be cancer-causing, such as human papillomavirus, hepatitis A virus, and hepatitis B virus, are contemplated for use in the present invention.

For example, in certain embodiments, the tumour antigens include, but are not limited to, p15, Hom/Mel-40, H-Ras, E2A-PRL, H4-RET, IGH-IGK, MYL-RAR, Epstein Barr virus antigens, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

In certain embodiments, the tumour antigens include viral proteins implicated in oncogenesis, such as antigens from Epstein Barr virus, human papillomavirus (HPV), including E6 and E7, and hepatitis B and C, and human T-cell lymphotropic virus.

It will be appreciated that such viral proteins, as well as various other viral proteins can also be targets for T cell activity in, for example, treatment against viral disease. In fact, the present invention may be useful in any infection where T cell activity is known to play a role in immunity (effectively all virus infections and many bacterial infections as well, such as tuberculosis). The infectious diseases described herein are provided by way of example only and are in no way intended to limit the scope of the invention. It will be appreciated that the present invention may be useful in the treatment of various other diseases and conditions.

Representative antigens for use in vaccination against pathogenic organisms are discussed below. Compounds, vaccines and compositions comprising one or more antigens prepared using those methods of immunisation are specifically contemplated.

Tuberculosis Antigens

It will be appreciated that a great many *M. tuberculosis* antigens have been characterised and are suitable for use in the present invention. All *M. tuberculosis* antigens, whether or not presently characterized, that are capable of eliciting an immune response are contemplated.

Exemplary *M. tuberculosis* antigens suitable for use include early secretary antigen target (ESAT)-6, Ag85A, Ag85B (MPT59), Ag85B, Ag85C, MPT32, MPT51, MPT59, MPT63, MPT64, MPT83, MPB5, MPB59, MPB64, MTC28, Mtb2, Mtb8.4, Mtb9.9, Mtb32A, Mtb39, Mtb41, TB10.4, TB10C, TB11B, TB12.5, TB13A, TB14, TB15, TB15A, TB16, TB16A, TB17, TB18, TB21, TB20.6, TB24, TB27B, TB32, TB32A, TB33, TB38, TB40.8, TB51, TB54, TB64, CFP6, CFP7, CFP7A, CFP7B, CFP8A, CFP8B, CFP9, CFP10, CFP11, CFP16, CFP17, CFP19, CFP19A, CFP19B, CFP20, CFP21, CFP22, CFP22A, CFP23, CFP23A, CFP23B, CFP25, CFP25A, CFP27, CFP28, CFP28B, CFP29, CFP30A, CFP30B, CFP50, CWP32, hspX (alpha-crystalline), APA, Tuberculin purified protein derivative (PPD), ST-CF, PPE68, LppX, PstS-1, PstS-2, PstS-3, HBHA, GroEL, GroEL2, GrpES, LHP, 19 kDa lipoprotein, 71 kDa, RD1-ORF2, RD1-ORF3, RD1-ORF4, RD1-ORF5, RD1-ORF8, RD1-ORF9A, RD1-ORF9B, Rv1984c, Rv0577, Rv1827, BfrB, Tpx. Rv1352, Rv1810, PpiA, Cut2, FbpB, FbpA, FbpC, DnaK, FecB, Ssb, RplL, FixA, FixB, AhpC2, Rv2626c, Rv1211, Mdh, Rv1626, Adk, ClpP, SucD (Belisle et al, 2005; U.S. Pat. No. 7,037,510; US 2004/0057963; US 2008/0199493; US 2008/0267990), or at least one antigenic portion or T-cell epitope of any of the above mentioned antigens.

Hepatitis Antigens

A number of hepatitis antigens have been characterised and are suitable for use in the present invention. Exemplary hepatitis C antigens include C—p22, E1—gp35, E2—gp70, NS1—p7, NS2—p23, NS3—p70, NS4A—p8, NS4B—p27, NS5A—p56/58, and NS5B—p68, and together with one or more antigenic portions or epitopes derived therefrom are each (whether alone or in combination) suitable for application in the present invention. All hepatitis antigens, whether or not presently characterized, that are capable of eliciting an immune response are contemplated.

Influenza Antigens

Many influenza antigens have been characterised and are suitable for use in the present invention. Exemplary influenza antigens suitable for use in the present invention include PB, PB2, PA, any of the hemagglutinin (HA) or neuramimidase (NA) proteins, NP, M, and NS, and together with one or more antigenic portions or epitopes derived therefrom are each (whether alone or in combination) suitable for application in the present invention. All influenza antigens, whether or not presently characterized, that are capable of eliciting an immune response are contemplated.

Anthrax Antigens

A number of B. anthracis antigens have been identified as potential candidates for vaccine development and are useful in the present invention. For example, PA83 is one such antigen for vaccine development. Currently, only one FDA licensed vaccine for anthrax is available called "Anthrax Vaccine Adsorbed" (AVA) or BioThrax®. This vaccine is derived from the cell-free supernatant of a non-encapsulated strain of B. anthracis adsorbed to aluminum adjuvant. PA is the primary immunogen in AVA. Other exemplary anthrax antigens suitable for use in the present invention include Protective antigen (PA or PA63), LF and EF (proteins), poly-gamma-(D-glutamate) capsule, spore antigen (endospore specific components), BclA (exosporium specific protein), BxpB (spore-associated protein), and secreted proteins. All anthrax antigens together with one or more antigenic portions or epitopes derived therefrom, whether or not presently characterized, that are capable of eliciting an immune response are contemplated.

Tularemia Antigens

A number of F. tularensis antigens have been identified as potential candidates for vaccine development and are useful in the present invention. For example, AcpA and IglC are antigens suitable for vaccine development. Other exemplary Tularemia antigens suitable for use in the present invention include O-antigen, CPS, outer membrane proteins (e.g. FopA), lipoproteins (e.g. Tul4), secreted proteins and lipopolysaccharide. All tularemia antigens together with one or more antigenic portions or epitopes derived therefrom, whether or not presently characterized, that are capable of eliciting an immune response are contemplated.

Brucellosis Antigens

A number of B. abortusis antigens have been identified as potential candidates for vaccine development and are useful in the present invention. For example, Omp16 is one such antigen for vaccine development. Other exemplary Brucellosis antigens suitable for use in the present invention include O-antigen, lipopolysaccharide, outer membrane proteins (e.g. Omp16), secreted proteins, ribosomal proteins (e.g. L7 and L12), bacterioferritin, p39 (a putative periplasmic binding protein), groEL(heat-shock protein), lumazine synthase, BCSP31 surface protein, PAL16.5 OM lipoprotein, catalase, 26 kDa periplasmic protein, 31 kDa Omp31, 28 kDa Omp, 25 kDa Omp, and 10 kDA Om lipoprotein. All brucellosis antigens together with one or more antigenic portions or epitopes derived therefrom, whether or not presently characterized, that are capable of eliciting an immune response are contemplated.

Meningitis Antigens

A number of N. meningitidis antigens have been identified as potential candidates for vaccine development and are useful in the present invention. For example, Cys6, PorA, PorB, FetA, and ZnuD are antigens suitable for vaccine development. Other exemplary Meningitis antigens suitable for use in the present invention include O-antigen, factor H binding protein (fHbp), TbpB, NspA, NadA, outer membrane proteins, group B CPS, secreted proteins and lipopolysaccharide. All menigitis antigens together with one or more antigenic portions or epitopes derived therefrom, whether or not presently characterized, that are capable of eliciting an immune response are contemplated.

Dengue Antigens

A number of Flavivirus antigens have been identified as potential candidates for vaccine development to treat dengue fever and are useful in the present invention. For example, dengue virus envelope proteins E1-E4 and the membrane proteins M1-M4 are antigens suitable for vaccine development. Other exemplary dengue antigens suitable for use in the present invention include C, preM, 1, 2A, 2B, 3, 4A, 4B and 5. All dengue antigens together with one or more antigenic portions or epitopes derived therefrom, whether or not presently characterized, that are capable of eliciting an immune response are contemplated.

Ebola Antigens

A number of ebola virus antigens have been identified as potential candidates for vaccine development to treat ebola infection and are useful in the present invention. For example, Filoviridae Zaire ebolavirus and Sudan ebolavirus virion spike glycoprotein precursor antigens ZEBOV-GP, and SEBOV-GP, respectively, are suitable for vaccine development. Other exemplary ebola antigens suitable for use in the present invention include NP, vp35, vp40, GP, vp30, vp24 and L. All ebola antigens together with one or more antigenic portions or epitopes derived therefrom, whether or not presently characterized, that are capable of eliciting an immune response are contemplated.

West Nile Antigens

A number of West Nile virus antigens have been identified as potential candidates for vaccine development to treat infection and are useful in the present invention. For example, Flavivirus envelope antigen (E) from West Nile virus (WNV) is a non-toxic protein expressed on the surface of WNV virions (WNVE) and are suitable for vaccine development. Other exemplary WNV antigens suitable for use in the present invention include Cp, Prm, NS1, NS2A, NS2B, NS3, NS4A, NS4B and NS5.

All West Nile antigens together with one or more antigenic portions or epitopes derived therefrom, whether or not presently characterized, that are capable of eliciting an immune response are contemplated.

The above-listed or referenced antigens are exemplary, not limiting, of the present invention.

The present invention also relates to pharmaceutical composition comprising an effective amount of a peptide conjugate of the present invention or a pharmaceutically acceptable salt or solvent thereof, and a pharmaceutically acceptable carrier.

The pharmaceutical compositions may comprise an effective amount of two or more peptide conjugates of the invention in combination. In some embodiments, the pharmaceutical compositions may comprise one or more peptide conjugates of the invention and one or more peptides as described herein.

The term "pharmaceutically acceptable carrier" refers to a carrier (adjuvant or vehicle) that may be administered to a subject together with the peptide conjugate of the present invention, or a pharmaceutically acceptable salt or solvent thereof, and a pharmaceutically acceptable carrier.

Pharmaceutically acceptable carriers that may be used in the compositions include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as a-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery. Oil solutions or suspensions may also contain a long-chain alcohol diluent or dispersant, or carboxymethyl cellulose or similar dispersing agents, which are commonly used in the formulation of pharmaceutically acceptable dosage forms such as emulsions and or suspensions.

The compositions are formulated to allow for administration to a subject by any chosen route, including but not limited to oral or parenteral (including topical, subcutaneous, intramuscular and intravenous) administration.

For example, the compositions may be formulated with an appropriate pharmaceutically acceptable carrier (including excipients, diluents, auxiliaries, and combinations thereof) selected with regard to the intended route of administration and standard pharmaceutical practice. For example, the compositions may be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

The compositions may be formulated to optimize bioavailability, immunogenicity, or to maintain plasma, blood, or tissue concentrations within the immunogenic or therapeutic range, including for extended periods. Controlled delivery preparations may also be used to optimize the antigen concentration at the site of action, for example.

The compositions may be formulated for periodic administration, for example to provide continued exposure. Strategies to elicit a beneficial immunological response, for example those that employ one or more "booster" vaccinations, are well known in the art, and such strategies may be adopted.

The compositions may be administered via the parenteral route. Examples of parenteral dosage forms include aqueous solutions, isotonic saline or 5% glucose of the active agent, or other well-known pharmaceutically acceptable excipients. Cyclodextrins, for example, or other solubilising agents well-known to those familiar with the art, can be utilized as pharmaceutical excipients for delivery of the therapeutic agent.

Examples of dosage forms suitable for oral administration include, but are not limited to tablets, capsules, lozenges, or like forms, or any liquid forms such as syrups, aqueous solutions, emulsions and the like, capable of providing a therapeutically effective amount of the composition. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent.

Examples of dosage forms suitable for transdermal administration include, but are not limited, to transdermal patches, transdermal bandages, and the like.

Examples of dosage forms suitable for topical administration of the compositions include any lotion, stick, spray, ointment, paste, cream, gel, etc., whether applied directly to the skin or via an intermediary such as a pad, patch or the like.

Examples of dosage forms suitable for suppository administration of the compositions include any solid dosage form inserted into a bodily orifice particularly those inserted rectally, vaginally and urethrally.

Examples of dosage of forms suitable for injection of the compositions include delivery via bolus such as single or multiple administrations by intravenous injection, subcutaneous, subdermal, and intramuscular administration or oral administration.

Examples of dosage forms suitable for depot administration of the compositions and include pellets of the peptide conjugates or solid forms wherein the peptide conjugates are entrapped in a matrix of biodegradable polymers, microemulsions, liposomes or are microencapsulated.

Examples of infusion devices for the compositions include infusion pumps for providing a desired number of doses or steady state administration, and include implantable drug pumps.

Examples of implantable infusion devices for compositions include any solid form in which the peptide conjugates are encapsulated within or dispersed throughout a biodegradable polymer or synthetic, polymer such as silicone, silicone rubber, silastic or similar polymer.

Examples of dosage forms suitable for transmucosal delivery of the compositions include depositories solutions for enemas, pessaries, tampons, creams, gels, pastes, foams, nebulised solutions, powders and similar formulations containing in addition to the active ingredients such carriers as are known in the art to be appropriate. Such dosage forms include forms suitable for inhalation or insufflation of the compositions, including compositions comprising solutions and/or suspensions in pharmaceutically acceptable, aqueous, or organic solvents, or mixture thereof and/or powders. Transmucosal administration of the compositions may utilize any mucosal membrane but commonly utilizes the nasal, buccal, vaginal and rectal tissues. Formulations suitable for nasal administration of the compositions may be administered in a liquid form, for example, nasal spray, nasal drops, or by aerosol administration by nebulizer, including aqueous or oily solutions of the polymer particles. Formulations may be prepared as aqueous solutions for example in saline, solutions employing benzyl alcohol or other suitable preservatives, absorption promoters to enhance bio-availability, fluorocarbons, and/or other solubilising or dispersing agents known in the art.

Examples of dosage forms suitable for buccal or sublingual administration of the compositions include lozenges, tablets and the like. Examples of dosage forms suitable for opthalmic administration of the compositions include inserts and/or compositions comprising solutions and/or suspensions in pharmaceutically acceptable, aqueous, or organic solvents.

Examples of formulations of compositions, including vaccines, may be found in, for example, Sweetman, S. C. (Ed.). Martindale. The Complete Drug Reference, 33rd Edition, Pharmaceutical Press, Chicago, 2002, 2483 pp.; Aulton, M. E. (Ed.) Pharmaceutics. The Science of Dosage Form Design. Churchill Livingstone, Edinburgh, 2000, 734 pp.; and, Ansel, H. C., Allen, L. V. and Popovich, N. G. Pharmaceutical Dosage Forms and Drug Delivery Systems, 7th Ed., Lippincott 1999, 676 pp. Excipients employed in the manufacture of drug delivery systems are described in various publications known to those skilled in the art including, for example, Kibbe, E. H. Handbook of Pharmaceutical Excipients, 3rd Ed., American Pharmaceutical Association, Washington, 2000, 665 pp. The USP also provides examples of modified-release oral dosage forms, including those formulated as tablets or capsules. See, for example, The United States Pharmacopeia 23/National Formulary 18, The United States Pharmacopeial Convention, Inc., Rockville Md., 1995 (hereinafter "the USP"), which also describes specific tests to determine the drug release capabilities of extended-release and delayed-release tablets and capsules. The USP test for drug release for extended-release and delayed-release articles is based on drug dissolution from the dosage unit against elapsed test time. Descriptions of various test apparatus and procedures may be found in the USP. Further guidance concerning the analysis of extended release dosage forms has been provided by the F.D.A. (See Guidance for Industry. Extended release oral dosage forms: development, evaluation, and application of in vitro/in vivo correlations. Rockville, Md.: Center for Drug Evaluation and Research, Food and Drug Administration, 1997).

While the composition may comprise one or more extrinsic adjuvants, advantageously in some embodiments this is not necessary. In some embodiments, the peptide conjugate comprises an epitope and is self adjuvanting.

The present invention provides a method of vaccinating or eliciting an immune response in a subject comprising administering to the subject an effective amount of a peptide conjugate of the present invention. The present invention also relates to use of a peptide conjugate of the invention for vaccinating or eliciting an immune response in a subject, and to use of a peptide conjugate of the invention in the manufacture of a medicament for vaccinating or eliciting an immune response in a subject.

The present invention also provides a method of vaccinating or eliciting an immune response in a subject comprising administering to the subject an effective amount of the pharmaceutical composition of the present invention. The present invention also relates to use of a pharmaceutical composition of the invention for vaccinating or eliciting an immune response in a subject, and to the use of one or more peptide conjugates of the present invention in the manufacture of a medicament for vaccinating or eliciting an immune response in a subject.

The administration or use of one or more peptides described herein and/or one or more peptide conjugates of the present invention, for example one or more peptide described herein in together with one or more peptide conjugates, for vaccinating or eliciting an immune response in the subject is contemplated herein.

Where two or more peptide conjugates, or one or more peptides and one or more peptide conjugates are administered or used, the two or more peptide conjugates, or one or more peptides and one or more peptide conjugates may be administered or used simultaneously, sequentially, or separately.

A "subject" refers to a vertebrate that is a mammal, for example, a human. Mammals include, but are not limited to, humans, farm animals, sport animals, pets, primates, mice and rats.

An "effective amount" is an amount sufficient to effect beneficial or desired results including clinical results. An effective amount can be administered in one or more administrations by various routes of administration.

The effective amount will vary depending on, among other factors, the disease indicated, the severity of the disease, the age and relative health of the subject, the potency of the compound administered, the mode of administration and the treatment desired. A person skilled in the art will be able to determine appropriate dosages having regard to these any other relevant factors.

The efficacy of a composition can be evaluated both in vitro and in vivo. For example, the composition can be tested in vitro or in vivo for its ability to induce a cell-mediated immune response. For in vivo studies, the composition can be fed to or injected into an animal (e.g., a mouse) and its effects on eliciting an immune response are then assessed. Based on the results, an appropriate dosage range and administration route can be determined.

The composition may be administered as a single dose or a multiple dose schedule. Multiple doses may be used in a primary immunisation schedule and/or in a booster immunisation schedule.

In certain embodiments, eliciting an immune response comprises raising or enhancing an immune response. In exemplary embodiments, eliciting an immune response comprises eliciting a humoral and a cell mediated response.

In certain embodiments, eliciting an immune response provides immunity.

The immune response is elicited for treating a disease or condition. A person skilled in the art will appreciate that the peptide conjugates described herein are useful for treating a variety of diseases and conditions, depending, for example, on the nature of epitope.

In some embodiments, the diseases or conditions are selected from those associated with the various antigens described herein.

In some embodiments an infectious disease, cancer, or viral re-activation post-bone marrow transplant or following induction of profound immunosuppression for any other reason.

The term "treatment", and related terms such as "treating" and "treat", as used herein relates generally to treatment, of a human or a non-human subject, in which some desired therapeutic effect is achieved. The therapeutic effect may, for example, be inhibition, reduction, amelioration, halt, or prevention of a disease or condition.

The compositions may be used to elicit systemic and/or mucosal immunity. Enhanced systemic and/or mucosal immunity may be reflected in an enhanced TH1 and/or TH2 immune response. The enhanced immune response may include an increase in the production of IgG1 and/or IgG2a and/or IgA.

EXAMPLES

1. Example 1

This example describes the preparation of a peptide conjugate of the invention 3 via a thiol-ene reaction.

1.1 General Details and Methods

Protected amino acids and coupling reagents were purchased from GL-Biochem (Shanghai). The resins used in the solid-supported syntheses were tentagel resins derivatised with a linker and the first (C-terminal) residue of the peptide sequence from Rapp Polymere GmbH (Tuebingen) and other solvents and reagents were obtained from Sigma (St Louis, Mo.) and Novabiochem.

The peptide synthesis described below was carried out using standard iterative Fmoc Solid-Phase Peptide Synthesis techniques on a Tribute peptide synthesiser (Protein Technologies International, Tucson, Ariz.).

A typical deprotection and coupling cycle carried out on a 0.1 mmol scale entailed removal of the Fmoc protecting group from the resin-bound amino-acid using two treatments of 20% piperidine in DMF (4 mL×5 min) then washing the resin with DMF. In a separate vessel the Fmoc amino acid (0.5 mmol) and coupling agent (1-[bis(dimethylamino)methylene]-1H-1,2,3-triazolo[4,5-b]pyridinium 3-oxid hexafluorophosphate (HATU), 0.45 mmol) were dissolved in DMF (1.5 mL) and base (4-methylmorpholine (NMM), 1 mmol) added. After mixing for 1 minute, this solution was transferred to the resin, which was agitated at room temperature (RT) for 1 hour, drained and washed.

Cleavage of the peptide (0.1 mmol scale) was achieved by suspending the resin in 5 mL trifluoroacetic acid (TFA) containing 5% (v/v) ethanedithiol (EDT) and agitating at room room temperature for 3 hours. Triisopropylsilane (TIPS) was then added to 1% (v/v) and agitation continued for a further five minutes before draining the TFA into chilled diethyl ether (40 mL). The precipitated material was pelleted by centrifugation, the ether discarded, the pellet washed once with ether (25 mL) and air-dried or lyophilised.

Reverse phase (RP)-HPLC was carried out using a Dionex Ultimate 3000 HPLC system. with UV detection at 210 nm or 225 nm. For semi-preparative purifications, a peptide sample was injected into a reverse-phase Phenomenex Gemini C18 column (5μ, 110 Å; 10×250 mm) equilibrated in a suitable mixture of eluent A (water/0.1% TFA) and eluent B (MeCN/0.1% TFA) then an increasing gradient of eluent B was generated to elute the constituent components. Analytical HPLC was performed similarly, using a Phenomenex Gemini C18 column (3p, 110 Å; 4.6×150 mm).

Low-resolution mass spectra were obtained using an Agilent Technologies 6120 Quadrapole mass spectrometer.

NMR spectra were obtained using a Bruker BRX400 spectrometer operating at 400 MHz for $^1$H NMR and at 100 MHz for $^{13}$C NMR.

1.2 Peptide Synthesis

Peptide 1 (sequence given in Table 1) was synthesised as described above in the general details and depicted below (Scheme 1).

The peptide is a combination of the well-known CMV pp65 peptide (NLVPMVATV [SEQ ID No: 122]), wherein the methionine residue is replaced with a Cys(tBu) residue to avoid unwanted side reactions at this location in the thiol-ene reaction, derivatised on the N-terminus with a polylysine solubilizing tag and a free thiol group.

Scheme 1

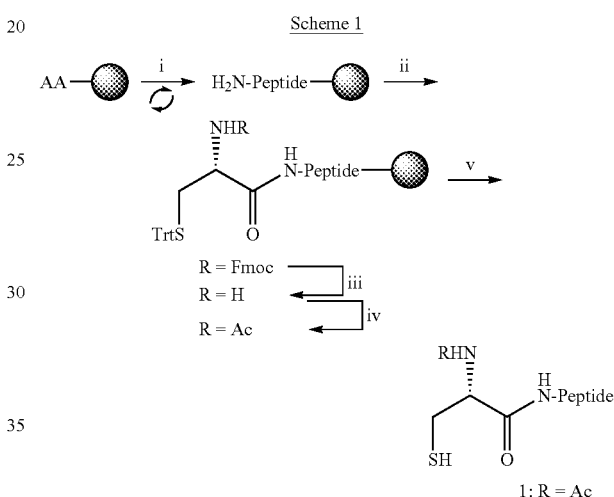

● = resin
AA = amino acid
(i) Iterative Fmoc-SPPS; (ii) Fmoc-Cys(Trt)-OH, HATU, NMM, DMF; (iii) 20% piperidine/DMF; (iv) Ac$_2$O/NMM, DMF; (v) TFA/EDT.

Following synthesis of the peptide sequence up to the penultimate amino acid using iterative Fmoc-SPPS, Fmoc-cysteine was introduced as the N-terminal residue of the on-resin peptide by reaction with Fmoc-Cys(Trt)-OH, HATU, and 4-methylmorpholine in DMF. The Fmoc group was removed using 20% piperidine in DMF.

The resulting amine group was converted to an acetamide by treatment with a mixture of 20% acetic anhydride in DMF (2 mL) and 4-methylmorpholine (1 mmol).

Following cleavage of the peptide from resin with TFA/EDT and its precipitation in ether, the solid was dissolved in 1:1 water/MeCN and lyophilised. The peptide was then purified by RP-HPLC to give material of >95%.

TABLE 1

Peptide 1

| Sequence | m/z | SEQ ID No. |
|---|---|---|
| 1 Ac-CSKKKKNLVPC(tBu)VATV | 999.9 [M + 2H$^+$] | 123 |

1.3 Peptide Conjugate Synthesis

Peptide conjugate 3 was synthesised from peptide 1 via a thiol-ene reaction as described and depicted below (Scheme 2).

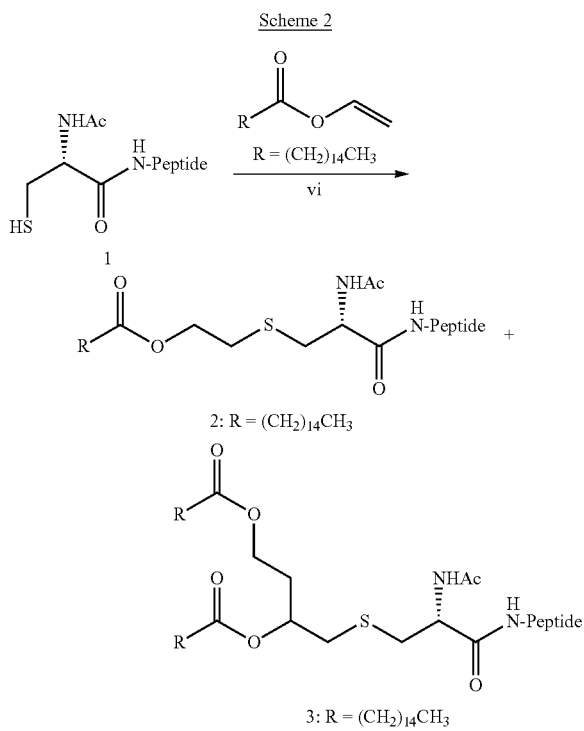

(vi) vinylpalmitate, DMPA, tBuSH, NMP, 365 nm, 83% conversion based on HPLC (49% 2; 34% 3).

Peptide substrate 1 (1.7 mg, 1 μmol) and vinyl palmitate (20 mg, 70 μmol, seventy equivalents) were weighed into a small polypropylene vial equipped with a magnetic stirrer bar and 100 μL degassed NMP added followed by 0.5 μmol DMPA and 3 μmol tBuSH (by adding 10 μL of a solution of 6.5 mg DMPA and 17 μL tBuSH in 0.5 mL degassed NMP). The vessel was flushed with nitrogen and irradiated for 30 minutes at 365 nm with vigorous stirring of the mixture.

Analysis of a sample of the reaction mixture by HPLC (see FIG. 1) indicated some residual starting material (peak a) and the formation of both the mono-pamitoylated peptide 2 and bis-pamitoylated peptide 3 (peaks b and c respectively).

Water and acetonitrile (200 μL of each) were added, the resulting mixture lyophilized and the components isolated by semi-preparative RP-HPLC.

1.4 Analysis of Peptide Conjugate 3

Figure 2:
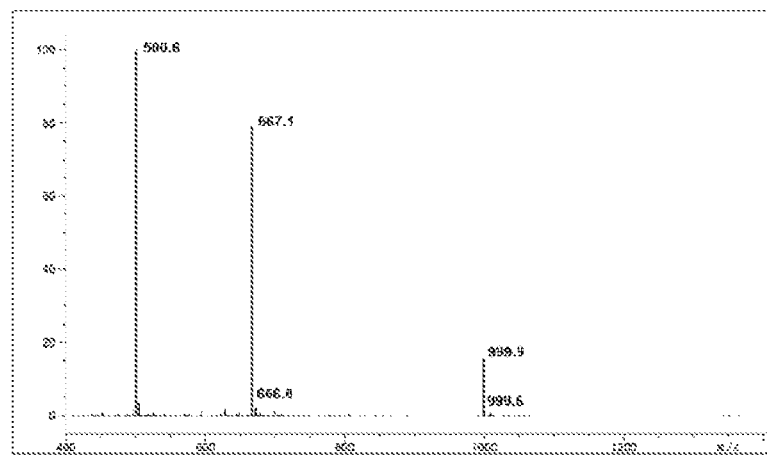
FIG. 2 is a low-resolution mass spectrum of peak b from FIG. 1: m/z (ESI) 999.9 [M+2H$^+$].
Figure 3:
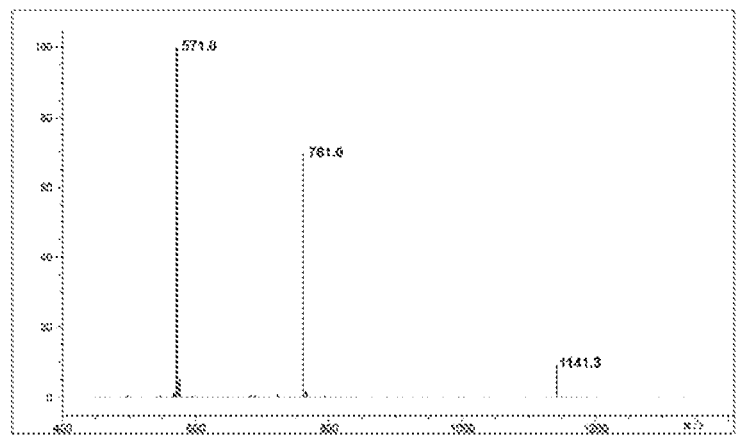
FIG. 3 is a low-resolution mass spectrum of peak c from FIG. 1: m/z (ESI) 1141.3 [M+2H$^+$].

The low-resolution mass spectra of peaks b and c from FIG. 1 are shown in FIGS. 2 and 3, respectively.

The mass spectrum of peak c confirms the introduction of a second 2-(palmitoyloxy)ethyl group to the peptide substrate (M+282).

Without wishing to be bound by theory, the it is believed that following irradiation of the reaction mixture containing the thiolated peptide, the thiyl radical that is generated then reacts with a molecule of vinyl palmitate to afford a radical intermediate 4 (Scheme 3) which then either (i) is quenched to give the mono-palmitoylated product 2, or (ii) reacts with another molecule of vinyl palmitate to give the more nonpolar bis-palmitoylated product 3. The two pathways are believed to be competitive, with the concentrations of vinyl palmitate used in this experiment (seventy equivalents) favouring telomerisation to provide 3. No higher order propagations (i.e. no products resulting from the addition of more than two molecules of vinyl palmitate) were observed.

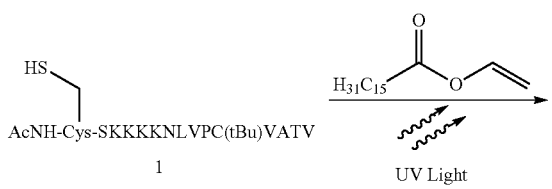

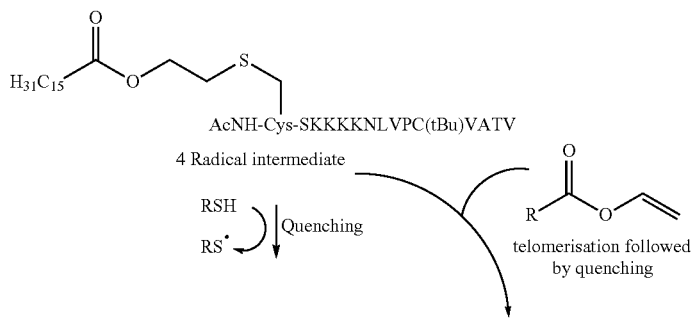

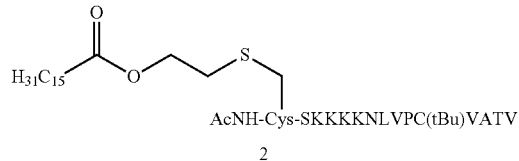
AcNH-Cys-SKKKKNLVPC(tBu)VATV
2

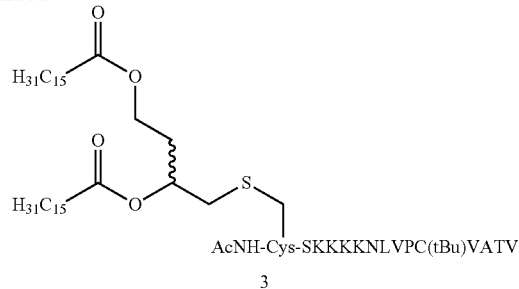
AcNH-Cys-SKKKKNLVPC(tBu)VATV
3

Some oxidation of products 2 and 3 was evident (FIG. 1 peaks e and f both M+16), presumably on the newly formed thioether. This is may be due to the difficulty of excluding oxygen from the small-scale system being used. These oxides can easily be reduced to the corresponding thioethers.

2. Example 2

This example investigates:
1. Murine and human TLR2 agonism of the present invention in two variations—homoPam2Cys(NH$_2$)-SKKKK and homoPam2Cys(NHAc)-SKKKK—as compared with known TLR2 agonists Pam1Cys-SKKK, Pam2Cys-SKKKK and Pam3Cys-SKKKK. In all cases agonists were prepared in-house and isolated via semi-preparative HPLC as described for Example 1, with the exception of Pam3Cys-SKKK which was purchased from InvivoGen. Further, retention of TLR2 agonism when conjugated to a short peptide epitope was assessed relative to Pam3Cys-SKKKK. In this example homoPam2Cys(NHAc)-SKKK-'NLV' was produced as described for present invention 3 (isolated by semi-preparative HPLC as described in Example 1) with the exception that the conjugate peptide sequence was NLVPMVATVK(Ac). A matched Pam2Cys-SKKKK-NLVPMVATVK(Ac) was also prepared.

2. Release and presentation of conjugated short synthetic peptides and long synthetic peptides to a cognate CD8+ T-cell clone. In this example homoPam2Cys(NHAc)-SKKKK-'NLV' was produced as described for present invention 3 (isolated by semi-preparative HPLC as described in Example 1) with the exception that the conjugate peptide sequence was NLVPMVATVK(Ac) rather than NLVP(Tbu)VATVK(Ac), in order to retain T-cell recognition of the peptide. Release and presentation was compared to that elicited by peptide-matched Pam1Cys-SKKKK and Pam2Cys-SKKKK constructs.
3. Processing and presentation of conjugated long synthetic peptide to a cognate CD8+ T-cell clone. homoPam2Cys(NHAc)-SKKK-'VPG' was produced as described for present invention 3 (isolated by semi-preparative HPLC as described in Example 1) with the exception that the conjugate peptide sequence was VPGVLLKEFTVSGNILTIRLTAADHR (SEQ ID No: 113). Processing and presentation of the HLA-A2-restricted epitope EFTVSGNIL (SEQ ID No: 114) from within this longer sequence was compared to that observed with long peptide only and by a peptide-matched Pam1Cys-SKKKK construct.

All constructs utilised in investigating TLR2 agonism and peptide processing and presentation to CD8+ T-cells are designated as in Table 2 below:

TABLE 2

| | Peptide conjugates | |
|---|---|---|
| Lipid/linker No. Component | Peptide | Peptide SEQ ID No. |
| 500 — | VPGVLLKEFTVSGNILTIRLTAADHR | 113 |
| 510 Pam1Cys-SKKKK | — | |
| 511 Pam1Cys-SKKKK | NLVPMVATVK(Ac) | 122 |
| 512 Pam1Cys-SKKKK | VPGVLLKEFTVSGNILTIRLTAADHR | 113 |
| 520 Pam2Cys-SKKKK | NA | |
| 521 Pam2Cys-SKKKK | NLVPMVATVK(Ac) | 122 |
| 530 Pam3Cys-SKKKK | — | |
| 540 Homo-Pam2Cys(NH$_2$)-SKKKK | — | |
| 550 Homo-Pam2Cys(NHAc)-SKKKK | — | |

TABLE 2-continued

Peptide conjugates

| No. | Lipid/linker Component | Peptide | Peptide SEQ ID No. |
|---|---|---|---|
| 551 | Homo-Pam2Cys(NHAc)-SKKKK | NLVPMVATVK(Ac) | 122 |
| 552 | Homo-Pam2Cys(NHAc)-SKKKK | VPGVLLKEFTVSGNILTIRLTAADHR | 113 |

Scheme 3A. Structures of Pam1Cys, Pam2Cys, homoPam2Cys(NH₂) and homoPam2Cys(NHAc) referred to in Table 2.

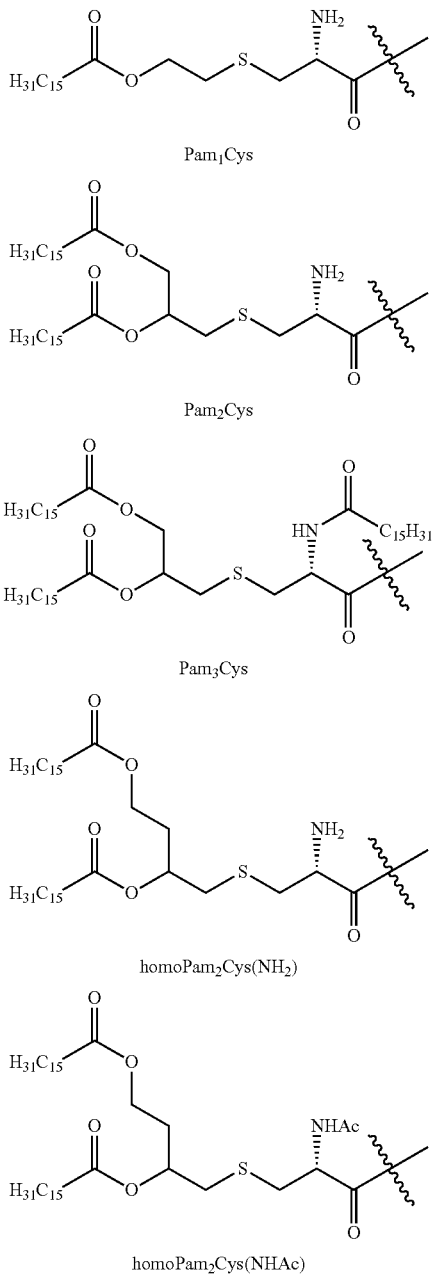

2.1 Toll-Like Receptor 2 (TLR2) Agonism Using HekBlue Cells

HEK-Blue™ Detection medium, HEK-Blue™-hTLR2 and HEK-Blue™-mTLR2 were purchased from Invivogen. These HEK-Blue cells were produced by co-transfection of both reporter gene SEAP (secreted embryonic alkaline phosphatase) and either human or murine TLR2, respectively. The SEAP reporter gene is under the control of the IFN-B minimal promoter fused to five AP-1 and five NFkB binding sites. Cells were cultured according to manufacturer's instructions.

On the day of the assay, TLR agonists 510, 520, 530, 540, 550 or PBS (negative control) were added at the indicated concentrations in 20 µl volume of endotoxin free water in a 96-well plate. HEK-Blue™-hTLR2 or HEK-Blue™-hTLR2 cells were resuspended at ~2.78×10⁵ cells/ml in HEK-Blue™ Detection medium and 180 µl of the cell suspension added to each well (~5×10⁴ cells). Cells were incubated for 10-12 h at 37° C. in 5% $CO_2$. SEAP expression was quantified using an EnSpire plate reader (PerkinElmer) at 635 nM. Data presented as mean+/−SD ABS or mABS (635 nm) values for triplicate wells following background subtraction.

2.2.1 Results

Figure 4A:
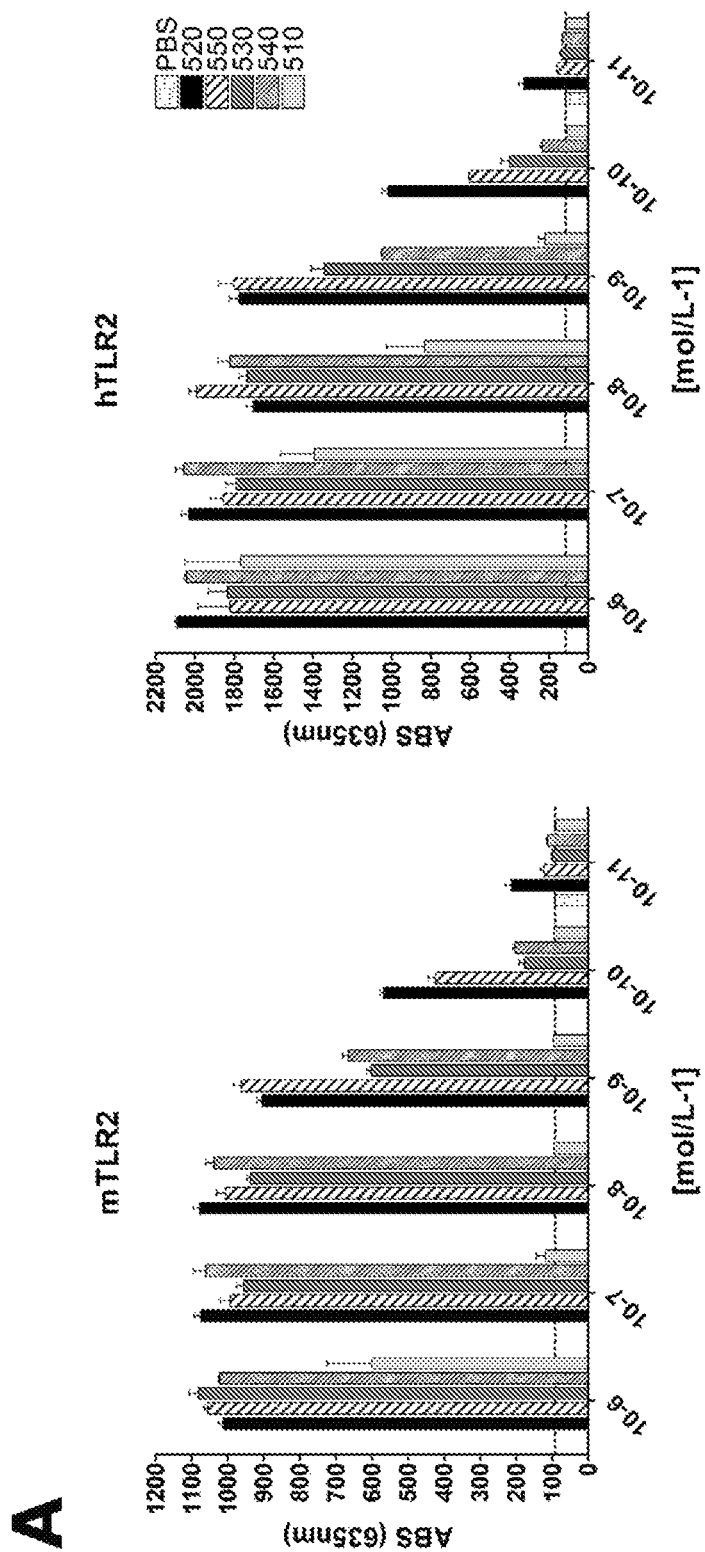
FIGS. 4A-4C are graphs showing the results of the TLR agonism assay using the peptide conjugates and HekBlue™, as described herein in the Examples. A: SEAP production in HEK-Blue™-mTLR2 cells (left) and HEK-Blue™-hTLR2 cells (right) elicited by agonists 520, 550, 530, 540, 510 or PBS. B: SEAP production in HEK-Blue™-mTLR2 cells (left) and HEK-Blue™-hTLR2 cells (right) elicited by agonists 520 (grey bars) and 530 (black bars). C: SEAP production in HEK-Blue™-mTLR2 cells (left) and HEK-Blue™-hTLR2 cells (right) elicited by agonists 550 (grey bars) and 530 (black bars).

In both HEK-Blue™-mTLR2 and HEK-Blue™-hTLR2 homoPam2Cys(NHAc)-SKKKK elicited equivalent SEAP production to the most potent agonist tested (Pam2Cys-SKKKK) at ≥1 nM and comparable production at sub-nM concentrations (FIG. 4A). In both systems homoPam2Cys(NHAc)-SKKKK was a demonstrably more potent agonist than Pam3Cys-SKKKK or homoPam2Cys(NH₂)-SKKKK. homoPam2Cys(NH₂)-SKKKK elicited equivalent SEAP production to Pam3Cys-SKKKK in HEK-Blue™-mTLR2, and comparable production in HEK-Blue™-hTLR2 (FIG. 4A). Both homoPam2Cys(NHAc/NH₂)-SKKKK were demonstrably more potent TLR2 agonists than Pam1CYs-SKKKK. Importantly, unlike Pam1Cys-SKKKK, which in not active in HEK-Blue™-mTLR2 at sub-µM concentrations, homoPam2Cys(NHAc/NH₂)-SKKKK are active in both HEK-Blue™-mTLR2 and -hTLR2 to sub-nM concentrations (FIG. 4A), potentiating future applications in transgenic murine models. These data indicate that homoPam2Cys(NHAc/NH₂)-SKKKK exhibit comparable biological function and activity to the known potent TLR1/2 and TLR2/6 agonists Pam3Cys and Pam2Cys.

Figure 4B:
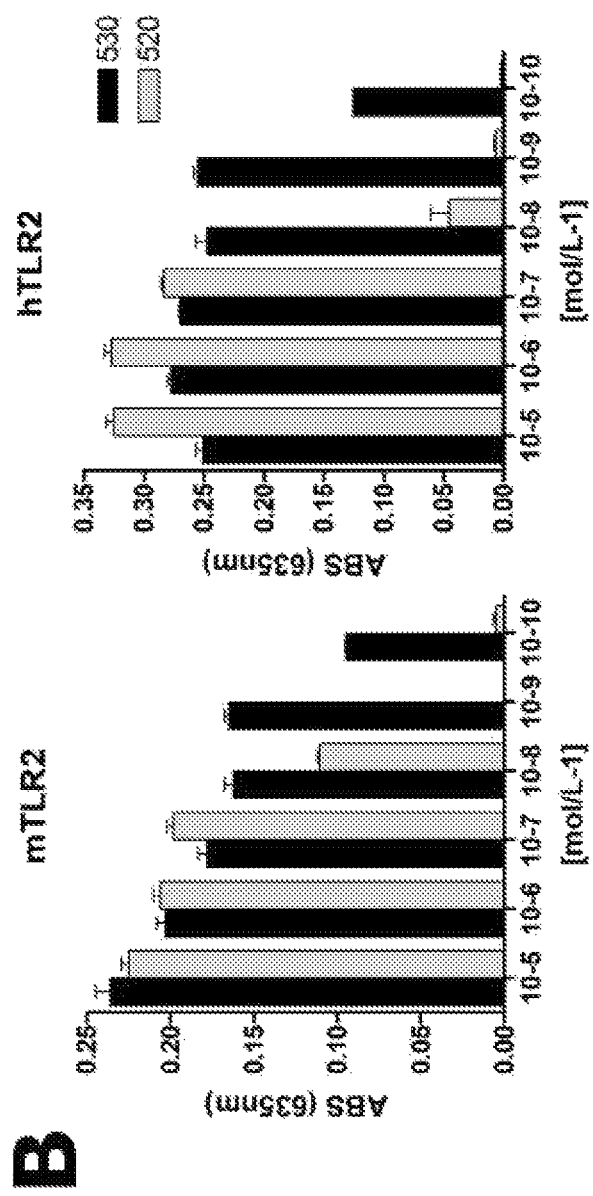
Figure 4C:
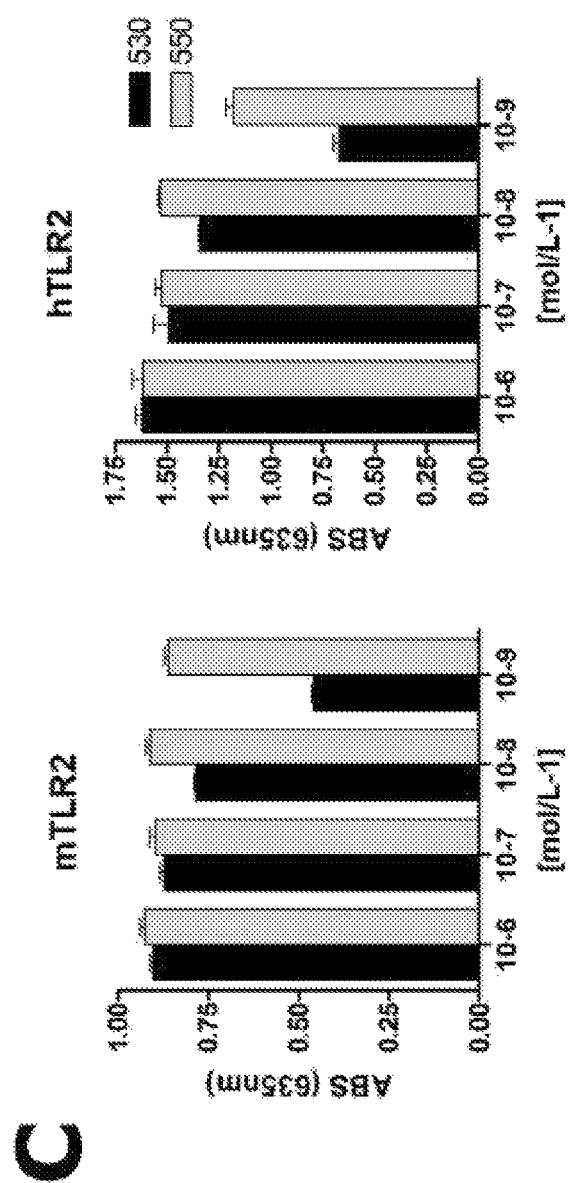

In both HEK-Blue™-mTLR2 and -hTLR2 conjugation of peptide NLVPMVATVK(Ac) to Pam2Cys-SKKKK induced a relative loss of agonism when compared to unconjugated Pam3Cys-SKKKK (FIG. 4B). Whether this was due to construct aggregation was not specifically determined. By contrast, conjugation of peptide NLVPMVATVK(Ac) to homoPam2Cys(NHAc)-SKKKK did not result in any loss of agonism, and homoPam2Cys(NHAc)-SKKKK-NLVPMVATVK(Ac) remained a more potent agonist than Pam3Cys- SKKKK, particularly at nM concentrations (FIG. 4C). These data suggest that homoPam2Cys retains solubility and bioactivity more robustly than Pam2Cys when conjugated to a hydrophobic peptide cargo, and may have some bearing on the relative in vivo bioavailability of these constructs.

2.2 Peptide Processing and Presentation to CD8+ T-Cell Clones

Epstein-Barr Virus-transformed TLR2+ HLA-A2+ lymphoblastoid B-cell lines (LCL) were used as antigen-presenting cells in all peptide processing and presentation assays. LCL were incubated for 16 h in RF10+peptide/construct as indicated at desired concentrations. Untreated LCL were incubated in RF10 only. LCL/construct incubation was performed in 96 well plates (U-bottom, BD Biosciences) or in 48wp (flat bottom, BD Biosciences) depending of the nature of the assay and the numbers of LCL required per treatment. Following incubation, LCL were thoroughly washed with RPMI 1640 to remove unbound construct/peptide.

To enable flow cytometric detection, CD8+ T cell clones were pre-stained with 0.5 µM CellTrace™ Violet ("CTV") (Life Technologies™) following manufacturer's protocols prior to seeding into APC wells. Loaded, washed LCL and CTV-stained T cell clones were seeded in 96 well plate wells (U-bottom) at a ratio of 4:1 (LCL: T cell) in duplicate (typical numbers of cells used were $1.25 \times 10^4$ cells/ml T cells and $5 \times 10^4$ cells/ml APC). Following seeding, plates were gently centrifuged ($\leq 300 \times g$, 3 minutes) to allow immediate interaction, and incubated for 26 hours in a standard cell culture incubator.

To detect T cell activation, samples were stained with anti-CD8:AlexaFluor700 and anti-CD137:PE antibodies (both Biolegend). Samples were incubated on ice for 30 minutes in the dark, and then washed twice with wash buffer to remove unbound antibody. DAPI (1 µg/ml final concentration) was added to each sample immediately prior to acquisition to allow live/dead exclusion.

Data acquisition was performed using a BD FACSAria II with FACSDiva software, and data analysis was performed using FlowJo software (Treestar). Data presented as the mean %+SD of live clonal cells positive for CD137 expression (FIGS. 4D-E).

Figures 4D, 4E:
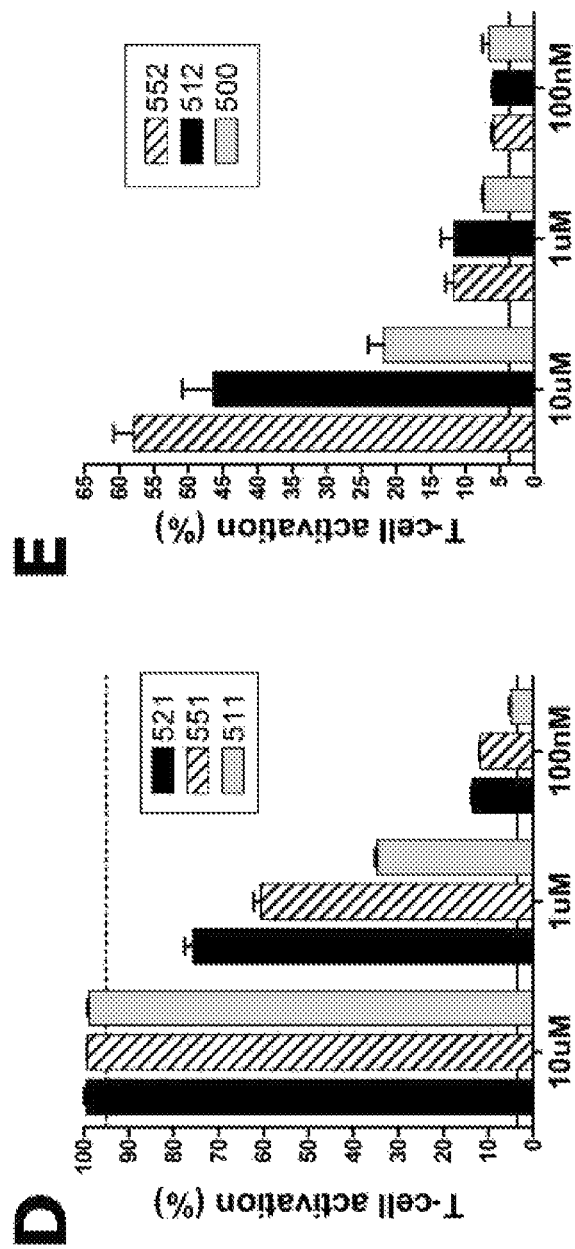
FIGS. 4D and 4E are graphs showing T cell clone activation in response to D: agonists 521 (black bars), 551 (cross-hatched bars) and 511 (grey bars); E: agonists 552 (cross-hatched bars), 512 (black bars) and 500 (grey bars).

2.2.1 Results homoPam2Cys(NHAc)-SKKKK-NLV (551) elicited comparable T-cell clone activation to NLV-bearing-Pam2Cys-SKKKK (521), and superior T-cell clone activation to NLV-bearing-Pam1Cys-SKKKK (511), following internalisation and peptide presentation by LCL (FIG. 4D). Dotted and solid lines in FIG. 4D represent background T-cell clone activation and activation elicited by co-incubation with LCL loaded with 10 nM free NLV peptide, respectively. As peptide NLVPMVATVK(Ac) represents the entirety of the T-cell epitope, no peptide processing is required in this system, and T-cell activation is determined by construct internalisation, peptide release and trafficking into the MHC I pathway of LCL.

homoPam2Cys(NHAc)-SKKKK-VPG (552) elicited superior T-cell clone activation to VPG-bearing-Pam1Cys-SKKKK (512), and both constructs were superior to VPG peptide alone (500), following internalisation and epitope presentation by LCL (FIG. 4E). As the release, through e.g peptidase activity, of minimal epitope EFTVSGNIL from within long peptide VPGVLLKEFTVSGNILTIRL-TAADHR is necessary for T-cell activation, these data suggest that conjugation of long synthetic peptides to homoPam2Cys moieties improves epitope processing and presentation by TLR2+ antigen-presenting cells, putatively through targeting the peptide to the endo/lysosomal pathway following surface TLR1/2 or TLR2/6 binding, and suggests that conjugation may improve the in vivo recognition of peptide epitopes by cognate T-cells. Dotted line in FIG. 4E represents background T-cell clone activation.

3. Example 3

This example demonstrates the preparation of an amino acid conjugate of the invention 6 via a thiol-ene reaction.

3.1 Method

Irradiation at 365 nm of a solution of 1 mL total volume comprised of Fmoc-Cys-OH (3.4 mg, 10 µmol), vinyl palmitate (141 mg, 500 µmol) and DMPA (0.5 mg, 2 µmol) dissolved in $CH_2Cl_2$ (approx. 850 µL) for 60 minutes afforded a product mixture composed of mono-palmitoylated Fmoc-Cys 5 as the major component and bis-palmitoylated Fmoc-Cys 6 (m/z ESI, 908.5 [M+H]) as the minor component (Scheme 4). After evaporation of the solvent each component could be isolated by column chromatography on silica, eluting firstly with 4:1 hexane/ethyl acetate then switching to 2:1 hexane/ethyl acetate and finally 1:1 hexane/ethyl acetate. This afforded 5 (4.6 mg, 75%) and 6 (0.9 mg, 10%).

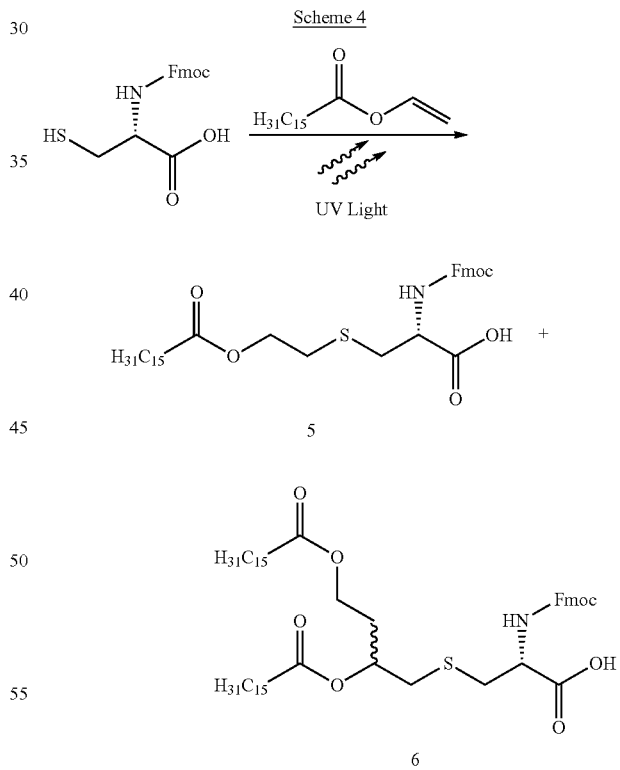

This method of synthesis is useful because the starting materials are cheap, the reaction can be performed on a large scale and the product is relatively easily isolated.

However, the conversion (by HPLC) to 6 was low and the mechanism of reaction dictates that the newly formed chiral centre may provide a mixture of epimers at the newly formed chiral centre.

4. Example 4

This example demonstrates the synthesis of an amino acid conjugate of the invention 6.

4.1 Method

A chemical synthesis was then undertaken from readily available 3-butenol, as outlined in scheme 5.

The bis-pamitoylated product 6 may be produced with different N-terminal protecting groups, by reaction with a protected cysteine bearing the desired protecting group.

The epoxide may be resolved (for example using kinetic hydrolysis: M. Tokunaga, J. F. Larrow, F. Kakiuchi, E. N. Jacobsen, *Science,* 1997, 277, 936-938) to afford the diastereomer of choice.

A solution of alkene 101 (2.00 g, 10.74 mmol) in CH$_2$Cl$_2$ (10 mL) was allowed to stir at r.t. A solution of mCPBA (2.78 g, 16.12 mmol) in CH$_2$Cl$_2$ (25 mL), which was dried over anhydrous Na$_2$SO$_4$, was added dropwise to the stirred solution over 30 min. The reaction mixture was allowed to stir at r.t. for 18 h. The mixture was then diluted with Et$_2$O (70 mL), filtered through a pad of Celite® and washed with sat. aq. Na$_2$S$_2$O$_3$ (30 mL), 2M aq. NaOH (30 mL) and brine (30 mL). The organic layer was dried over anhydrous MgSO$_4$ and concentrated in vacuo. The crude was purified by flash column chromatography (petroleum ether-EtOAc, 3:1) to give 102 (1.85 g, 85%) as a colourless oil.

Scheme 5

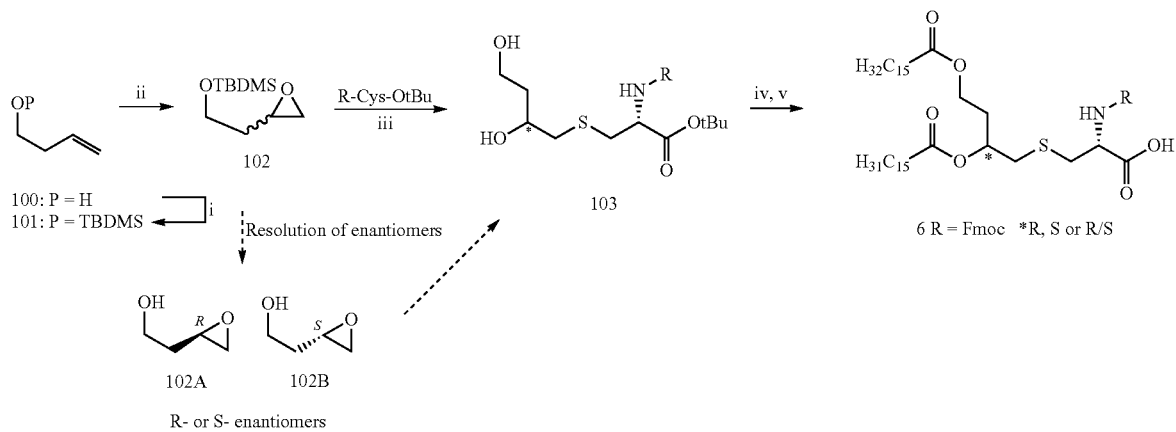

(i) TBDMS—Cl, imidazole, CH$_2$Cl$_2$; (ii) mcpba; (iii) CH$_2$Cl$_2$, HCl/H$_2$SO$_4$; (iv) Palmitic acid, DIC, DMAP, THF; (v) Trifluoroacetic acid Step i

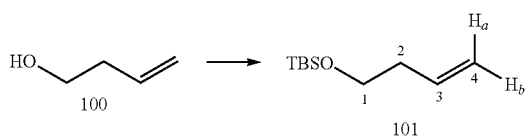

To a stirred solution of tert-butyldimethylsilyl chloride (10.60 g, 70 mmol) and imidazole (4.77 g, 70 mmol) in CH$_2$Cl$_2$ (200 mL) at r.t. was added 3-buten-1-ol 100 (5.98 mL, 69 mmol) dropwise over 10 min. The reaction mixture was allowed to stir at r.t. for 90 min. The mixture was then diluted Et$_2$O (150 mL) and washed with water (3×100 mL) and brine (50 mL). The organic layer was dried over anhydrous MgSO$_4$ and concentrated in vacuo. The crude was purified by filtration through silica gel to give 101 (11.99 g, 91%) as a colourless liquid.

Step ii

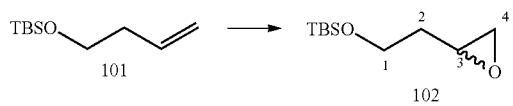

Step iii

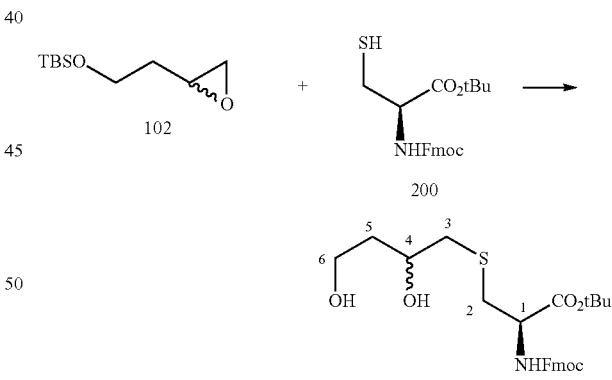

A solution of thiol 200 (0.53 g, 1.34 mmol) in CH$_2$Cl$_2$ (4 mL) and a freshly prepared mixture of methanol, conc. hydrochloric acid and conc. sulfuric acid (100:7:1, 2 mL) was allowed to stir at 0° C. for 30 min. Epoxide 102 was then added to the mixture and the resultant solution was allowed to reflux at 40° C. for 19 h. The mixture was then diluted with CH$_2$Cl$_2$ (30 mL), filtered through a pad of Celite® and washed with brine (30 mL). The aqueous layer was extracted with CH$_2$Cl$_2$ (3×30 mL) and the combined organic extracts were dried over anhydrous MgSO$_4$ and concentrated in vacuo. The crude was purified by flash column chromatography (hexanes-EtOAc, 1:3) to give 103 (0.50 g, 77%) as a colourless oil.

Step iv

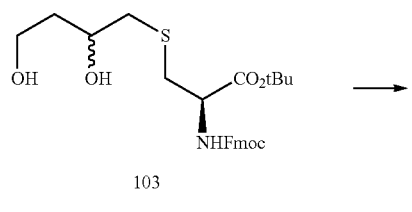

103

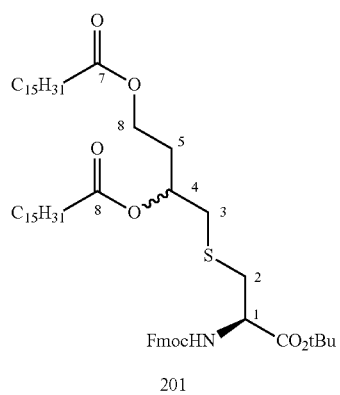

201

To a stirred solution of diol 103 (0.327 g, 0.67 mmol) and palmitic acid (0.516 g, 2.01 mmol) in THF (9 mL) at r.t. was added diisopropylcarbodiimide (0.414 mL, 2.68 mmol) and 4-dimethylaminopyridine (0.01 g, 0.07 mmol). The reaction mixture was allowed to stir at r.t. for 19 h. The mixture was then diluted with EtOAc (30 mL), filtered through a bed of Celite® and concentrated in vacuo. The crude was purified by flash column chromatography ($CH_2Cl_2$) to give 201 (0.301 g, 47%) as yellow oil.

Step v

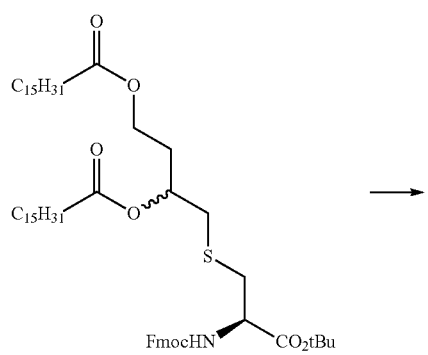

201

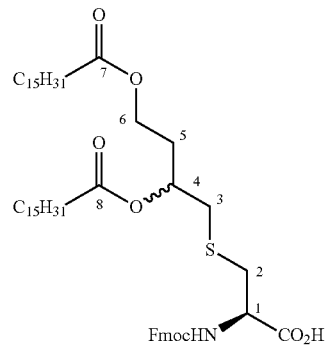

6

A solution of diester 201 (0.35 g, 0.364 mmol) in trifluoroacetic acid (2 mL) was allowed to stir at r.t. for 1 h after which the mixture was concentrated in vacuo. The crude was purified by flash column chromatography (hexanes-EtOAc, 9:1→0:1) to give 6 (0.33 g, quant.) as a colourless oil.

Fmoc-Cys-OH is described in the literature: H.-K. Cui, Y. Guo, Y. He, F.-L. Wang, H.-H.

Chang, Y. 3. Wang, F.-M. Wu, C.-L. Tian, L. Lu, *Angew. Chem. Int. Eng.*, 2013, 52(36), 9558-9562.

4.2 Analysis of Amino Acid Conjugate 6

Amino acid conjugate 6 synthesised by the method described above in section 4.1 had the same analytical properties as those for the 6 obtained on irradiation of a solution of Fmoc-Cysteine and vinyl palmitate as described in Example 3 (the mass specta were the same).

Figure 5:
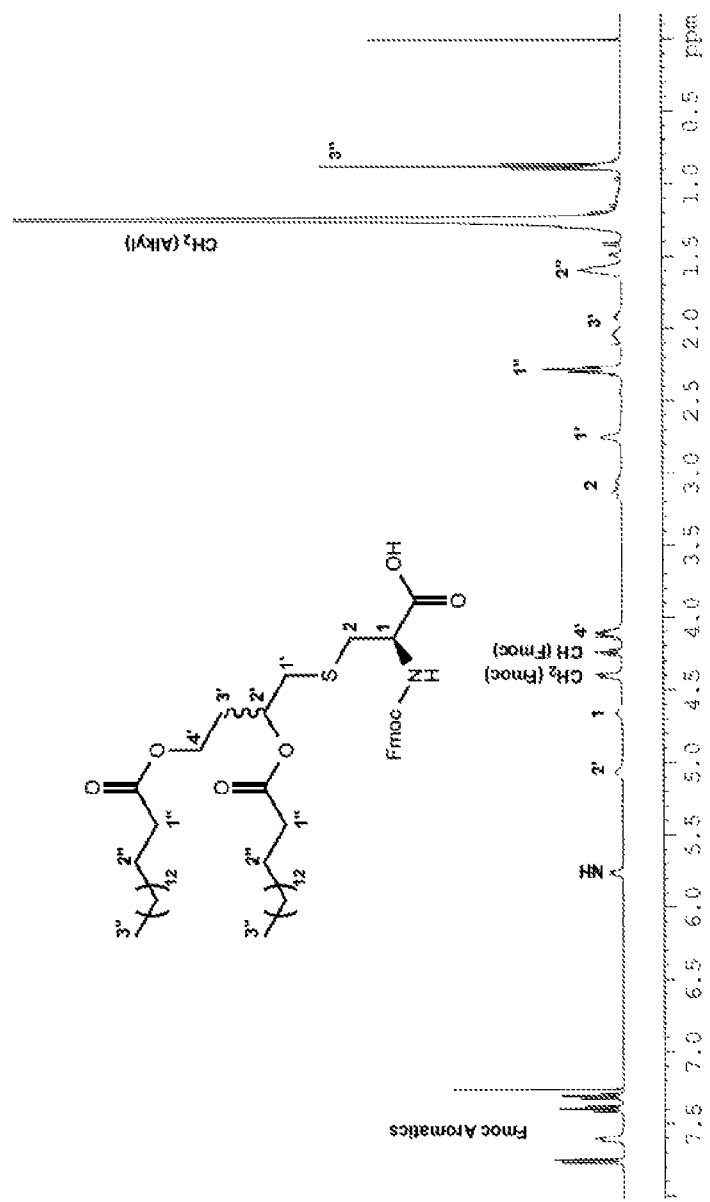
FIG. 5 is an $^1$H NMR spectrum of bis-pamitolyated peptide 3.

The $^1H$ NMR spectrum of bis-pamitoylated Fmoc-Cys 6 is shown in FIG. 5.

Characterisation data is as follows: $^1H$ NMR (400 Mhz, $CDCl_3$) δ 7.75 (2H, d, Fmoc Ar—H), 7.60 (2H, d, Fmoc Ar—H), 7.39 (2H, t, Fmoc Ar—H), 7.31 (2H, t, Fmoc Ar—H), 5.75 (1H, broad d, NH), 5.06 (1H, m, H-2'), 4.66 (1H, m, H-1), 4.40 (2H, d, $CH_2$ (Fmoc)), 4.26 (1H, t, CH (Fmoc)), 4.11 (2H, m, H-4'), 3.13 (1H, 2×dd, H-2), 3.06 (1H, 2×dd, H-2), 2.76 (2H, m, H-1'), 2.28 (4H, m, H-1"), 2.03, (1H, m, H-3'), 1.94 (1H, m, H-3'), 1.59 (4H, m, H-2"), 1.24 (48H, m, 14×$CH_2$ (palmitoyl)), 0.88 (6H, t, 2×$CH_3$ (Palmitoyl)). MS (ESI-TOF): m/z [M+H] 908.6065; $C_{54}H_{86}NO_8S$ requires [M+H] 908.6069.

4.3 Preparation and Use of Enantiopure Epoxides 102A and 102B

Diastereomerically pure amino acid conjugate 6 may be prepared using enantiopure epoxide 102A or enantiopure epoxide 102B produced stereospecifically from an enantiomerically pure starting material. The resultant enantiopure epoxide may be reacted with thiol 200 in a procedure analogous to that described above in step (iii) of section 4.1 or with disulfide 804 as described below to provide the corresponding diastereomerically pure diol 103A or 103B, which may then be converted to the corresponding diastereomerically pure conjugate 6A or 6B as described herein.

Enantiopure epoxide 102A and enantiopure epoxide 102B were prepared from L-aspartic acid and D-aspartic acid, respectively, by following the procedure described in Volkmann, R. A. et al. *J. Org. Chem.*, 1992, 57, 4352-4361 for the preparation of (R)-(2-hydroxyethyl)oxirane (102A) from L-aspartic acid.

(S)-2-Bromosuccinic Acid

To a solution of sodium bromide (15.46 g, 150.24 mmol) in 6N $H_2SO_4$ (33 mL) at 0° C. was added L-aspartic acid (5.00 g, 37.56 mmol). To the resultant mixture was added sodium nitrite (3.11 g, 45.07 mmol) portionwise over 90 min. The reaction mixture was allowed to stir at 0° C. for a further 2 h. The mixture was then diluted with H$_2$O (17 mL) and extracted with Et$_2$O (100 mL). The aqueous layer was diluted with brine (20 mL) and further extract with Et$_2$O (3×100 mL). The combined organic extracts were dried over anhydrous Na$_2$SO$_4$ and concentrated in vacuo to give the title compound (2.98 g, 41%) as a white solid. The crude was used in subsequent synthetic steps without further purification. $[\alpha]_D^{19.7}$-71.5 (c 0.46 in EtOAc) (lit −73.5 (c 6.0 in EtOAc); $\delta_H$ (400 MHz; DMSO) 12.8 (2H, br s, 2×CO$_2$H), 4.54 (1H, dd, J=8.5, 6.4 Hz, H-1), 3.10 (1H, dd, J=17.2, 8.6 Hz, H-2), 2.90 (1H, dd, J=17.1, 6.4 Hz, H-2); $\delta_C$ (100 MHz; DMSO) 171.0 (C, CO$_2$H), 170.1 (C, CO$_2$H), 40.5 (CH, C-1), 39.5 (CH$_2$, C-2). Spectroscopic data was consistent with that reported in literature.

(R)-2-Bromosuccinic Acid (R)-2-Bromosuccinic acid was prepared by following the procedure described above for the preparation of (S)-2-bromosuccinic acid, but using D-aspartic acid instead of L-aspartic acid. $[\alpha]_D^{20.2}$ +66.5 (c 0.2 in EtOAc). The remaining spectroscopic data was identical to that observed for (S)-2-bromosuccinic acid.

(S)-2-Bromo-1,4-butanediol

To a solution of (S)-2-bromosuccinic acid (2.98 g, 15.20 mmol) in THF (35 mL) at −78° C. was added BH$_3$.DMS complex (4.33 mL, 45.61 mmol) dropwise over 90 min. The reaction was allowed to stir at −78° C. for 2 h and then warmed to r.t. and allowed to stir for a further 60 h. The reaction was then cooled to 0° C. and MeOH (15 mL) was added slowly. The mixture was then concentrated in vacuo and the residue diluted with MeOH (15 mL). This process was repeated 3 times to give the title compound (2.55 g, quant.) as a yellow oil. The crude was used in subsequent synthetic steps without further purification. $[\alpha]_D^{19.6}$-36.8 (c 0.5 in CHCl$_3$); $\delta_H$ (400 MHz, CDCl$_3$) 4.34 (1H, dq, J=7.7, 5.3 Hz, H-2), 3.92-3.78 (4H, m, H-1, H-4), 2.40 (2H, br s, 2×OH), 2.20-2.06 (2H, m, H-3); $\delta_C$ (100 MHz; CDCl$_3$) 67.1 (CH$_2$, C-1), 60.1 (CH$_2$, C-4), 55.2 (CH, C-2), 37.8 (CH$_2$, C-3). Spectroscopic data was consistent with that reported in literature.

(R)-2-Bromo-1,4-butanediol (R)-2-Bromo-1,4-butanediol was prepared by following the procedure described above for the preparation of (S)-2-bromo-1,4-butanediol, but using (R)-2-bromosuccinic acid instead of (S)-2-bromosuccinic acid. $[\alpha]_D^{21.3}$ +20.0 (c 0.17 in CHCl$_3$). The remaining spectroscopic data was identical to that observed for (S)-2-bromo-1,4-butanediol.

(R)-(2-Hydroxyethyl)oxirane (102A)

To a solution of (S)-2-bromo-1,4-butanediol (2.31 g, 13.76 mmol) in CH$_2$Cl$_2$ (46 mL) at r.t. was added Cs$_2$CO$_3$ (8.74 g, 24.77 mmol). The resultant mixture was allowed to stir at r.t. for 72 h. The reaction was then filtered through a pad of Celite® and concentrated in vacuo to give the title compound as a yellow oil with quantitative conversion. The crude material was used in subsequent synthetic steps without further purification. $[\alpha]_D^{22.9}$ +35.0 (c 0.61 in CHCl$_3$); $\delta_H$ (400 MHz; CDCl$_3$) 3.83-3.79 (2H, m, H-1), 3.12-3.08 (1H, m, H-3), 2.81 (1H, dd, J=4.8, 4.1 Hz, H-4), 2.60 (1H, dd, J=4.8, 2.8 Hz, H-4), 2.03-1.95 (1H, m, H-2), 1.78 (1H, t, J=5.4 Hz, OH), 1.71 (1H, dq, J=14.6, 5.9 Hz, H-2); $\delta_C$ (100 MHz; CDCl$_3$) 60.0 (CH$_2$, C-1), 50.5 (CH, C-3), 46.5 (CH$_2$, C-4), 34.6 (CH$_2$, C-2). Spectroscopic data was consistent with that reported in literature.

(S)-(2-hydroxyethyl)oxirane (102B)

(S)-(2-Hydroxyethyl)oxirane (102B) was prepared by following the procedure described above for the preparation of (R)-(2-hydroxyethyl)oxirane (102A), but using (R)-2-bromo-1,4-butanediol instead of (S)-2-bromo-1,4-butanediol. $[\alpha]_D^{22.9}$ −35.2 (c 0.23 in CHCl$_3$). The remaining spectroscopic data was identical to that observed for (S)-2-bromo-1,4-butanediol.

Preparation of Diastereomerically Pure 6A

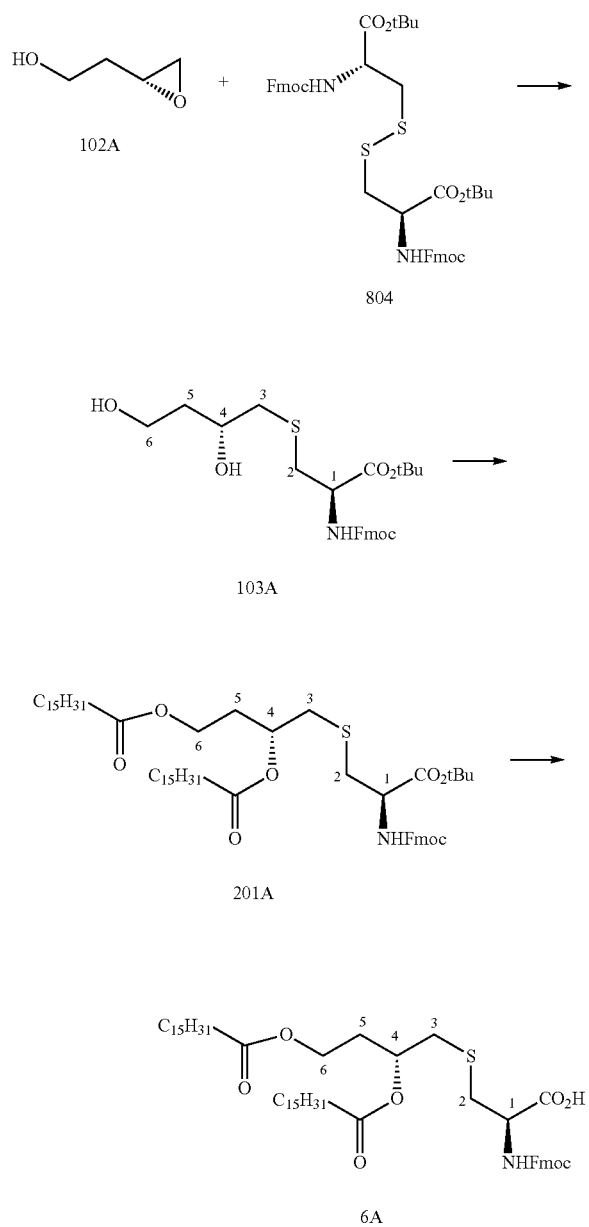

To a stirred solution of disulfide 804 (1.59 g, 2.06 mmol) in CH$_2$Cl$_2$ (10 mL) at 0° C. was added zinc powder (0.94 g, 14.42 mmol) and a freshly prepared mixture of methanol, conc. hydrochloric acid and conc. sulfuric acid (100:7:1, 5 mL). The resultant mixture was allowed to stir at 0° C. for 30 min after which was added epoxide 102A (0.73 g, 8.24 mmol). The reaction mixture was allowed to stir at 55° C. for 17 h. The mixture was then diluted with CH$_2$Cl$_2$ (30 mL), filtered through a pad of Celite® and washed with brine (50 mL). The aqueous layer was extracted with CH$_2$Cl$_2$ (3×50 mL) and the combined organic extracts were dried over anhydrous MgSO$_4$ and concentrated in vacuo. The crude was purified by flash column chromatography (hexanes-EtOAc, 1:3) to give 103A (1.72 g, 88%) as a colourless oil.

R$_f$ 0.15 (hexanes-EtOAc 1:3); [a]$_D^{20.2}$ −3.5 (c 0.32 in CHCl$_3$); ν$_{max}$(neat)/cm$^{-1}$ 3347, 2976, 1703, 1518, 1449, 1413, 1369, 1335, 1249, 1151; δ$_H$ (400 MHz; CDCl$_3$) 7.77 (2H, d, J=7.5, FmocH), 7.61 (2H, d, J=7.2 Hz, FmocH), 7.40 (2H, t, J=7.4 Hz, FmocH), 7.32 (2H, t, J=7.5 Hz, FmocH), 5.81 (1H, d, J=8.0 Hz, NH), 4.53-4.50 (1H, m, H-1), 4.40 (2H, d, J=6.8 Hz, FmocCH$_2$), 4.23 (1H, t, J=7.0 Hz, FmocCH), 3.94-3.88 (1H, m, H-4), 3.85-3.81 (2H, m, H-6), 3.03 (1H, dd, J=14.0, 4.2 Hz, H-2), 2.94 (1H, dd, J=14.3, 6.1 Hz, H-2), 2.82 (1H, dd, J=14.0, 2.9 Hz, H-3), 2.56 (1H, dd, J=14.0, 9.0 Hz, H-3), 1.74-1.71 (1H, m, H-5), 1.50 (9H, s, C(CH$_3$)$_3$); δ$_C$ (100 MHz; CDCl$_3$) 141.3 (C, Fmoc), 127.8 (CH, Fmoc), 127.1 (CH, Fmoc), 125.1 (CH, Fmoc), 120.0 (CH, Fmoc), 83.1 (C, C(CH$_3$)$_3$), 69.9 (CH, C-4), 67.2 (CH$_2$, FmocCH$_2$), 61.2 (CH$_2$, C-6), 54.7 (CH, C-1), 47.1 (CH, FmocCH), 41.2 (CH$_2$, C-3), 37.5 37.5 (CH$_2$, C-5), 35.7 (CH$_2$, C-2), 28.0 (3×CH$_3$, C(CH$_3$)$_3$); HRMS (ESI+) [M+Na]$^+$ 510.1921 calc for C$_{26}$H$_{33}$NNaO$_6$S 510.1921.

Diastereomerically pure diol 103A was then converted to diastereomerically pure conjugate 6A by following procedures analgous to those described in steps iv and v of section 4.1 above.

Preparation of Diastereomerically Pure 6B

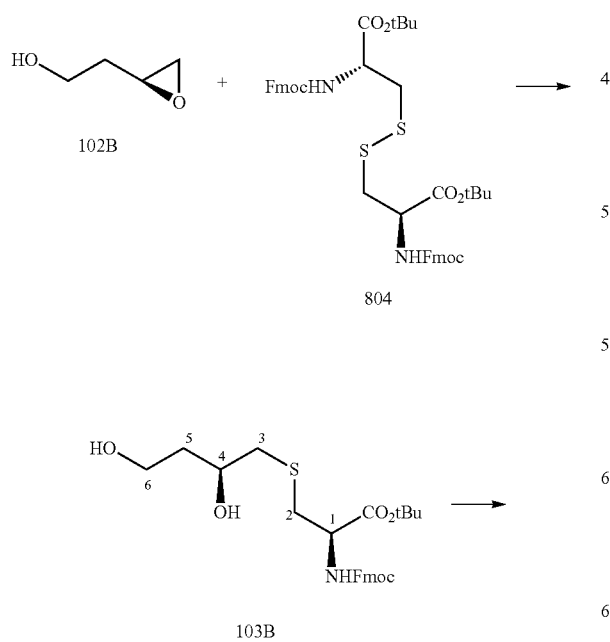

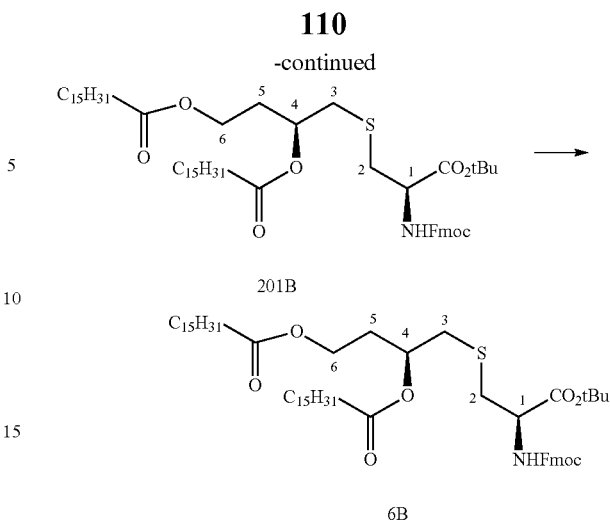

To a stirred solution of disulfide 804 (2.01 g, 2.53 mmol) in CH$_2$Cl$_2$ (14 mL) at 0° C. was added zinc powder (1.15 g, 17.51 mmol) and a freshly prepared mixture of methanol, conc. hydrochloric acid and conc. sulfuric acid (100:7:1, 7 mL). The resultant mixture was allowed to stir at 0° C. for 30 min after which was added epoxide 102B (0.89 g, 10.11 mmol). The reaction mixture was allowed to stir at 55° C. for 17 h. The mixture was then diluted with CH$_2$Cl$_2$ (30 mL), filtered through a pad of Celite® and washed with brine (50 mL). The aqueous layer was extracted with CH$_2$Cl$_2$ (3×50 mL) and the combined organic extracts were dried over anhydrous MgSO$_4$ and concentrated in vacuo. The crude was purified by flash column chromatography (hexanes-EtOAc, 3:1) to give the 103B (2.17 g, 88%) as a colourless oil.

R$_f$ 0.15 (hexanes-EtOAc 1:3); [a]$_D^{22}$ +8.5 (c 0.3 in CHCl$_3$); ν$_{max}$(neat)/cm$^{-1}$ 3347, 2976, 1703, 1518, 1449, 1413, 1369, 1335, 1249, 1151; δ$_H$ (400 MHz; CDCl$_3$) 7.77 (2H, d, J=7.5 Hz, FmocH), 7.61 (2H, d, J=7.4 Hz, FmocH), 7.40 (2H, t, J=7.4 Hz, FmocH), 7.32 (2H, t, J=7.5 Hz, FmocH), 5.74 (1H, d, J=7.0 Hz, NH), 4.51-4.47 (1H, m, H-1), 4.42-4.39 (2H, m, FmocCH$_2$), 4.24 (1H, t, J=7.0 Hz, FmocCH), 3.93 (1H, br s, H-4), 3.85-3.81 (2H, m, H-6), 3.31 (1H, br s, OH-4), 3.00-2.78 (2H, m, H-2), 2.80 (1H, dd, J=13.5, 3.2 Hz, H-3), 2.55 (1H, dd, J=13.8, 8.4, Hz, H-3), 2.36 (1H, br s, OH-6) 1.73 (2H, q, J=5.3, H-5), 1.50 (9H, s, C(CH$_3$)$_3$); δ$_C$ (100 MHz; CDCl$_3$) 141.3 (C, Fmoc), 127.8 (CH, Fmoc), 127.1 (CH, Fmoc), 125.1 (CH, Fmoc), 120.0 (CH, Fmoc), 83.1 (C, C(CH$_3$)$_3$), 69.9 (CH, C-4), 67.2 (CH$_2$, FmocCH$_2$), 61.2 (CH$_2$, C-6), 54.7 (CH, C-1), 47.1 (CH, FmocCH), 41.2 (CH$_2$, C-3), 37.5 37.5 (CH$_2$, C-5), 35.7 (CH$_2$, C-2), 28.0 (3×CH$_3$, C(CH$_3$)$_3$); HRMS (ESI+) [M+Na]$^+$ 510.1921 calc for C$_{26}$H$_{33}$NNaO$_6$S 510.1921.

Diastereomerically pure diol 103B was then converted to diastereomerically pure conjugate 6B by following procedures analgous to those described in steps iv and v of section 4.1 above.

5. Example 5

Peptide conjugates of the invention 10A and 10B comprising the peptide sequence SKKKKVPGVLLKEFTVSG-NILTIRLTAADHR [SEQ ID No: 112] were prepared using 6 as described and depicted below (Scheme 6).

Scheme 6

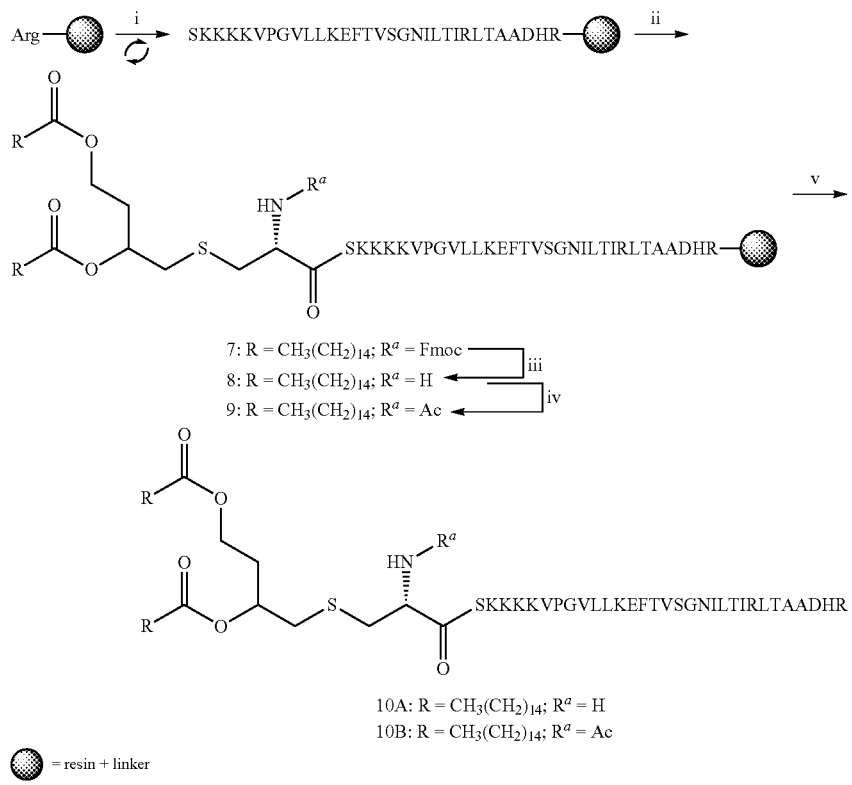

= resin + linker

AA = amino acid
(i) Iterative Fmoc-SPPS; (ii) bis-pamitoylated Fmoc-Cys-OH 6, PyBOP, collidine, DMF;
(iii) 20% piperidine/DMF; (iv) Ac$_2$O/NMM, DMF; (v) TFA/EDT.

The desired peptide sequence was synthesised using standard iterative Fmoc SPPS techniques as previously described.

After coupling the penultimate amino acid residue, the resin-bound peptide chain was then derivatised with the amino acid conjugate 6 using PyBOP (benzotriazol-1-yl-oxytripyrrolidinophosphonium hexafluorophosphate) and collidine in DMF. The conditions for coupling of the amino acid conjugate reduce the propensity of the α-carbon of the amino acid to epimerise on activation. The amino acid conjugate (0.075 mmol) and PyBOP (0.1 mmol) were combined and dissolved in DMF (0.3 mL). Neat 2,4,6-trimethylpyridine (0.1 mmol) was added. After mixing for 30 seconds the solution was transferred to 0.025 mmol of resin, which was then agitated for 90 minutes, drained and washed (DMF).

The Fmoc group was then removed using 20% piperidine in DMF to provide 8.

Peptide 8 was then converted to the corresponding acetamide 9 by treatment with a mixture of 20% acetic anhydride in DMF (2 mL) and 4-methylmorpholine (1 mmol).

Alternatively, peptide 8 was cleaved from the resin to provide the corresponding peptide conjugate 10A. Resin (0.015 mmol) in 1 mL of trifluoroacetic acid containing 5% (v/v) ethanedithiol was agitated at room temperature for 3 hours. The supernatant was then drained through a sinter into chilled diethyl ether (10 mL). The resin was then washed with a further 1 mL of TFA, which was also added to the ether. The precipitated material was pelleted by centrifugation and the pellet washed once with ether (5 mL) before being dissolved in 1:1 MeCN/Water (+0.1% tfa) and lyophilised.

Peptide 9 was cleaved from the resin using the same procedure.

Purification of 10A and 10B was performed by semi-preparative HPLC using a Phenomenex Gemini C18 (5p, 110A) 10×250 mm column with eluent A being water (+0.1% tfa) and eluent B being MeCN (+0.1% tfa). After injection of the crude peptide sample on to the column a gradient of 5% B to 95% B over 30 minutes was generated at a flow of 4 mL/min and the desired product material collected on elution from the column and freeze-dried.

10A: m/z (ESI) 1363.8 [M+3H$^+$]. HPLC analysis: Column: Phenomenex Proteo C12 (4$_\mu$, 90 Å, 4.6×250 mm); eluent A, water/0.1% TFA; eluent B: MeCN/0.1% TFA; gradient: 5-95% B over 30 min @ 1 mL/min. Retention time: 23.4 mins.

10B: m/z (ESI) 1377.7 [M+3H$^+$]. HPLC analysis: Column: Phenomenex Proteo C12 (4$_\mu$, 90 Å, 4.6×250 mm); eluent A, water/0.1% TFA; eluent B: MeCN/0.1% TFA; gradient: 5-95% B over 30 min @ 1 mL/min. Retention time: 25.2 mins.

6. Example 6

The thiol-ene reaction of peptide 1 and vinyl palmitate was carried out according to the general procedure below under a variety of conditions, as summarised in Table 2.

6.1 Synthesis of Peptide 1

Peptide 1 was prepared as described below.

Aminomethyl polystyrene resin (100 mg, 0.1 mmol, loading 1.0 mmol/g) was reacted with Fmoc-Val-HMPP (HMPP=hydroxymethylphenoxy acetic acid) (105 mg, 0.2 mmol) and DIC (31 μL, 0.2 mmol) in a mixture of dichloromethane and DMF (2 mL, 1.9:0.1 v/v) for 1 hour at room temperature. The completion of the coupling was monitored using the Kaiser test and the coupling procedure was repeated with freshly prepared reagent upon incomplete coupling. Solid phase peptide synthesis of the remainder of the peptide sequence was performed using a Tribute peptide synthesizer (Protein technologies Inc.) using HATU/DIPEA for 40 minutes at room temperature for each coupling step and 20% solution of piperidine in DMF (v/v), repeated twice for 5 minutes at room temperature, for each Fmoc-deprotection step.

Following synthesis of the peptide sequence, N-terminal acetylation was completed using 20% solution of acetic anhydride in DMF (v/v) and DIPEA (0.25 mL) for 15 minutes at room temperature.

The resin-bound peptide was cleaved by treatment with TFA/TIPS/H$_2$O/DODT (10 mL, 94:1:2.5:2.5 v/v/v/v) for 2 hours at room temperature. Following evaporation of TFA by a flow of nitrogen, the peptide was precipitated in cold diethyl ether, isolated by centrifugation, washed twice with cold diethyl ether, dissolved in acetonitrile:water containing 0.1% TFA (1:1, v/v), and lyophilised to afford the crude peptide.

Purification by RP-HPLC using a semi-preparative Gemini C-18 column (phenomenex, 5μ 10.0×250 mm) afforded peptide 1 (74 mg, 43% based on 0.1 mmol scale), [(M+2H)$^{2+}$, calcd. 858.5, found 858.6 Da)].

6.2 General Procedure for Thiolene Reaction

Stock solution 1: DMPA (6.5 mg, 25.3 μmol) in degassed N-methyl-2-pyrrolidone (0.5 mL).

Stock solution 2: vinyl palmitate in degassed N-methyl-2-pyrrolidone (requisite concentration)

Peptide 1 (1.71 mg, 1.0 μmol) was dissolved in stock solution 1 (10 μL, 0.5 μmol) followed by addition of tert-butylthiol and/or triisopropylsilane, and trifluoroacetic acid (5% v/v) and stock solution 2. The reaction mixture was irradiated at wavelength of 365 nm using a UV lamp at room temperature, with samples removed for LC-MS analysis at 30 minute intervals thereafter. An analytical sample was prepared by quenching with Milli-Q water and analysed using a Gemini C-18 column (Phenomenex, 5μ 4.6×150 mm).

TABLE 3

Conjugation of peptide 10 and vinyl palmitate 1 in NMP$^a$ using DMPA$^b$ as radical initiator

| Entry | Vinyl Palmitate$^c$ 1 (equiv.) | $^t$BuSH$^c$ (equiv.) | TIPS$^c$ (equiv.) | Conversion$^f$ (%) | Products$^f$ |
|---|---|---|---|---|---|
| 1 | 7 | 0 | 0 | 58 | 2 (84%) 3 (16%) |
| 2 | 7 | 3 | 0 | 69 | 2 (97%) 3 (3%) |
| 3 | 70 | 3 | 0 | 84 | 2 (65%) 3 (35%) |
| 4 | 70 | 80 | 0 | 93 | 2 (76%) 3 (24%) |
| 5 | 70 | 80 | 40 | 94 | 2 (88%) 3 (12%) |
| 6 | 70 | 40 | 40 | 88 | 2 (95%) 3 (5%) |

TABLE 3-continued

Conjugation of peptide 10 and vinyl palmitate 1 in NMP$^a$ using DMPA$^b$ as radical initiator

| Entry | Vinyl Palmitate$^c$ 1 (equiv.) | $^t$BuSH$^c$ (equiv.) | TIPS$^c$ (equiv.) | Conversion$^f$ (%) | Products$^f$ |
|---|---|---|---|---|---|
| 7 | 70 | 80 | 80 | 94 | 2 (95%)$^g$ 3 (5%) |
| 8 | 70 | 0 | 80 | 78 | 2 (67%) 3 (33%) |
| 9 | 7 | 80 | 80 | 60 | 2 (98%) 3 (2%) |
| 10 | 20 | 80 | 80 | 81 | 2 (>99%) 3 (<1%) |
| 11 | 35 | 80 | 80 | 92 | 2 (97%) 3 (3%) |
| 12 | 100 | 80 | 80 | 90 | 2 (95%) 3 (5%) |
| 13$^d$ | 70 | 80 | 80 | 26 | 2 (>99%) 3 (<1%) |
| 14$^e$ | 70 | 80 | 80 | 91 | 2 (96%) 3 (4%) |

$^a$30 minute reaction time with 5% TFA per final reaction volume;
$^b$0.5 molar equivalent relative to peptide 1;
$^c$molar equivalent relative to peptide 1;
$^d$dimethylsulfoxide as solvent;
$^e$N,N'-dimethylformamide as solvent;
$^f$conversion of peptide 1, mono-adduct 2 and bis-adduct 3 is based on the integration of corresponding peaks on RP-HPLC profile at 210 nm. The relative amounts of 2 and 3 are cited as percentages;
$^g$72% isolated yield after RP-HPLC purification.

7. Example 7

This example demonstrates the synthesis of a amino acid conjugates of the invention from various starting materials.

7.1 Synthesis of Amino Acid Conjugate 806 from Alcohol 800

Step i

To a stirred solution of 4-pentyn-1-ol 800 (5 mL, 53.72 mmol) in CH$_2$Cl$_2$ (150 mL) at r.t. was added imidazole (3.66 g, 53.72 mmol) and tert-butyldimethylsilyl chloride (8.10 g, 53.72 mmol). The reaction mixture was allowed to stir at r.t. for 24 h. The mixture was then diluted with Et$_2$O (200 mL) and washed with water (3×100 mL) and brine (100 mL). The organic layer was dried over anhydrous Na$_2$SO$_4$ and concentrated in vacuo. The crude was purified by filtration through silica gel to give the title compound 801 (10.64 g, quant.) as a colourless liquid. Alkyne 801 was used in subsequent synthetic steps without characterisation.

Step ii

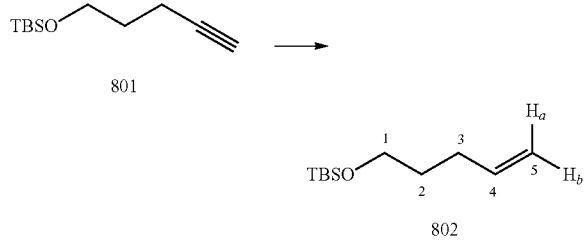

To a stirred solution of alkyne 801 (14.08 g, 70.00 mmol) in hexanes (150 mL) at r.t. was added quinoline (11.75 mL, 100.00 mmol) and Lindar's catalyst (1.408 g). The reaction mixture was connected to a H$_2$-filled balloon (1 atm) and allowed to stir at r.t. for 5 h. The mixture was then filtered through a pad of Celite® and concentrated in vacuo. The crude product was purified by flash column chromatography (petroleum ether-EtOAc, 9:1) to give the title compound 802 (14.09 g, 99%) as a colourless liquid.

$R_f$ 0.88 (petroleum ether-EtOAc 9:1); $\delta_H$ (400 MHz; CDCl$_3$) 5.82 (1H, ddt, J=17.0, 10.2, 6.7 Hz, H-4), 5.02 (1H, d, J=17.1 Hz, H$_a$-5), 4.95 (1H, d, J=10.4 Hz, H$_b$-5), 3.62 (2H, t, J=6.5 Hz, H-1), 2.10 (2H, q, J=7.2 Hz, H-3), 1.61 (2H, p, J=7.0 Hz, H-2), 0.90 (9H, s, SiC(CH$_3$)$_3$), 0.05 (6H, s, Si(CH$_3$)$_2$); $\delta_C$ (100 MHz; CDCl$_3$) 138.6 (CH, C-4), 114.5 (CH$_2$, C-5), 62.6 (CH$_2$, C-1), 32.0 (CH$_2$, C-2), 30.5 (CH$_2$, C-3), 26.0 (3×CH$_3$, SiC(CH$_3$)$_3$), 18.4 (C, SiC(CH$_3$)$_3$), −5.3 (2×CH$_3$, Si(CH$_3$)$_2$). Spectroscopic data was consistent with that reported in literature.

Step iii

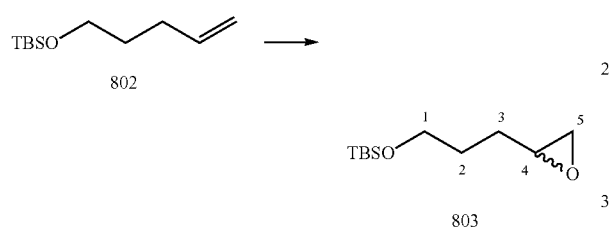

To a stirred solution of alkene 802 (8.646 g, 43.16 mmol) in CH$_2$Cl$_2$ (100 mL) at r.t. was added mCPBA (8.191 g, 47.47 mmol). The reaction mixture was allowed to stir at r.t. for 15 h. The mixture was then filtered through Celite®, diluted with Et$_2$O (100 mL) and washed with sat. aq. NaHCO$_3$ (3×100 mL) and brine (100 mL). The organic layer was dried over anhydrous Na$_2$SO$_4$ and concentrated in vacuo. The crude product was purified by flash column chromatography (petroleum ether-EtOAc, 9:1) to give the title compound 803 (8.09 g, 87%) as a colourless liquid.

$R_f$ 0.51 (petroleum ether-EtOAc 9:1); $\delta_H$ (400 MHz; CDCl$_3$) 3.70-3.60 (2H, m, H-1), 2.96-2.92 (1H, m, H-4), 2.75 (1H, dd, J=5.0, 4.0 Hz, H-5), 2.47 (1H, dd, J=5.0, 2.8 Hz, H-5), 1.73-1.53 (4H, m, H-2, H-3), 0.89 (9H, s, SiC(CH$_3$)$_3$), 0.04 (6H, s, Si(CH$_3$)$_2$); $\delta_C$ (100 MHz; CDCl$_3$) 62.7 (CH$_2$, C-1), 52.2 (CH, C-4), 47.1 (CH$_2$, C-5), 29.1 (CH$_2$, C-2), 29.0 (CH$_2$, C-3), 25.9 (3×CH$_3$, SiC(CH$_3$)$_3$), 18.3 (C, SiC(CH$_3$)$_3$), −5.3 (2×CH$_3$, Si(CH$_3$)$_2$). Spectroscopic data was consistent with that reported in literature.

Step iv

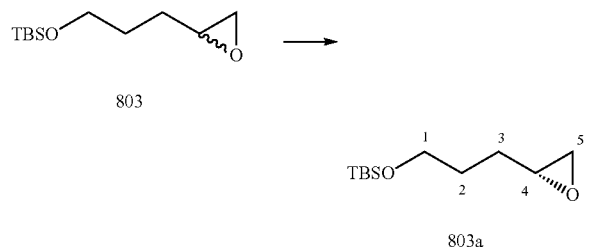

To a stirred solution of racemic epoxide 803 (8.272 g, 38.24 mmol), (R,R)-(+)-N,N'-bis(3,5-di-tert-butylsalicylidene)-1,2-cyclohexanediaminocobalt(II) (0.121 g, 0.19 mmol) and glacial acetic acid (0.04 mL, 0.76 mmol) in THF (0.35 mL) at 0° C. was added water (0.38 mL) dropwise. The reaction mixture was allowed to stir at r.t. for 48 h. The mixture was then concentrated in vacuo. The crude product was purified by flash column chromatography (petroleum ether-EtOAc, 9:1) to give the title compound 803a (4.12 g, 49%) as a yellow oil.

$R_f$ 0.51 (petroleum ether-EtOAc 9:1); $[\alpha]_D^{21.4}$ +4.65 (c 1.15 in CHCl$_3$); $\delta_H$ (400 MHz; CDCl$_3$) 3.70-3.60 (2H, m, H-1), 2.96-2.92 (1H, m, H-4), 2.75 (1H, dd, J=5.0, 4.0 Hz, H-5), 2.47 (1H, dd, J=5.0, 2.8 Hz, H-5), 1.73-1.53 (4H, m, H-2, H-3), 0.89 (9H, s, SiC(CH$_3$)$_3$), 0.04 (6H, s, Si(CH$_3$)$_2$); $\delta_C$ (100 MHz; CDCl$_3$) 62.7 (CH$_2$, C-1), 52.2 (CH, C-4), 47.1 (CH$_2$, C-5), 29.1 (CH$_2$, C-2), 29.0 (CH$_2$, C-3), 25.9 (3×CH$_3$, SiC(CH$_3$)$_3$), 18.3 (C, SiC(CH$_3$)$_3$), −5.3 (2×CH$_3$, Si(CH$_3$)$_2$). Spectroscopic data was consistent with that reported in literature.

Step v

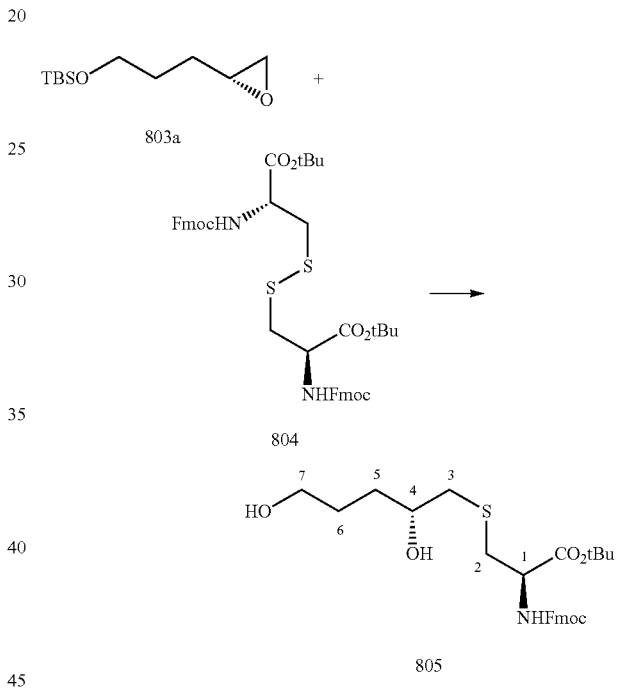

To a stirred solution of disulfide 804 (0.751 g, 0.94 mmol), which is commercially available, in CH$_2$Cl$_2$ (5 mL) at 0° C. was added zinc powder (0.508 g, 7.78 mmol) and a freshly prepared mixture of methanol, conc. hydrochloric acid and conc. sulfuric acid (100:7:1, 2 mL). The resultant mixture was allowed to stir at 0° C. for 30 min. The mixture was then allowed to stir at 65° C. for 5 min after which was added epoxide 803a (0.839 g, 3.88 mmol). The reaction mixture was allowed to stir at 65° C. for 19 h. The mixture was then diluted with EtOAc (50 mL), filtered through a pad of Celite® and washed with brine (50 mL). The aqueous layer was extracted with EtOAc (3×50 mL) and the combined organic extracts were dried over anhydrous Na$_2$SO$_4$ and concentrated in vacuo. The crude product was purified by flash column chromatography (hexanes-EtOAc, 1:3) to give the title compound 805 (0.568 g, 60%) as a colourless oil.

$R_f$ 0.34 (hexane-EtOAc 1:3); $[\alpha]_D^{21.0}$ −26.7 (c 0.03 in CHCl$_3$); $\nu_{max}$(neat)/cm$^{-1}$ 3321, 2931, 1706, 1532, 1450, 1369, 1248, 1152, 1050; $\delta_H$ (400 MHz; CHCl$_3$) 7.76 (2H, d, J=7.5 Hz, FmocH), 7.61 (2H, d, J=7.2 Hz, FmocH), 7.40

(2H, t, J=7.4 Hz, FmocH), 7.31 (2H, t, J=7.4 Hz, FmocH), 5.90 (1H, d, J=7.8 Hz, NH), 4.51 (1H, dd, J=12.3, 5.2 Hz, H-1), 4.39 (2H, d, J=7.1 Hz, FmocCH$_2$), 4.23 (1H, t, J=7.1 Hz, FmocCH), 3.73-3.58 (3H, m, H-4, H-7), 3.03 (1H, dd, J=13.9, 4.4 Hz, H-2), 2.95 (1H, dd, J=13.9, 5.7 Hz, H-2), 2.80 (1H, dd, J=13.6, 2.9 Hz, H-3), 2.53 (1H, dd, J=13.6, 8.9 Hz, H-3), 1.72-1.61 (4H, m, H-5, H-6), 1.49 (9H, s, C(CH$_3$)$_3$)); δ$_C$ (100 MHz; CHCl$_3$) 169.8 (C, CO$_2$tBu), 156.1 (C, FmocCO), 143.9 (C, Fmoc), 141.1 (C, Fmoc), 127.9 (CH, Fmoc), 127.2 (CH, Fmoc), 125.3 (CH, Fmoc), 120.1 (CH, Fmoc), 83.2 (C, C(CH$_3$)$_3$), 70.1 (CH, C-4), 67.3 (CH$_2$, FmocCH$_2$), 62.8 (CH$_2$, C-7), 54.7 (CH, C-1), 47.2 (CH, FmocCH), 41.2 (CH$_2$, C-3), 35.5 (CH$_2$, C-2), 33.4 (CH$_2$, C-5), 29.2 (CH$_2$, C-6), 28.1 (3×CH$_3$, C(CH$_3$)$_3$); HRMS (ESI+) [M+Na]$^+$ 524.2077 calc for C$_{27}$H$_{35}$NNaO$_6$S 524.2075.

Step vi

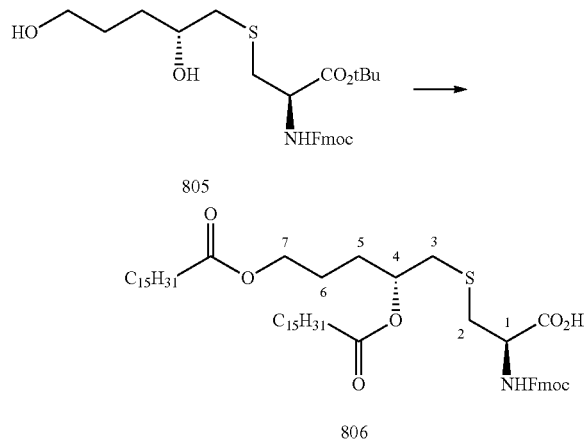

To a stirred solution of diol 805 (0.114 g, 0.243 mmol) and palmitic acid (0.180 g, 0.702 mmol) in THF (3 mL) at r.t. was added N,N'-diisopropylcarbodiimide (0.145 mL, 0.936 mmol) and 4-dimethylaminopyridine (0.011 g, 0.094 mmol). The reaction mixture was allowed to stir at r.t. for 17 h. The mixture was then filtered through a pad of Celite®, diluted with EtOAc (30 mL), washed with 1M citric acid (30 mL) and brine (30 mL) and concentrated in vacuo. The residue was then redissolved in TFA (3 mL) and allowed to stir at r.t for 45 min. The reaction mixture was again concentrated in vacuo. The crude product was purified by flash column chromatography (hexanes-EtOAc, 9:1→0:1) to give the title compound 806 (0.220 g, 98%) as a colourless oil.

R$_f$ 0.15 (petroleum ether-EtOAc 1:1); [a]$_D^{21.3}$ +10.0 (c 0.08 in CHCl$_3$); v$_{max}$(neat)/cm$^{-1}$ 2919, 2851, 1723, 1521, 1521, 1221, 1108, 1054; δ$_H$ (400 MHz; CHCl$_3$) 7.76 (2H, d, J=7.5 Hz, FmocH), 7.62 (2H, d, J=7.4 Hz, FmocH), 7.39 (2H, t, J=7.4 Hz, FmocH), 7.30 (2H, td, J=11.2, 0.9 Hz, FmocH), 5.78 (1H, d, J=7.6 Hz, NH), 5.04-4.95 (1H, m, H-4), 4.60 (1H, dd, J=12.2, 5.2 Hz, H-1), 4.38 (2H, d, J=7.2 Hz, FmocCH$_2$), 4.24 (2H, t, J=7.1 Hz, FmocCH), 4.13-3.99 (2H, m, H-7), 3.16 (1H, dd, J=13.9, 4.5 Hz, H-2), 3.04 (1H, dd, J=14.0, 5.3 Hz, H-2), 2.78-2.70 (2H, m, H-3), 2.34-2.25 (4H, m, 2×PamCH$_{2a}$alkyl), 1.74-1.56 (8H, m, 2×PamCH$_{2β}$alkyl, H-5, H-6), 1.32-1.22 (48H, m, 24×PamCH$_2$alkyl), 0.88 (6H, t, J=6.9 Hz, 2×PamCH$_3$alkyl); δ$_C$ (100 MHz; CHCl$_3$) 174.3 (C, CO$_2$H), 174.0 (C, PamCO$_2$), 173.5 (C, PamCO$_2$), 156.0 (C, FmocCO), 143.7 (C, Fmoc), 141.3 (C, Fmoc), 127.8 (CH, Fmoc), 127.1 (CH, Fmoc), 121.2 (CH, Fmoc), 120.0 (CH, Fmoc), 72.1 (CH, C-4), 67.5 (CH$_2$, FmocCH$_2$), 63.8 (CH$_2$, C-7), 53.6 (CH, C-1), 47.1 (CH, FmocCH), 36.5 (CH$_2$, C-3), 34.6 (CH$_2$, PamCH$_{2a}$alkyl), 34.5 (CH$_2$, PamCH$_{2a}$alkyl), 34.3 (CH$_2$, C-2), 31.9 (2×CH$_2$, PamCH$_2$alkyl), 29.7-29.2 (21×CH$_2$, PamCH$_2$alkyl, C-5), 25.0 (2×CH$_2$, PamCH$_{2β}$alkyl), 24.6 (CH$_2$, C-6), 22.7 (2×CH$_2$, PamCH$_2$alkyl), 14.1 (2×CH$_3$, PamCH$_3$alkyl); HRMS (ESI+) [M+Na]$^+$ 944.6045 calc for C$_{55}$H$_{87}$NNaO$_8$S 944.6028.

7.1.2 Synthesis of Amino Acid Conjugate 811 from Alcohol 807

Step i

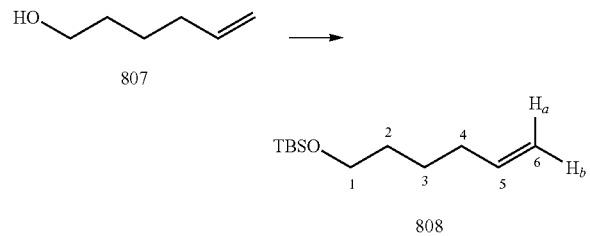

To a stirred solution of 5-hexen-1-ol 807 (5.00 mL, 41.64 mmol) in CH$_2$Cl$_2$ (150 mL) at r.t. was added imidazole (2.86 g, 43.06 mmol) and tert-butyldimethylsilyl chloride (6.34 g, 42.06 mmol). The reaction mixture was allowed to stir at r.t. for 19 h. The mixture was then diluted with EtOAc (400 mL), washed with water (200 mL) and brine (200 mL), dried over anhydrous Na$_2$SO$_4$ and concentrated in vacuo. The crude product was purified by flash column chromatography (petroleum ether) to give the title compound 808 (8.846 g, quant.) as a colourless oil.

R$_f$ 0.90 (petroleum ether-EtOAc 9:1); δ$_H$ (400 MHz; CDCl$_3$) 5.81 (1H, ddt, J=17.1, 10.1, 6.7 Hz, H-5), 5.00 (1H, dq, J=17.2, 1.7 Hz, H$_a$-6), 4.94 (1H, d, J=10.5 Hz, H$_b$-6), 3.61 (2H, t, J=6.2 Hz, H-1), 2.06 (2H, q, J=7.1 Hz, H-4), 1.59-1.50 (2H, m, H-2), 1.47-1.39 (2H, m, H-3), 0.89 (9H, s, SiC(CH$_3$)$_3$), 0.05 (6H, s, Si(CH$_3$)$_2$); δ$_C$ (100 MHz; CDCl$_3$) 139.0 (CH, C-5), 114.3 (CH$_2$, C-6), 63.1 (CH$_2$, C-1), 33.5 (CH$_2$, C-4), 32.3 (CH$_2$, C-2), 26.0 (3×CH$_3$, SiC(CH$_3$)$_3$), 25.2 (CH$_2$, C-3), 18.4 (C, SiC(CH$_3$)$_3$), −5.3 (2×CH$_3$, Si(CH$_3$)$_2$). Spectroscopic data was consistent with that reported in literature.

Step ii

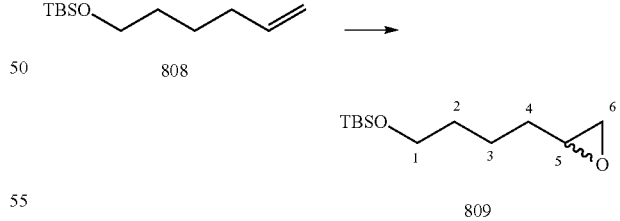

To a stirred solution of alkene 808 (7.58 g, 35.35 mmol) in CH$_2$Cl$_2$ (150 mL) at r.t. was added mCPBA (9.15 g, 53.05 mmol) portionwise. The reaction mixture was allowed to stir at r.t. for 18 h. The mixture was then diluted with Et$_2$O (200 mL), filtered through Celite®, washed with 2M aq. NaOH (200 mL) and brine (200 mL), dried over anhydrous Na$_2$SO$_4$ and concentrated in vacuo. The crude product was purified by flash column chromatography (petroleum ether-EtOAc, 9:1) to give the title compound 809 (6.91 g, 85%) as a colourless oil.

$R_f$ 0.60 (petroleum ether-EtOAc 9:1); $\delta_H$ (400 MHz; CDCl$_3$) 3.61 (2H, t, J=6.0 Hz, H-1), 2.93-2.88 (2H, m, H-5), 2.74 (1H, dd, J=5.0, 4.0 Hz, H-6), 2.46 (1H, dd, J=5.0, 3.0 Hz, H-6), 1.63-1.46 (6H, m, H-2, H-3, H-4), 0.89 (9H, s, SiC(CH$_3$)$_3$), 0.04 (6H, s, Si(CH$_3$)$_2$); $\delta_C$ (100 MHz; CDCl$_3$) 63.0 (CH$_2$, C-1), 52.3 (CH, C-5), 47.1 (CH$_2$, C-6), 32.6 (CH$_2$, C-4), 32.3 (CH$_2$, C-2), 26.0 (3×CH$_3$, SiC(CH$_3$)$_3$), 22.3 (CH$_2$, C-3), 18.4 (C, SiC(CH$_3$)$_3$), −5.3 (2×CH$_3$, Si(CH$_3$)$_2$). Spectroscopic data was consistent with that reported in literature.

Step iii

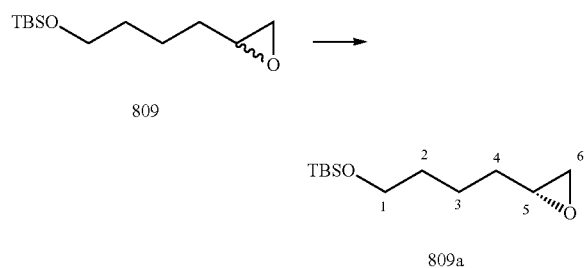

809

809a

To a stirred solution of racemic epoxide 809 (5.887 g, 25.56 mmol), (R,R)-(+)-N,N'-bis(3,5-di-tert-butylsalicylidene)-1,2-cyclohexanediaminocobalt(II) (0.083 g, 0.13 mmol) and glacial acetic acid (0.03 mL, 0.51 mmol) in THF (0.3 mL) at 0° C. was added water (0.253 mL) dropwise. The reaction mixture was allowed to stir at r.t. for 48 h. The mixture was then concentrated in vacuo. The crude product was purified by flash column chromatography (petroleum ether-EtOAc, 9:1) to give the title compound 809a (2.913 g, 49%) as a yellow oil.

$R_f$ 0.60 (petroleum ether-EtOAc 9:1); $[\alpha]_D^{20.4}$ +5.0 (c 0.02 in CHCl$_3$); $\delta_H$ (400 MHz; CDCl$_3$) 3.61 (2H, t, J=6.0 Hz, H-1), 2.93-2.88 (2H, m, H-5), 2.74 (1H, dd, J=5.0, 4.0 Hz, H-6), 2.46 (1H, dd, J=5.0, 3.0 Hz, H-6), 1.63-1.46 (6H, m, H-2, H-3, H-4), 0.89 (9H, s, SiC(CH$_3$)$_3$), 0.04 (6H, s, Si(CH$_3$)$_2$); $\delta_C$ (100 MHz; CDCl$_3$) 63.0 (CH$_2$, C-1), 52.3 (CH, C-5), 47.1 (CH$_2$, C-6), 32.6 (CH$_2$, C-4), 32.3 (CH$_2$, C-2), 26.0 (3×CH$_3$, SiC(CH$_3$)$_3$), 22.3 (CH$_2$, C-3), 18.4 (C, SiC(CH$_3$)$_3$), −5.3 (2×CH$_3$, Si(CH$_3$)$_2$). Spectroscopic data was consistent with that reported in literature.

Step iv

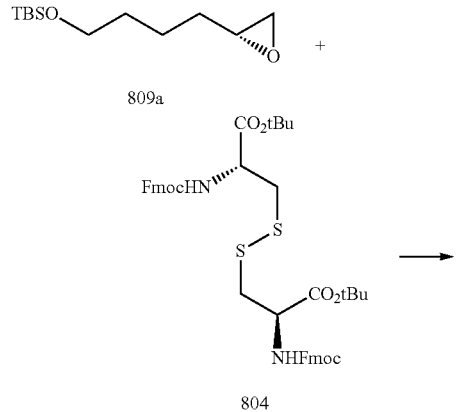

809a

804

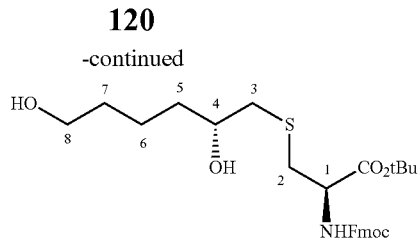

810

To a stirred solution of disulfide 804 (0.500 g, 0.649 mmol) in CH$_2$Cl$_2$ (5 mL) at 0° C. was added zinc powder (0.300 g, 4.54 mmol) and a freshly prepared mixture of methanol, conc. hydrochloric acid and conc. sulfuric acid (100:7:1, 2 mL). The resultant mixture was allowed to stir at 0° C. for 30 min. The mixture was then allowed to stir at 65° C. for 5 min after which was added epoxide 809a (0.600 g, 2.60 mmol). The reaction mixture was allowed to stir at 65° C. for 19 h. The mixture was then diluted with EtOAc (50 mL), filtered through a pad of Celite® and washed with brine (50 mL). The aqueous layer was extracted with EtOAc (3×50 mL) and the combined organic extracts were dried over anhydrous Na$_2$SO$_4$ and concentrated in vacuo. The crude product was purified by flash column chromatography (hexanes-EtOAc, 4:1→1:3) to give the title compound 810 (0.553 g, 83%) as a colourless oil.

$R_f$ 0.39 (hexane-EtOAc 1:3); $[\alpha]_D^{21.2}$ −25.0 (c 0.07 in CHCl$_3$); $\nu_{max}$(neat)/cm$^{-1}$ 3343, 2934, 2862, 1705, 1513, 1450, 1369, 1344, 1248, 1152; $\delta_H$ (400 MHz; CHCl$_3$) 7.76 (2H, d, J=7.5 Hz, FmocH), 7.61 (2H, d, J=7.0 Hz, FmocH), 7.40 (2H, t, J=7.4 Hz, FmocH), 7.30 (2H, td, J=11.2, 1.1 Hz, FmocH), 5.88 (1H, d, J=7.8 Hz, NH), 4.52 (1H, dd, J=12.5, 5.2 Hz, H-1), 4.39 (2H, d, J=8.1 Hz, FmocCH$_2$), 4.23 (1H, t, J=7.1 Hz, FmocCH), 3.70-3.59 (3H, m, H-4, H-8), 3.03 (1H, dd, J=13.7, 4.7 Hz, H-2), 2.94 (1H, dd, J=13.7, 5.4 Hz, H-2), 2.80 (1H, dd, J=13.6, 3.4 Hz, H-3), 2.51 (1H, dd, J=13.4, 8.7 Hz, H-3), 1.60-1.38 (15H, m, H-5, H-6, H-7, C(CH$_3$)$_3$); $\delta_C$ (100 MHz; CHCl$_3$) 169.7 (C, CO$_2$Bu), 156.0 (C, FmocCO), 143.8 (C, Fmoc), 141.3 (C, Fmoc), 127.8 (CH, Fmoc), 127.1 (CH, Fmoc), 125.2 (CH, Fmoc), 120.0 (CH, Fmoc), 83.1 (C, C(CH$_3$)$_3$), 69.8 (CH, C-4), 67.2 (CH$_2$, FmocCH$_2$), 62.5 (CH$_2$, C-8), 54.6 (CH, C-1), 47.1 (CH, FmocCH), 41.1 (CH$_2$, C-3), 35.8 (CH$_2$, C-5), 35.4 (CH$_2$, C-2), 32.4 (CH$_2$, C-7), 28.0 (3×CH$_3$, C(CH$_3$)$_3$), 21.9 (CH$_2$, C-6); HRMS (ESI+) [M+Na]$^+$ 538.2226 calc for C$_{28}$H$_{37}$NNaO$_6$S 538.2234.

Step v

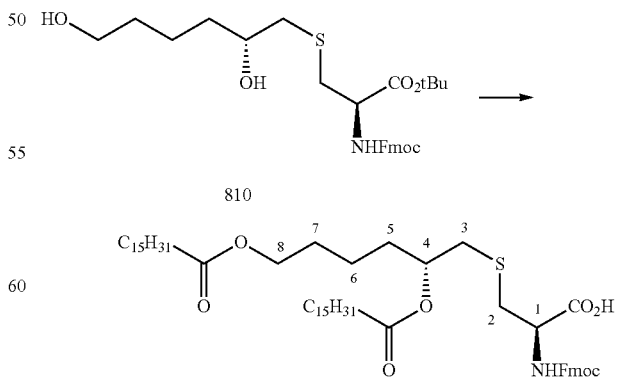

810

811

To a stirred solution of diol 810 (0.190 g, 0.370 mmol) and palmitic acid (0.284 g, 1.10 mmol) in THF (3 mL) at r.t. was added N,N'-diisopropylcarbodiimide (0.226 mL, 1.47 mmol) and 4-dimethylaminopyridine (0.018 g, 0.147 mmol). The reaction mixture was allowed to stir at r.t. for 17 h. The mixture was then filtered through a pad of Celite®, diluted with EtOAc (50 mL), washed with 1M citric acid (30 mL) and brine (30 mL) and concentrated in vacuo. The residue was then redissolved in TFA (3 mL) and allowed to stir at r.t. for 45 min. The reaction mixture was again concentrated in vacuo. The crude product was purified by flash column chromatography (hexanes-EtOAc, 9:1→0:1) to give the title compound 811 (0.301 g, quant.) as a colourless oil.

$R_f$ 0.20 (petroleum ether-EtOAc 1:1); $[a]_D^{21.2}$ +10.0 (c 0.07 in CHCl$_3$); $v_{max}$(neat)/cm$^{-1}$ 3331, 2917, 2850, 1728, 1692, 1532, 1467, 1451, 1244, 1221, 1198, 1175; $\delta_H$ (400 MHz; CHCl$_3$) 7.76 (2H, d, J=7.5 Hz, FmocH), 7.62 (2H, d, J=7.2 Hz, FmocH), 7.40 (2H, t, J=7.4 Hz, FmocH), 7.30 (2H, td, J=11.2, 1.0 Hz, FmocH), 5.82 (1H, d, J=7.9 NH), 5.03-4.92 (1H, m, H-4), 4.71-4.60 (1H, m, H-1), 4.40 (2H, d, J=7.0 Hz, FmocCH$_2$), 4.24 (1H, t, J=7.1 Hz, FmocCH), 4.11-4.00 (2H, m, H-8), 3.15 (1H, dd, J=13.9, 4.4 Hz, H-2), 3.04 (1H, dd, J=13.8, 5.8 Hz, H-2), 2.78-2.65 (2H, m, H-3), 2.31 (2H, t, J=7.6 Hz, PamCH$_{2a}$alkyl), 2.28 (2H, t, J=7.6 Hz, PamCH$_{2a}$alkyl), 1.74-1.55 (8H, m, 2×PamCH$_{2\beta}$alkyl, H-5, H-7), 1.45-1.17 (50H, m, 24×PamCH$_2$alkyl, H-6), 0.88 (6H, t, J=6.8 Hz, 2×PamCH$_3$alkyl); $\delta_C$ (100 MHz; CHCl$_3$) 174.3 (C, CO$_2$H), 174.0 (C, PamCO$_2$), 173.9 (C, PamCO$_2$), 156.1 (C, FmocCO), 143.7 (C, Fmoc), 141.3 (C, Fmoc), 127.8 (CH, Fmoc), 127.1 (CH, Fmoc), 125.2 (CH, Fmoc), 120.0 (CH, Fmoc), 72.4 (CH, C-4), 67.4 (CH$_2$, FmocCH$_2$), 64.0 (CH$_2$, C-8), 53.6 (CH, C-1), 47.1 (CH, FmocCH), 36.6 (CH$_2$, C-3), 34.6 (CH$_2$, PamCH$_{2a}$alkyl), 34.5 (CH$_2$, PamCH$_{2a}$alkyl), 34.4 (CH$_2$, C-2), 32.7 (CH$_2$, C-5), 32.0 (2×CH$_2$, PamCH$_2$alkyl), 29.7-29.3 (20×CH$_2$, PamCH$_2$alkyl), 28.3 (CH$_2$, C-7), 25.0 (2×CH$_2$, PamCH$_{2\beta}$alkyl), 25.0 (2×CH$_2$, PamCH$_{2\beta}$alkyl), 22.7 (2×CH$_2$, PamCH$_2$alkyl), 21.7 (CH$_2$, C-6), 14.4 (2×CH$_3$, PamCH$_3$alkyl); HRMS (ESI+) [M+Na]$^+$ 958.6239 calc for C$_{56}$H$_{89}$NNaO$_8$S 958.6238.

7.1.3 Synthesis of Amino Acid Conjugate 820 from Alkene 814
A) Synthesis of Alkene 814 from Alcohol 812
Step i

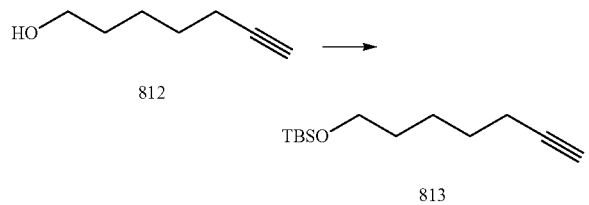

To a stirred solution of 6-heptyn-1-ol 812 (3.33 mL, 26.75 mmol) in CH$_2$Cl$_2$ (80 mL) at r.t. was added imidazole (1.76 g, 27.01 mmol) and tert-butyldimethylsilyl chloride (4.07 g, 27.01 mmol). The reaction mixture was allowed to stir at r.t. for 24 h. The mixture was then diluted with Et$_2$O (100 mL) and washed with water (3×100 mL) and brine (100 mL). The organic layer was dried over anhydrous Na$_2$SO$_4$ and concentrated in vacuo. The crude product was purified by filtration through silica gel to give alkyne 813 (5.68 g, quant.) as a colourless liquid. Alkyne 813 was used in subsequent synthetic steps without characterisation.
Step ii

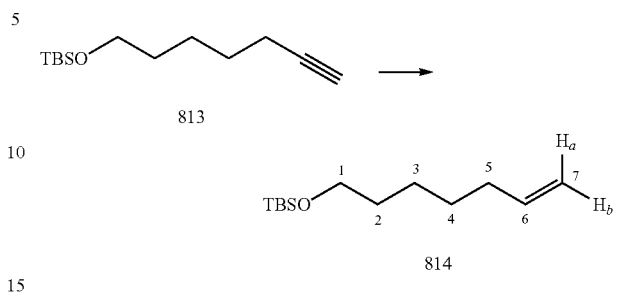

To a stirred solution of alkyne 813 (5.34 g, 25.18 mmol) in hexanes (140 mL) at r.t. was added quinoline (4.18 mL, 35.26 mmol) and Lindar's catalyst (0.53 g). The reaction mixture was connected to a H2-filled balloon (1 atm) and allowed to stir at r.t. for 2 h. The mixture was then filtered through a pad of Celite® and concentrated in vacuo. The crude product was purified by flash column chromatography (petroleum ether-EtOAc, 9:1) to give the title compound 814 (5.34 g, quant.) as a colourless liquid.

$R_f$ 0.91 (petroleum ether-EtOAc 9:1); $\delta_H$ (400 MHz; CDCl$_3$) 5.81 (1H, ddt, J=17.0, 10.3, 6.7 Hz, H-6), 4.99 (1H, dd, J=17.0 Hz, H$_a$-7) 4.93 (1H, dd, J=10.1 Hz, H$_b$-7), 3.60 (2H, t, J=6.6 Hz, H-1), 2.05 (2H, q, J=7.0 Hz, H-5), 1.56-1.31 (6H, m, H-2, H-3, H-4), 0.89 (9H, s, SiC(CH$_3$)$_3$), 0.05 (6H, s, Si(CH$_3$)$_2$); $\delta_C$ (100 MHz; CDCl$_3$) 139.1 (CH, C-6), 114.2 (CH$_2$, C-7), 63.2 (CH$_2$, C-1), 33.8 (CH$_2$, C-5), 33.7 (CH$_2$, C-4), 28.7 (CH$_2$, C-3), 26.0 (3×CH$_3$, SiC(CH$_3$)$_3$), 25.3 (CH$_2$, C-2), 18.4 (C, SiC(CH$_3$)$_3$), −5.3 (2×CH$_3$, Si(CH$_3$)$_2$). Spectroscopic data was consistent with that reported in literature.

B) Synthesis of Alkene 814 from Alcohol 815
Step i

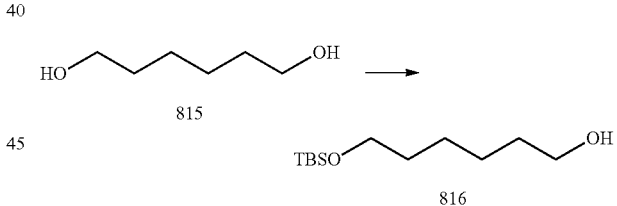

To a stirred solution of 1,6-hexanediol (815) (16.00 g, 135.39 mmol) in CH$_2$Cl$_2$ (150 mL) at r.t. was added imidazole (9.22 g, 135.39 mmol) and tert-butyldimethylsilyl chloride (20.41 g, 135.39 mmol). The reaction mixture was allowed to stir at r.t. for 19 h. The mixture was then filtered, washed with H$_2$O (100 mL) and brine (100 mL), dried over anhydrous Na$_2$SO$_4$ and concentrated in vacuo. The crude product was purified by flash column chromatography (petroleum ether-EtOAc, 4:1) to give the title compound 816 (25.13 g, 80%) as a colourless liquid. Alcohol 816 was used in subsequent synthetic steps without characterisation.
Step ii

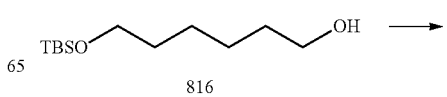

123

-continued

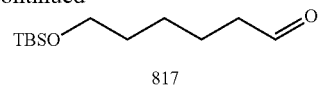
817

To a stirred solution of alcohol 816 (4.90 g, 21.10 mmol) in CH$_2$Cl$_2$ (11 mL) at 0° C. was added dimethylsulfoxide (11.08 mL, 154.05 mmol), Et$_3$N (14.71 mL, 105.52 mmol) and sulfur trioxide pyridine complex (9.89 g, 63.31 mmol). The reaction mixture was allowed to stir for 30 min. The mixture was then quenched with water (20 mL) and extracted with EtOAc (2×50 mL). The combined organic extracts were washed with water (50 mL) and brine (50 mL), dried over anhydrous Na$_2$SO$_4$ and concentrated in vacuo. The crude product was purified by flash column chromatography (petroleum ether-EtOAc, 9:1) to give the title compound 817 (4.71 g, 97%) as a colourless oil. Aldehyde 817 was used in subsequent synthetic steps without characterization.
Step iii

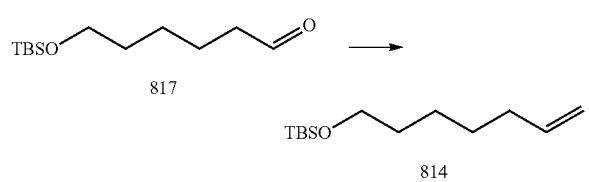

To a stirred solution of methyltriphenylphosphonium bromide (4.60 g, 12.89 mmol) in THF (30 mL) at −78° C. was added a solution of n-butyllithium (7.16 mL, 1.8 M, 12.89 mmol) dropwise. The resultant mixture was warmed to r.t. and allowed to stir for 1 h. The reaction mixture was then cooled to −78° C. and aldehyde 817 (2.56 g, 11.21 mmol) in THF (6 mL) was added dropwise. The reaction mixture was allowed to stir at −78° C. for 3 h and then warmed to r.t. and allowed to stir for a further 15 h. The mixture was then quenched with sat. aq. NH$_4$Cl (10 mL) and extracted with EtOAc (3×70 mL). The combined organic extracts were washed with water (2×50 mL) and brine (50 mL), dried over anhydrous Na$_2$SO$_4$ and concentrated in vacuo. The crude product was purified by flash column chromatography (petroleum ether-EtOAc, 99:1) to give the title compound 814 (2.50 g, 98%) as a colourless liquid.

R$_f$ 0.91 (petroleum ether-EtOAc 9:1); δ$_H$ (400 MHz; CDCl$_3$) 5.81 (1H, ddt, J=17.0, 10.3, 6.7 Hz, H-6), 4.99 (1H, dd, J=17.0 Hz, H$_a$-7) 4.93 (1H, dd, J=10.1 Hz, H$_b$-7), 3.60 (2H, t, J=6.6 Hz, H-1), 2.05 (2H, q, J=7.0 Hz, H-5), 1.56-1.31 (6H, m, H-2, H-3, H-4), 0.89 (9H, s, SiC(CH$_3$)$_3$), 0.05 (6H, s, Si(CH$_3$)$_2$); δ$_C$ (100 MHz; CDCl$_3$) 139.1 (CH, C-6), 114.2 (CH$_2$, C-7), 63.2 (CH$_2$, C-1), 33.8 (CH$_2$, C-5), 33.7 (CH$_2$, C-4), 28.7 (CH$_2$, C-3), 26.0 (3×CH$_3$, SiC(CH$_3$)$_3$), 25.3 (CH$_2$, C-2), 18.4 (C, SiC(CH$_3$)$_3$), −5.3 (2×CH$_3$, Si(CH$_3$)$_2$). Spectroscopic data was consistent with that reported in literature.
C) Synthesis of Amino Acid Conjugate 820 from Alkene 814
Step i

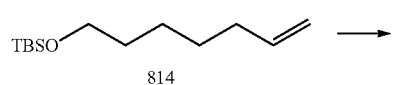
814

124

-continued

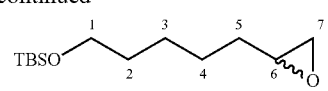
818

To a stirred solution of alkene 814 (4.30 g, 18.40 mmol) in CH$_2$Cl$_2$ (40 mL) at r.t. was added mCPBA (4.46 g, 25.84 mmol). The reaction mixture was allowed to stir at r.t. for 7 h. The mixture was then filtered through Celite®, diluted with Et$_2$O (60 mL) and washed with sat. aq. NaHCO$_3$ (3×100 mL) and brine (100 mL). The organic layer was dried over anhydrous Na$_2$SO$_4$ and concentrated in vacuo. The crude product was purified by flash column chromatography (petroleum ether-EtOAc, 9:1) to give the title compound 818 (4.30 g, 96%) as a colourless liquid.

R$_f$ 0.63 (petroleum ether-EtOAc 9:1); δ$_H$ (400 MHz; CDCl$_3$) 3.60 (2H, t, J=6.5 Hz, H-1), 2.92-2.88 (1H, m, H-6), 2.74 (1H, t, J=4.5 Hz, H-7), 2.46 (1H, dd, J=5.0, 2.8 Hz, H-7), 1.56-1.36 (8H, m, H-2, H-3, H-4, H-5), (9H, s, SiC(CH$_3$)$_3$), 0.04 (6H, s, Si(CH$_3$)$_2$); δ$_C$ (100 MHz; CDCl$_3$) 63.1 (CH$_2$, C-1), 52.3 (CH, C-6), 47.1 (CH$_2$, C-7), 32.8 (CH$_2$, C-5), 32.5 (CH$_2$, C-2), 26.0 (3×CH$_3$, SiC(CH$_3$)$_3$), 25.8 (CH$_2$, C-4), 25.7 (CH$_2$, C-3), 18.4 (C, SiC(CH$_3$)$_3$), −5.3 (2×CH$_3$, Si(CH$_3$)$_2$). Spectroscopic data was consistent with that reported in literature.
Step ii

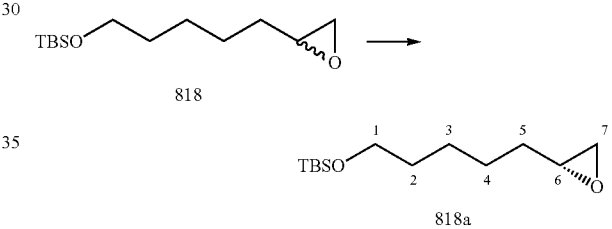

To a stirred solution of racemic epoxide 818 (2.23 g, 9.13 mmol), (R,R)-(+)-N,N'-bis(3,5-di-tert-butylsalicylidene)-1,2-cyclohexanediaminocobalt(II) (0.03 g, 0.05 mmol) and glacial acetic acid (0.01 mL, 0.18 mmol) in THF (0.1 mL) at 0° C. was added water (0.09 mL) dropwise. The reaction mixture was allowed to stir at r.t. for 48 h. The mixture was then concentrated in vacuo. The crude product was purified by flash column chromatography (petroleum ether-EtOAc, 9:1) to give the title compound 818a (1.09 g, 49%) as a yellow oil.

R$_f$ 0.63 (petroleum ether-EtOAc 9:1); [a]$_D^{21.3}$ +4.2 (c 0.90 in CHCl$_3$); δH (400 MHz; CDCl$_3$) 3.60 (2H, t, J=6.5 Hz, H-1), 2.92-2.88 (1H, m, H-6), 2.74 (1H, t, J=4.5 Hz, H-7), 2.46 (1H, dd, J=5.0, 2.8 Hz, H-7), 1.56-1.36 (8H, m, H-2, H-3, H-4, H-5), (9H, s, SiC(CH$_3$)$_3$), 0.04 (6H, s, Si(CH$_3$)$_2$); δ$_C$ (100 MHz; CDCl$_3$) 63.1 (CH$_2$, C-1), 52.3 (CH, C-6), 47.1 (CH$_2$, C-7), 32.8 (CH$_2$, C-5), 32.5 (CH$_2$, C-2), 26.0 (3×CH$_3$, SiC(CH$_3$)$_3$), 25.8 (CH$_2$, C-4), 25.7 (CH$_2$, C-3), 18.4 (C, SiC(CH$_3$)$_3$), −5.3 (2×CH$_3$, Si(CH$_3$)$_2$). Spectroscopic data was consistent with that reported in literature.
Step iii

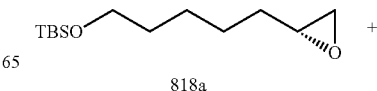
818a +

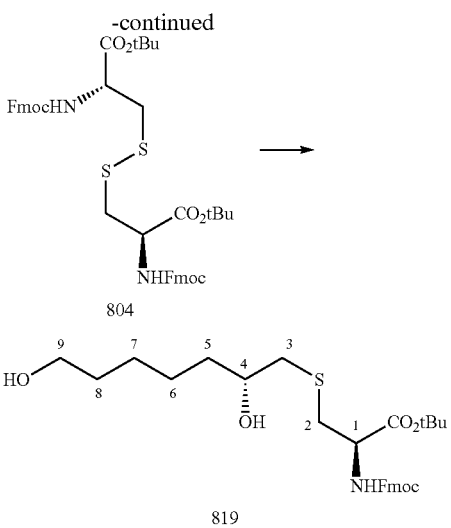

804

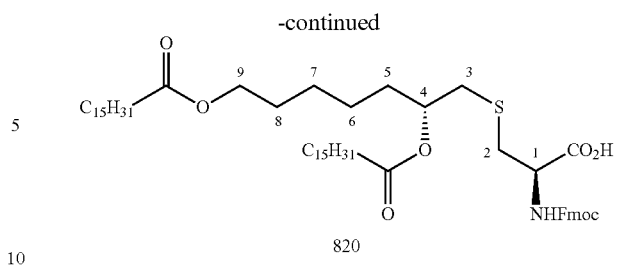

820

To a stirred solution of diol 819 (0.168 g, 0.317 mmol) and palmitic acid (0.244 g, 0.951 mmol) in THF (4.6 mL) at r.t. was added N,N'-diisopropylcarbodiimide (0.191 mL, 1.269 mmol) and 4-dimethylaminopyridine (0.016 g, 0.127 mmol). The reaction mixture was allowed to stir at r.t. for 17 h. The mixture was then filtered through a pad of Celite®, diluted with EtOAc (30 mL), washed with 1M citric acid (30 mL) and brine (30 mL) and concentrated in vacuo. The residue was then redissolved in TFA (3 mL) and allowed to stir at r.t. for 45 min. The reaction mixture was again concentrated in vacuo. The crude product was purified by flash column chromatography (hexanes-EtOAc, 9:1→0:1) to give the title compound 820 (0.301 g, quant.) as a colourless oil.

$R_f$ 0.21 (petroleum ether-EtOAc 1:1); $[a]_D^{20.8}$ +7.5 (c 0.24 in CHCl$_3$); $v_{max}$(neat)/cm$^{-1}$ 3319, 2919, 2851, 1722, 1521, 1471, 1450, 1221, 1055; $\delta_H$ (400 MHz; CDCl$_3$) 7.76 (2H, d, J=7.6 Hz, FmocH), 7.61 (2H, d, J=7.3 Hz, FmocH), 7.40 (2H, t, J=7.7 Hz, FmocH), 7.30 (2H, td, J=11.2, 1.1 Hz, FmocH), 5.82, (1H, d, J=7.7 Hz, NH), 5.00-4.94 (1H, m, H-4), 4.64 (1H, dd, J=12.3, 5.6 Hz, H-1), 4.40 (2H, d, J=7.1 Hz, FmocCH), 4.24 (1H, t, J=7.1 Hz, FmocCH$_2$), 4.10-4.00 (2H, m, H-9), 3.14 (1H, dd, J=13.8, 4.3 Hz, H-2), 3.04 (1H, dd, J=13.8, 5.6 Hz, H-2), 2.76-2.67 (2H, m H-3), 2.31 (2H, t, J=7.6 Hz, PamCH$_{2a}$alkyl), 2.28 (2H, t, J=7.6 Hz, PamCH$_{2a}$alkyl), 1.65-1.56 (8H, m, 2×PamCH$_{2\beta}$alkyl, H-8, H-5), 1.39-1.18 (52H, m, 24×PamCH$_2$alkyl, H-6, H-7), 0.88 (6H, t, J=6.9 Hz, 2×PamCH$_3$alkyl); $\delta_C$ (100 MHz; CDCl$_3$) 174.4 (C, CO$_2$H), 156.1 (C, FmocCO), 143.7 (C, Fmoc), 141.3 (C, Fmoc), 127.8 (CH, Fmoc), 127.1 (CH, Fmoc), 125.2 (CH, Fmoc), 120.0 (CH, Fmoc), 72.4 (CH, C-4), 67.5 (CH$_2$, FmocCH$_2$), 64.2 (CH$_2$, C-9), 53.6 (CH, C-1), 47.1 (CH, FmocCH), 36.5 (CH$_2$, C-3), 34.6 (CH$_2$, C-2), 34.3 (2×CH$_2$, PamCH$_{2a}$alkyl), 33.0 (CH$_2$, C-5), 31.9 (2×CH$_2$, PamCH$_2$alkyl) 29.7-28.4 (21×CH$_2$, PamCH$_2$alkyl, C-8), 25.5 (CH$_2$, C-7), 25.0 (2×CH$_2$, PamCH$_{2\beta}$alkyl), 24.8 (CH$_2$, C-6), 22.7 (2×CH$_2$, PamCH$_2$alkyl), 14.1 (2×CH$_3$, PamCH$_3$alkyl); HRMS (ESI+) [M+Na]$^+$972.6358 calc for C$_{57}$H$_{91}$NNaO$_8$S 972.6392.

819

To a stirred solution of disulfide 804 (0.30 g, 0.375 mmol) in CH$_2$Cl$_2$ (1 mL) at 0° C. was added zinc powder (0.20 g, 3.01 mmol) and a freshly prepared mixture of methanol, conc. hydrochloric acid and conc. sulfuric acid (100:7:1, 1 mL). The resultant mixture was allowed to stir at 0° C. for 30 min after which was added epoxide 818a (0.344 g, 1.13 mmol). The reaction mixture was allowed to stir at 70° C. for 17 h. The mixture was then diluted with EtOAc (30 mL), filtered through a pad of Celite® and washed with brine (30 mL). The aqueous layer was extracted with EtOAc (3×30 mL) and the combined organic extracts were dried over anhydrous MgSO$_4$ and concentrated in vacuo. The crude product was purified by flash column chromatography (hexanes-EtOAc, 1:3) to give the title compound 819 (0.350 g, 88%) as a colourless oil.

$R_f$ 0.4 (hexane-EtOAc 1:3); $[a]_D^{20.8}$ −20.0 (c 0.03 in EtOAc); $v_{max}$(neat)/cm$^{-1}$ 3365, 3933, 1703, 1514, 1450, 1369, 1343, 1248, 1151, 1046; $\delta_H$ (400 MHz; MeOD) 7.79 (2H, d, J=7.5 Hz, FmocH), 7.68 (2H, d, J=7.4 Hz, FmocH), 7.39 (2H, t, J=7.4 Hz, FmocH), 7.31 (2H, t, J=4.7 Hz, FmocH), 4.34 (2H, d, J=7.1 Hz, FmocCH), 4.28 (1H, dd, J=8.2, 5.1 Hz, H-1), 4.23 (1H, t, J=7.0 Hz, FmocCH$_2$), 3.72-3.61 (1H, m, H-4), 3.57-3.79 (2H, m, H-9), 3.01 (1H, dd, J=13.8, 5.0 Hz, H-2), 2.86 (1H, dd, J=13.7, 8.3 Hz, H-2), 2.69 (1H, dd, J=13.4, 4.9 Hz, H-3), 2.60 (1H, dd, J=13.4, 7.0 Hz, H-3), 1.57-1.34 (17H, m, H-5, H-6, H-7, H-8, C(CH$_3$)$_3$); $\delta_C$ (100 MHz; MeOD) 171.8 (C, CO$_2$tBu), 158.1 (C, FmocCO), 145.3 (C, Fmoc), 142.6 (C, Fmoc), 128.8 (CH, Fmoc), 128.2 (CH, Fmoc), 126.4 (CH, Fmoc), 121.0 (CH, Fmoc), 83.3 (C, C(CH$_3$)$_3$), 71.9 (CH, C-4), 68.2 (CH$_2$, FmocCH$_2$), 62.9 (CH$_2$, C-9), 56.5 (CH, C-1), 50.2 (CH, FmocCH), 40.8 (CH$_2$, C-3), 37.3 (CH$_2$, C-5), 35.5 (CH$_2$, C-2), 33.6 (CH$_2$, C-8), 28.3 (3×CH$_3$, C(CH$_3$)$_3$), 26.9 (CH$_2$, C-7), 26.6 (CH$_2$, C-6); HRMS (ESI+) [M+Na]$^+$ 552.2390 calc for C$_{29}$H$_{39}$NNaO$_6$S 552.2393.
Step iv

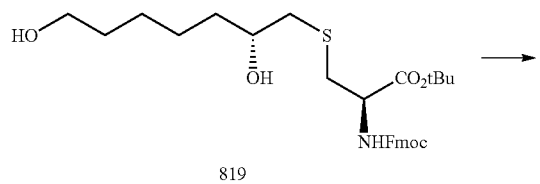

819

8. Example 8

This example demonstrates the TLR agonism of (R)- and (S)-constructs of Pam2Cys-SKKKK, homoPam2Cys-SKKKK and Pam3Cys-SKKKK.
8.1 Method
Enantiopure epimeric (R)- and (S)-versions of Pam2Cys-SKKKK, homoPam2Cys-SKKKK and Pam3Cys-SKKKK were produced in-house using methods analogous to those described in the Examples herein (Examples 4 and 5). Further, paired SKKKK-NH$_2$ and SKKKK-NAc agonist sets were prepared, in order to assess the impact of C-terminal modification on TLR agonism by h-Pam-2-Cys and Pam-2-Cys. The agonists prepared are listed in Table 4.
The TLR2 agonism of the agonists in Table 4 were investigated in HEK-Blue™-mTLR2 (FIG. 6A) and HEK- Blue™-hTLR2 (FIG. 6B) cells by following a procedure analogous to that described in section 2.1 of Example 2 across a 6-$\log_{10}$ dilution series ($10^{-6}$ M to $10^{-11}$ M). (R/S)-Pam-1-Cys-$NH_2$ was tested only at $10^{-6}$ and $10^{-9}$ M. Data presented as mean+/−SD absorbance (635 nm) values for triplicate wells following background subtraction, with dotted lines representing absorbance in wells treated with media only.

TABLE 4

Enantiopure TLR agonists

Figure 6A:
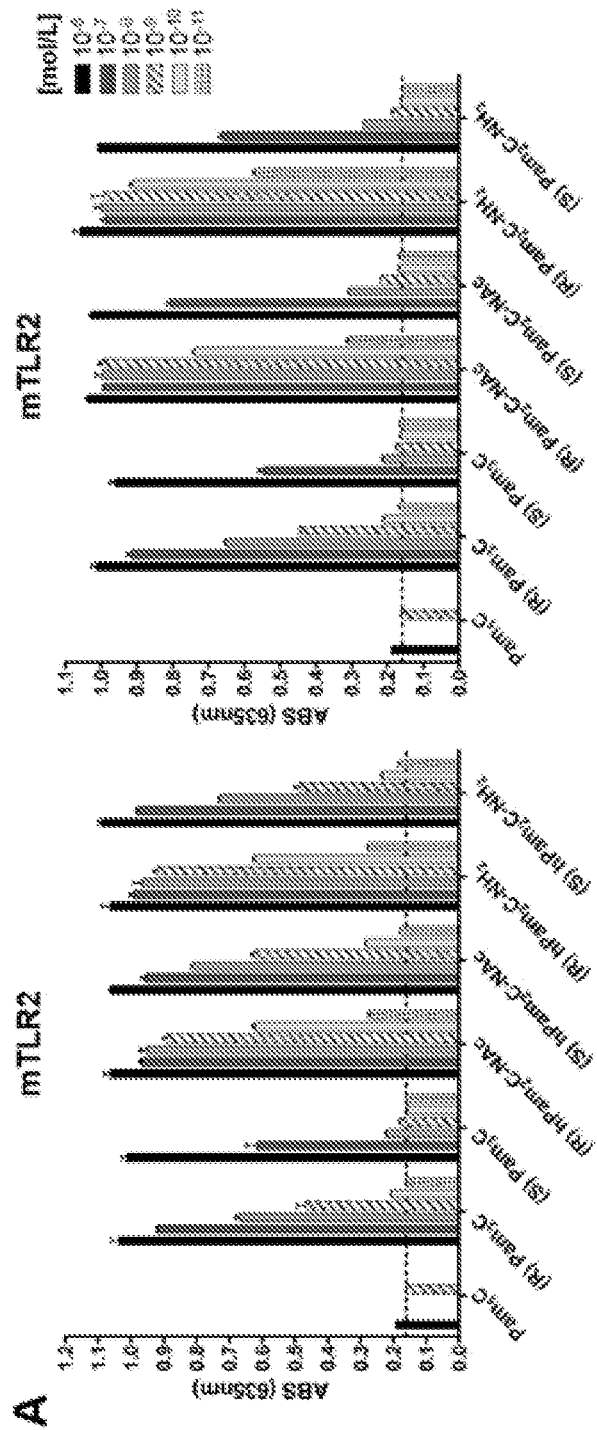
FIGS. 6A and 6B are graphs showing the results of TLR agonism assays in HEK-Blue™-mTLR2 (FIG. 6A) and HEK-Blue™-hTLR2 (FIG. 6B) cells using Pam1Cys-SKKKK-NH$_2$ and the (R)- and (S)-Pam2Cys-SKKKK, Pam3Cys-SKKKK, and homoPam2Cys-SKKKK constructs listed in Table 4, as described in Example 8, at various concentrations: $10^{-6}$ mol/L (black bars), $10^{-7}$ mol/L (dary grey bars), $10^{-8}$ mol/L (medium grey bars), $10^{-9}$ mol/L (diagonal cross-hatched bars), $10^{-10}$ mol/L (light grey bars), and $10^{-11}$ mol/L (square hatched bars).
Figure 6B:
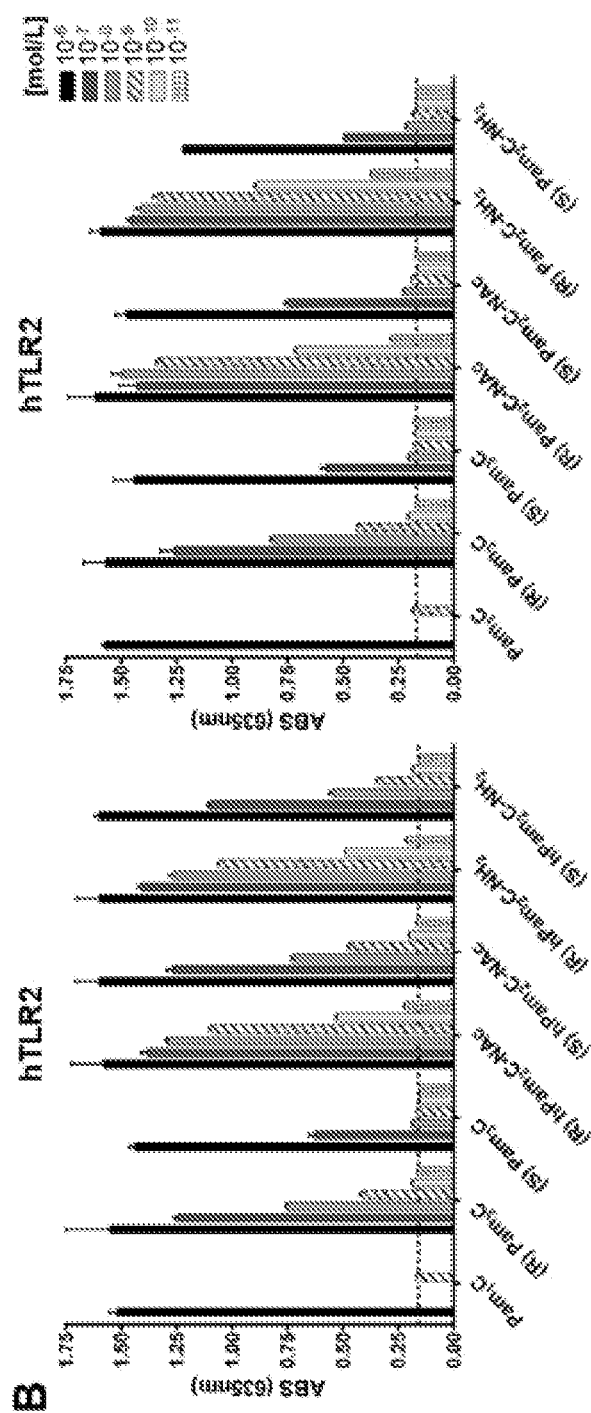

| Agonist | Label in FIGS. 6A and 6B |
|---|---|
| Pam1Cys-SKKKK-$NH_2$ | $Pam_1C$ |
| (R)-Pam2Cys-SKKKK-$NH_2$ | (R) $Pam_2$C-$NH_2$ |
| (S)-Pam2Cys-SKKKK-$NH_2$ | (S) $Pam_2$C-$NH_2$ |
| (R)-Pam2Cys-SKKKK-NHAc | (R) $Pam_2$C-NAc |
| (S)-Pam2Cys-SKKKK-NHAc | (S) $Pam_2$C-NAc |
| (R)-homo-Pam2Cys-SKKKK-$NH_2$ | (R) $hPam_2$C-$NH_2$ |
| (S)-homoPam2Cys-SKKKK-$NH_2$ | (S) $hPam_2$C-$NH_2$ |
| (R)-homoPam2Cys-SKKKK-NHAc | (R) $hPam_2$C-NAc |
| (S)-homoPam2Cys-SKKKK-NHAc | (S) $hPam_2$C-NAc |
| (R)-Pam3Cys-SKKKK-$NH_2$ | (R) $Pam_3$C |
| (S)-Pam3Cys-SKKKK-$NH_2$ | (S) $Pam_3$C |

Scheme 7. Structures of Pam1Cys-, (R)- and (S)-Pam2Cys, (R)- and (S)-Pam3Cys-, and (R)- and (S)-homoPam2Cys- referred to in Table 4.

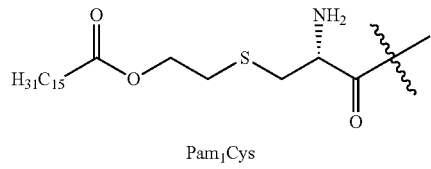

Pam₁Cys

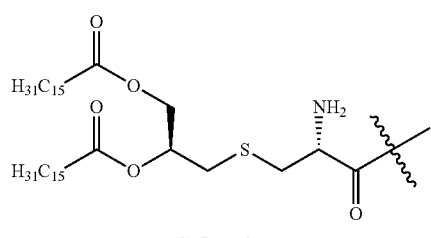

(S)-Pam₂Cys

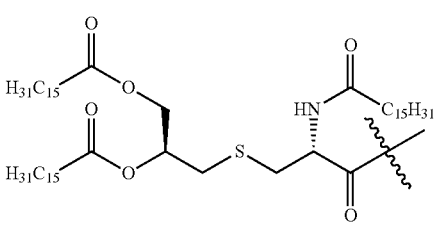

(S)-Pam₃Cys

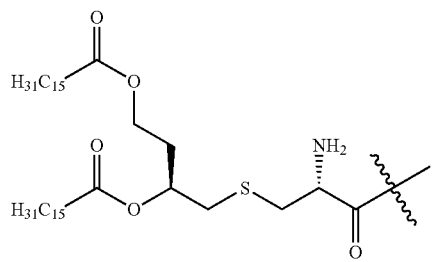

(S)-homoPam₂Cys

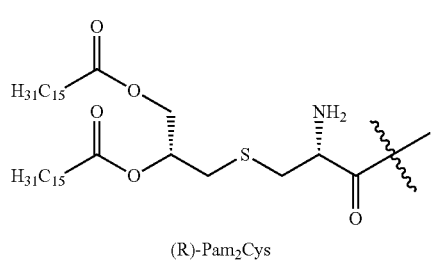

(R)-Pam₂Cys

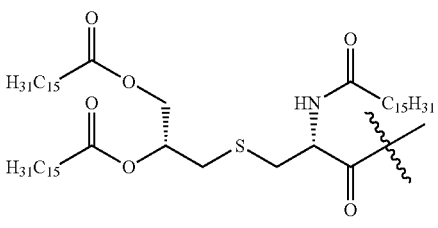

(R)-Pam₃Cys

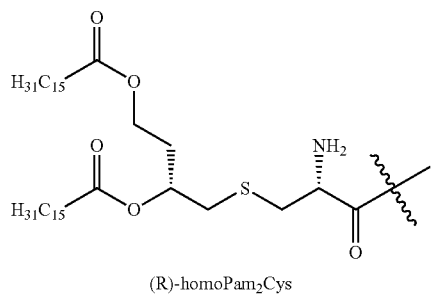

(R)-homoPam₂Cys 8.2 Results 8.2.1 Construct Bioactivity for mTLR2 and hTLR2

Pam1Cys-SKKKK-NH$_2$ exhibited agonism for hTLR2 at $10^{-6}$ M but not $10^{-9}$ M, and exhibited no agonism at any concentration for mTLR2. By contrast, all Pam2Cys, homoPam2Cys and Pam3Cys constructs tested exhibited agonism for both mTLR2 and hTLR2. Typically, epimer- and C-terminus-matched homoPam2Cys and Pam2Cys constructs exhibited comparable strength and pattern of agonism across the dilution series, and were markedly more potent agonists than epimer-matched Pam3Cys for both mTLR2 and hTLR2 (eliciting NFκB production at ≥10-fold lower concentrations than Pam3Cys).

8.2.2 Effect of (R)- Vs (S)-Stereochemistry

In all construct sets tested, paired (R)-versions exhibited more potent agonism than (S)-versions for both mTLR2 and hTLR2. (R)-Pam3Cys maintained NFκB production at ~≥10-fold lower concentration than (S)-Pam3Cys for both mTLR2 and hTLR2. (R)-homoPam2Cys maintained NFκB production at ~≥10-fold lower concentration than (S)-homoPam2Cys for both mTLR2 and hTLR2, irrespective of C-terminal modification. (R)-Pam2Cys maintained NFκB production at ~≥100-fold lower concentration than (S)-Pam2Cys for both mTLR2 and hTLR2, irrespective of C-terminal modification. Interestingly, while (R)-homoPam2Cys and (R)-Pam2Cys were comparable agonists across the log$_{10}$ dilution series in both mTLR2 and hTLR2, (S)-homoPam2Cys was a more potent agonist than (S)-Pam2Cys in both mTLR2 and hTLR2, eliciting NFκB production at ~≥10-100-fold lower concentration. (S)-Pam2Cys exhibited a similar strength and pattern of agonism to (S)-Pam3Cys.

8.2.3 Effect of C-Terminal —NH$_2$ and —NAc

No differential agonism was observed for either mTLR2 or HTLR2 when comparing epimer-matched homoPam2Cys-SKKKK bearing C-terminal —NH$_2$ and C-terminal —NAc. No differential agonism was observed for hTLR2 when comparing epimer-matched Pam2Cys-SKKKK bearing C-terminal —NH$_2$ and C-terminal —NAc. No differential agonism was observed for mTLR2 when comparing (S)-Pam2Cys-SKKKK bearing C-terminal —NH$_2$ and C-terminal —NAc. An increase in NKκB production at $10^{-10}$ and $10^{-11}$ M only was observed when comparing (R)-Pam2Cys-SKKKK-NH$_2$ to (R)-Pam2Cys-SKKKK-NAc for mTLR2.

9. Example 9

Peptide conjugates of the invention 821 and 822 comprising the peptide sequence SKKKKKISQAVHAA-HAEINEAGRESIINFEKLTEWT [SEQ ID No: 127] were prepared using 6 as described and depicted below (Scheme 8).

The peptide sequence (SEQ ID No: 127)
SKKKK<u>ISQAVHAAHAEINEAGRES</u><u>IINFEKLTEWT</u> includes two immunogenic peptide epitopes (underlined), linked by a single E, derived from the ovalbumin (OVA) protein (the major constituent of chicken egg white). OVA is useful as a model antigen in mice, for example, as tumour cells can be engineered/transfected to express it.

Details of the epitopes are as follows:

SIINFEKL: H-K2$^b$ restricted (murine MHC class I), recognised by CD8$^+$ T cells. OVA amino acids 257-264.

ISQAVHAAHAEINEAGR: I-Ad restricted (murine MHC class II), recognised by CD4$^+$ T cells. OVA amino acids 323-339.

Scheme 8.

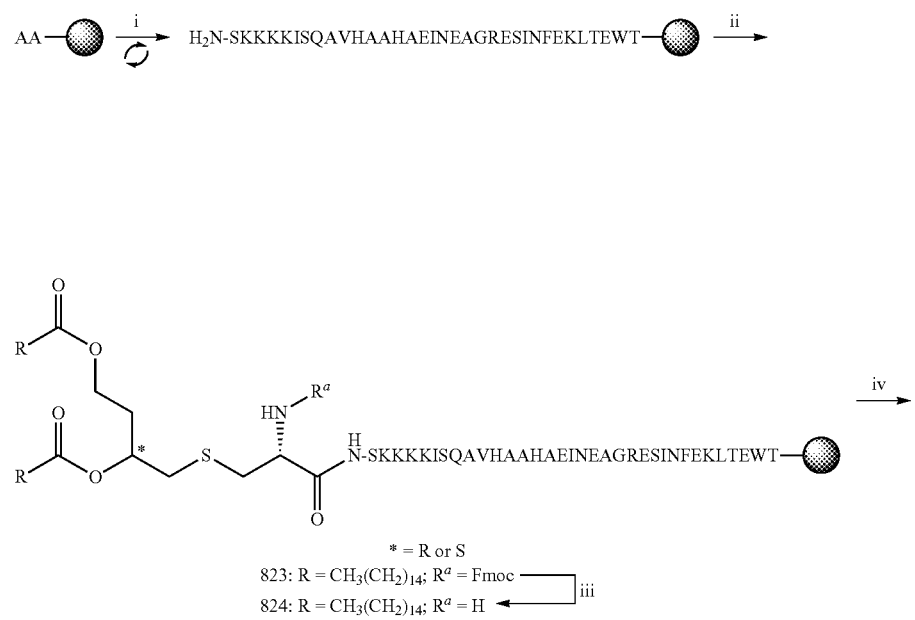

-continued

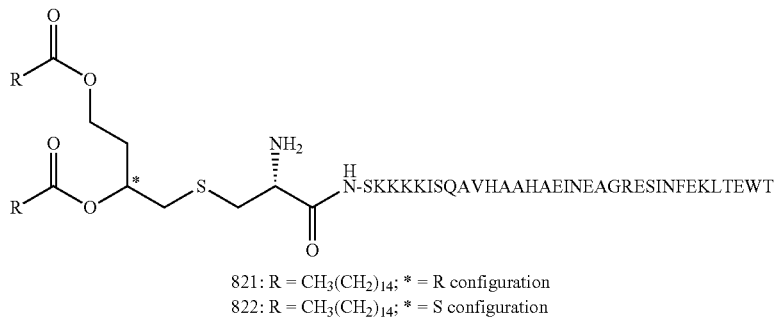

821: R = CH$_3$(CH$_2$)$_{14}$; * = R configuration
822: R = CH$_3$(CH$_2$)$_{14}$; * = S configuration ● = resin + linker
AA = amino acid
(i) Iterative Fmoc-SPPS; (ii) (R)- or (S)- bis-pamitoylated Fmoc-Cys-OH 6, PyBOP, collidine, DMF; (iii) 20% piperidine/DMF; (iv) TFA/EDT/water.

The desired peptide sequence was synthesised using standard iterative Fmoc SPPS techniques as previously described.

After coupling the penultimate amino acid residue, the resin-bound peptide chain was then derivatised with the desired diastereomer of amino acid conjugate 6 using PyBOP (benzotriazol-1-yl-oxytripyrrolidinophosphonium hexafluorophosphate) and collidine in DMF. The conditions for coupling of the amino acid conjugate reduce the propensity of the α-carbon of the amino acid to epimerise on activation. The amino acid conjugate (0.032 mmol) and PyBOP (0.033 mmol) were combined and dissolved in DMF (0.25 mL). Neat 2,4,6-trimethylpyridine (0.05 mmol) was added. After mixing for 30 seconds the solution was transferred to 0.016 mmol of resin, which was then agitated for 90 minutes, drained and washed (DMF) to afford 823.

The Fmoc group was then removed using 20% piperidine in DMF to provide 824.

Peptide 824 was cleaved from the resin to provide the peptide conjugate 821 with the R configuration at the indicated position (Scheme 8) or the peptide conjugate 822 with the S configuration at the indicated position. Resin (0.016 mmol) in 1.5 mL of trifluoroacetic acid containing 2.5% (v/v) ethanedithiol and 2.5% v/v water was agitated at room temperature for 2 hours. The supernatant was then drained through a sinter into chilled diethyl ether (10 mL). The resin was then washed with a further 1 mL of TFA, which was also added to the ether. The precipitated material was pelleted by centrifugation and the pellet washed once with ether (5 mL) before being dissolved in 1:1 MeCN/Water (+0.1% tfa) and lyophilised.

Purification of 821 and 822 was performed by semi-preparative HPLC using a Phenomenex Gemini C18 (5µ, 110 Å) 10×250 mm column with eluent A being water (+0.1% tfa) and eluent B being MeCN (+0.1% tfa). After injection of the crude peptide sample on to the column the following gradient was generated: 5% B to 45% B over 3 minutes followed by 45% B to 65% B over 16 minutes at a flow of 4 mL/min. The desired product material collected on elution from the column and freeze-dried.

| No. | Structure |
|-----|-----------|
| 821 | 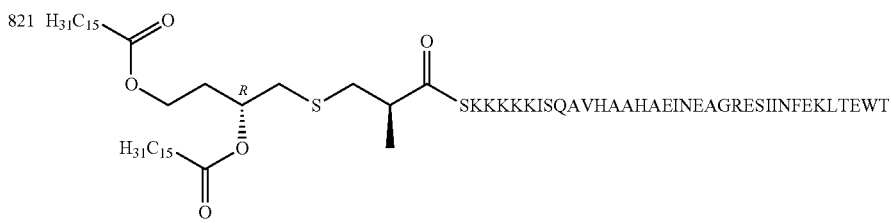 |
| 822 | 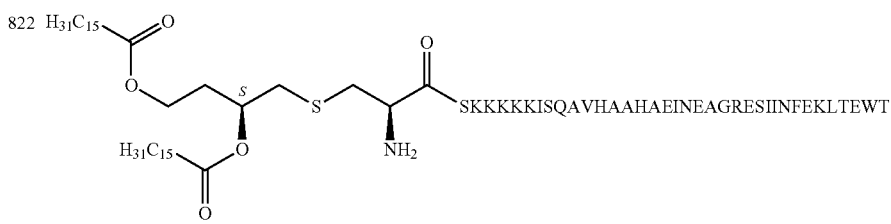 |

821: m/z (ESI) 1191.5 [M+4H⁺]. HPLC analysis: Column: Phenomenex Gemini C18 (34, 110 Å, 4.6×150 mm); eluent A, water/0.1% TFA; eluent B: MeCN/0.1% TFA; gradient: 5-95% B over 30 min @ 1 mL/min. Retention time: 20.9 mins.

822: m/z (ESI) 1191.5 [M+4H⁺]. HPLC analysis: Column: Phenomenex Gemini C18 (34, 110 Å, 4.6×150 mm); eluent A, water/0.1% TFA; eluent B: MeCN/0.1% TFA; gradient: 5-95% B over 30 min @ 1 mL/min. Retention time: 20.8 mins.

It is not the intention to limit the scope of the invention to the abovementioned examples only. As would be appreciated by a skilled person in the art, many variations are possible without departing from the scope of the invention.

The invention claimed is:

1. A compound of the formula (I):

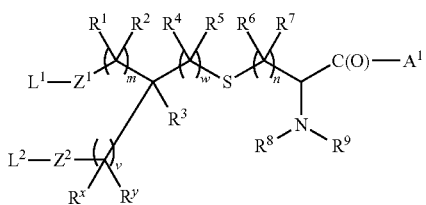

wherein
  m and w are each independently an integer from 0 to 7 and v is an integer from 0 to 5,
  provided that:
    the sum of m, v, and w is at least 3; and
    the sum of m and w is from 0 to 7;
  n is 1 or 2;
  Z1 and Z2 are each independently selected from the group consisting of —O—, —NR—, —S—, —S(O)—, —SO$_2$—, —C(O)O—, —OC(O)—, —C(O)NR—, —NRC(O)—, —C(O)S—, —SC(O)—, —OC(O)O—, —NRC(O)O—, —OC(O)NR—, and —NRC(O)NR—;
  R1, R2, Rx, Ry, R4, R5, R6, and R7 at each instance of m, v, w, and n are each independently hydrogen or C1-6aliphatic;
  R, R3, and R8 are each independently hydrogen or C1-6aliphatic;
  R9 is hydrogen, C1-6aliphatic, an amino protecting group, L3—C(O)—, or A2;
  L1 and L2 are each independently selected from C5-21aliphatic or C4-20heteroaliphatic;
  L3 is C1-21aliphatic or C2-20heteroaliphatic;
  A1 is an amino acid, a peptide, OH, OP1, NH$_2$, or NHP2, wherein P1 is a carboxyl protecting group, and wherein P2 is a carboxamide protecting group;
  A2 is an amino acid or a peptide;
  wherein any aliphatic or heteroaliphatic present in any of R, R1, R2, R3, R4, R5, R6, R7, R8, R9, Rx, Ry, L1, L2, and L3 is optionally substituted;
  wherein 1) A1 is a peptide comprising 8 to 220 amino acids and comprises an epitope or 2) R9 is A2 and is a peptide comprising an epitope;

or a pharmaceutically acceptable salt or solvate thereof.

2. The compound of claim 1, wherein Z1 and Z2 are each independently selected from the group consisting of —C(O)O—, —C(O)NR—, and —C(O)S—.

3. The compound of claim 1, wherein the compound is a compound of the formula (IA):

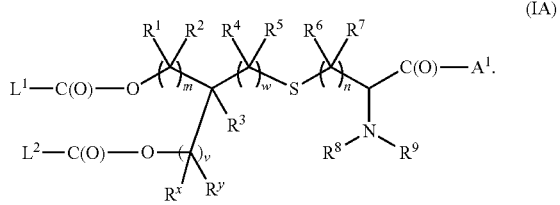

4. The compound of claim 1, wherein m and w are each independently from 0 to 5; and/or wherein the sum of m and w is from 2 to 7.

5. The compound of claim 1, wherein m is from 1 to 3; wherein w is 1 or 2; wherein n is 1; and/or wherein v is from 0 to 3.

6. The compound of claim 1, wherein L1 and L2 are each independently C5-21alkyl.

7. The compound of claim 6, wherein L1 and L2 are each independently linear C15alkyl.

8. The compound of claim 1, wherein L3 is methyl or linear C15alkyl.

9. The compound of claim 8, wherein L3 is methyl.

10. The compound of claim 1, wherein R1 and R2 at each instance of m are each independently C1-6alkyl or hydrogen; wherein R3 is C1-6alkyl or hydrogen; wherein R4 and R5 at each instance of w are each independently C1-6alkyl or hydrogen; wherein Rx and Ry at each instance of v are each independently C1-6alkyl or hydrogen; wherein R6 and R7 at each instance of n are each independently C1-6alkyl or hydrogen; wherein R8 is independently C1-6alkyl or hydrogen; and/or wherein R9 is C1-6alkyl, hydrogen, an amino protecting group, L3-C(0), or A2.

11. The compound of claim 1, wherein the compound is a compound of the formula (IF):

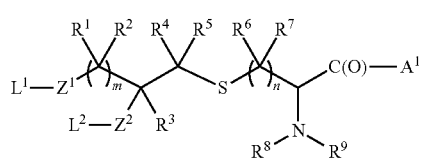

wherein m is an integer from 2 to 6; or a compound of the formula (IB):

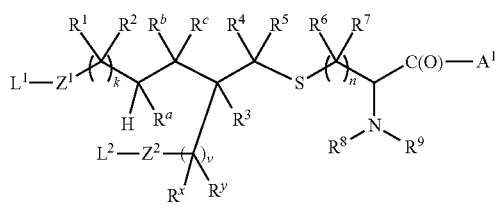

wherein k is an integer from 0 to 4, and wherein Ra, Rb, and Rc are each independently hydrogen or C1-6aliphatic.

12. The compound of claim 11, wherein k is 0 to 3; and/or wherein Ra, Rb, and Rc are each independently selected from hydrogen or C1-6alkyl.

13. The compound of claim 1, wherein the compound is a compound of the formula (ID):

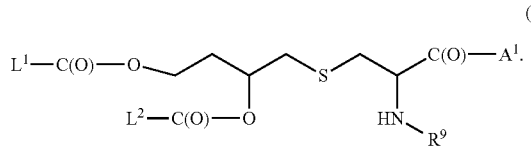

14. The compound of claim 1, wherein the compound of formula (I) has the formula (IEE-3):

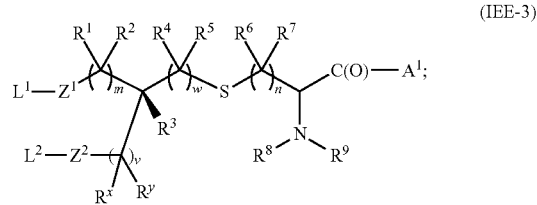

has the formula (IEE-4):

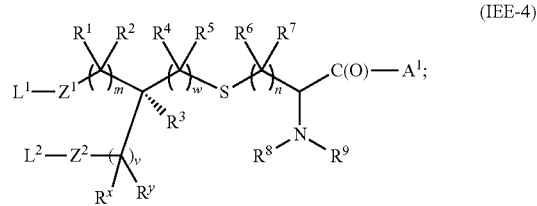

or has the formula (IE):

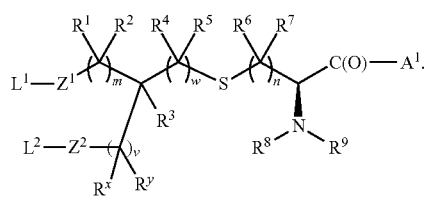

15. The compound of claim 1, wherein the amino acid of the peptide conjugate to which the lipid moieties are conjugated is an N-terminal amino acid residue; and/or wherein A1 is serine or a peptide comprising serine as the first N-terminal amino acid residue.

16. The compound of claim 1, wherein A1 and/or A2 is a peptide comprising a solubilising group.

17. The compound of claim 1, wherein the peptide comprises an amino acid sequence selected from the group consisting of 8 or more contiguous amino acids from the amino acid sequence of any one of SEQ ID NOs 1-121.

18. A pharmaceutical composition comprising an effective amount of a peptide conjugate compound of claim 1 or a pharmaceutically acceptable salt or solvate thereof, and a pharmaceutically acceptable carrier.

* * * * *

UNITED STATES PATENT AND TRADEMARK OFFICE
CERTIFICATE OF CORRECTION

PATENT NO. : 11,464,853 B2
APPLICATION NO. : 16/076912
DATED : October 11, 2022
INVENTOR(S) : Margaret Anne Brimble et al.

It is certified that error appears in the above-identified patent and that said Letters Patent is hereby corrected as shown below:

On the Title Page

Item (71)
Line 1, delete "Applicants:" and insert -- Applicant: --
Line 2, delete "Margaret Anne"
Line 3, delete "Brimble, Auckland (NZ); Geoffrey"
Line 4, delete "Martyn Williams, Auckland (NZ);"
Line 5, delete "Peter Roderick Dunbar, Auckland"
Line 6, delete "(NZ)"

Signed and Sealed this
Fourteenth Day of February, 2023

Katherine Kelly Vidal
*Director of the United States Patent and Trademark Office*